US008236512B1

(12) United States Patent
Zhao et al.

(10) Patent No.: US 8,236,512 B1
(45) Date of Patent: Aug. 7, 2012

(54) METHODS OF DEVELOPING TERPENE SYNTHASE VARIANTS

(75) Inventors: Lishan Zhao, Emeryville, CA (US); Lan Xu, San Diego, CA (US); Patrick Westfall, Novato, CA (US); Andrew Main, Berkeley, CA (US)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 13/363,588

(22) Filed: Feb. 1, 2012

Related U.S. Application Data

(60) Provisional application No. 61/438,948, filed on Feb. 2, 2011.

(51) Int. Cl.
*G01N 33/53* (2006.01)
*C12P 1/00* (2006.01)

(52) U.S. Cl. ............................................. 435/7.6

(58) Field of Classification Search .................. None
See application file for complete search history.

(56) References Cited

U.S. PATENT DOCUMENTS

| | | | |
|---|---|---|---|
| 7,927,794 | B2 | 4/2011 | Keasling et al. |
| 7,935,156 | B2 | 5/2011 | Renninger et al. |
| 2002/0035058 | A1 | 3/2002 | Brown et al. |
| 2009/0053797 | A1 | 2/2009 | Shiba et al. |
| 2010/0003716 | A1 | 1/2010 | Cervin et al. |

OTHER PUBLICATIONS

Amman et al. "'ATG vectors' for regulated high-level expression of cloned genes in *Escherichia coli*." Gene, 1985, vol. 40, pp. 183-190.
Arthington-Skaggs et al. "Quantitation of Ergosterol Content: Novel Method for Determination of Fluconazole Susceptibility of *Candida albicans*." Journal of Clinical Microbiology, Oct. 1999, vol. 37, No. 10, pp. 3332-3337.
Bennetzen et al. "Codon Selection in Yeast." Journal of Biological Chemistry, Mar. 25, 1982, vol. 257, No. 6, pp. 3026-3031.
Cane et al. "Pre-steady-state kinetic analysis of the trichodiene synthase reaction pathway." Biochemistry, Jul. 8, 1997, vol. 36, No. 27, pp. 8332-8339.
Cane "Enzymic formation of sesquiterpenes," Chemical Reviews, Nov. 1990, vol. 90, pp. 1089-1103.
Crock et al. "Isolation and bacterial expression of a sesquiterpene synthase cDNA clone from peppermint (*Mentha x piperita*, L.) that produces the aphid alarm pheromone (E)-β-farnesene." PNAS USA Nov. 25, 1997, vol. 94, No. 24, pp. 12833-12838.
Cregg et al. "*Pichia pastoris* as a host system for transformations." Molecular and Cellular Biology, Dec. 1985, vol. 5, No. 12, pp. 3376-3385.
Crockett et al. "Sensitive assay for cholesterol in biological membranes reveals membrane-specific differences in kinetics of cholesterol oxidase." Journal of Experimental Zoology, Feb. 1995, vol. 271, No. 3, pp. 190-195.
Deshpande "Ethanol production from cellulose by coupled saccharification/fermentation using *Saccharomyces cerevisiae* and cellulase complex from *Sclerotiun rolfsii* UV-8 mutant." Applied Biochemistry and Biotechnology, Sep. 1992, vol. 36, pp. 227-234.
Dijken et al. "An interlaboratory comparison of physiological and genetic properties of four *Saccharomyces cerevisiae* strains." Enzyme and Microbial Technology, 2000, vol. 26, pp. 706-714.
Eyre-Walker "Synonymous codon bias is related to gene length in *Escherichia coli*: selection for translational accuracy?" Molecular Biology and Evolution, Jul. 1996, vol. 13, No. 6, pp. 864-872.
Fisch et al. "A strategy of exon shuffling for making large peptide repertoires displayed on filamentous bacteriophage." PNAS USA, Jul. 1996, vol. 93, No. 15, pp. 7761-7766.
Frey et al. "Identification of ergosterol in vesicular-arbuscular mycorrhizae." Biology and Fertility of Soils, Aug. 1992, vol. 13, No. 4, pp. 229-234.

Geiser et al. "Integration of PCR Fragments at any Specific Site within Cloning Vectors without the Use of Restriction Enzymes and DNA Ligase." BioTechniques, Jul. 2001, vol. 31, No. 1, pp. 88-92.
Gouy et al. "Codon usage in bacteria: correlation with gene expressivity." Nucleic Acids Research, Nov. 25, 1982, vol. 10, No. 22, pp. 7055-7074.
Greenhagen et al. "Identifying and manipulating structural determinates linking catalytic specificities in terpene synthases." PNAS USA, Jun. 27, 2006, vol. 103, No. 26, pp. 9826-9831.
Griggs et al. "Regulated expression of the GAL4 activator gene in yeast provides a sensitive genetic switch for glucose repression." PNAS USA, Oct. 1991, vol. 88, No. 19, pp. 8597-8601.
Kovach et al. "Four new derivatives of the broad-host-range cloning vector pBBR1MCS, carrying different antibiotic-resistance cassettes" Gene, Dec. 1995, vol. 166, No. 1, pp. 175-176.
Lutz et al. "Independent and tight regulation of transcriptional units in *Escherichia coli* via the LacR/O, the TetR/O and AraC/I1-I2 regulatory elements." Nucleic Acids Research, Mar. 15, 1997, vol. 25, No. 6, pp. 1203-1210.
Mathis et al. "Pre-steady-state study of recombinant sesquiterpene cyclases." Biochemistry Jul. 8, 1997, vol. 36, No. 27, pp. 8340-8348.
Mumberg et al. "Regulatable promoters of *Saccharomyces cerevisiae*: comparison of transcriptional activity and their use for heterologous expression." Nucleic Acids Research, Dec. 25, 1994, vol. 22, No. 25, pp. 5767-5768.
Nakamura et al. "Codon usage tabulated from international DNA sequence databases: status for the year 2000." Nucleic Acids Research, Jan. 2000, vol. 28, No. 1, p. 292. Nixon et al. "Assembly of an active enzyme by the linkage of two protein modules," PNAS USA, Feb. 18, 1997, vol. 94, No. 15, pp. 1069-1073.
Nogi et al. "Nucleotide sequence of the yeast regulatory gene GAL80." Nucleic Acids Research, Dec. 21, 1984 vol. 12, No. 24, pp. 9287-9298.
O'Maille et al. "Quantitative exploration of the catalytic landscape separating divergent plant sesquiterpene synthases." Nature Chemical Biology, Oct. 2008, vol. 4, pp. 617-623.
Picaud et al, "Expression, purification and characterization of recombinant (E)-β-farnesene synthase from *Artemisia annua*." Phytochemistry May 2005, vol. 66, No. 9, pp. 961-967.
Seitz et al. "Ergosterol as a measure of fungal growth." Physiology and Biochemistry, 1979, vol. 69, pp. 1202-1203.
Voynova et al. "*Staphylococcus aureus* Mevalonate Kinase: Isolation and Characterization of an Enzyme of the Isoprenoid Biosynthetic Pathway." Journal of Bacteriology, Jan. 2004, vol. 186, No. 1, pp. 61-67.
Withers et al. "Identification of Isopentenol Biosynthetic Genes from *Bacillus subtilis* by a Screening Method Based on Isoprenoid Precursor Toxicity." Applied and Environmental Microbiology, Oct. 2007, vol. 73, No. 19, pp. 6277-6283.
Yoshikuni et al. "Designed divergent evolution of enzyme function." Nature, Apr. 2006, vol. 440, pp. 1078-1082.
Yoshikuni et al. "Redesigning Enzymes Based on Adaptive Evolution for Optimal Function in Synthetic Metabolic Pathways." Chemistry & Biology, Jun. 23, 2008, vol. 15, No. 6, pp. 607-618.
International Search Report for PCT Application No. PCT/US12/23446, mailed on May 4, 2012, 3 pages.
Written Opinion for PCT Application No. PCT/US12/23446, mailed on May 4, 2012, 5 pages.

*Primary Examiner* — Suzanne M Noakes

(74) *Attorney, Agent, or Firm* — Sheridan Ross, P.C.

(57) ABSTRACT

The present disclosure relates to methods of developing terpene synthase variants through engineered host cells. Particularly, the disclosure provides methods of developing terpene synthase variants with improved in vivo performance that are useful in the commercial production of terpene products. Further encompassed in the present disclosure are superior terpene synthase variants and host cells comprising such terpene synthase variants.

29 Claims, 26 Drawing Sheets

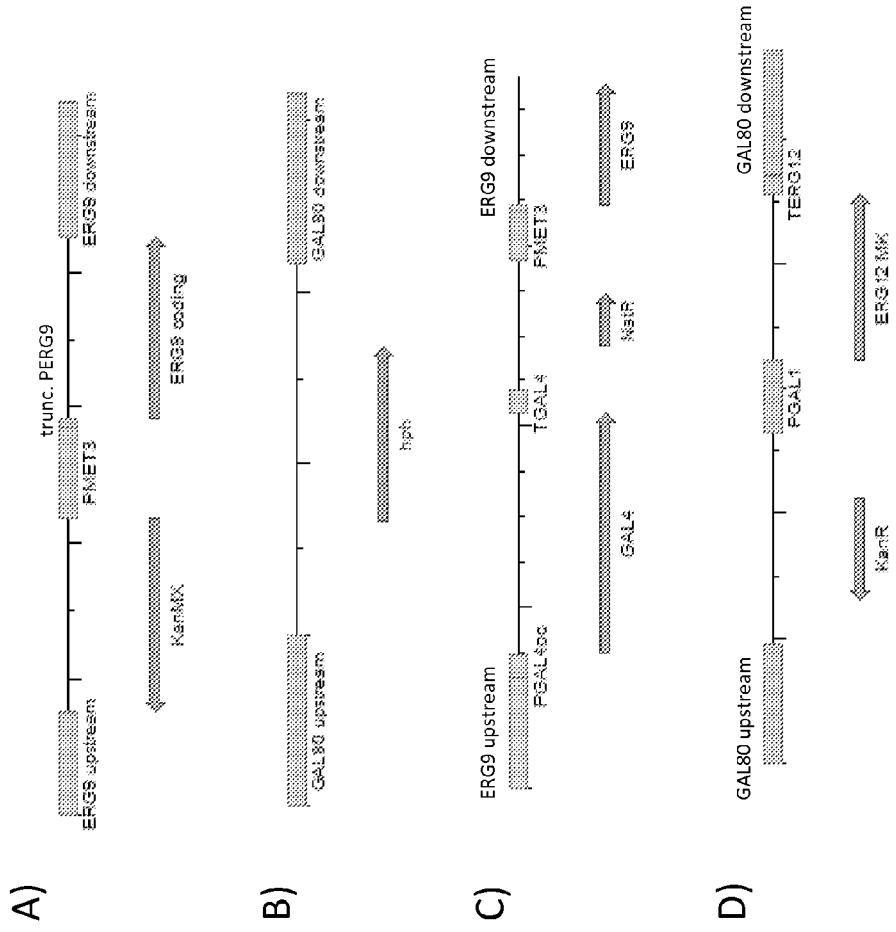

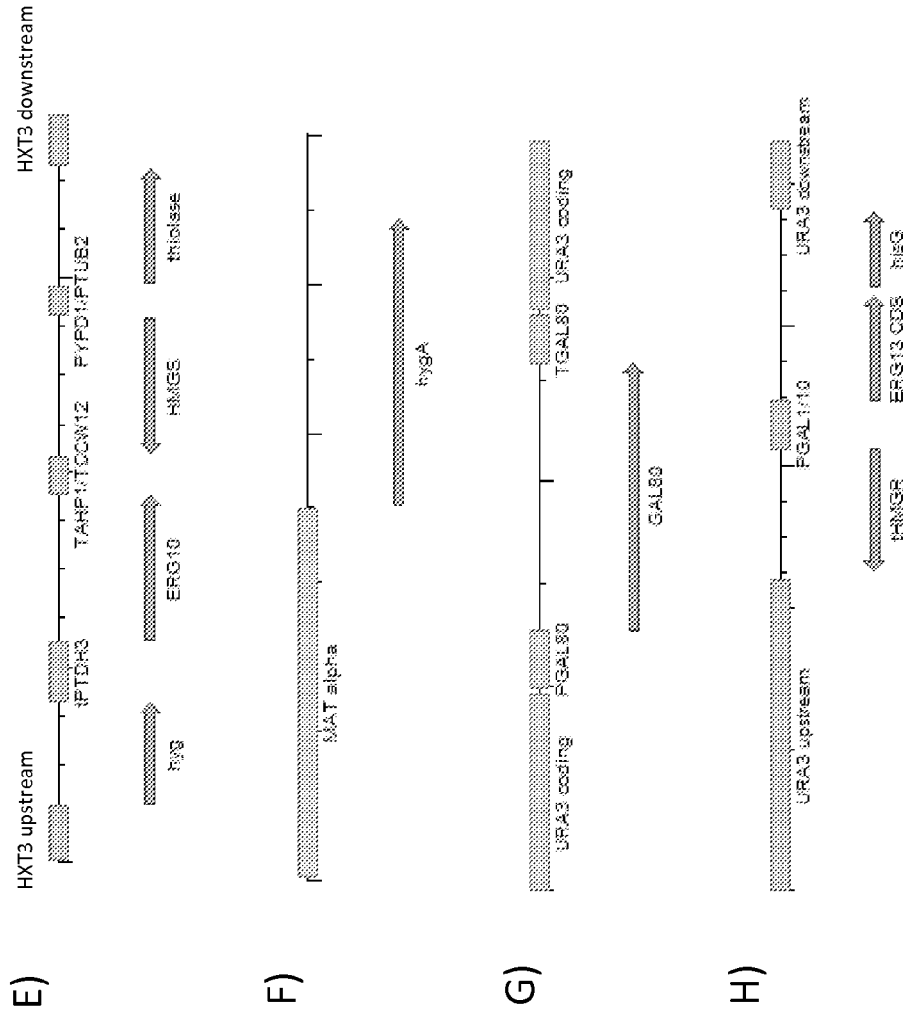

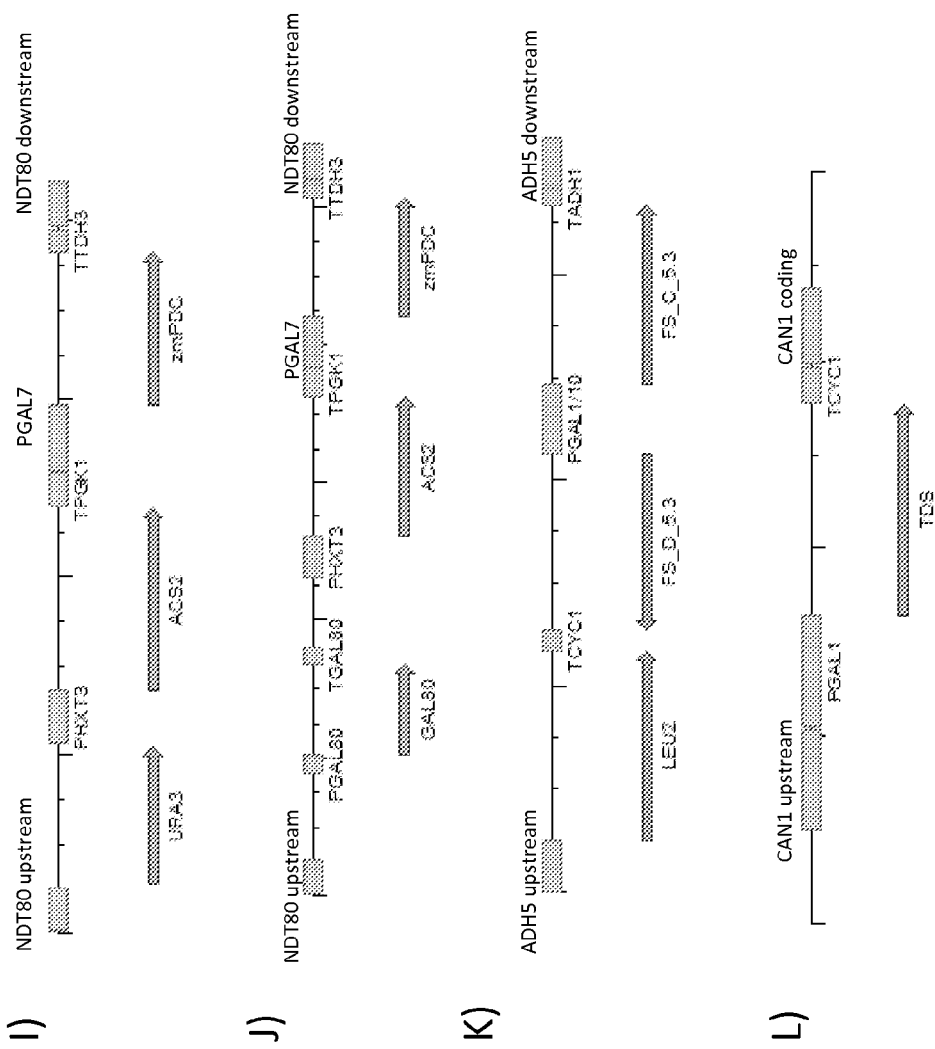

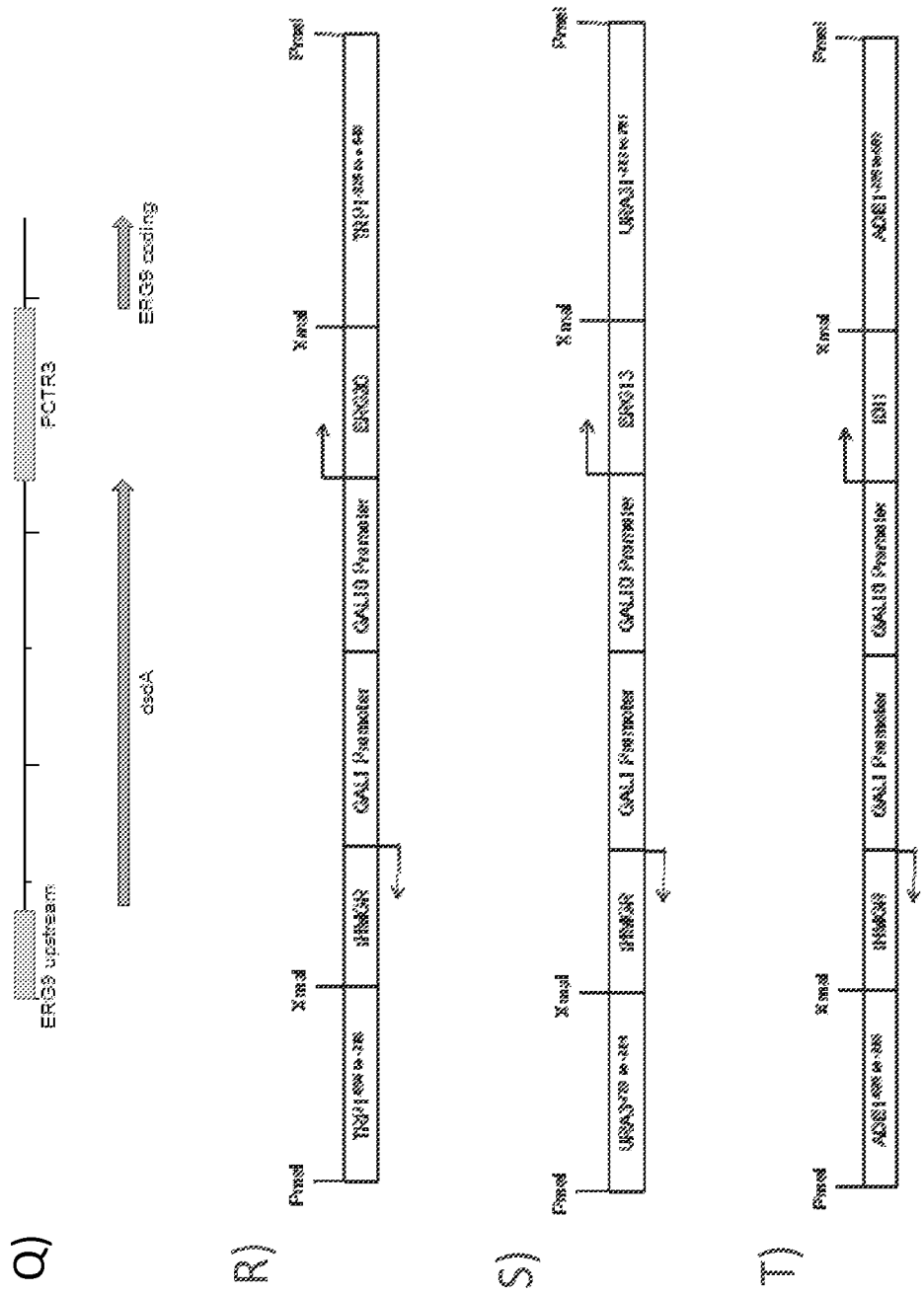

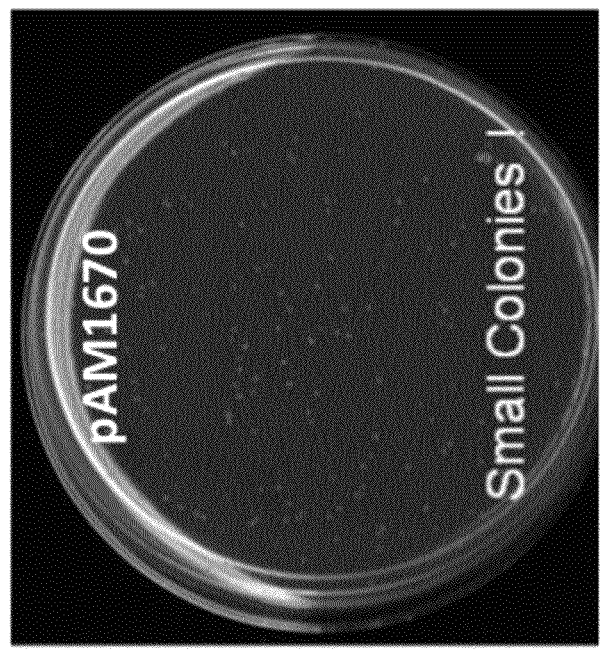
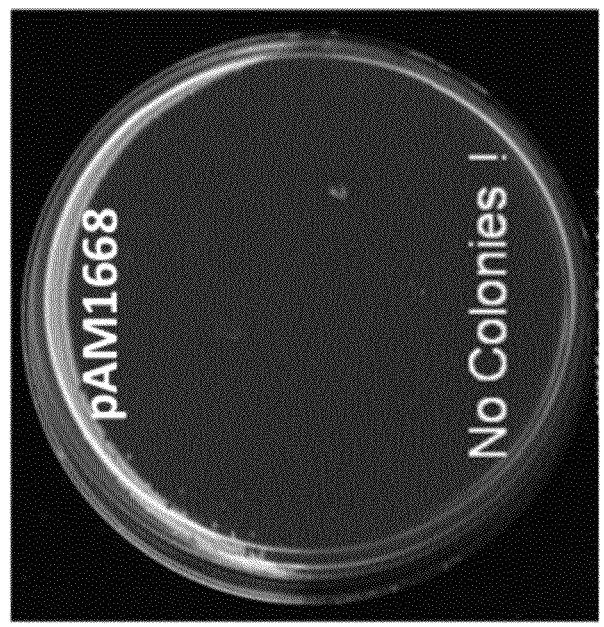
Figure 3

A)

Figure 13:
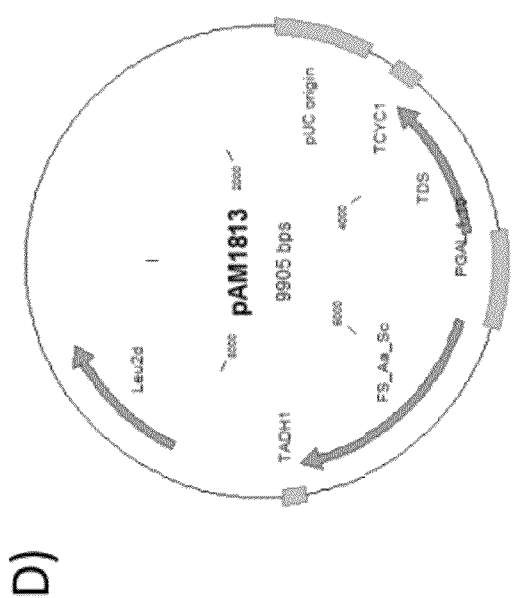

Figure 13
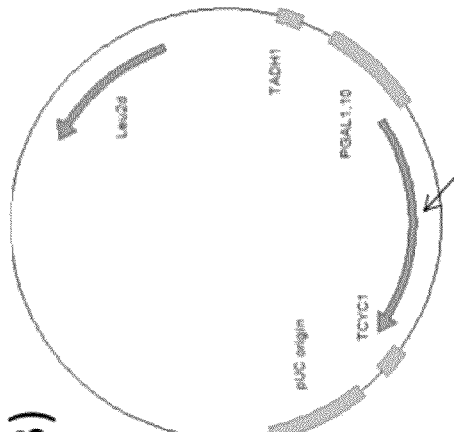
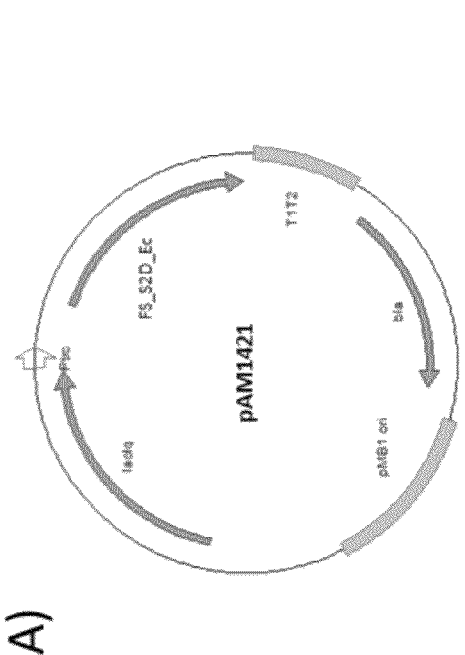
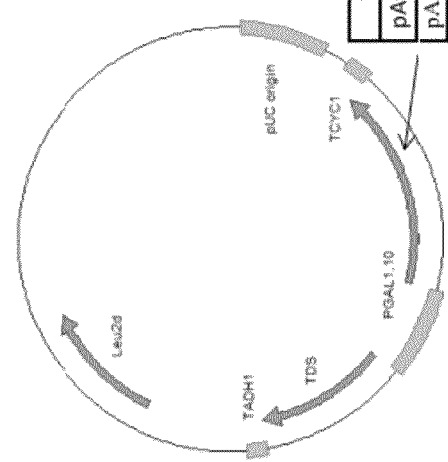

D)

METHODS OF DEVELOPING TERPENE SYNTHASE VARIANTS

1. CROSS REFERENCE TO RELATED APPLICATION

This application claims the benefit of priority under 35 U.S.C. §119(e) to U.S. Provisional Patent Application Ser. No. 61/438,948 filed Feb. 2, 2011, which is incorporated herein by reference.

2. FIELD OF THE INVENTION

The present disclosure relates to methods of developing terpene synthase variants through engineered host cells. Particularly, the disclosure provides methods of developing terpene synthase variants with improved in vivo performance that are useful in the commercial production of terpene products. Further encompassed in the present disclosure are superior terpene synthase variants, and host cells comprising such terpene synthase variants.

3. BACKGROUND

Terpenes are a large class of hydrocarbons that are produced in many organisms. They are derived by linking units of isoprene ($C_5H_8$), and are classified by the number of isoprene units present. Hemiterpenes consist of a single isoprene unit. Isoprene itself is considered the only hemiterpene. Monoterpenes are made of two isoprene units, and have the molecular formula $C_{10}H_{16}$. Examples of monoterpenes are geraniol, limonene, and terpineol. Sesquiterpenes are composed of three isoprene units, and have the molecular formula $C_{15}H_{24}$. Examples of sesquiterpenes are farnesenes, farnesol and patchoulol. Diterpenes are made of four isoprene units, and have the molecular formula $C_{20}H_{32}$. Examples of diterpenes are cafestol, kahweol, cembrene, and taxadiene. Sesterterpenes are made of five isoprene units, and have the molecular formula $C_{25}H_{40}$. An example of a sesterterpenes is geranylfarnesol. Triterpenes consist of six isoprene units, and have the molecular formula $C_{30}H_{48}$. Tetraterpenes contain eight isoprene units, and have the molecular formula $C_{40}H_{64}$. Biologically important tetraterpenes include the acyclic lycopene, the monocyclic gamma-carotene, and the bicyclic alpha- and beta-carotenes. Polyterpenes consist of long chains of many isoprene units. Natural rubber consists of polyisoprene in which the double bonds are cis.

When terpenes are chemically modified (e.g., via oxidation or rearrangement of the carbon skeleton) the resulting compounds are generally referred to as terpenoids, which are also known as isoprenoids. Isoprenoids play many important biological roles, for example, as quinones in electron transport chains, as components of membranes, in subcellular targeting and regulation via protein prenylation, as photosynthetic pigments including carotenoids, chlorophyll, as hormones and cofactors, and as plant defense compounds with various monoterpenes, sesquiterpenes, and diterpenes. They are industrially useful as antibiotics, hormones, anticancer drugs, insecticides, and chemicals.

Terpenes are biosynthesized through condensations of isopentenyl pyrophosphate (isopentenyl diphosphate or IPP) and its isomer dimethylallyl pyrophosphate (dimethylallyl diphosphate or DMAPP). Two pathways are known to generate IPP and DMAPP, namely the mevalonate-dependent (MEV) pathway of eukaryotes, and the mevalonate-independent or deoxyxylulose-5-phosphate (DXP) pathway of prokaryotes. Plants use both the MEV pathway and the DXP pathway. IPP and DMAPP in turn are condensed to polyprenyl diphosphates (e.g., geranyl disphosphate or GPP, farnesyl diphosphate or FPP, and geranylgeranyl diphosphate or GGPP) through the action of prenyl disphosphate synthases (e.g., GPP synthase, FPP synthase, and GGPP synthase, respectively).

The polyprenyl diphosphate intermediates are converted to more complex isoprenoid structures by terpene synthases. Terpene synthases are organized into large gene families that form multiple products. Examples of terpene synthases include sesquiterpene synthases, which convert FPP into sesquiterpenes. An example of a sesquiterpene synthase is farnesene synthase, which converts FPP to farnesene. The reaction mechanism of terpene synthases has been extensively investigated and is well understood. Overall, three steps are required to convert a diphosphate substrate such as FPP to its isoprenoid product: a) formation of enzyme-substrate complex (ES), b) formation of an enzyme-bound reactive carbocation intermediate, subsequent rearrangements, and the formation of product (EP), and c) release of product from the enzyme-product complex. In vitro kinetic and pre-steady state kinetic studies on terpene synthase catalyzed reactions have shown that the overall rate-limiting step for the reactions is the release of product (Cane et al. (1997) *Biochemistry*, 36(27):8332-9, and Mathis et al. (1997) *Biochemistry* 36(27): 8340-8). The turnover rates of terpene synthases are low, generally measured at less than 0.5 per second (Cane, D.C. (1990) *Chem. Rev.* 90:1089-1103).

Terpene synthases are important in the regulation of pathway flux to an isoprenoid because they operate at metabolic branch points and often compete with other metabolic enzymes for a prenyl diphosphate pool. For example, FPP is the precursor to many cellular molecules including squalene, dolichols, and the cofactor heme. In engineered microbes where the production of sesquiterpenes such as farnesene is desired, the terpene synthases hold the key to high yield production of such terpenes. However, because they are slow enzymes, terpene synthases are often the bottlenecks in the metabolic pathways. In addition, they can suffer from other shortcomings such as substrate inhibition that limit the kinetic capacity required for efficient production of terpenes in engineered microbial hosts (Crock et al. (1997) *Proc. Natl. Acad. Sci. USA* 94:12833-12838).

Hence, there are potentially enormous benefits to improving the catalytic efficiency of terpene synthases so that these enzymes would no longer limit the overall metabolic flux to an isoprenoid. Attempts to engineer terpene synthases for altered product specificity as well as the use of rational approaches such as those based on structural guidance or adaptive evolution have been described previously (Greenhagen et al. (2006) *Proc. Natl. Acad. Sci. USA* 103:9826-9831; O'Maille et al. (2008) *Nat. Chem. Biol.* 4:617-623; Yoshikuni et al. (2006) *Nature* 440:1078-1082; Yoshikuni et al. (2008) *Chem. Biol.* 15:607-618). However, these studies have fallen short of improving the kinetic capacity of terpene synthases while also maintaining their product specificity. In addition, the application of conventional protein engineering strategies, such as directed evolution, has been devoid for terpene synthases primarily because of the lack of available and effective high throughput screening methods (Yoshikuni et al. (2008) (supra)). There thus remains a need for reliable and high throughput methods for improving the catalytic efficiency of terpene synthases, and for terpene synthase variants that have such improved catalytic efficiency.

4. SUMMARY OF THE INVENTION

The present disclosure relates to methods of developing terpene synthase variants through engineered host cells. Particularly, the disclosure provides methods of developing terpene synthase variants with improved in vivo performance. The methods also allow for the continued improvement of the in vivo performance of these enzymes.

In one aspect, the present invention provides a screening method for a sesquiterpene synthase variant with improved in vivo performance, comprising the steps of:
a) engineering a host cell expressing a control sesquiterpene synthase to comprise an elevated level of FPP, wherein the elevated level of FPP reduces the viability of the host cell compared to a parent cell not comprising the elevated level of FPP;
b) expressing in the host cell a test sesquiterpene synthase instead of the control sesquiterpene synthase, wherein the test sesquiterpene synthase is a variant of the control sesquiterpene synthase; and
c) identifying the test sesquiterpene synthase as having improved in vivo performance compared to the control sesquiterpene synthase by an increase in viability of the host cell expressing the test sesquiterpene synthase compared to the host cell expressing the control terpene synthase.

In some embodiments, the host cell is plated on an agar plate, and a host cell comprising a test terpene synthase variant with improved in vivo performance is identified by colony growth. In some embodiments, the method further comprises selecting and/or isolating the test sesquiterpene synthase having improved in vivo performance.

In some embodiments, a collection of sesquiterpene synthase variants is expressed in a collection of host cells. In some embodiments, the collection of sesquiterpene synthase variants comprises from 2 to 5, from 5 to 10, from 10 to 50, from 50 to 100, from 100 to 500, from 500 to 1,000, from 1,000 to 10,000, from 10,000 to 100,000, from 100,000 to 1,000,000, and more, sesquiterpene synthase variants.

In some embodiments, the screening method is used in an iterative fashion, wherein the test sesquiterpene synthase identified in an iteration is used as the control sesquiterpene synthase of the next iteration, and wherein the host cell in an iteration comprises such elevated level of FPP that it has reduced viability in the presence of the test sesquiterpene synthase identified in the previous iteration compared to a parent cell not comprising the elevated level of FPP.

In another aspect, provided herein is a composition comprising two cell subpopulations derived from a common population of host cells comprising an elevated level of FPP, wherein:
a) the first subpopulation comprises a control sesquiterpene synthase, wherein the elevated level of FPP reduces the viability of cells of the first subpopulation compared to the viability of a parent cell not comprising the elevated level of FPP; and
b) the second subpopulation comprises a test sesquiterpene synthase, wherein the test sesquiterpene synthase is a variant of the control sesquiterpene synthase.

In some embodiments, the viability of the cells of the second subpopulation is greater than the viability of the cells of the first subpopulation.

In another aspect, the present invention provides a second screening method for identifying terpene synthase variants with improved in vivo performance, comprising the steps of:
a) providing a host cell expressing a control terpene synthase and having a growth rate;
b) expressing in the host cell a test terpene synthase instead of the control terpene synthase, wherein the test terpene synthase is a variant of the control terpene synthase; and
d) identifying the test terpene synthase as having improved in vivo performance compared to the control terpene synthase by a decreased growth rate of the host cell expressing the test terpene synthase compared to the growth rate of the host cell expressing the control terpene synthase.

In yet another aspect, the present invention provides a competition method for identifying and/or ranking the in vivo performance of terpene synthase variants, comprising the steps of:
a) dividing a population of host cells into a control population and a test population;
b) expressing in the control population a control terpene synthase and a comparison terpene synthase, wherein the control terpene synthase can convert a polyprenyl diphosphate to a first terpene, and wherein the comparison terpene synthase can convert a polyprenyl diphosphate to a second terpene;
c) expressing in the test population the comparison terpene synthase and a test terpene synthase, wherein the test terpene synthase is a variant of the control terpene synthase, and wherein the comparison terpene synthase is expressed at similar levels in the test population and in the control population; and
d) measuring a ratio of the first terpene over the second terpene in the test population and in the control population.

In separate embodiments, the competition method is applied to identify and/or to rank terpene synthases selected from the group consisting of monoterpene synthases, diterpene synthases, sesquiterpene synthases, sesterterpene synthases, triterpene synthases, tetraterpene synthases, and polyterpene synthases.

In some embodiments, the competition method is used to screen a library of mutant terpene synthases on the basis that compared to the control terpene synthase, a terpene synthase variant with improved in vivo performance is capable of diverting more flux from a polyprenyl diphosphate substrate to its terpene product, thus, giving a higher ratio of terpene of interest/comparison terpene (i.e., first terpene/second terpene). In such embodiments, it is important that the test terpene synthase is expressed at a similar level in the test population as the control terpene synthase is expressed in the control population.

In other embodiments, the competition method is used to identify a promoter of a desired strength. In such embodiments, the control terpene synthase and the test terpene synthase are identical, and the control population and test population differ in the expression level of the control terpene synthase.

In another aspect, provided herein is a composition comprising two cell subpopulations derived from a common population of host cells, wherein:
a) the first subpopulation comprises a control terpene synthase and a comparison terpene synthase, wherein the control terpene synthase converts a polyprenyl diphosphate to a first terpene, and wherein the comparison sesquiterpene synthase converts the polyprenyl diphosphate to a second terpene; and
b) the second subpopulation comprises a test terpene synthase and the comparison terpene synthase, wherein the control terpene synthase converts the polyprenyl diphosphate to the first terpene, and wherein the test terpene synthase is a variant of the control terpene synthase.

In some embodiments, the ratio of the first terpene over the second terpene is greater in the second subpopulation compared to that in the first subpopulation. In yet another aspect, provided herein are isolated β-farnesene synthase variants, and isolated nucleic acids comprising a nucleotide sequence encoding such β-farnesene synthase variants, having an amino acid sequence as given in SEQ ID NO: 111 but comprising one or more amino acid substitutions at positions selected from the group consisting of positions 2, 3, 4, 6, 9, 11, 18, 20, 24, 35, 38, 50, 61, 72, 80, 89, 105, 115, 144, 196, 211, 251, 280, 288, 319, 348, 357, 359, 369, 371, 385, 398, 423, 433, 434, 442, 444, 446, 460, 467, 488, 495, 505, 526, 531, 556, 572, and 575 of SEQ ID NO: 111.

In yet another aspect, the present invention provides a genetically modified host cell that comprises:
(a) a heterologous β-farnesene synthase, wherein the heterologous β-farnesene synthase is a variant of a β-farnesene synthase encoded by SEQ ID NO: 111; and
(b) a MEV pathway or DXP pathway enzyme;
wherein the host cell makes at least 15% more of a β-farnesene compared to a parent cell that comprises the MEV pathway or DXP pathway enzyme and the β-farnesene synthase encoded by SEQ ID NO: 111.

In yet another aspect, provided herein is a method of producing β-farnesene comprising the steps of:
(a) obtaining a plurality of genetically modified host cells comprising:
 i) a first heterologous nucleotide sequence encoding a variant of a β-farnesene synthase encoded by SEQ ID NO: 111; and
 ii) a second heterologous nucleotide sequence encoding a MEV pathway or DXP pathway enzyme;
(b) culturing said genetically modified host cells in a medium comprising a carbon source under conditions suitable for making the β-farnesene; and
(c) recovering the β-farnesene from the medium.

5. BRIEF DESCRIPTION OF THE FIGURES

The present disclosure is best understood when read in conjunction with the accompanying figures, which serve to illustrate the preferred embodiments. It is understood, however, that the disclosure is not limited to the specific embodiments disclosed in the figures.

FIGS. 1A-Z provides maps of several chromosomal integration constructs used in the generation of host cells of the invention.

Figure 2:
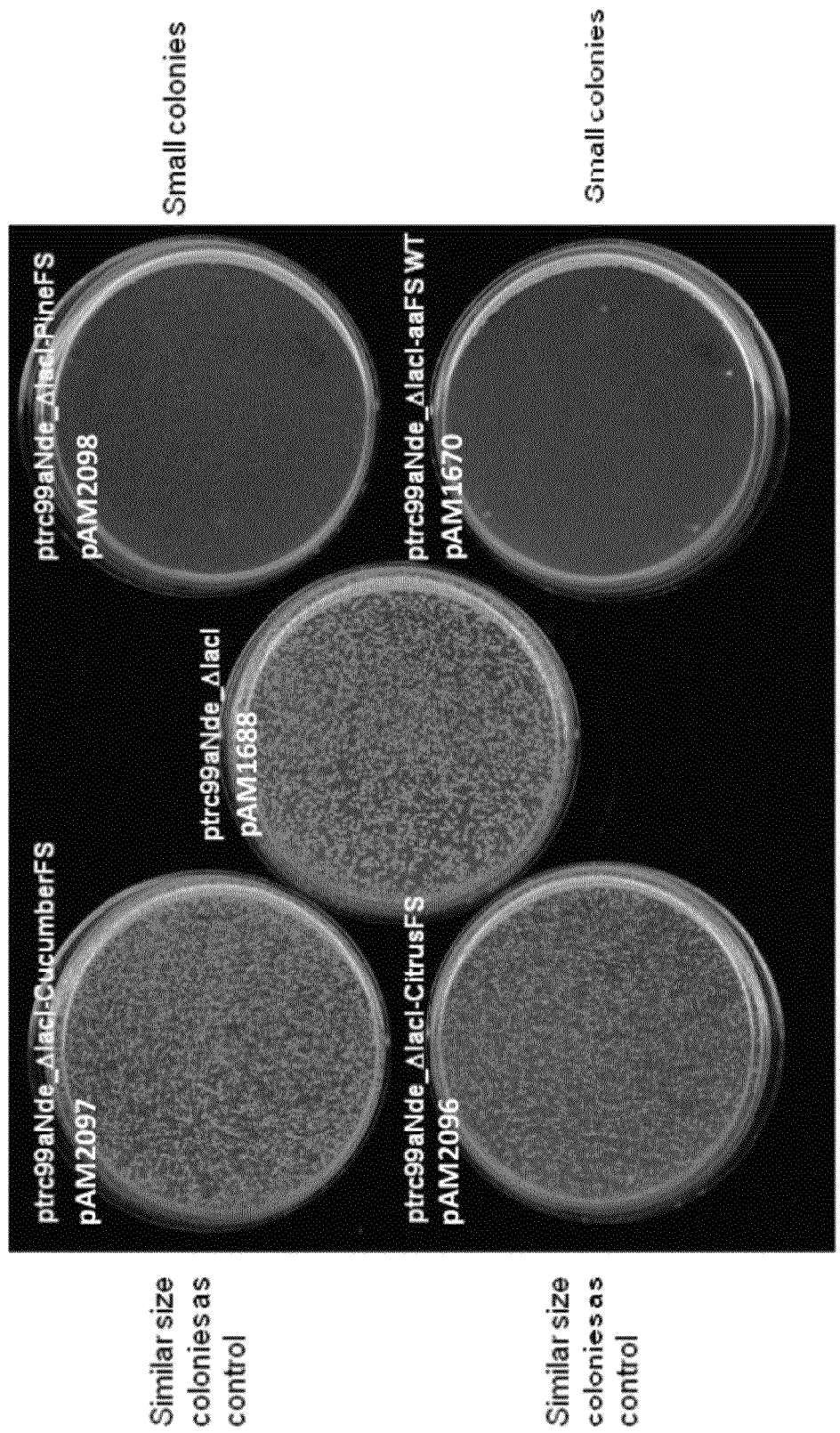

FIG. 2 provides an image of several agar plates on which were plated *Escherichia coli* host cells comprising active and inactive sesquiterpene synthases for FPP starvation-based selection.

FIG. 3 provides an image of two agar plates on which were plated *Escherichia coli* host cells comprising active and inactive sesquiterpene synthases for FPP toxicity-based growth selection.

Figure 4:
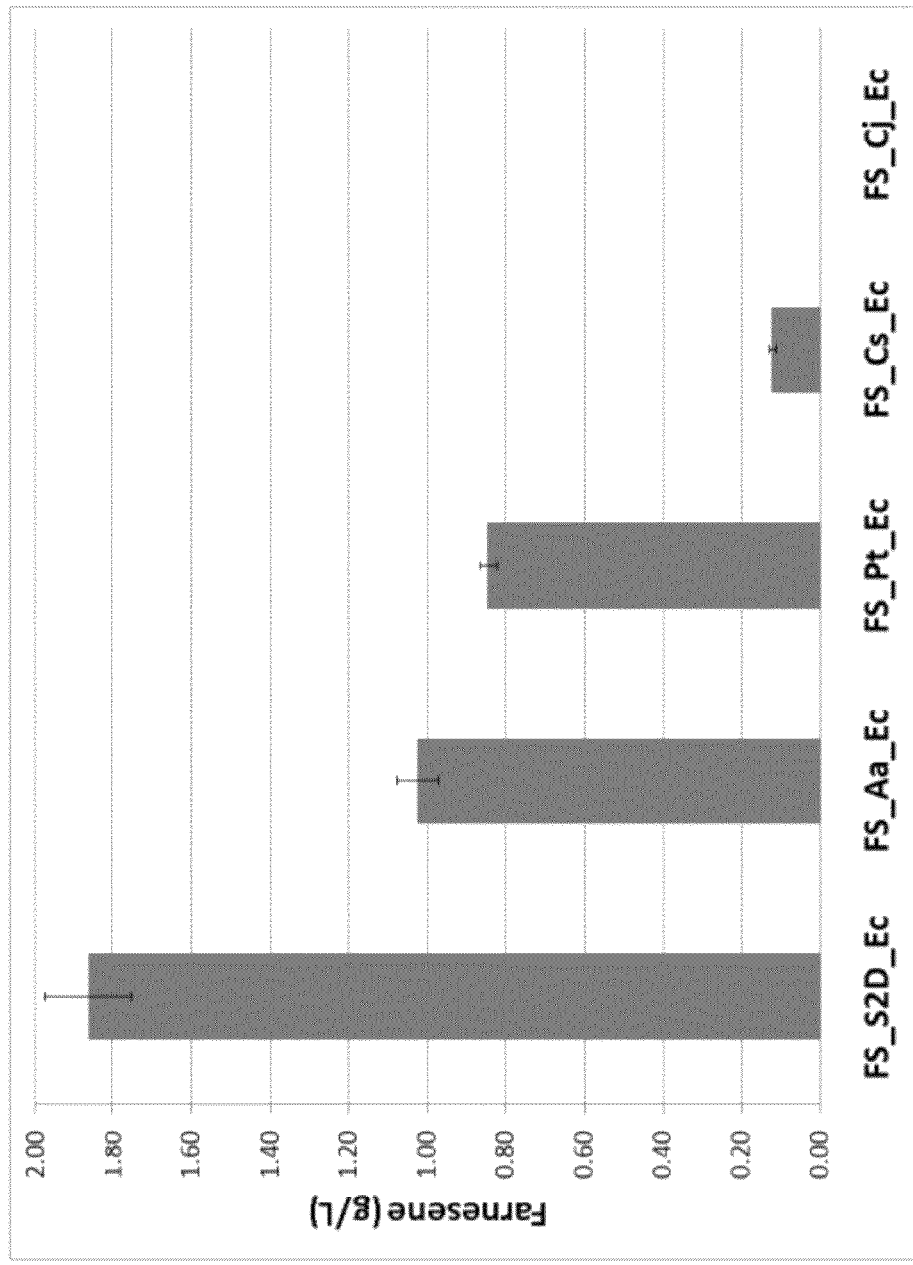

FIG. 4 provides farnesene titers obtained by GC analysis of *Escherichia coli* host cells comprising various farnesene synthase coding sequences.

Figure 5:
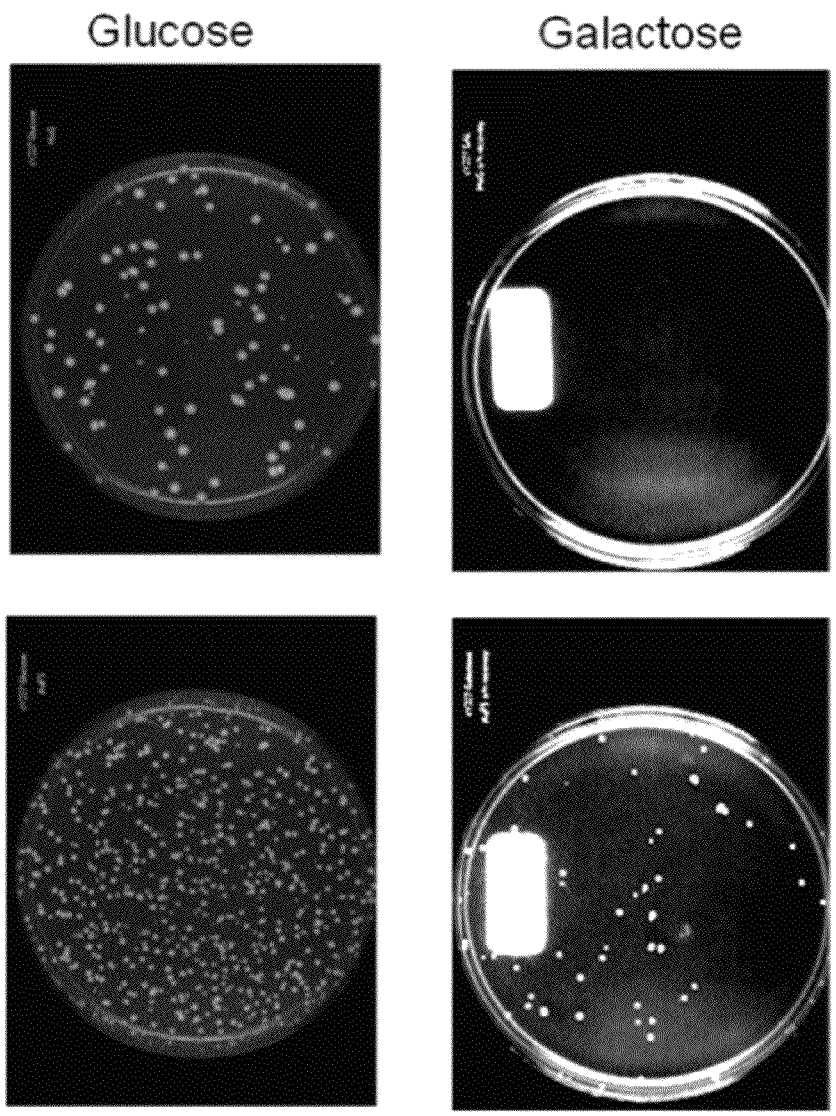

FIG. 5 provides an image of agar plates on which were plated *Saccharomyces cerevisiae* host cells comprising active and inactive sesquiterpene synthases for FPP toxicity-based growth selection.

Figure 6:
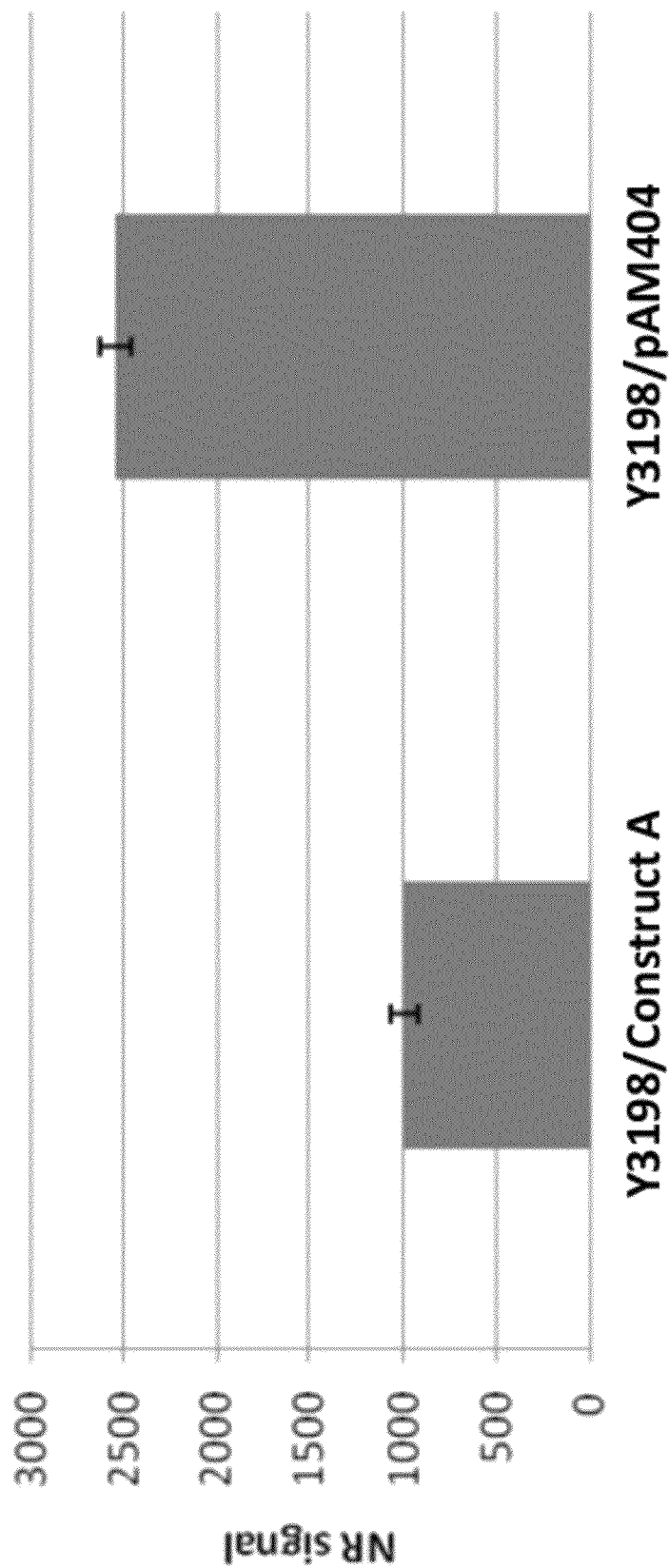

FIG. 6 provides farnesene titers obtained by Nile Red fluorescence analysis of *Saccharomyces cerevisiae* host cells comprising either chromosomally intergrated or extrachromosomally maintained farnesene synthase coding sequences.

Figure 7:
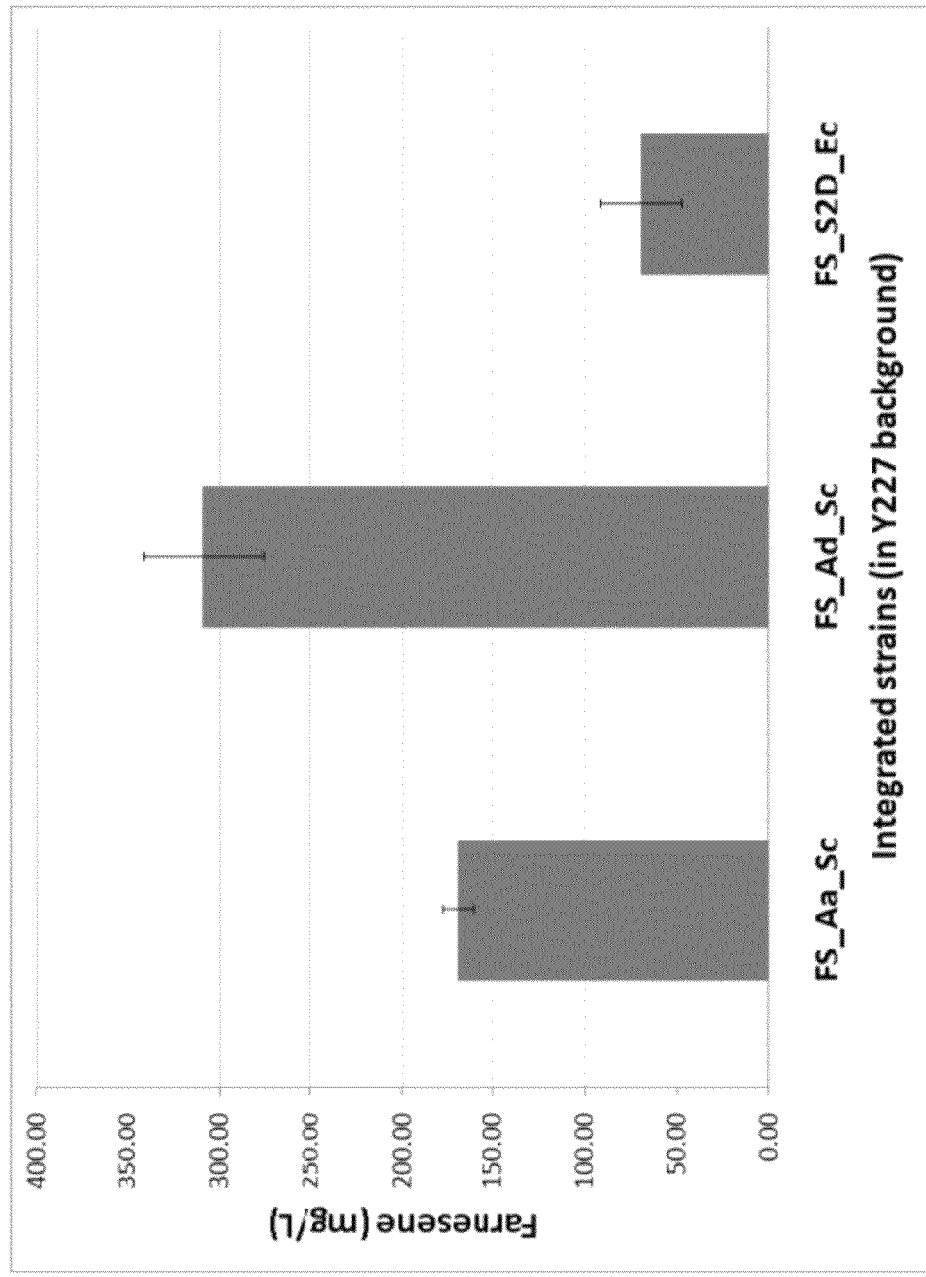

FIG. 7 provides farnesene titers obtained by GC analysis of *Saccharomyces cerevisiae* host cells ranked by sesquiterpene synthase competition.

Figure 8:
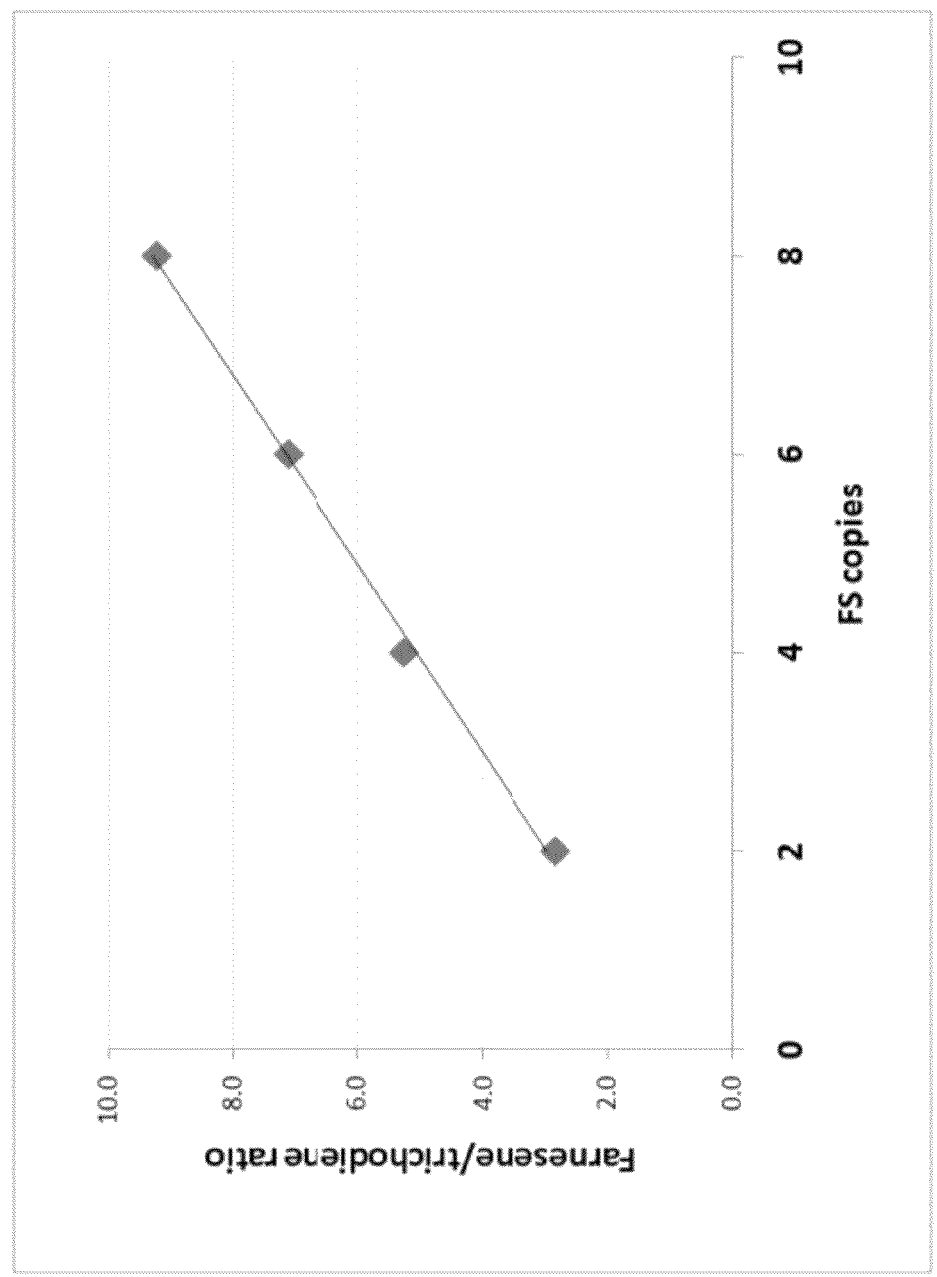

FIG. 8 provides farnesene/trichodiene titer ratios obtained by GC analysis of *Saccharomyces cerevisiae* host cells comprising increasing copy numbers of farnesene synthase coding sequences.

Figure 9:
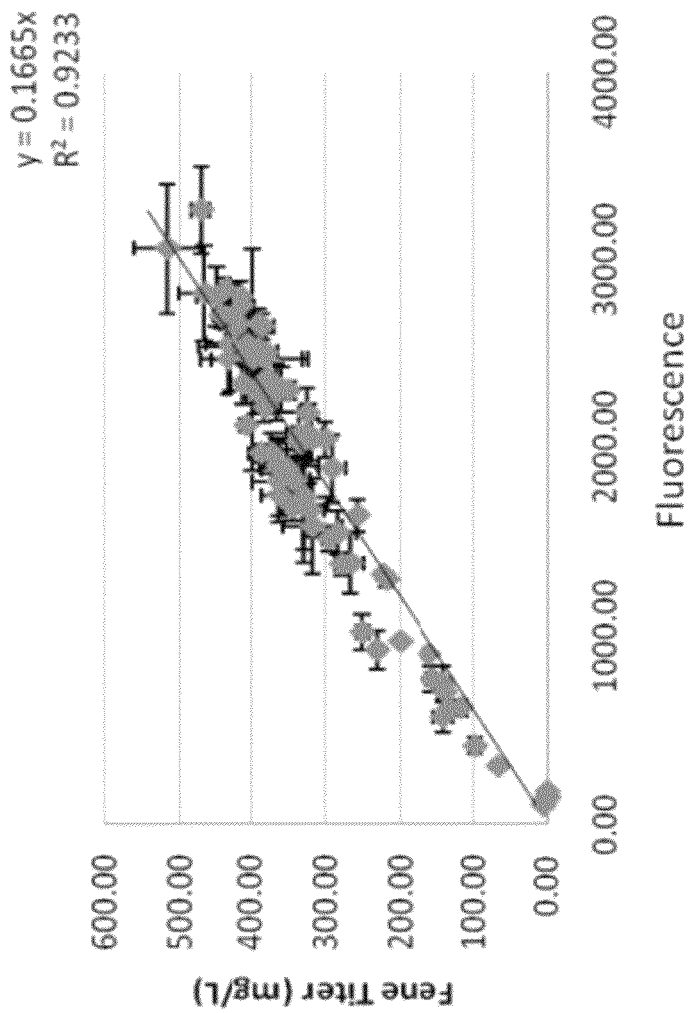

FIG. 9 provides a comparison of farnesene titers obtained by GC analysis versus Nile Red fluorescence analysis of *Escherichia coli* host cells of a sesquiterpene synthase library.

Figure 10:
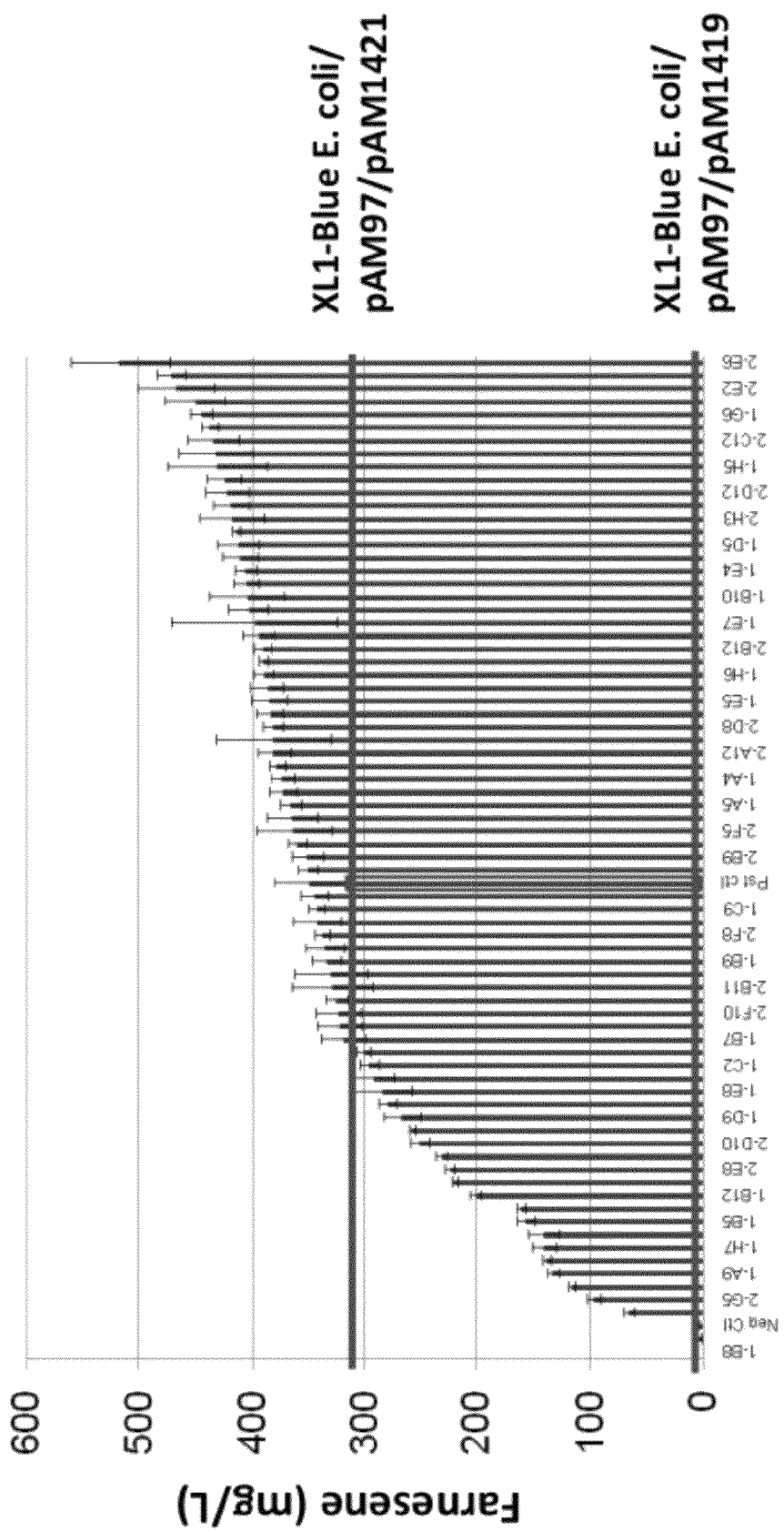

FIG. 10 provides farnesene titers obtained by GC analysis of *Escherichia coli* host strains identified from a library of FS variants screened by Nile Red fluorescence.

Figure 11:
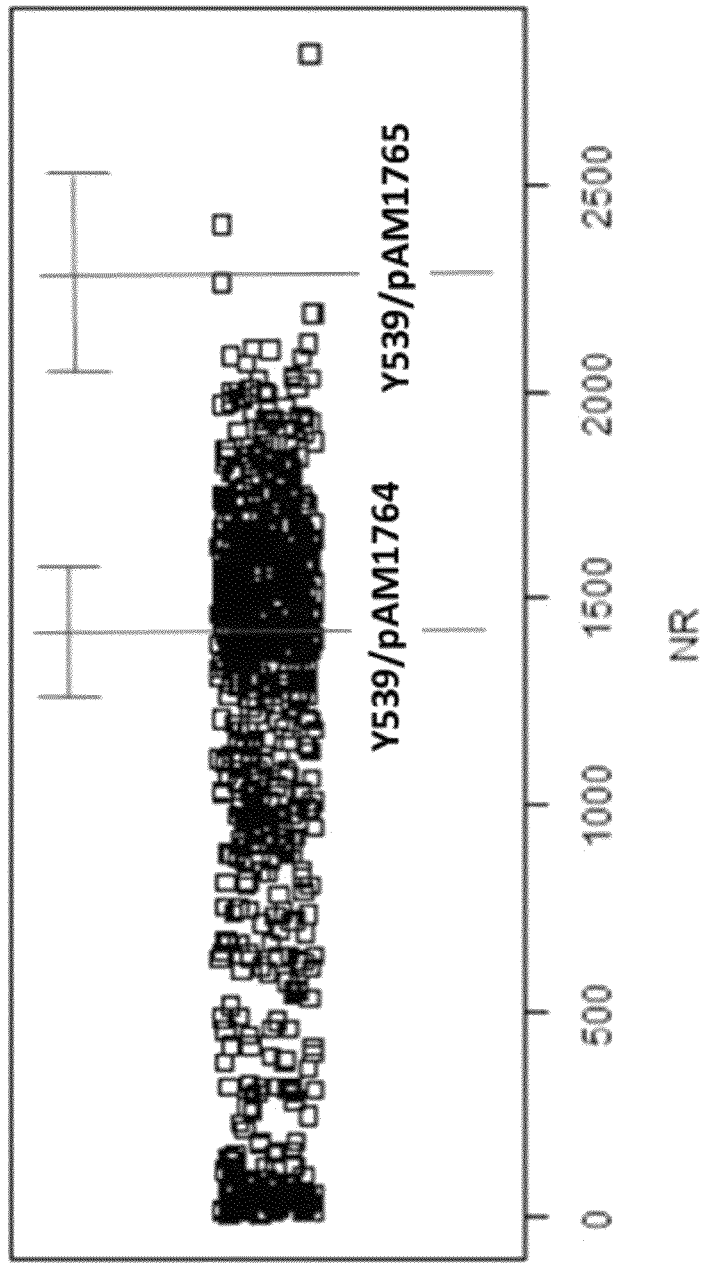
Figure 11:
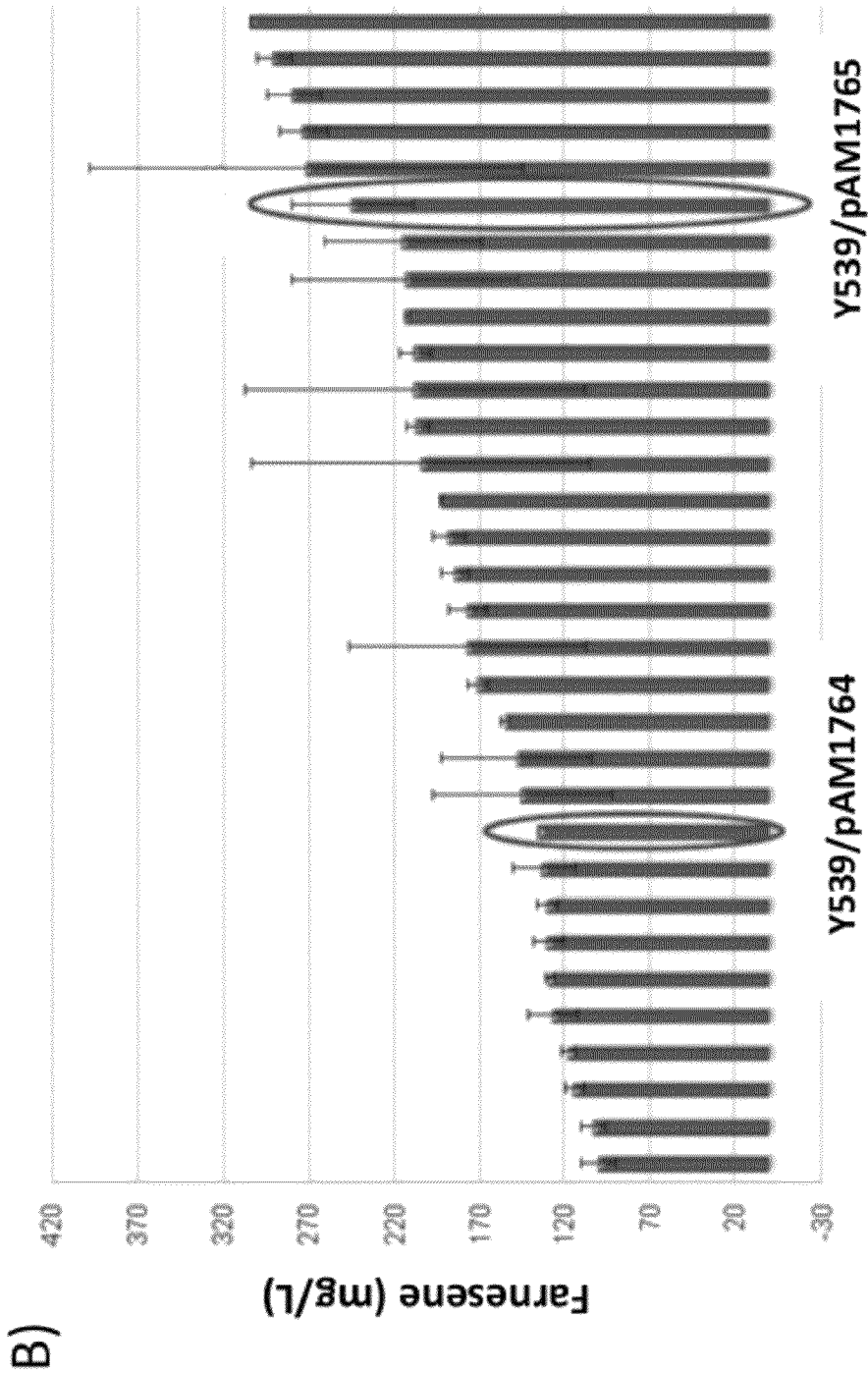

FIG. 11 provides farnesene titers obtained by Nile Red fluorescence (A) and GC analysis (B) of *Saccharomyces cerevisiae* host strains identified from a library of FS variants screened by FPP toxicity based growth selection.

Figure 12:
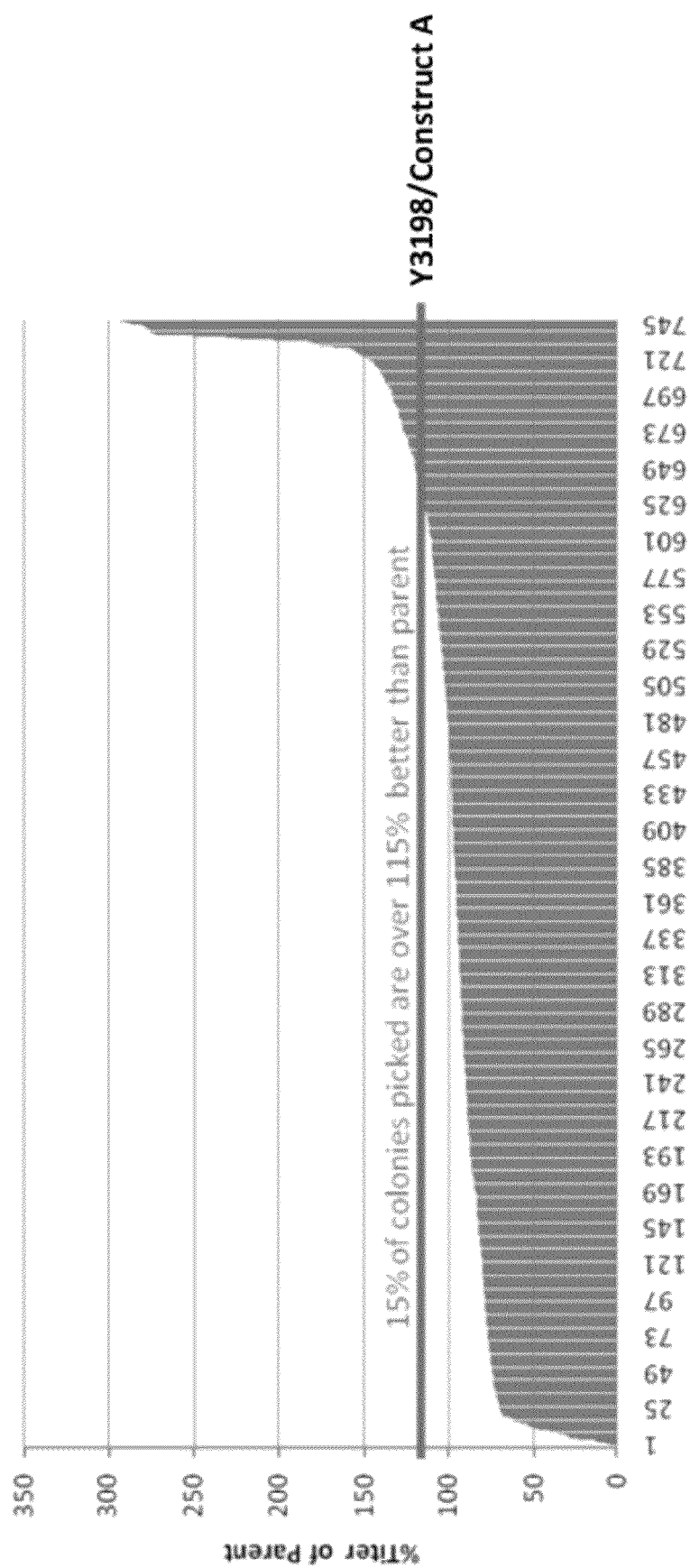

FIG. 12 provides farnesene titers obtained by Nile Red fluorescence analysis of *Saccharomyces cerevisiae* host strains identified from a library of FS variants by FPP toxicity-based growth selection.

FIG. 13 provides maps of various expression plasmids used in the generation of host cells of the invention.

Figure 14:
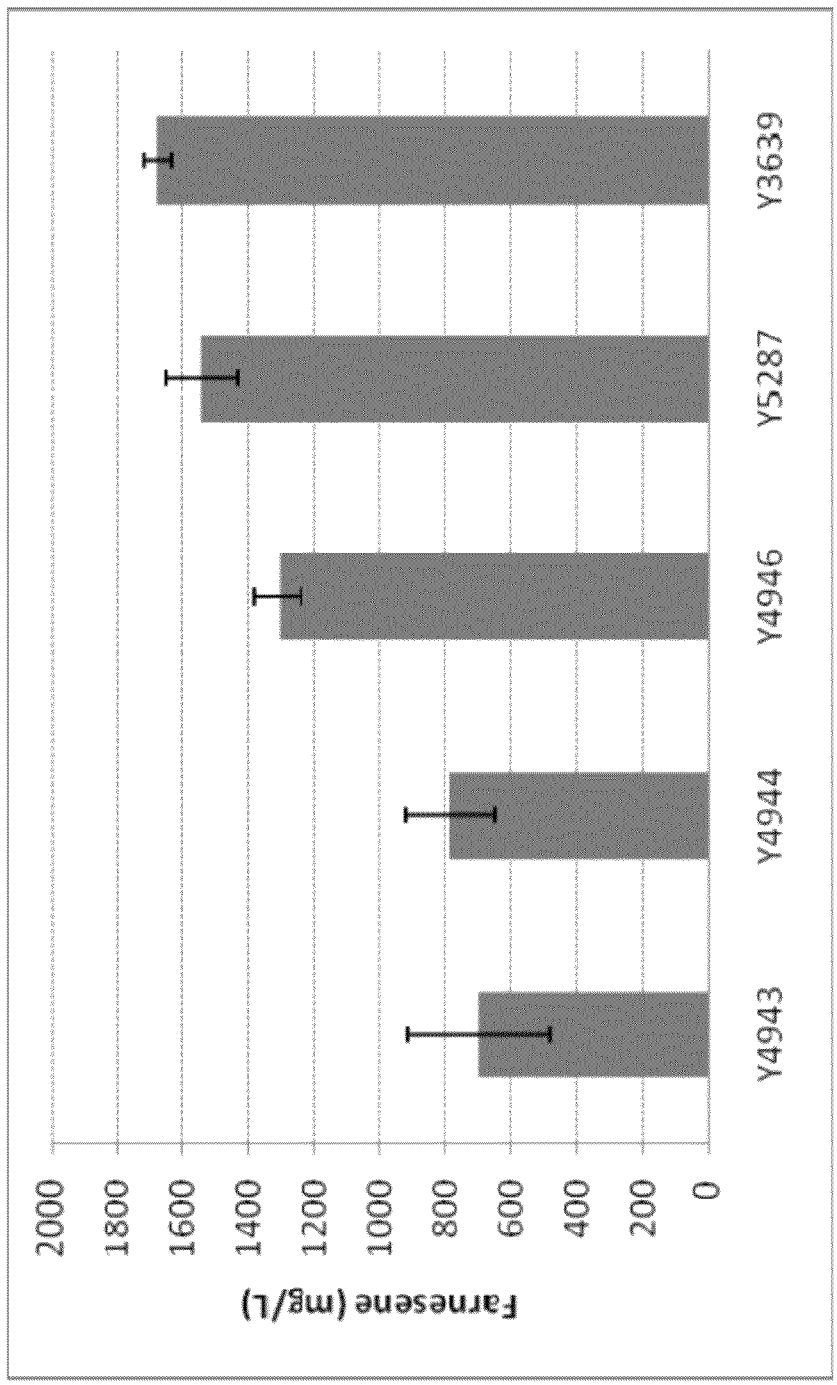

FIG. 14 provides farnesene titers obtained by GC analysis of *Saccharomyces cerevisiae* host strains comprising single chromosomally integrated copies of FS variant coding sequences.

Figure 15:
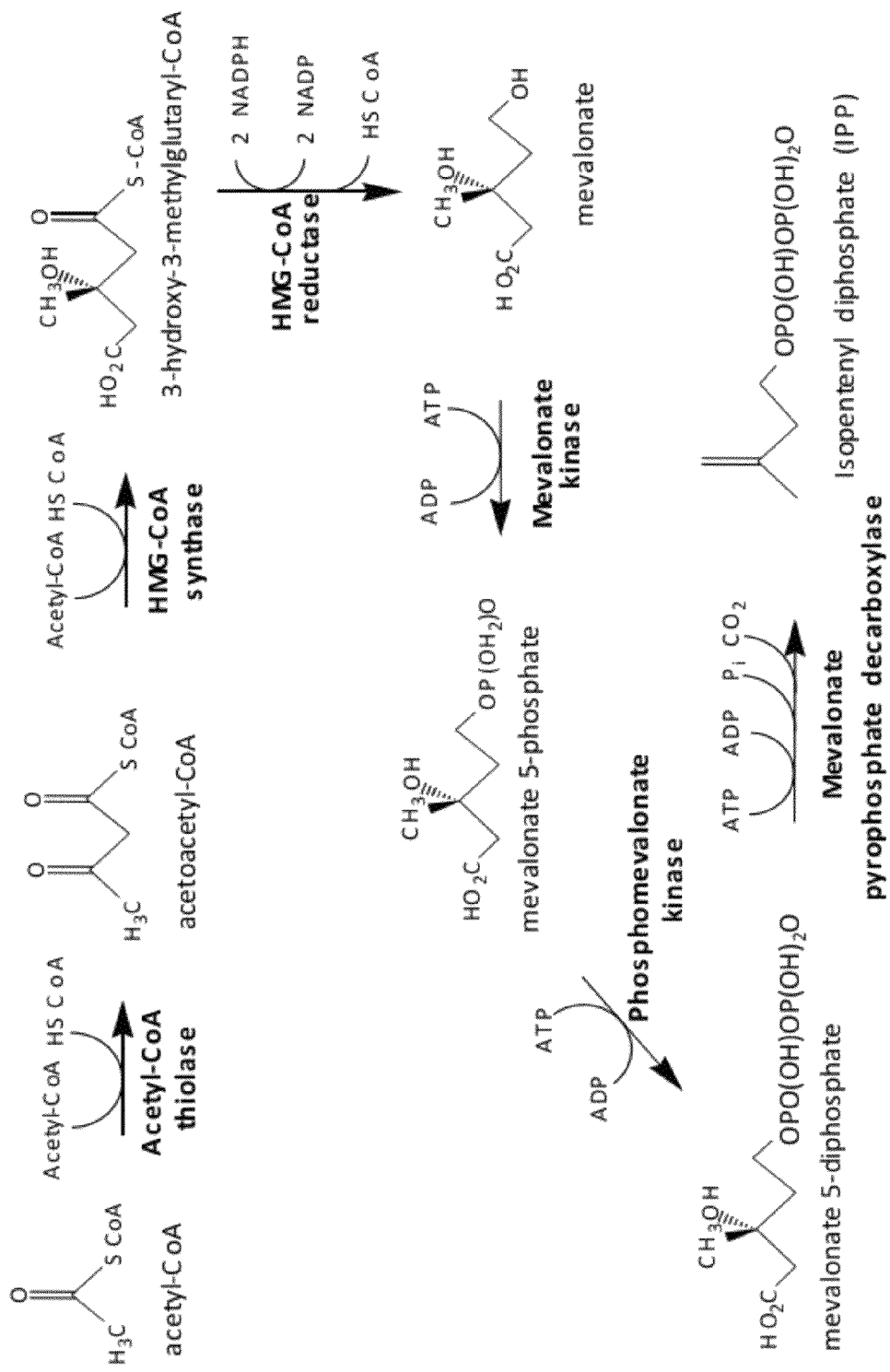

FIG. 15 provides a schematic representation of the MEV pathway for the production of IPP and DMAPP.

Figure 16:
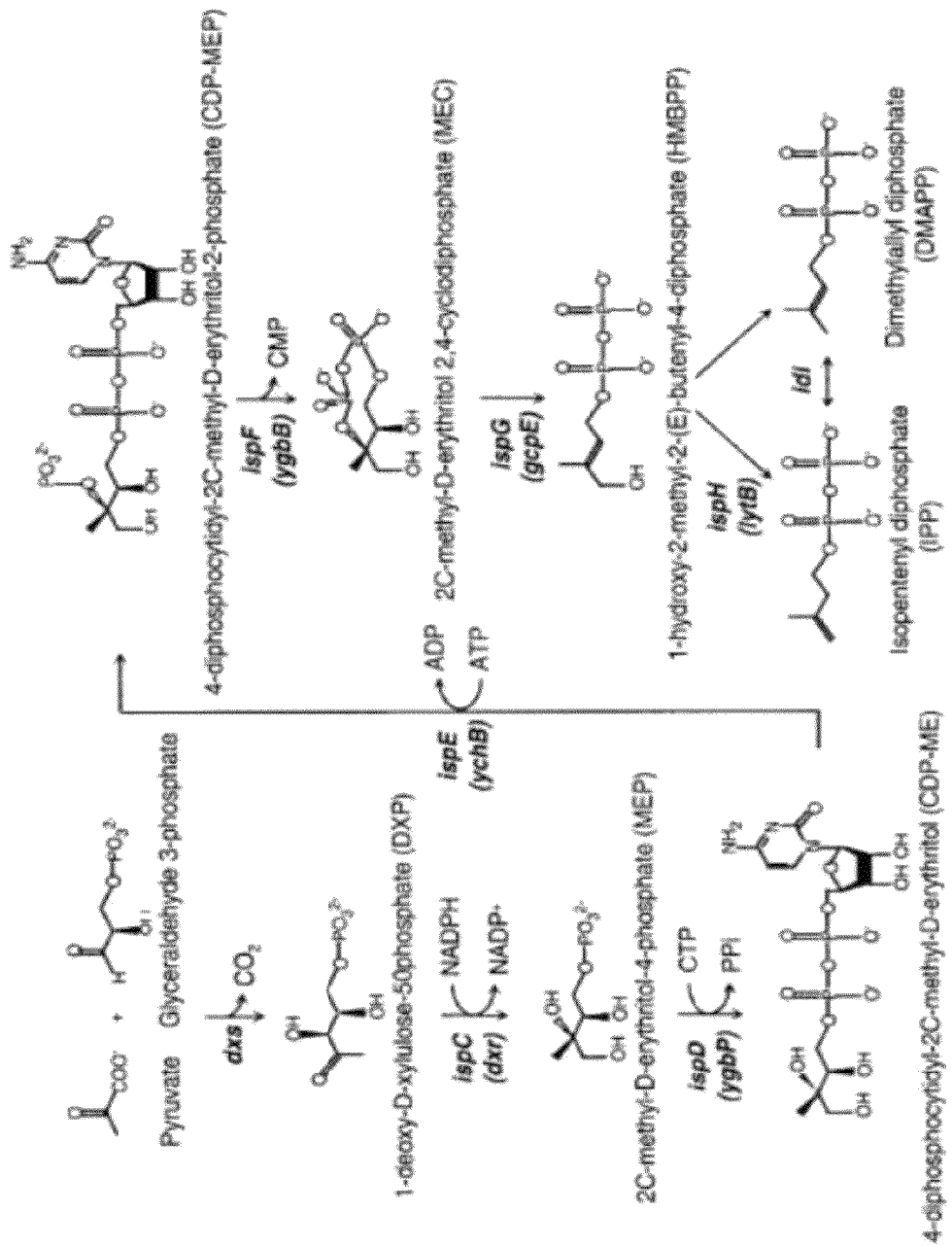

FIG. 16 provides a schematic representation of the DXP pathway for the production of IPP and DMAPP.

Figure 17:
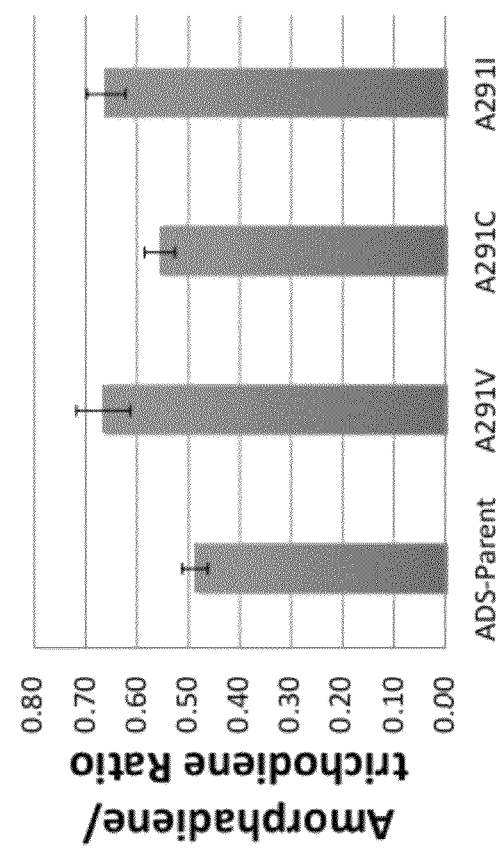

FIG. 17 provides amorphadiene/trichodiene titer ratios obtained by GC analysis of *Saccharomyces cerevisiae* host cells comprising coding sequences for amorphadiene synthase variants.

Figure 18:
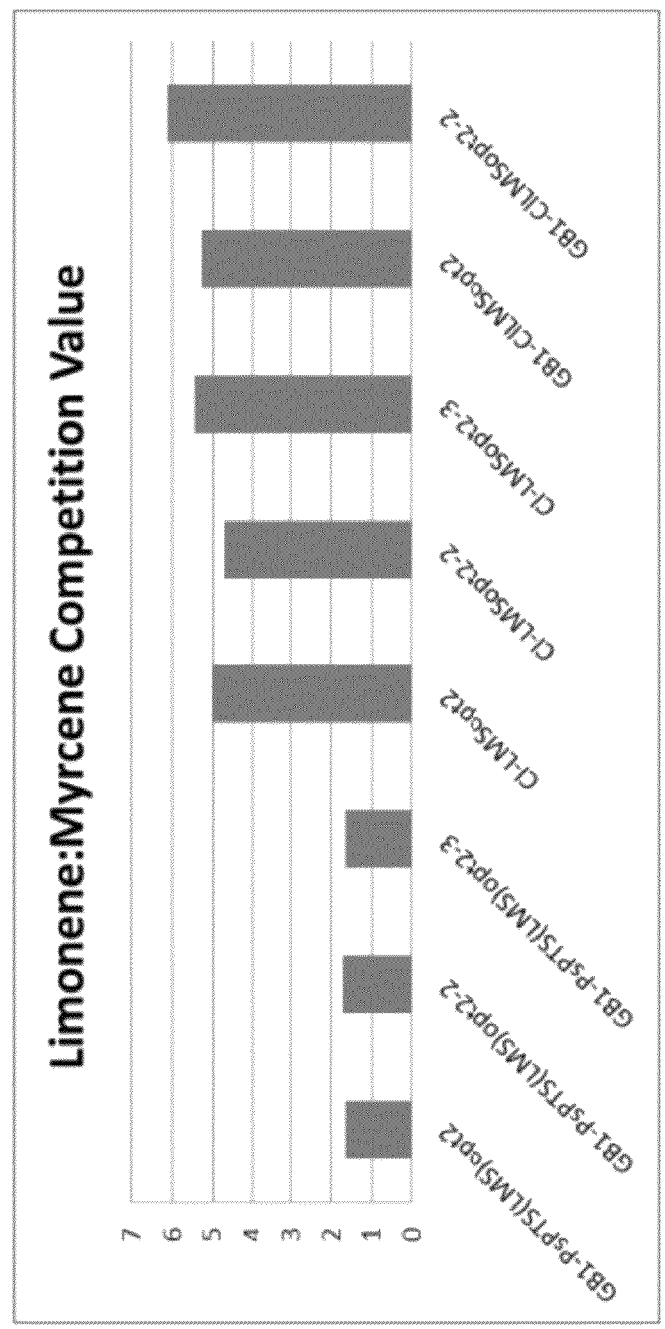

FIG. 18 provides limonene/myrcene titer ratios obtained by GC analysis of *Saccharomyces cerevisiae* host cells comprising coding sequences for limonene synthase variants.

6. DETAILED DESCRIPTION OF THE EMBODIMENTS

6.1 Definitions

The following terms used herein shall have the meanings as indicated below.

As used herein, the term "terpene synthase variant" refers to a terpene synthase that compared to a selected terpene synthase has a different nucleotide or amino acid sequence. For example, compared to the wild-type sequence of the selected terpene synthase, the terpene synthase variant may comprise nucleotide additions, deletions, and/or substitutions that may or may not result in changes to the corresponding amino acid sequence. In some embodiments where nucleotide changes do not result in changes to the amino acid sequence, the changes may nonetheless effect improved activity of the synthase, for example, through codon optimization. In other embodiments, the terpene synthase variant comprises amino acid additions, deletions, and/or substitutions. Accordingly, as used herein, the term "sesquiterpene synthase variant" refers to a sesquiterpene synthase that compared to a selected sesquiterpene synthase has a different nucleotide or amino acid sequence. For example, compared to the selected sesquiterpene synthase, the sesquiterpene synthase variant may comprise nucleotide additions, deletions, and/or substitutions that may or may not result in changes to the corresponding amino acid sequence. In other embodiments, the terpene synthase variant comprises amino acid additions, deletions and/or substitutions.

As used herein, the term "engineered host cell" refers to a host cell that is generated by genetically modifying a parent cell using genetic engineering techniques (i.e., recombinant technology). The engineered host cell may comprise additions, deletions, and/or modifications of nucleotide sequences to the genome of the parent cell.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

As used herein, the term "naturally occurring" refers to what is found in nature. For example, a terpene synthase that is present in an organism that can be isolated from a source in nature and that has not been intentionally modified by a human in the laboratory is a naturally occurring terpene synthase. Conversely, as used herein, the term "naturally not occurring" refers to what is not found in nature but is created by human intervention.

As used herein, the term "biosynthetic enzyme" refers to an enzyme that functions in a biosynthetic pathway leading to the production of a naturally occurring molecule.

As used herein, the term "in vivo performance" refers to the ability of a terpene synthase to convert a polyprenyl diphosphate substrate to a terpene when expressed in a host cell. Accordingly, the term "improved in vivo performance" refers to an increased ability of a terpene synthase to convert a polyprenyl diphosphate substrate to a terpene when expressed in a host cell.

As used herein, the term "parent cell" refers to a cell that has an identical genetic background as a host cell disclosed herein except that it does not comprise the elevated intracellular level of FPP or does not comprise a particular heterologous nucleotide sequence, and that serves as the starting point for introducing said elevated intracellular level of FPP or said heterologous nucleotide sequence leading to the generation of a host cell disclosed herein.

6.2 General Overview

The present disclosure relates to methods of developing terpene synthase variants through engineered host cells. Particularly, the disclosure provides methods of developing terpene synthase variants with improved in vivo performance. The methods also allow for the continued improvement of the in vivo performance of these enzymes.

In one aspect, the present invention provides a screening method for terpene synthase variants with improved in vivo performance. In some embodiments, terpene synthase variants with improved in vivo performance are identified by their ability to rescue engineered host cells from cell death. The engineered host cells comprise genetic modifications that cause elevated intracellular levels of FPP. Because FPP is highly toxic to cells and thus reduces cell viability (Withers et al. (2007) Appl. Environ. Microbiol. 73:6277-6283), to achieve a viability that is comparable to that of a parent cell that does not comprise the elevated level of intracellular FPP, the engineered host cells require a sufficiently active sesquiterpene synthase to reduce the intracellular levels of FPP.

The presently provided screening method thus comprises the following steps:

a) engineering a host cell expressing a control sesquiterpene synthase to comprise an elevated level of FPP, wherein the elevated level of FPP reduces the viability of the host cell compared to a parent cell not comprising the elevated level of FPP;

b) expressing in the host cell a test sesquiterpene synthase instead of the control sesquiterpene synthase, wherein the test sesquiterpene synthase is a variant of the control sesquiterpene synthase; and c) identifying the test sesquiterpene synthase as having improved in vivo performance compared to the control sesquiterpene synthase by an increase in viability of the host cell expressing the test sesquiterpene synthase compared to the host cell expressing the control sesquiterpene synthase.

In some embodiments, the method further comprises selecting and/or isolating the test sesquiterpene synthase having improved in vivo performance.

It is most convenient if the elevated level of FPP in the host cell is inducible. Induction may occur in response to an inducing agent or specific growth conditions such as, for example, temperature. The elevated level of FPP in the host cell may range from about 10% to at least about 1,000-fold, or more, higher than the level of FPP of the parent cell.

The reduced viability of the host cell expressing the control sesquiterpene synthase compared to the parent cell may range from decreased cell growth to lethality. Thus, in some embodiments, the host cell expressing the control sesquiterpene synthase produces a reduced number of progeny cells in a liquid culture or on an agar plate compared to the parent cell. In other embodiments, the host cell expressing the control sesquiterpene synthase produces no progeny cells in a liquid culture or on an agar plate compared to the parent cell. Accordingly, the increase in viability of the host cell expressing the test sesquiterpene synthase instead of the control sesquiterpene synthase may be apparent in liquid culture by a higher number of progeny cells, or on an agar plate by a larger colony size, compared to the number of progeny cells or colony size produced by the host cell expressing the control sesquiterpene synthase.

The elevated level of FPP in the host cell may be effected by modifying the expression and/or activity of an enzyme involved in the production of FPP or its precursors in the host cell. In some such embodiments, the expression and/or activity of an enzyme of the MEV or DXP pathway is modified. In some such embodiments, the expression and/or activity of a HMG-CoA reductase and/or a mevalonate kinase is modified. Alternatively, the elevated level of FPP in the host cell may be effected by modifying the expression and/or activity of an enzyme involved in the utilization of FPP or its precursors in the host cell. In some such embodiments, the expression and/or activity of a squalene synthase is modified.

The control sesquiterpene synthase may be a naturally occurring sesquiterpene synthase or a naturally not occurring sesquiterpene synthase. The test sequiterpene synthase may differ from the control sesquiterpene synthase by comprising one or more amino acid substitutions, deletions, and/or additions. In addition or alternatively, the test sequiterpene synthase may comprise identical amino acids as the control sesquiterpene synthase but the codons encoding these amino acids may differ between the test sesquiterpene synthase and the control sesquiterpene synthase. In some such embodiments, the codons are optimized for usage in the host cell.

In some embodiments, the control sesquiterpene synthase is selected from the group consisting of a β-farnesene synthase, an α-farnesene synthase, a trichodiene synthase, a patchoulol synthase, an amorphadiene synthase, a valencene synthase, a farnesol synthase, a nerolidol synthase, and a nootkatone synthase. In some such embodiments, the control sesquiterpene synthase is a β-farnesene synthase of *Artemisia annua*. In some such embodiments, the control sesquiterpene synthase has an amino acid sequence as given in SEQ ID NO: 111.

To be able to compare the viability of the host cell in the presence of the test sesquiterpene synthase to that of the host cell in the presence of the control sesquiterpene synthase, it is necessary to ensure similar expression levels of the control sesquiterpene synthase and the test sesquiterpene synthase in the host cell. This can be accomplished by placing the nucleotide sequences encoding the sesquiterpene synthases in the two host cells under the control of the same regulatory elements.

To prevent a competitive growth situation in which fast growing false positive host cells comprising a growth promoting mutation rather than an improved sesquiterpene synthase variant take over a host cell culture, one embodiment of the screening method involves an agar-plate based selection system. In this embodiment, the host cell is plated on an agar plate, and a host cell comprising a test sesquiterpene synthase variant with improved in vivo performance is identified by colony growth.

One major advantage of the presently disclosed screening method is its continued capacity to select for better and better sesquiterpene synthase variants in an iterative fashion, wherein a test sesquiterpene synthase identified in an iteration is used as the control sesquiterpene synthase in a subsequent iteration. Thus, this method can be distinguished from other assays known in the art that aim to identify only whether a particular sesquiterpene synthase may be active in a biosynthetic pathway, and do not seek to identify synthases having improved activity over a control, e.g., parent synthase. In some embodiments, the FPP level in the host cell is checked and potentially increased at each iteration (e.g., by increasing or decreasing expression levels of enzymes, adding or subtracting enzymes, increasing or decreasing copy numbers of genes, replacing promoters controlling expression of enzymes, or altering enzymes by genetic mutation) to a level that causes reduced viability when the host cell expresses the new control sesquiterpene synthase (i.e., the test sesquiterpene synthase of the previous iteration). Alternatively, or in addition, at each iteration, the expression of the control sesquiterpene synthase can be reduced (e.g., by decreasing expression of or by using weaker promoters or by reducing the stability of the control sesquiterpene synthase transcript or polypeptide) to provide reduced control sesquiterpene synthase activity. In the next iteration, a test sesquiterpene synthase can then be identified that has yet increased in vivo performance compared to the test sesquiterpene synthase of the previous iteration.

Another major advantage of the presently disclosed screening method is its simplicity and capacity for high-throughput implementation. Sesquiterpene synthase variants that can reduce the intracellular FPP levels in the engineered host cell to non-toxic levels are identified simply based on cell viability, making other costly and time consuming screening methods virtually unnecessary. Thus, in one embodiment, the method is used to screen a collection of sesquiterpene synthase variants (e.g., a library of mutant sesquiterpene synthases) for sesquiterpene synthase variants with improved in vivo performance. In such an embodiment, not a single test sesquiterpene synthase is expressed in a host cell but a collection of test sesquiterpene synthases are expressed in a collection of host cells. The host cells can then be grown on agar plates, and host cells expressing sesquiterpene synthase variants with improved in vivo performance can be identified based on colony growth. In some embodiments, the collection of sesquiterpene synthase variants comprises from 2 to 5, from 5 to 10, from 10 to 50, from 50 to 100, from 100 to 500, from 500 to 1,000, from 1,000 to 10,000, from 10,000 to 100,000, from 100,000 to 1,000,000, and more, sesquiterpene synthase variants.

Another major advantage of the presently disclosed screening method is that selection for improved sesquiterpene synthases occurs in vivo rather than in vitro. As a result, improvements of multiple enzyme properties that enhance the in vivo performance of the sesquiterpene synthase variant can be obtained.

In another aspect, the present invention provides a second screening method for identifying terpene synthase variants with improved in vivo performance. In this second screening method, terpene synthase variants with improved in vivo performance are identified by their ability to starve host cells of a polyprenyl diphosphate (e.g., FPP). In the presence of a highly active terpene synthase variant, the intracellular pool of its polyprenyl diphosphate substrate in a host cell may be depleted, causing the cell to not be able to maintain basic cellular processes required for cell survival.

The presently provided second screening method thus comprises the following steps:
a) providing a host cell expressing a control terpene synthase and having a growth rate;
b) expressing in the host cell a test terpene synthase instead of the control terpene synthase, wherein the test terpene synthase is a variant of the control terpene synthase; and
d) identifying the test terpene synthase as having improved in vivo performance compared to the control terpene synthase by a decreased growth rate of the host cell expressing the test terpene synthase compared to the host cell expressing the control terpene synthase.

The control terpene synthase may be a monoterpene synthase, a sesquiterpene synthase, a diterpene synthase, a sesterterpene synthase, a triterpene synthase, a tetraterpene synthase, or a polyterpene synthase. In some embodiments, the control terpene synthase is a sesquiterpene synthase. In some such embodiments, the control terpene synthase is a β-farnesene synthase. In some such embodiments, the control terpene synthase is a β-farnesene synthase of *Artemisia annua*. In some such embodiments, the control terpene synthase has an amino acid sequence as given in SEQ ID NO: 111.

The polyprenyl diphosphate substrate that becomes depleted in the host cell in the presence of the test terpene synthase may be FPP. Aside from sesquiterpenes, a number of other compounds are synthesized from FPP that are essential for the viability and growth of the host cell. Such compounds include but are not limited to squalene, lanosterol, ergosterol, cycloartenol, cholesterol, steroid hormones, and vitamin D. Thus, in some embodiments, a host cell expressing the test terpene synthase may comprise reduced amounts of cholesterol or ergosterol in its cell membrane. Methods for the quantification of cholesterol or ergosterol in cells are known in the art (e.g., Crockett and Hazel (2005) J. Experimental Zoology, 271(3): 190-195; Arthington-Skaggs et al. (1999) J Clin Microbiol. 37(10): 3332-3337; Seitz et al. (1979) Physiol. Biochem. 69: 1202-1203). In some embodiments, the basic cellular process required for cell survival that cannot be maintained in the host cell in the presence of the test terpene synthase is the production and/or maintenance of a cell membrane. In other embodiments, the polyprenyl diphosphate substrate that becomes depleted in the host cell in the presence of the test terpene synthase is GPP or GGPP.

In yet another aspect, the present invention provides a competition method for identifying and/or ranking the in vivo performance of terpene synthase variants. The competition method employs a known terpene synthase as the comparison enzyme against which the terpene synthase variants are compared. Both the comparison terpene synthase and each of the terpene synthase variants are co-expressed in a host cell in which they then compete for the same polyprenyl diphosphate substrate (e.g., GPP, FPP, or GGPP) to produce their corresponding terpenes. Since the performance of the comparison enzyme remains constant in the host cells, any changes in the ratios of titers of the terpene products produced by the comparison terpene synthase and the terpene synthase variants are the direct result of the activities of the terpene synthase variants. Consequently, such ratios can be used to identify terpene synthase variants with improved in vivo performance, and/or to rank or quantitatively compare the terpene synthase variants for their in vivo kinetic capacities in diverting polyprenyl diphosphate substrates to the production of terpenes.

The presently provided competition method thus comprises the following steps:

a) dividing a population of host cells into a control population and a test population;

b) expressing in the control population a control terpene synthase and a comparison terpene synthase, wherein the control terpene synthase can convert a polyprenyl diphosphate to a first terpene, and wherein the comparison terpene synthase can convert a polyprenyl diphosphate to a second terpene;

c) expressing in the test population the comparison terpene synthase and a test terpene synthase, wherein the test terpene synthase is a variant of the control terpene synthase, and wherein the comparison terpene synthase is expressed at similar levels in the test population and in the control population; and d) measuring a ratio of the first terpene over the second terpene in the test population and in the control population.

Notably, the presently disclosed competition method can be applied to a wide variety of terpene synthases. Thus, in separate embodiments, the competition method is applied to identify and/or rank terpene synthases selected from the group consisting of monoterpene synthases, diterpene synthases, sesquiterpene synthases, sesterterpene synthases, triterpene synthases, tetraterpene synthases, and polyterpene synthases. Accordingly, in separate embodiments, the first terpene and the second terpene are selected from the group consisting of monoterpenes, sesquiterpenes, diterpenes, sesterterpenes, triterpenes, tetraterpenes, and polyterpenes. In some such embodiments, the first terpene or the second terpene is selected from the group consisting of a β-farnesene, an α-farnesene, a trichodiene, a patchoulol, an amorphadiene, a valencene, a farnesol, a nerolidol, a limonene, a myrcene, and a nootkatone.

The control terpene synthase may be a naturally occurring terpene synthase or a naturally not occurring synthase. The test terpene synthase may comprise amino acid substitutions, deletions, or additions compared to the control terpene synthase, or comprise identical amino acids encoded by different codons in the nucleotide sequences encoding the control terpene synthase and test terpene synthase. In some embodiments, the control terpene synthase is a sesquiterpene synthase. In some such embodiments, the sesquiterpene synthase is selected from the group consisting of a β-farnesene synthase, an α-farnesene synthase, a trichodiene synthase, a patchoulol synthase, an amorphadiene synthase, a valencene synthase, a farnesol synthase, a nerolidol synthase, and a nootkatone synthase. In some such embodiments, the control sesquiterpene synthase is a β-farnesene synthase of *Artemisia annua*. In some such embodiments, the control sesquiterpene synthase has an amino acid sequence as given in SEQ ID NO: 111.

To be able to compare the ratios of first terpene/second terpene of the control population and the test population, it is necessary to ensure similar expression levels of the comparison terpene synthase. This can be accomplished by placing the nucleotide sequences encoding the comparison terpene synthase in the two host cell populations under the control of the same regulatory elements. In embodiments in which the competition method is used to identify a terpene synthase variant, the expression levels of the control terpene synthase and the test terpene synthase in the two cell populations must also be similar. In other embodiments in which the competition method is used, for example, to identify regulatory elements (e.g., promoters) that provide a desired expression level, the test terpene synthase differs from the control terpene synthase not in nucleotide or amino acid sequence but in expression level. In such embodiments, different regulatory elements are used for the expression of the control terpene synthase and the test terpene synthase.

There are numerous utilities for the presently disclosed competition method. In some embodiments, the method is used to screen for terpene synthase variants with improved in vivo performance (e.g., from a library of mutant terpene synthases) on the basis that compared to the control terpene synthase, a terpene synthase variant with improved in vivo performance is capable of diverting more flux from a polyprenyl diphosphate substrate to its terpene product, thus, giving a higher ratio of terpene of interest/comparison terpene (i.e., first terpene/second terpene). In such embodiments, it is important that the test terpene synthase is expressed at a similar level in the test population as the control terpene synthase is expressed in the control population.

A similar assay can be used to rank the strength of a series of promoters (see Example 16, for example, in which such an assay was used to identify promoters suitable for use in expressing the control sesquiterpene synthase in the first screening method disclosed herein). In such an embodiment, the control terpene synthase and the test terpene synthase are actually identical, but they are under regulatory control of different prometers such that the control population and the test population do not differ in the type of test terpene synthase they comprise but in the level of expression of the test terpene synthase. In such an embodiment, comparing the ratio of the first terpene over the second terpene in the test population and in the control population provides information not about the activity of the test terpene synthase but about the strength of the promoter driving the expression of the test terpene synthase.

In addition, this system can be used to modulate the ratio of two or more terpene products made by various cells so that the combined mixture of the various cells with a defined ratio possesses the desired properties of a commercially useful product.

Major advantages of the presently disclosed competition method are that it eliminates cell-to-cell variations in enzyme expression and activity, that it is robust, and that it can be used even when the overall pathway flux to the polyprenyl diphosphate substrate is limiting in the host cell. The latter is important because assays that are based on absolute terpene titer measurements may mask improvements in enzyme activities when terpene titers are capped by the overall pathway flux to the polyprenyl disphosphate substrate.

Enzymes developed using the presently disclosed screening method and/or competition method can be subjected to additional means of optional screening including, but not limited to, a fluorescent screen and/or a direct quantitation of terpene product by gas chromatography. More specifically, this includes a Nile Red-based high throughput fluorescent assay for measuring production of a sesquiterpene such as farnesene, and a gas chromatography (GC)-based direct quantitation method for measuring the titer of a sesquiterpene such as farnesene. The improved enzymes can also be further improved by genetic engineering methods such as induced mutations and the like. As a result, improvements of multiple enzyme properties that enhance the final enzyme performance are successively accomplished, and the most effective enzyme variants are identified.

The present disclosure also pertains to superior farnesene synthase variants, and host cells comprising such farnesene synthase variants. The farnesene synthase variants were developed using the methods disclosed herein, and show more than a 200% improvement in in vivo performance. The farnesene synthase variants have improved catalytic efficiency, i.e., they are able to catalyze their reaction at a faster rate. As such, they are more suitable for commercial production of sesquiterpene products such as farnesene where high yield production is of major importance.

Thus, in yet another aspect, provided herein are isolated β-farnesene synthase variants, and isolated nucleic acids comprising a nucleotide sequence encoding such β-farnesene synthase variants, having an amino acid sequence as given in SEQ ID NO: 111 but comprising one or more amino acid substitutions at positions selected from the group consisting of positions 2, 3, 4, 6, 9, 11, 18, 20, 24, 35, 38, 50, 61, 72, 80, 89, 105, 115, 144, 196, 211, 251, 280, 288, 319, 348, 357, 359, 369, 371, 385, 398, 423, 433, 434, 442, 444, 446, 460, 467, 488, 495, 505, 526, 531, 556, 572, and 575 of SEQ ID NO: 111.

In yet another aspect, the present invention provides a genetically modified host cell that comprises:
 (a) a heterologous β-farnesene synthase, wherein the heterologous β-farnesene synthase is a variant of a β-farnesene synthase encoded by SEQ ID NO: 111; and
 (b) a MEV pathway or DXP pathway enzyme;
wherein the host cell makes at least 15% more of a β-farnesene compared to a parent cell that comprises the MEV pathway or DXP pathway enzyme and the β-farnesene synthase encoded by SEQ ID NO: 111.

In some embodiments, the heterologous β-farnesene synthase comprises one or more amino acid substitutions at positions selected from the group consisting of positions 2, 3, 4, 6, 9, 11, 18, 20, 24, 35, 38, 50, 61, 72, 80, 89, 105, 115, 144, 196, 211, 251, 280, 288, 319, 348, 357, 359, 369, 371, 385, 398, 423, 433, 434, 442, 444, 446, 460, 467, 488, 495, 505, 526, 531, 556, 572, and 575 of SEQ ID NO: 111.

In some embodiments, the MEV pathway enzyme is a HMG-CoA reductase. In some embodiments, the MEV pathway enzyme is a mevalonate kinase. Additional exemplary enzymes of the MEV pathway are provided in Section 5.4 below.

In yet another aspect, provided herein is a method of producing a β-farnesene comprising the steps of:
 (a) obtaining a plurality of genetically modified host cells comprising:
  i) a first heterologous nucleotide sequence encoding a variant of a β-farnesene synthase encoded by SEQ ID NO: 111; and
  ii) a second heterologous nucleotide sequence encoding a MEV pathway or DXP pathway enzyme;
 (b) culturing said genetically modified host cells in a medium comprising a carbon source under conditions suitable for making the β-farnesene; and
 (c) recovering the β-farnesene from the medium.

In some embodiments, the MEV pathway enzyme is a HMG-CoA reductase. In some embodiments, the MEV pathway enzyme is a mevalonate kinase. Additional exemplary enzymes of the MEV pathway are provided in Section 5.4 below.

6.3 Selecting Host Cells

Host cells useful in the practice of the present invention include archae, prokaryotic, or eukaryotic cells.

Suitable prokaryotic hosts include but are not limited to any of a variety of gram-positive, gram-negative, or gram-variable bacteria. Examples include but are not limited to cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas.* Examples of prokaryotic strains include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei,* and *Staphylococcus aureus.*

Suitable archae hosts include but are not limited to cells belonging to the genera: *Aeropyrum, Archaeglobus, Halobacterium, Methanococcus, Methanobacterium, Pyrococcus, Sulfolobus,* and *Thermoplasma.* Examples of archae strains include but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi,* and *Aeropyrum pernix.*

Suitable eukaryotic hosts include but are not limited to fungal cells, algal cells, insect cells, and plant cells. Examples include but are not limited to cells belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma, Ascomycota, Basidiomycota, Dothideomycetes,* and *Xanthophyllomyces* (formerly *Phaffia*). Examples of eukaryotic strains include but are not limited to: *Pichia pastoris, Pichia finlandica, Pichia trehalophila, Pichia koclamae, Pichia membranaefaciens, Pichia opuntiae, Pichia thermotolerans, Pichia salictaria, Pichia quercuum, Pichia pijperi, Pichia stiptis, Pichia methanolica, Pichia* sp., *Saccharomyces cerevisiae, Saccharomyces* sp., *Schizosaccharomyces pombe, Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa,* and *Chlamydomonas reinhardtii.*

In a particular embodiment, the host cell is an *Escherichia coli* cell. In another particular embodiment, the host cell is a *Saccharomyces cerevisiae* cell. In some embodiments, the host cell is a *Saccharomyces cerevisiae* cell selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the host cell is a *Saccharomyces cerevisiae* cell selected from the group consisting of PE-2, CAT-1, VR-1, BG-1, CR-1, and SA-1. In a particular embodiment, the host cell is a *Saccharomyces cerevisiae* of strain PE-2. In another particular embodiment, the host cell is a *Saccharomyces cerevisiae* of strain CAT-1. In another particular embodiment, the host cell is a *Saccharomyces cerevisiae* of strain BG-1.

In some embodiments, the host cell is a cell that is suitable for industrial fermentation, e.g., bioethanol fermentation. In particular embodiments, the host cell is conditioned to subsist under high solvent concentration, high temperature, expanded substrate utilization, nutrient limitation, osmotic stress, acidity, sulfite and bacterial contamination, or combinations thereof, which are recognized stress conditions of the industrial fermentation environment.

6.4 Host Cells With Elevated Intracellular FPP Levels In some embodiments, compared to a parent cell, a host cell comprises an elevated intracellular level of FPP, wherein the elevated intracellular level of FPP decreases the viability of the host cell.

In some embodiments, the host cell comprises an intracellular level of FPP that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the intracellular level of FPP of the parent cell, on a per unit volume of cell culture basis.

In some embodiments, the host cell comprises an intracellular level of FPP that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the intracellular level of FPP of the parent cell, on a per unit dry cell weight basis.

In some embodiments, the host cell comprises an intracellular level of FPP that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 60%, at least about 75-fold, at least about 100-fold, at least about 200-fold, at least about 300-fold, at least about 400-fold, at least about 500-fold, or at least about 1,000-fold, or more, higher than the intracellular level of FPP of the parent cell, on a per unit volume of cell culture per unit time basis.

In some embodiments, the host cell comprises an intracellular level of FPP that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the intracellular level of FPP of the parent cell, on a per unit dry cell weight per unit time basis.

In most embodiments, the elevated intracellular level of FPP in the host cell is inducible by an inducing compound. Such a host cell can be manipulated with ease in the absence of the inducing compound. The inducing compound is then added to induce the elevated level of FPP in the host cell. In other embodiments, the elevated intracellular level of FPP in the host cell is inducible by changing culture conditions, such as, for example, the growth temperature. The inducible elevation of intracellular FPP level thus provides a molecular on and off switch for the reduced viability phenotype of the host cell.

The elevation of intracellular FPP level can be effected through targeted genetic engineering of the host cell. A number of enzymes are known to function in the production or utilization of FPP and its precursors, and any one of these enzymes can be manipulated to change the level of FPP in a host cell.

In some embodiments, the production of FPP in the host cell is increased by increasing production of cellular acetyl-CoA in the host cell.

In some embodiments, the production of FPP in the host cell is increased by increasing the production of IPP and/or DMAPP in the host cell. In some such embodiments, the production of IPP and DMAPP in the host cell is increased by increasing the activity of one or more enzymes of the MEV pathway. A schematic representation of the MEV pathway is described in FIG. 15. In general, the pathway comprises six steps:

In the first step, two molecules of acetyl-coenzyme A are enzymatically combined to form acetoacetyl-CoA. An enzyme known to catalyze this step is, for example, acetyl-CoA thiolase. Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp.

KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

In other such embodiments, the production of IPP and DMAPP in the host cell is increased by increasing the activity of one or more enzymes of the DXP pathway. A schematic representation of the DXP pathway is described in FIG. 16. In general, the DXP pathway comprises seven steps:

In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2. 4. 1), (NC_005296, locus tag RPA0952; *Rhodopseudomonas palustris* CGA009), (NC_004556, locus tag PD1293; *Xylella fastidiosa Temecula1*), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2. 4. 1), and (NC_007492, locus tag Pfl_1107; *Pseudomonas fluorescens* NO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2. 4. 1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2. 4. 1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2. 4. 1), and (NC_002947, locus_tag PP1618; *Pseudomonas putida* KT2440).

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2. 4. 1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, the production of FPP in the host cell is increased by increasing the isomerization of IPP to DMAPP. In some such embodiments, the isomerization of IPP to DMAPP is increased by increasing the activity of an IPP isomerase. Illustrative examples of nucleotide sequences encoding IPP isomerases include but are not limited to: (NC_000913, 3031087 . . . 3031635; *Escherichia coli*), and (AF082326; *Haematococcus pluvialis*).

In some embodiments, the production of FPP in the host cell is increased by increasing the condensation of IPP and DMAPP to FPP. In some such embodiments, the condensation of IPP and DMAPP or of IPP and geranyl pyrophosphate ("GPP") to FPP is increased by increasing the activity of a FPP synthase. Illustrative examples of nucleotide sequences that encode FPP synthases include but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM_202836; *Arabidopsis thaliana), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP 873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans serovar Copenhageni str. Fiocruz* L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa Temeculal*).

In some embodiments, the production of FPP in the host cell is increased by inhibiting reactions that divert intermediates from productive steps towards formation of FPP. Such reactions include but are not limited to side reactions of the TCA cycle that lead to fatty acid biosynthesis, alanine biosynthesis, the aspartate superpathway, gluconeogenesis, heme biosynthesis, glutamate biosynthesis, and conversion of acetyl-CoA to acetate via the action of phosphotransacetylase.

In some embodiments, a host cell that comprises an elevated intracellular level of FPP is obtained by decreasing the consumption of FPP in the host cell. In some such embodiments, the consumption of FPP in the host cell is decreased by decreasing the activity of a farnesyl-diphosphate farnesyl transferase or squalene synthase that can convert FPP to squalene. In other such embodiments, the consumption of FPP in the host cell is decreased by decreasing the activity of a sesquiterpene synthase in the host cell.

A host cell comprising an elevated intracellular level of FPP can be generated by genetically modifying a parent cell using genetic engineering techniques (i.e., recombinant technology), classical microbiological techniques, or a combination of such techniques. The host cell may also be a naturally occurring genetic variant that is non-viable under certain growth conditions due to an elevated intracellular level of FPP.

A host cell that comprises such an elevated intracellular level of FPP that it has reduced cell viability can be identified by comparing the growth of the host cell on a solid medium with that of a parent cell that does not comprise the elevated intracellular level of FPP. A host cell that comprises an elevated level of intracellular FPP should produce fewer or smaller colonies on the solid agar medium compared to its parent cell. A host cell that comprises the elevated intracellular level of FPP only under certain growth conditions can be identified by first growing the host cell under conditions under which the host cell does not comprise an elevated intracellular level of FPP and under which it has the same viability as its parent cell ("permissive growth conditions"), and then replica-plating the host cell and growing it under conditions under which the host cell does comprise the elevated intracellular level of FPP ("restrictive growth condition") to identify host cells that has reduced viability only under restrictive growth conditions but that does not have reduced viability under permissive growth conditions. Such restrictive growth conditions can include but are not limited to the presence of a specific nutrient in the culture medium, the presence of a specific nutrient at a specific level in the culture medium, the presence of an inducing compound in the culture medium, the presence of a repressing compound in the culture medium, and a specific growth temperature.

6.5 Terpene Synthases

The methods provided herein are focused on developing terpene synthase variants with improved in vivo performance.

In some embodiments, the terpene synthase variant is a variant of a naturally occurring terpene synthase. In other embodiments, the terpene synthase variant is a variant of a naturally not occurring terpene synthase.

In some such embodiments, the terpene synthase variant differs from a naturally occurring terpene synthase or from a naturally not occurring terpene synthase by one or more amino acid substitutions, deletions, and/or additions. In some embodiments, the terpene synthase differs from a naturally occurring terpene synthase or from a naturally not occurring terpene synthase by comprising one, two, three, four, five, six, seven, eight, nine, ten, or more additional amino acids. In some embodiments, the terpene synthase variant differs from a naturally occurring terpene synthase or from a naturally not occurring terpene synthase by comprising one, two, three, four, five, six, seven, eight, nine, ten, or more amino acid substitutions. In some embodiments, the terpene synthase variant differs from a naturally occurring terpene synthase or from a naturally not occurring terpene synthase by lacking one, two, three, four, five, six, seven, eight, nine, ten, or more amino acids.

In some embodiments, the terpene synthase variant has from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to 99% amino acid sequence identity to the amino acid sequence of a naturally occurring terpene synthase or of a naturally not occurring terpene synthase.

In some embodiments, the terpene synthase variant comprises a consensus amino acid sequence. A consensus amino acid sequence is derived by aligning three or more amino acid sequences, and identifying amino acids that are shared by at least two of the sequences. In some embodiments, the terpene synthase variant comprises a consensus sequence derived from two or more naturally occurring terpene synthases.

In some embodiments, the terpene synthase variant is a hybrid terpene synthase. Hybrid terpene synthases comprise stretches of contiguous amino acids from two or more different terpene synthases. Hybrid terpene synthases can be generated using any known method, including but not limited to exon shuffling, domain swapping, and the like (e.g., Nixon et al. (1997) *Proc. Natl. Acad. Sci. USA* 94:1069-1073; Fisch et al. (1996) *Proc Natl Acad Sci USA* 93(15):7761-7766).

In some embodiments, a nucleic acid comprising a nucleotide sequence encoding a terpene synthase variant hybridizes under stringent hybridization conditions to a nucleic acid encoding a naturally occurring terpene synthase. In another embodiment, a nucleic acid comprising a nucleotide sequence encoding a terpene synthase variant hybridizes under moderate hybridization conditions to a nucleic acid encoding a naturally occurring terpene synthase. In yet another embodiment, a nucleic acid comprising a nucleotide sequence encoding a terpene synthase variant hybridizes under low stringency hybridization conditions to a nucleic acid encoding a naturally occurring terpene synthase.

In some embodiments, the nucleotide sequence encoding the terpene synthase variant is altered from the nucleotide sequence encoding a naturally occurring terpene synthase to reflect the codon preferences for a particular host cell (i.e., is codon-optimized for expression in a particular host cell). The use of preferred codons for a particular host cell generally increases the likelihood of translation, and hence expression, of the nucleotide sequence. Codon usage tables that summarize the percentage of time a specific organism uses a specific codon to code a specific amino acid are available for many organisms, and can be used as a reference in designing suitable nucleotide sequences. In some embodiments, the nucleotide sequence encoding the terpene synthase is altered to reflect the codon preferences of *Saccharomyces cerevisiae* (see, e.g., Bennetzen and Hall (1982) *J. Biol. Chem.* 257(6): 3026-3031). In some embodiments, the nucleotide sequence encoding the terpene synthase is altered to reflect the codon preferences for *Escherichia coli* (see, e.g., Gouy and Gautier (1982) *Nucleic Acids Res.* 10(22):7055-7074; Eyre-Walker (1996) *Mol. Biol. Evol.* 13(6):864-872; Nakamura et al. (2000) *Nucleic Acids Res.* 28(1):292).

A nucleic acid comprising a nucleotide sequence encoding a terpene synthase can be obtained using any of a variety of known recombinant techniques and synthetic procedures. The nucleic acid can be prepared from genomic DNA, cDNA, or RNA, all of which can be extracted directly from a cell or can be recombinantly produced by various amplification processes including but not limited to PCR and rt-PCR. Direct chemical synthesis methods are also well known in the art.

A nucleic acid comprising a nucleotide sequence encoding a terpene synthase variant can be obtained using any of a variety of known methods. For example, nucleic acids can be isolated from cells that were treated with chemical mutagens or radiation, or from cells that have deficiencies in DNA repair. Suitable chemical mutagens include, but are not limited to, ethyl methanesulfonate (EMS), methyl methanesulfonate (MMS), N-nitroso urea (ENU), N-methyl-N-nitro-N'-nitrosoguanidine, 4-nitroquino line N-oxide, diethylsulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and acridine dyes (see, for example Thomas D. Brock in *Biotechnology: A Textbook of Industrial Microbiology, Second Edition* (1989) Sinauer Associates, Inc., Sunderland, Mass., or Deshpande Mukund V., *Appl. Biochem. Biotechnol.* 36, 227 (1992)). Suitable radiation exposures include but are not limited to ultraviolet radiation (optionally in combination with exposure to chemical agents such as, for example, trimethylpsoralen), γ-irradiation, X-rays, and fast neutron bombardment. A suitable method for introducing deficiencies in DNA repair in a cell includes but is not limited to the expression of a mutant DNA repair enzyme that generates a high frequency of mutations in the genome of the cell (on the order of about 1 mutation/100 genes to about 1 mutation/10,000 genes). Examples of genes encoding DNA repair enzymes include but are not limited to Mut H, Mut S, Mut L, and Mut U, and the homologs thereof in other species (for example, MSH 1-6, PMS1-2, MLH 1, GTBP, and ERCC-1). Other methods for obtaining a nucleic acid comprising a nucleotide sequence encoding a terpene synthase variant include manipulation of cell-free in vitro systems (e.g., using error-prone PCR for the amplification of a nucleic acid), random or targeted insertion in the genome of a cell of a mobile DNA element (e.g., a transposable element), or in vitro DNA shuffling (e.g., exon shuffling, domain swapping, and the like; see, for example, Ausubel et al., *Current Protocols In Molecular Biology*, John Wiley and Sons, New York (current edition); and Sambrook et al., *Molecular Cloning, A Laboratory Manual*, 3d. ed., Cold Spring Harbor Laboratory Press, Cold Spring Harbor, N.Y. (2001)).

In some embodiments, the terpene synthase variants are variants of a sesquiterpene synthase selected from the group consisting of a β-farnesene synthase, an α-farnesene synthase, a trichodiene synthase, a patchoulol synthase, an amorphadiene synthase, a valencene synthase, a farnesol synthase, a nerolidol synthase, and a nootkatone synthase.

In some embodiments, the terpene synthase variant is a β-farnesene synthase variant. In some such embodiments, the β-farnesene synthase variant is derived from a β-farnesene synthase of *Artemisia annua*. The sequence of the β-farnesene synthase of *Artemisia annua* has been previously described (Picaud, et al, (2005) *Phytochemistry* 66 (9):961-967). The nucleotide sequence of the β-farnesene synthase of *Artemisia annua* is deposited under GenBank accession number AY835398, and SEQ ID NO: 112 as provided herein. The amino acid sequence of the β-farnesene synthase of *Artemisia annua* is deposited under GenBank accession number AAX39387, and SEQ ID NO: 111 as provided herein.

In some embodiments, the β-farnesene synthase variant has an amino acid sequence as given in SEQ ID NO: 111 but comprising an amino acid substitution at position 2 from serine to aspartate (S2D mutation). In some embodiments, the β-farnesene synthase variant has an amino acid sequence as given in SEQ ID NO: 111 but comprising an amino acid substitution at position 3 from threonine to asparagine (T3N mutation). In some embodiments, the β-farnesene synthase variant has an amino acid sequence as given in SEQ ID NO: 111 but comprising an amino acid substitution at position 4 from leucine to serine (L4S mutation). In some embodiments, the β-farnesene synthase variant has an amino acid sequence as given in SEQ ID NO: 111 but comprising an amino acid substitution at position 6 from isoleucine to threonine (I6T mutation). In some embodiments, the β-farnesene synthase variant has an amino acid sequence as given in SEQ ID NO: 111 but comprising an amino acid substitution at position 9 from valine to aspartic acid (V9D mutation). In some embodiments, the β-farnesene synthase variant has an amino acid sequence as given in SEQ ID NO: 111 but comprising an amino acid substitution at position 11 from phenylalanine to serine (F11S mutation). In some embodiments, the β-farnesene synthase variant has an amino acid sequence as given in SEQ ID NO: 111 but comprising an amino acid substitution at position 20 from valine to glutamic acid (V20E mutation). In some embodiments, the β-farnesene synthase variant has an amino acid sequence as given in SEQ ID NO: 111 but comprising an amino acid substitution at position 24 from valine to aspartic acid (V24D mutation). In some embodiments, the β-farnesene synthase variant has an amino acid sequence as given in SEQ ID NO: 111 but comprising an amino acid substitution at position 35 from methionine to threonine (M35T mutation). In some embodiments, the β-farnesene synthase variant has an amino acid sequence as given in SEQ ID NO: 111 but comprising an amino acid substitution at position 38 from asparagine to serine (N38S mutation). In some embodiments, the β-farnesene synthase variant has an amino acid sequence as given in SEQ ID NO: 111 but comprising an amino acid substitution at position 50 from aspartic acid to asparagine (D50N mutation). In some embodiments, the β-farnesene synthase variant has an amino acid sequence as given in SEQ ID NO: 111 but comprising an amino acid substitution at position 61 from leucine to glutamine (L61Q mutation). In some embodiments, the β-farnesene synthase variant has an amino acid sequence as given in SEQ ID NO: 111 but comprising an amino acid substitution at position 72 from glutamic acid to lysine (E72K mutation). In some embodiments, the β-farnesene synthase variant has an amino acid sequence as given in SEQ ID NO: 111 but comprising an amino acid substitution at position 72 from glutamic acid to valine (E72V mutation). In some embodiments, the β-farnesene synthase variant has an amino acid sequence as given in SEQ ID NO: 111 but comprising an amino acid substitution at position 80 from asparagine to aspartic acid (N80D mutation). In some embodiments, the β-farnesene synthase variant has an amino acid sequence as given in SEQ ID NO: 111 but comprising an amino acid substitution at position 89 from isoleucine to valine (I89V mutation). In some embodiments, the β-farnesene synthase variant has an amino acid sequence as given in SEQ ID NO: 111 but comprising an amino acid substitution at position 105 from glutamic acid to aspartic acid (E105D mutation). In some embodiments, the β-farnesene synthase variant has an amino acid sequence as given in SEQ ID NO: 111 but comprising an amino acid substitution at position 115 from isoleucine to methionine (I115M mutation). In some embodiments, the β-farnesene synthase variant has an amino acid sequence as given in SEQ ID NO: 111 but comprising an amino acid substitution at position 115 from isoleucine to valine (I115V mutation). In some embodiments, the β-farnesene synthase variant has an amino acid sequence as given in SEQ ID NO: 111 but comprising an amino acid substitution at position 144 from phenylalanine to tyrosine (F144Y mutation). In some embodiments, the β-farnesene synthase variant has an amino acid sequence as given in SEQ ID NO: 111 but comprising an amino acid substitution at position 196 from threonine to serine (T196S mutation). In some embodiments, the β-farnesene synthase variant has an amino acid sequence as given in SEQ ID NO: 111 but comprising an amino acid substitution at position 211 from serine to threonine (S211T mutation). In some embodiments, the β-farnesene synthase variant has an amino acid sequence as given in SEQ ID NO: 111 but comprising an amino acid substitution at position 251 from leucine to methionine (L251M mutation). In some embodiments, the β-farnesene synthase variant has an amino acid sequence as given in SEQ ID NO: 111 but comprising an amino acid substitution at position 280 from leucine to glutamine (L280Q mutation). In some embodiments, the β-farnesene synthase variant has an amino acid sequence as given in SEQ ID NO: 111 but comprising an amino acid substitution at position 288 from tyrosine to phenylalanine (Y288F mutation). In some embodiments, the β-farnesene synthase variant has an amino acid sequence as given in SEQ ID NO: 111 but comprising an amino acid substitution at position 319 from threonine to serine (T319S mutation). In some embodiments, the β-farnesene synthase variant has an amino acid sequence as given in SEQ ID NO: 111 but comprising an amino acid substitution at position 357 from glutamic acid to valine (E357V mutation). In some embodiments, the β-farnesene synthase variant has an amino acid sequence as given in SEQ ID NO: 111 but comprising an amino acid substitution at position 359 from glutamic acid to threonine (E359T mutation). In some embodiments, the β-farnesene synthase variant has an amino acid sequence as given in SEQ ID NO: 111 but comprising an amino acid substitution at position 369 from valine to leucine (V369L mutation). In some embodiments, the β-farnesene synthase variant has an amino acid sequence as given in SEQ ID NO: 111 but comprising an amino acid substitution at position 371 from leucine to methionine (L371M mutation). In some embodiments, the β-farnesene synthase variant has an amino acid sequence as given in SEQ ID NO: 111 but comprising an amino acid substitution at position 385 from threonine to alanine (T385A mutation). In some embodiments, the β-farnesene synthase variant has an amino acid sequence as given in SEQ ID NO: 111 but comprising an amino acid substitution at position 398 from isoleucine to valine (I398V mutation). In some embodiments, the β-farnesene synthase variant has an amino acid sequence as given in SEQ ID NO: 111 but comprising an amino acid substitution at position 423 from valine to isoleucine (V423I mutation). In some embodiments, the β-farnesene synthase variant has an amino acid sequence as given in SEQ ID NO: 111 but comprising an amino acid substitution at position 433 from methionine to isoleucine (M433I mutation). In some embodiments, the β-farnesene synthase variant has an amino acid sequence as given in SEQ ID NO: 111 but comprising an amino acid substitution at position 434 from isoleucine to threonine (I434T mutation). In some embodiments, the β-farnesene synthase variant has an amino acid sequence as given in SEQ ID NO: 111 but comprising an amino acid substitution at position 442 from glycine to alanine (G442A mutation). In some embodiments, the β-farnesene synthase variant has an amino acid sequence as given in SEQ ID NO: 111 but comprising an amino acid substitution at position 442 from glycine to aspartic acid (G442D mutation). In some embodiments, the β-farnesene synthase variant has an amino acid sequence as given in SEQ ID NO: 111 but comprising an amino acid substitution at position 444 from isoleucine to leucine (I444L mutation). In some embodiments, the β-farnesene synthase variant has an amino acid sequence as given in SEQ ID NO: 111 but comprising an amino acid substitution at position 446 from threonine to asparagine (T446N mutation). In some embodiments, the β-farnesene synthase variant has an amino acid sequence as given in SEQ ID NO: 111 but comprising an amino acid substitution at position 460 from isoleucine to valine (I460V mutation). In some embodiments, the β-farnesene synthase variant has an amino acid sequence as given in SEQ ID NO: 111 but comprising an amino acid substitution at position 467 from valine to isoleucine (V467I mutation). In some embodiments, the β-farnesene synthase variant has an amino acid sequence as given in SEQ ID NO: 111 but comprising an amino acid substitution at position 488 from serine to phenylalanine (S488F mutation). In some embodiments, the β-farnesene synthase variant has an amino acid sequence as given in SEQ ID NO: 111 but comprising an amino acid substitution at position 495 from glutamic acid to glycine (E495G mutation). In some embodiments, the β-farnesene synthase variant has an amino acid sequence as given in SEQ ID NO: 111 but comprising an amino acid substitution at position 505 from glutamic acid to valine (E505V mutation). In some embodiments, the β-farnesene synthase variant has an amino acid sequence as given in SEQ ID NO: 111 but comprising an amino acid substitution at position 526 from threonine to serine (T526S mutation). In some embodiments, the β-farnesene synthase variant has an amino acid sequence as given in SEQ ID NO: 111 but comprising an amino acid substitution at position 531 from proline to serine (P531S mutation). In some embodiments, the β-farnesene synthase variant has an amino acid sequence as given in SEQ ID NO: 111 but comprising an amino acid substitution at position 556 from alanine to valine (A556V mutation). In some embodiments, the β-farnesene synthase variant has an amino acid sequence as given in SEQ ID NO: 111 but comprising an amino acid substitution at position 572 from methionine to lysine (M572K mutation). In some embodiments, the β-farnesene synthase variant has an amino acid sequence as given in SEQ ID NO: 111 but comprising an amino acid substitution at position 575 from a stop codon to lysine (stop575K mutation). In some embodiments, the β-farnesene synthase variant has an amino acid sequence as given in SEQ ID NO: 111 but comprising an amino acid substitution at position 348 from arginine to lysine (R348K mutation). In some embodiments, the β-farnesene synthase variant has an amino acid sequence as given in SEQ ID NO: 111 but comprising an amino acid substitution at position 18 from leucine to isoleucine (L18I mutation).

6.6 Genetically Engineering Host Cells

The methods provided herein include obtaining a host cell that is genetically engineered to comprise an elevated intracellular FPP level or to express a terpene synthase or a terpene synthase variant. Such a genetically engineered host cell may comprise insertions, deletions, or modifications of nucleotides in such a manner as to provide the desired effect of elevating the intracellular level of FPP or of expressing the terpene synthase or the terpene synthase variant. Such genetic modifications may result in a decrease or increase or modification in copy number or activity of a specific enzyme.

For example, the copy number of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be archived for example by modifying the stability of the mRNA, modifying the sequence of the ribosome binding site, modifying the distance or sequence between the ribosome binding site and the start codon of the enzyme coding sequence, modifying the entire intercistronic region located "upstream of or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

The methods provided herein further include steps of expressing a terpene synthase or a terpene synthase variant in a host cell that does not naturally express such terpene synthase or terpene synthase variant. Expression of a terpene synthase or a terpene synthase variant in a host cell can be accomplished by introducing into the host cells a nucleic acid comprising a nucleotide sequence encoding the terpene synthase or terpene synthase variant under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

In some embodiments, it is essential that expression levels of terpene synthases or terpene synthase variants in two or more host cells are similar. This can be accomplished using nucleic acids comprising nucleotide sequences encoding the terpene synthase or terpene synthase variant under the control of the same regulatory elements. Such nucleic acids can be used as extrachromosomal expression vectors or to integrate the nucleotide sequences encoding the terpene synthase or the terpene synthase variant and the regulatory elements into the chromosome of the host cell. Comparable expression levels can also be accomplished by targeting nucleic acids comprising nucleotide sequences encoding the terpene synthase or terpene synthase variant to identical locations in the two or more host cells, thus placing the nucleotide sequences under the control of the same endogenous regulatory elements. In addition to the use of similar regulatory elements, comparable expression levels may also depend on similar copy numbers of the nucleotide sequences in the two or more host cells. Copy numbers can be controlled by the use of similar or identical origins of replications in extrachromosomal expression vectors, or by the use of similar types and numbers of chromosomal integration constructs for the integration of the nucleotide sequences into the chromosome of the two or more host cells. A number of additional features of the nucleic acids can affect the expression level of the encoded terpene synthases or terpene synthase variants (e.g., protein or mRNA stability, sequence of the ribosome binding site, distance between the ribosome binding site and start codon, nature of the upstream and downstream sequences, hairpins and other specialized sequences, and codon usage), and all of these can be modified to ensure similar expression levels when required in the provided methods.

Nucleic acids can be introduced into microorganisms by any method known to one of skill in the art without limitation (see, for example, Hinnen et al. (1978) *Proc. Natl. Acad. Sci. USA* 75:1292-3; Cregg et al. (1985) *Mol. Cell. Biol.* 5:3376-3385; Goeddel et al., eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include but are not limited to spheroplasting, electroporation, PEG 1000 mediated transformation, and lithium acetate or lithium chloride mediated transformation.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include but are not limited to the BLA, NAT1, PAT, AUR1-C, PDR4, SMR1, CAT, mouse dhfr, HPH, DSDA, $KAN^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevi-* siae confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the KAN$^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional rende a parent cell incapable of growing in media without supplementation with one or more nutrients. Such gene products include but are not limited to the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and α-aminoadipic acid (aAA), respectively, that prevent growth of the prototrophic strains but allows growth of the URA3, TRP1, and LYS2 mutants, respectively.

In other embodiments, the selectable marker rescues other non-lethal deficiencies or phenotypes that can be identified by a known selection method.

6.7 Growing Host Cells

The present invention provides methods for developing terpene synthase variants with improved in vivo performance, and for producing terpenes. The methods generally involve growing a host cell under suitable conditions in a suitable medium comprising a carbon source.

Suitable conditions and suitable media for growing microorganisms are well known in the art. In some embodiments, the suitable medium is supplemented with one or more additional agents, such as, for example, an inducing compound (e.g., when one or more nucleotide sequences encoding a gene product are under the control of an inducible promoter), a repressing compound (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

In one aspect, the present invention provides a method for identifying a terpene synthase with improved in vivo performance based on the growth rate of a host cell comprising a test terpene synthase. The growth rate of a host cell can be determined, for example, by growing the host cell in liquid medium for a defined period of time, then plating all or an aliquot of the culture on an agar plate, and finally scoring the number of colonies that arise on the agar plate. Alternatively, the growth rate of a host cell is determined by measuring the biomass of a culture after a defined period of time. Biomass can be measured by determining the density of the liquid culture, e.g. by UV spectrometry, or by quantifying biomass index molecules such as hexoseamine and ergosterol (Frey et al. (1992) Biol. Fertil. Soils 13: 229-234; Newell (1992) p. 521-561. In G. C. Carroll and D. T. Wicklow (ed.), The fungal community: its organization and role in the ecosystem, 2nd ed. Marcel Dekker Inc., New York).

6.8 Producing Terpenes

The present invention provides methods for producing terpenes.

In some embodiments, the terpene is produced in an amount greater than about 10 grams per liter of fermentation medium. In some such embodiments, the terpene is produced in an amount from about 10 to about 50 grams, more than about 15 grams, more than about 20 grams, more than about 25 grams, or more than about 30 grams per liter of cell culture.

In some embodiments, the terpene is produced in an amount greater than about 50 milligrams per gram of dry cell weight. In some such embodiments, the terpene is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the terpene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the terpene produced by a host cell that does not comprise the first heterologous nucleotide sequence, on a per unit volume of cell culture basis.

In some embodiments, the terpene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the terpene produced by a host cell that does not comprise the first heterologous nucleotide sequence, on a per unit dry cell weight basis.

In some embodiments, the terpene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the terpene produced by a host cell that does not comprise the first heterologous nucleotide sequence, on a per unit volume of cell culture per unit time basis.

In some embodiments, the terpene is produced in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2. 5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of the terpene produced by a host cell that does not comprise the first heterologous nucleotide sequence, on a per unit dry cell weight per unit time basis.

6.9 Extracting and Quantifying Terpenes

The terpene produced by the genetically modified host cell of the invention may be isolated from the fermentation using any suitable separation and purification methods known in the art.

In some embodiments, an organic phase comprising the terpene is separated from the fermentation by centrifugation. In other embodiments, an organic phase comprising the terpene separates from the fermentation spontaneously. In yet other embodiments, an organic phase comprising the terpene is separated from the fermentation by adding a deemulsifier and/or a nucleating agent into the fermentation reaction. Illustrative examples of deemulsifiers include flocculants and coagulants. Illustrative examples of nucleating agents include droplets of the terpene itself and organic solvents such as dodecane, isopropyl myristrate, and methyl oleate.

In some embodiments, the terpene is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

In some embodiments, the terpene is pure, e.g., at least about 40% pure, at least about 50% pure, at least about 60% pure, at least about 70% pure, at least about 80% pure, at least about 90% pure, at least about 95% pure, at least about 98% pure, or more than 98% pure, where "pure" in the context of an terpene refers to an terpene that is free from other terpenes or contaminants.

Terpene production can be readily quantified using well-known methods known in the art including but are not limited to gas chromatography (GC), gas chromatography-mass spectrometry (GC/MS), nuclear magnetic resonance (NMR), RAMAN spectroscopy, optical absorption (UV/VIS), infrared spectroscopy (IR), high performance liquid chromatography (HPLC), liquid chromatography-mass spectrometry (LC/MS), ion chromatography-mass spectrometry, thin layer chromatography, pulsed amperometric detection, and UV-vis spectrometry.

Terpenes produced by host cells can be recovered using any of a variety of methods including but not limited to chromatography, extraction, solvent extraction, membrane separation, electrodialysis, reverse osmosis, distillation, chemical derivatization, and crystallization.

Additional processing steps to improve terpene quantification or isolation include but are not limited to breaking open the host cells. Suitable methods include but are not limited to vortexing, sonication, and the use of glass beads. Other processing steps can include centrifugation to remove unwanted cell debris from the supernatant.

7. EXAMPLES

The following specific examples are intended to illustrate the disclosure and should not be construed as limiting the scope of the claims.

Example 1

This example describes methods for making DNA constructs useful in the generation and characterization of terpene synthase variants.

Expression plasmid pAM36-MevT66 was generated by inserting the MevT66 operon into vector pAM36. Vector pAM36 was generated by removing the tet resistance gene from and adding an oligonucleotide cassette containing AscI-SfiI-AsiSI-XhoI-PacI-FsII-PmeI restriction sites into the pACYC184 vector (GenBank accession number XO6403). The MevT66 operon encoded the set of MEV pathway enzymes that together transform the ubiquitous precursor acetyl-CoA to (R)-mevalonate, namely acetoacetyl-CoA thiolase, HMG-CoA synthase, and HMG-CoA reductase. The MevT66 operon was synthetically generated and comprised the atoB gene of *Escherichia coli* (GenBank accession number NC_000913 REGION: 2324131 . . . 2325315; encodes an acetoacetyl-CoA thiolase) codon-optimized for expression in *Escherichia coli*, the coding sequence of the ERG13 gene of *Saccharomyces cerevisiae* (GenBank accession number X96617, REGION: 220 . . . 1695; encodes a HMG-CoA synthase) codon-optimized for expression in *Escherichia coli*, and a truncated coding sequence of the HGM1 gene of *Saccharomyces cerevisiae* (GenBank accession number M22002, REGION: 1777.3285; encodes a truncated HMG-CoA reductase) codon-optimized for expression in *Escherichia coli*. The synthetically generated MevT66 operon was cloned into a cloning vector such as a standard pUC or pACYC origin vector, from which it was again PCR amplified with flanking SfiI and AsiSI restriction sites, the amplified DNA fragment was digested using SfiI and AsiSI restriction endonucleases, the approximately 4.2 kb DNA fragment comprising the MevT66 operon was gel purified, and the purified DNA fragment was inserted into the SfiI and AsiSI restriction sites of the pAM36 vector, yielding expression plasmid pAM36-MevT66.

Expression plasmid pMevB-Cm was generated by inserting the MevB operon into the pBBR1MCS-1 vector. The MevB operon encodes the set of enzymes that together convert (R)-mevalonate to IPP, namely mevalonate kinase, phosphomevalonate kinase, and mevalonate pyrophosphate carboxylase. The coding sequences of the ERG12 gene (GenBank accession number X55875, REGION: 580.1911; encodes a mevalonate kinase), the coding sequence of the ERG8 gene (GenBank accession number Z49939, REGION: 3363.4718; encodes a phosphomevalonate kinase), and the coding sequence of the MVD 1 gene (GenBank accession number X97557, REGION: 544.1734; encodes a mevalonate pyrophosphate carboxylase) were PCR amplified from *Saccharomyces cerevisiae* genomic DNA. By choosing appropriate primer sequences, the stop codons of the ERG12 and ERG8 coding sequences were changed from TAA to TAG during PCR amplification to introduce ribosome binding sites. The PCR products were spliced together into the MevB operon by sequence overlap extension (SOE; Ho, et al, 1989). After the addition of 3' A overhangs, the MevB operon was ligated into the TA cloning vector pCR4 (Invitrogen, Carlsbad, Calif.). The MevB operon was excised again by digesting the cloning construct using PstI restriction endonuclease, the approximately 4.2 kb DNA fragment comprising the MevB operon was gel purified, and purified DNA fragment was ligated into the PstI restriction site of vector pBBR1MCS-1 (Kovach et al., Gene 166(1): 175-176 (1995)), yielding expression plasmid pMevB-Cm.

Expression plasmid pMBI was generated by inserting the MBI operon into the pBBR1MCS-3 vector. The MBI operon encodes the same enzymes as the MevB operon, as well as an isopentenyl pyrophosphatase isomerase that catalyzes the conversion of IPP to DMAPP. The MBI operon was generated by PCR amplifying from *Escherichia coli* genomic DNA the coding sequence of the idi gene (GenBank accession number AF119715) using primers that contained an XmaI restriction site at their 5' ends. The PCR product was digested using XmaI restriction endonuclease, the 0.5 kb DNA fragment comprising the idi coding sequence was gel purified, and the purified DNA fragment was inserted into the XmaI restriction site of expression plasmid pMevB-Cm, placing idi at the 3' end of the MevB operon. The MBI operon was then subcloned into the SalI and SadI restriction sites of vector pBBR1MCS-3 (Kovach et al., Gene 166(1): 175-176 (1995)), yielding expression plasmid pMBI.

Expression plasmid pMBIS was generated by inserting the ispA gene into expression plasmid pMBI. The ispA gene encodes a farnesyl pyrophosphate synthase that catalyzes the condensation of IPP and DMAPP to FPP. The coding sequence of the ispA gene (GenBank accession number D00694, REGION: 484.1383) was PCR amplified from *Escherichia coli* genomic DNA using a forward primer with a SacII restriction site and a reverse primer with a SadI restriction site. The amplified PCR product was digested using SacII and SadI restriction endonucleases, the 0.9 kb DNA fragment comprising the ispA coding sequence was gel purified, and the purified DNA fragment was ligated into the SacII and SadI restriction sites of pMBI, placing the ispA coding sequence 3' of idi and the MevB operon, and yielding expression plasmid pMBIS.

Expression plasmid pAM25 was generated by inserting the MevT66 operon into the pAM29 vector. The pAM29 vector was created by assembling the p15A origin of replication and kanamycin resistance conferring gene from the pZS24-MCS1 vector (Lutz and Bujard (1997) Nucl Acids Res. 25:1203-1210) with an oligonucleotide-generated lacUV5 promoter. The DNA synthesis construct comprising the MevT66 operon (see description for pAM36-MevT66 above) was digested using EcoRI and Hind III restriction endonucleases, the approximately 4.2 kb DNA fragment comprising the MevT66 operon was gel purified, and the purified DNA fragment was ligated into the EcoRI and HindIII restriction sites of pAM29, yielding expression plasmid pAM25.

Expression plasmid pAM41 was generated by replacing in expression plasmid pAM25 the truncated coding sequence of the HMG1 gene, which encodes a truncated version of the *Saccharomyces cerevisiae* HMG-CoA reductase, with the coding sequence of the mvaA gene, which encodes the *Staphylococcus aureus* HMG-CoA reductase (GenBank accession number BA000017, REGION: 2688925.2687648). The coding sequence of the mvaA gene was PCR amplified from *Staphyloccocus aureus* subsp. *aureus* (ATCC 70069) genomic DNA using primers comprising SpeI restriction sites, the PCR product was digested using SpeI restriction endonuclease, and the approximately 1.3 kb DNA fragment comprising the mvaA coding sequence was gel purified. Expression plasmid pAM25 was digested using HindIII restriction endonuclease, terminal overhangs were blunted using T4 DNA polymerase, the linear vector backbone was partially digested using SpeI restriction endonuclease, and the approximately 4.8 kb DNA fragment lacking the truncated HMG1 coding sequence was gel purified. The purified DNA fragments were ligated, yielding expression plasmid pAM41.

Expression plasmid pAM43 was generated by inserting the MBIS operon into expression plasmid pAM36-MevT66. The MBIS operon was PCR amplified from pMBIS using primers comprising a 5' XhoI restriction site and a 3' PacI restriction site, the amplified PCR product was digested using XhoI and PacI restriction endonucleases, the approximately 5.4 kb DNA fragment comprising the MBIS operon was gel purified, and the purified DNA fragment was ligated into the XhoI PacI restriction site of expression plasmid pAM36-MevT66, yielding expression plasmid pAM43.

Expression plasmid pAM45 was generated by inserting lacUV5 promoters in front of the MBIS and MevT66 operons of expression plasmid pAM43. A DNA fragment comprising a nucleotide sequence encoding the lacUV5 promoter was synthesized from oligonucleotides, and inserted into the AscI SfiI and AsiSI XhoI restriction sites of pAM43, yielding expression plasmid pAM45.

Expression plasmid pAM52 was generated by replacing in expression plasmid pAM41 the coding sequence of the ERG13 gene, which encodes the *Saccharomyces cerevisiae* HMG-CoA synthase, with the coding sequence of the mvaS gene, which encodes the *Staphylococcus aureus* HMG-CoA synthase (GenBank accession number BA000017, REGION: 2689180 . . . 2690346). The coding sequence of the mvaS gene was PCR amplified from *Staphyloccocus aureus* subsp. *aureus* (ATCC 70069) genomic DNA, and the amplified DNA fragment was used as a PCR primer to replace the coding sequence of the HMG1 gene in pAM41 according to the method of Geiser et al. (BioTechniques 31:88-92 (2001)), yielding expression plasmid pAM52.

Expression plasmid pAM97 was generated by replacing in expression plasmid pAM45 the MevT66 operon with the (atoB(opt):mvaS:mvaA) operon of expression plasmid pAM52. Expression plasmid pAM45 was digested using AsiSI and SfiI restriction endonucleases, and the approximately 8.3 kb DNA fragment lacking the MevT66 operon was gel purified. The (atoB(opt):mvaS:mvaA) operon of pAM52 was PCR amplified using primers comprising a SfiI and AsiSI restriction site, the PCR product was digested using SfiI and AsiSI restriction endonucleases, and the approximately 3.8 kb DNA fragment comprising the (atoB(opt):mvaS:mvaA)

operon was gel purified. The purified DNA fragments were ligated, yielding expression plasmid pAM97.

Expression plasmid pAM765 was generated by replacing in expression plasmid pAM97 the coding sequence of the ERG12 gene, which encodes the *Saccharomyces cerevisiae* mevalonate kinase, with the coding sequence of the mvaK1 gene, which encodes the *Staphylococcus aureus* mevalonate kinase (GenBank accession number AAG02424). The *Staphylococcus aureus* mevalonate kinase is less sensitive to feedback inhibition by FPP (Voynova et al. (2004) *J. Bacteriol.* 186:61-67), and so expression plasmid pAM765 can cause greater production of FPP in a host cell than expression plasmid pAM97. The coding sequence of the mvaK1 gene was PCR amplified from an expression plasmid, and the approximately 0.9 kb PCR product was gel purified. The PMK-PMD-idi-ispA operon was PCR amplified from pAM97, and the approximately 4.1 kb PCR product was gel purified. The purified PCR products were stitched together, and the stitched product was gel purified. The purified stitched product and pAM97 were digested using XhoI and SacI restriction endonucleases, the digested DNA fragments were gel purified, and the purified DNA fragments were ligated, yielding expression plasmid pAM765 (SEQ ID NO: 1).

Plasmid pAM489 was generated by inserting the $P_{GAL10}$-ERG20_$P_{GAL1}$-tHMGR insert of vector pAM471 into vector pAM466. Vector pAM471 was generated by inserting DNA fragment $P_{GAL10}$-ERG20_$P_{GAL1}$-tHMGR, which comprises the coding sequence of the ERG20 gene of *Saccharomyces cerevisiae* (ERG20 nucleotide positions 1 to 1208; A of ATG start codon is nucleotide 1) (ERG20), the genomic locus containing the divergent GAL1 and GAL10 promoter of *Saccharomyces cerevisiae* (GAL1 nucleotide position −1 to −668) ($P_{GAL}$), and a truncated coding sequence of the HMG1 gene of *Saccharomyces cerevisiae* (HMG1 nucleotide positions 1586 to 3323) (tHMGR), into the TOPO Zero Blunt II cloning vector (Invitrogen, Carlsbad, Calif.). Vector pAM466 was generated by inserting DNA fragment TRP1$^{-856\ to\ +548}$, which comprises a segment of the wild-type TRP1 locus of *Saccharomyces cerevisiae* that extends from nucleotide position −856 to position 548 and harbors a non-native internal XmaI restriction site between bases −226 and −225, into the TOPO TA pCR2.1 cloning vector (Invitrogen, q Carlsbad, Calif.). DNA fragments $P_{GAL10}$-ERG20_$P_{GAL1}$-tHMGR and TRP1$^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, Mass.), DNA fragments corresponding to the $P_{GAL10}$-ERG20_$P_{GAL1}$-tHMGR insert and the linearized pAM466 vector were gel purified, and 4 molar equivalents of the purified insert was ligated with 1 molar equivalent of the purified linearized vector, yielding pAM489. FIG. 1R shows a map and SEQ ID NO: 2 the nucleotide sequence of the TRP1_$P_{GAL10}$-ERG20_$P_{GAL1}$-tHMGR TRP insert of pAM489.

TABLE 1

PCR amplifications performed to generate pAM489

| PCR Round | Template | Primer 1 | Primer 2 | PCR Product |
|---|---|---|---|---|
| 1 | 100 ng of Y051 genomic DNA | 61-67-CPK001-G (SEQ ID NO: 3) | 61-67-CPK002-G (SEQ ID NO: 4) | TRP1$^{-856\ to\ -226}$ |
| | | 61-67-CPK003-G (SEQ ID NO: 5) | 61-67-CPK004-G (SEQ ID NO: 6) | TRP1$^{-225\ to\ +548}$ |
| | 100 ng of EG123 genomic DNA | 61-67-CPK025-G (SEQ ID NO: 7) | 61-67-CPK050-G (SEQ ID NO: 8) | ERG20 |
| | 100 ng of Y002 genomic DNA | 61-67-CPK051-G (SEQ ID NO: 9) | 61-67-CPK052-G (SEQ ID NO: 10) | $P_{GAL1/10}$ |
| | | 61-67-CPK053-G (SEQ ID NO: 11) | 61-67-CPK031-G (SEQ ID NO: 12) | tHMGR |
| 2 | 100 ng each of TRP1$^{-856\ to\ -226}$ and TRP1$^{-225\ to\ +548}$ purified PCR products | 61-67-CPK001-G (SEQ ID NO: 3) | 61-67-CPK004-G (SEQ ID NO: 6) | TRP1$^{-856\ to\ +548}$ |
| | 100 ng each of ERG20 and $P_{GAL1/10}$ purified PCR products | 61-67-CPK025-G (SEQ ID NO: 7) | 61-67-CPK052-G (SEQ ID NO: 10) | ERG20-$P_{GAL1/10}$ |
| 3 | 100 ng each of ERG20-$P_{GAL1/10}$ and tHMGR purified PCR products | 61-67-CPK025-G (SEQ ID NO: 7) | 61-67-CPK031-G (SEQ ID NO: 12) | $P_{GAL10}$-ERG20_$P_{GAL1}$-tHMGR |

Plasmid pAM491 was generated by inserting the $P_{GAL10}$-ERG13_$P_{GAL1}$-tHMGR insert of vector pAM472 into vector pAM467. Vector pAM472 was generated by inserting DNA fragment $P_{GAL10}$-ERG13_$P_{GAL1}$-tHMGR, which comprises the coding sequence of the ERG13 gene of *Saccharomyces cerevisiae* (ERG13 nucleotide positions 1 to 1626) (ERG13), the genomic locus containing the divergent GAL1 and GAL 10 promoter of *Saccharomyces cerevisiae* (GAL1 nucleotide position −1 to −668) ($P_{GAL}$), and a truncated ORF of the HMG1 gene of *Saccharomyces cerevisiae* (HMG1 nucleotide position 1586 to 3323) (tHMGR), into the TOPO Zero Blunt II cloning vector. Vector pAM467 was generated by inserting DNA fragment URA3$^{-723\ to\ 701}$, which comprises a segment of the wild-type URA3 locus of *Saccharomyces cerevisiae* that extends from nucleotide position −723 to position −224 and harbors a non-native internal XmaI restriction site between bases −224 and −223, into the TOPO TA pCR2.1 cloning vector. DNA fragments $P_{GAL10}$-ERG13_$P_{GAL1}$-tHMGR and URA3$^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERG13-$P_{GAL}$-tHMGR insert and the linearized pAM467 vector were gel purified, and 4 molar equivalents of the purified insert was ligated with 1 molar equivalent of the purified linearized vector, yielding pAM491. FIG. 1S shows a map and SEQ ID NO: 13 the nucleotide sequence of the URA3_$P_{GAL10}$-ERG13_$P_{GAL1}$-tHMGR_URA3 insert of pAM491.

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 14) | 61-67-CPK006-G (SEQ ID NO: 15) | URA3$^{-723\ to\ -224}$ |
| | | 61-67-CPK007-G (SEQ ID NO: 16) | 61-67-CPK008-G (SEQ ID NO: 17) | URA3$^{-223\ to\ 701}$ |
| | 100 ng of Y002 genomic DNA | 61-67-CPK032-G (SEQ ID NO: 18) | 61-67-CPK054-G (SEQ ID NO: 19) | ERG13 |
| | | 61-67-CPK052-G (SEQ ID NO: 20) | 61-67-CPK055-G (SEQ ID NO: 21) | P$_{GAL1/10}$ |
| | | 61-67-CPK031-G (SEQ ID NO: 22) | 61-67-CPK053-G (SEQ ID NO: 23) | tHMGR |
| 2 | 100 ng each of URA3$^{-723\ to\ -224}$ and uRA3$^{-223\ to\ 701}$ purified PCR products | 61-67-CPK005-G (SEQ ID NO: 14) | 61-67-CPK008-G (SEQ ID NO: 17) | URA3$^{-723\ to\ 701}$ |
| | 100 ng each of ERG13 and P$_{GAL1/10}$ purified PCR products | 61-67-CPK032-G (SEQ ID NO: 18) | 61-67-CPK052-G (SEQ ID NO: 20) | ERG13-P$_{GAL1/10}$ |
| 3 | 100 ng each of ERG13-P$_{GAL1/10}$ and tHMGR purified PCR products | 61-67-CPK031-G (SEQ ID NO: 22) | 61-67-CPK032-G (SEQ ID NO: 18) | P$_{GAL10}$-ERG13_P$_{GAL1}$-tHMGR |

Plasmid pAM493 was generated by inserting the P$_{GAL10}$-IDI1_P$_{GAL1}$-tHMGR insert of vector pAM473 into vector pAM468. Vector pAM473 was generated by inserting DNA fragment P$_{GAL10}$-IDI1_P$_{GAL1}$-tHMGR, which comprises the coding sequence of the IDI1 gene of Saccharomyces cerevisiae (IDI1 nucleotide position 1 to 1017) (IDI1), the genomic locus containing the divergent GAL1 and GAL10 promoter of Saccharomyces cerevisiae (GAL1 nucleotide position -1 to -668) (P$_{GAL}$), and a truncated ORF of the HMG1 gene of Saccharomyces cerevisiae (HMG1 nucleotide positions 1586 to 3323) (tHMGR), into the TOPO Zero Blunt II cloning vector. Vector pAM468 was generated by inserting DNA fragment ADE1$^{-825\ to\ 653}$, which comprises a segment of the wild-type ADE1 locus of Saccharomyces cerevisiae that extends from nucleotide position -225 to position 653 and harbors a non-native internal XmaI restriction site between bases -226 and -225, into the TOPO TA pCR2.1 cloning vector. DNA fragments P$_{GAL10}$-IDI1_P$_{GAL1}$-tHMGR and ADE1$^{-825\ to\ 653}$ were generated by PCR amplification as outlined in Table 3. For the construction of pAM493, 400 ng of pAM473 and 100 ng of pAM468 were digested to completion using XmaI restriction enzyme, DNA fragments corresponding to the P$_{GAL10}$-IDI1_P$_{GAL1}$-tHMGR insert and the linearized pAM468 vector were gel purified, and 4 molar equivalents of the purified insert was ligated with 1 molar equivalent of the purified linearized vector, yielding vector pAM493. FIG. 1T shows a map and SEQ ID NO: 24 the nucleotide sequence of the ADE1_P$_{GAL10}$-IDI1_P$_{GAL1}$-tHMGR_ADE1 insert of pAM493.

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 25) | 61-67-CPK010-G (SEQ ID NO: 26) | ADE1$^{-825\ to\ -226}$ |
| | | 61-67-CPK011-G (SEQ ID NO: 27) | 61-67-CPK012-G (SEQ ID NO: 28) | ADE1$^{-225\ to\ 653}$ |
| | 100 ng of Y002 genomic DNA | 61-67-CPK047-G (SEQ ID NO: 29) | 61-67-CPK064-G (SEQ ID NO: 30) | IDI1 |
| | | 61-67-CPK052-G SEQ ID NO: 31) | 61-67-CPK065-G (SEQ ID NO: 32) | P$_{GAL1/10}$ |
| | | 61-67-CPK031-G (SEQ ID NO: 12) | 61-67-CPK053-G (SEQ ID NO: 33) | tHMGR |
| 2 | 100 ng each of ADE1$^{-825\ to\ -226}$ and ADE1$^{-225\ to\ 653}$ purified PCR products | 61-67-CPK009-G (SEQ ID NO: 25) | 61-67-CPK012-G (SEQ ID NO: 28) | ADE1$^{-825\ to\ 653}$ |
| | 100 ng each of IDI1 and P$_{GAL1/10}$ purified PCR products | 61-67-CPK047-G (SEQ ID NO: 29) | 61-67-CPK052-G (SEQ ID NO: 31) | IDI1-P$_{GAL1/10}$ |
| 3 | 100 ng each of IDI1-P$_{GAL1/10}$ and tHMGR purified PCR products | 61-67-CPK031-G (SEQ ID NO: 12) | 61-67-CPK047-G (SEQ ID NO: 29) | P$_{GAL10}$-IDI1_P$_{GAL1}$-tHMGR |

Figure 1D:
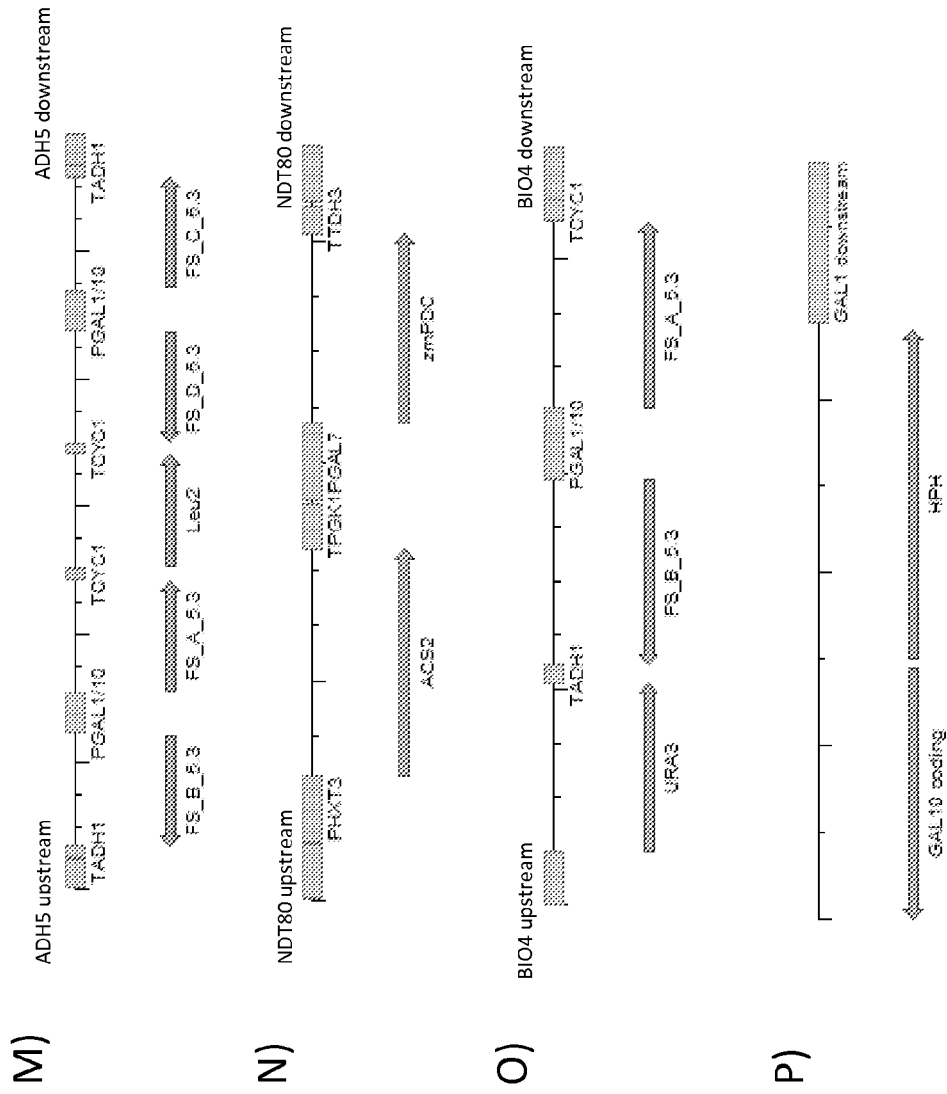

Plasmid pAM495 was generated by inserting the $P_{GAL10}$-ERG10_$P_{GAL1}$-ERG12 insert of pAM474 into vector pAM469. Vector pAM474 was generated by inserting DNA fragment $P_{GAL10}$-ERG10_$P_{GAL1}$-ERG12, which comprises the coding sequence of the ERG10 gene of *Saccharomyces cerevisiae* (ERG10 nucleotide position 1 to 1347) (ERG10), the genomic locus containing the divergent GAL1 and GAL10 promoter of *Saccharomyces cerevisiae* (GAL1 nucleotide position −1 to −668) ($P_{GAL}$), and the coding sequence of the ERG12 gene of *Saccharomyces cerevisiae* (ERG12 nucleotide position 1 to 1482) (ERG12), into the TOPO Zero Blunt II cloning vector. Vector pAM469 was generated by inserting DNA fragment $HIS3^{-32\ to\ -1000}$_HISMX_$HIS3^{504\ to\ -1103}$, which comprises two segments of the HIS locus of *Saccharomyces cerevisiae* that extend from nucleotide position −32 to position −1000 and from nucleotide position 504 to position 1103, a HISMX marker, and a non-native XmaI restriction site between the $HIS3^{504\ to\ -1103}$ sequence and the HISMX marker, into the TOPO TA pCR2.1 cloning vector. DNA fragments $P_{GAL10}$-ERG10_$P_{GAL1}$-ERG12 and $HIS3^{-32\ to\ -1000}$_HISMX_$HIS3^{504\ to\ -1103}$ were generated by PCR amplification as outlined in Table 4. For construction of pAM495, 400 ng of pAM474 and 100 ng of pAM469 were digested to completion using XmaI restriction enzyme, DNA fragments corresponding to the $P_{GAL10}$-ERG10_$P_{GAL1}$-ERG12 insert and the linearized pAM469 vector were gel purified, and 4 molar equivalents of the purified insert was ligated with 1 molar equivalent of the purified linearized vector, yielding vector pAM495. FIG. 1D shows a map and SEQ ID NO: 34 the nucleotide sequence of the $HIS3\_P_{GAL10}$-ERG10_$P_{GAL1}$-ERG12_HIS3 insert of pAM495.

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 35) | 61-67-CPK014alt-G (SEQ ID NO: 36) | $HIS3^{-32\ to\ -1000}$ |
| | | 61-67-CPK017-G (SEQ ID NO: 37) | 61-67-CPK018-G (SEQ ID NO: 38) | $HIS3^{504\ to\ -1103}$ |
| | | 61-67-CPK035-G (SEQ ID NO: 39) | 61-67-CPK056-G (SEQ ID NO: 40) | ERG10 |
| | | 61-67-CPK057-G (SEQ ID NO: 41) | 61-67-CPK058-G (SEQ ID NO: 42) | $P_{GAL}$ |
| | | 61-67-CPK040-G (SEQ ID NO: 43) | 61-67-CPK059-G (SEQ ID NO: 44) | ERG12 |
| | 10 ng of plasmid pAM330 DNA ** | 61-67-CPK015a1t-G (SEQ ID NO: 45) | 61-67-CPK016-G (SEQ ID NO: 46) | HISMX |
| 2 | 100 ng each of $HIS3^{504\ to\ -1103}$ and HISMX PCR purified products | 61-67-CPK015alt-G (SEQ ID NO: 45) | 61-67-CPK018-G (SEQ ID NO: 38) | HISMX_$HIS3^{504\ to\ -1103}$ |
| | 100 ng each of ERG10 and $P_{GAL}$ purified PCR products | 61-67-CPK035-G (SEQ ID NO: 39) | 61-67-CPK058-G (SEQ ID NO: 42) | ERG10-$P_{GAL1/10}$ |
| 3 | 100 ng each of $HIS3^{-32\ to\ -1000}$ and HISMX_$HIS3^{504\ to\ -1103}$ purified PCR products | 61-67-CPK013-G (SEQ ID NO: 35) | 61-67-CPK018-G (SEQ ID NO: 38) | $HIS3^{-32\ to\ -1000}$_HISMX_$HIS3^{504\ to\ -1103}$ |
| | 100 ng each of ERG10-$P_{GAL1/10}$ and ERG12 purified PCR products | 61-67-CPK035-G (SEQ ID NO: 39) | 61-67-CPK040-G (SEQ ID NO: 43) | $P_{GAL10}$-ERG10_$P_{GAL1}$-ERG12 |

** The HISMX marker in pAM330 originated from pFA6a-HISMX6-PGAL1 as described by van Dijken et al. ((2000) Enzyme Microb. Technol. 26(9-10):706-714).

Plasmid pAM497 was generated by inserting the $P_{GAL10}$-ERG8_$P_{GAL1}$-ERG19 insert of pAM475 into vector pAM470. Vector pAM475 was generated by inserting DNA fragment $P_{GAL10}$-ERG8_$P_{GAL1}$-ERG19, which comprises the coding sequence of the ERG8 gene of *Saccharomyces cerevisiae* (ERG8 nucleotide position 1 to 1512) (ERG8), the genomic locus containing the divergent GAL1 and GAL10 promoter of *Saccharomyces cerevisiae* (GAL1 nucleotide position −1 to −668) ($P_{GAL}$), and the coding sequence of the ERG19 gene of *Saccharomyces cerevisiae* (ERG19 nucleotide position 1 to 1341) (ERG19), into the TOPO Zero Blunt II cloning vector. Vector pAM470 was generated by inserting DNA fragment LEU2$^{-100\ to\ 450}$_HISMX_LEU2$^{1096\ to\ 1770}$, which comprises two segments of the LEU2 locus of *Saccharomyces cerevisiae* that extend from nucleotide position −100 to position 450 and from nucleotide position 1096 to position 1770, a HISMX marker, and a non-native XmaI restriction site between the LEU2$^{1096\ to\ 1770}$ sequence and the HISMX marker, into the TOPO TA pCR2.1 cloning vector. DNA fragments $P_{GAL10}$-ERG8_$P_{GAL1}$-ERG19 and LEU2$^{-100\ to\ 450}$_HISMX_LEU2$^{1096\ to\ 1770}$ were generated by PCR amplification as outlined in Table 5. For the construction of pAM497, 400 ng of pAM475 and 100 ng of pAM470 were digested to completion using XmaI restriction enzyme, DNA fragments corresponding to the ERG8-$P_{GAL}$-ERG19 insert and the linearized pAM470 vector were purified, and 4 molar equivalents of the purified insert was ligated with 1 molar equivalent of the purified linearized vector, yielding vector pAM497. FIG. 1V for a map and SEQ ID NO: 47 the nucleotide sequence of the LEU2_$P_{GAL10}$-ERG8_$P_{GAL1}$-ERG19LEU2 insert of pAM497.

the Quikchange Multi Site-Directed Mutagenesis Kit, yielding vector pAM1419 (SEQ ID NO: 60).

Expression plasmid pAM1421 (FIG. 13A) were generated by inserting into vector pAM1419 the FS_S2D_Ec coding sequence. Vector pAM1419 was digested using BamHI and NdeI restriction endonucleases, the approximately 4.15 kb linearized vector backbone was gel purified, and the purified DNA fragment was digested with Calf Intestinal Alkaline Phosphatse (CIP) to remove 5' phosphate groups. The b-farnesene synthase gene of *Artemisia annua* (GenBank accession number AY835398; Picaud, et al, 2005) comprising an amino acid substitution at position 2 from serine to aspartate (S2D) and codon-optimized for expression in *Escherichia coli* (FS_S2D_Ec coding sequence; SEQ ID NO: 61) with flanking BamHI and NdeI restriction sites was PCR amplified from other expression plasmids, the PCR product was digested using BamHI and NdeI restriction endonucleases, and then gel purified. Purified linearized vector and digested PCR product were ligated using T4 DNA ligase, yielding expression plasmid pAM 1421.

Expression plasmid pAM353 was generated by inserting into the pRS425-Gall vector (Mumberg et. al. (1994) Nucl. Acids. Res. 22(25): 5767-5768) the coding sequence of the β-farnesene synthase gene of *Artemisia annua* (GenBank accession number AY835398) codon-optimized for expression in *Saccharomyces cerevisiae* (FS_Aa_Sc coding sequence; SEQ ID NO: 68). The FS_Aa_Sc coding sequence was generated synthetically and was flanked by 5' BamHI and 3' XhoI restriction sites such that it could be cloned into compatible restriction sites of a cloning vector such as a standard pUC or pACYC origin vector. The FS_Aa_Sc cod-

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 48) | 61-67-CPK020-G (SEQ ID NO: 49) | LEU2$^{-100\ to\ 450}$ |
|  |  | 61-67-CPK023-G (SEQ ID NO: 50) | 61-67-CPK024-G (SEQ ID NO: 51) | LEU2$^{1096\ to\ 1770}$ |
|  | 10 ng of plasmid pAM330 DNA ** | 61-67-CPK021-G (SEQ ID NO: 52) | 61-67-CPK022-G (SEQ ID NO: 53) | HISMX |
|  | 100 ng of Y002 genomic DNA | 61-67-CPK041-G (SEQ ID NO: 54) | 61-67-CPK060-G (SEQ ID NO: 55) | ERG8 |
|  |  | 61-67-CPK061-G (SEQ ID NO: 56) | 61-67-CPK062-G (SEQ ID NO: 57) | $P_{GAL}$ |
|  |  | 61-67-CPK046-G (SEQ ID NO: 58) | 61-67-CPK063-G (SEQ ID NO: 59) | ERG19 |
| 2 | 100 ng each of LEU2$^{1096\ to\ 1770}$ and HISMX purified PCR products | 61-67-CPK021-G (SEQ ID NO: 52) | 61-67-CPK024-G (SEQ ID NO: 51) | HISMX_LEU2$^{1096\ to\ 1770}$ |
|  | 100 ng each of ERG8 and $P_{GAL}$ purified PCR products | 61-67-CPK041-G (SEQ ID NO: 54) | 61-67-CPK062-G (SEQ ID NO: 57) | ERG8-$P_{GAL}$ |
| 3 | 100 ng of LEU2$^{-100\ to\ 450}$ and HISMX-LEU2$^{1096\ to\ 1770}$ purified PCR products | 61-67-CPK019-G (SEQ ID NO: 48) | 61-67-CPK024-G (SEQ ID NO: 51) | LEU2$^{-100\ to\ 450}$ HISMX_LEU2$^{1096\ to\ 1770}$ |
|  | 100 ng each of ERG8-$P_{GAL}$ and ERG19 purified PCR products | 61-67-CPK041-G (SEQ ID NO: 54) | 61-67-CPK046-G (SEQ ID NO: 58) | $P_{GAL1}$-ERG8_$P_{GAL1}$-ERG19 |

** The HISMX marker in pAM330 originated from pFA6a-HISMX6-PGAL1 as described by van Dijken et al. ((2000) Enzyme Microb. Technol. 26(9-10):706-714).

Vector pAM1419 was generated by removing from vector pTrc99A (Amman et al., Gene 40:183-190 (1985)) two NcoI restriction sites. The NcoI restriction site in the multiple cloning site of vector pTrc99A was first changed to a NdeI restriction site using the Quikchange Multi Site-Directed Mutagenesis Kit (Stratagene Cloning Systems, La Jolla, Calif.) according to manufacturer recommended protocols. A second NdeI restriction site outside of the multiple cloning site at position 2699 of vector pTrc99A was then also removed using ing sequence was excised again by digesting the construct using BamHI and XhoI restriction endonucleases, the approximately 1.7 kb DNA fragment comprising the FS_Aa_Sc coding sequence was gel purified, and the purified DNA fragment was ligated into the BamHI XhoI restriction site of the pRS425-Gall vector, yielding expression plasmid pAM353.

Expression plasmid pAM404 (FIG. 13B) was generated by inserting into vector pAM178 (SEQ ID NO: 69) the FS_Aa_Sc coding sequence. Vector pAM178 was digested using BamHI and NheI restriction endonucleases, and the approximately 7.3 kb vector backbone was gel purified. The FS_Aa_Sc coding sequence with flanking BamHI and NheI restriction sites was PCR amplified from pAM353, the PCR product was digested using BamHI and NheI restriction endonucleases, and the approximately 1.7 kb DNA fragment comprising the FS_Aa_Sc coding sequence was gel purified. The two gel purified DNA fragments were ligated, yielding expression plasmid pAM404.

The expression plasmids shown in Table 6 and FIG. 13B were generated by replacing in expression plasmid pAM404 the FS_Aa_Sc coding sequence with the indicated coding sequences. Vector pAM404 was digested using BamHI and NheI restriction endonucleases, and the approximately 7.3 kb linearized vector backbone lacking the FS_Aa_Sc coding sequence was gel purified. The FS_S2D_Ec coding sequence was PCR amplified from another expression plasmid using primers that overlap with terminal sequences of the linearized pAM404 vector backbone. The IS_Pn_Sc and TDS_Pn_Sc coding sequence were extracted by restriction endonuclease digestion from other expression vectors. The DNA fragments were gel purified. The FS_S2D_Ec coding sequence was inserted into the purified linearized vector via homologous recombination by transforming strain Y539 and selecting host cell transformants on Complete Synthetic Medium (CSM) lacking leucine (CSM-L) with 2% glucose as a sole carbon source. The IS_Pn_Sc and TDS_Fs_Sc coding sequences were ligated into the purified linearized vector using T4 DNA ligase.

TABLE 6

Construction of pAM404-derived expression plasmids

| Expression Plasmid | Coding Sequence | Size of Coding Sequence (bp) |
|---|---|---|
| pAM1765 | FS_S2D_Ec (SEQ ID NO: 61) | 1.7 |
| pAM1795 | TDS_Fs_Sc (SEQ ID NO: 70) | 1.1 |
| pAM1549 | IS_Pn_Sc (SEQ ID NO: 71) | 1.8 |

FS_S2D_Ec = β-farnesene synthase gene of Artemisia annua (GenBank accession number AY835398; Picaud, et al, 2005) comprising an amino acid substitution at position 2 from serine to aspartate (S2D) and codon-optimized for expression in *Escherichia coli*
TDS_Fs_Sc = coding sequence of the trichodiene synthase gene of Fusarium sporotrichioides (GenBank accession number AF364179; Holn, et al, 1989) codon-optimized for expression in *Saccharomyces cerevisiae*
IS_Pn_Sc = isoprene synthase gene of Populus nigra (GenBank accession number AM410988; Fortunati, et al, 2008) codon-optimized for expression in *Saccharomyces cerevisiae*

Expression plasmid pAM1812 (SEQ ID NO: 72; FIG. 13C) was generated by inserting into expression plasmid pAM404 the TDS_Fs_Sc coding sequence. Expression plasmid pAM404 was digested using NotI restriction endonuclease, and the approximately 9.0 kb linearized plasmid was gel purified. The TDS_Fs_Sc coding sequence was PCR amplified from expression plasmid pAM1795 using primers that overlap with terminal sequences of the linearized pAM404, and the 1.2 kb PCR product comprising the TDS_Fs_Sc coding sequence was gel purified. The two gel purified DNA fragments were ligated via homologous recombination by transforming strain Y539 with both purified DNA fragments and selecting host cell transformants on CSM-L with 2% glucose as a sole carbon source.

The expression plasmids shown in Table 7 and FIG. 13C were generated by replacing in expression plasmid pAM1812 the FS_Aa_Sc coding sequence with the indicated coding sequences. Expression plasmid pAM1812 was digested using BamHI and NheI restriction endonucleases, and the approximately 7.2 kb linear plasmid lacking the FS_Aa_Sc coding sequence was gel purified. The coding sequences were extracted by BamHI and NheI restriction endonuclease digestion from other expression vectors, and the DNA fragment comprising the coding sequence were gel purified. The purified DNA fragments were finally ligated using T4 DNA ligase, yielding the expression plasmids.

TABLE 7

Construction of pAM1812-derived expression plasmids

| Expression Plasmid | Coding Sequence | Size of Coding Sequence (kb) |
|---|---|---|
| pAM1895 | FS_S2D_Ec (SEQ ID NO: 61) | 1.7 |
| pAM1896 | FS_Ad_Sc (SEQ ID NO: 73) | 2.3 |
| pAM1948 | IS_Pn_Sc (SEQ ID NO: 71) | 1.8 |

FS_S2D_Ec = β-farnesene synthase gene of Artemisia annua (GenBank accession number AY835398) comprising an amino acid substitution at position 2 from serine to aspartate (S2D) and codon-optimized for expression in *Escherichia coli*
FS_Ad_Sc = α-farnesene synthase of Actinidia deliciosa (GenBank Accession No. FJ265785; Nieuwenhuizen, et al, 2009) codon-optimized for expression in *Saccharomyces cerevisiae*
IS_Pn_Sc = isoprene synthase of Populus nigra (Accession No. AM410988; Fortunati, et al, 2008) codon-optimized for expression in *Saccharomyces cerevisiae*

Expression plasmid pAM1813 (FIG. 13D) was generated by inserting into expression plasmid pAM1795 the coding sequence of the FS_Aa_Sc coding sequence. Expression plasmid pAM1795 was digested using NotI restriction endonuclease, and the approximately 8.4 kb linearized plasmid was gel purified. The FS_Aa_Sc coding sequences was PCR amplified using primers that overlap with terminal sequences of the linearized pAM404, and the PCR product comprising the FS_Aa_Sc coding sequences was gel purified. The purified PCR product was ligated via homologous recombination by transforming it into strain Y539 and selecting host cell transformants on CSM-L with 2% glucose as a sole carbon source. Note that pAM1812 and pAM1813 are identical except that the promoters for TDS and FS are switched. Using promoters of different strengths allows variation of the farnesene/trichodiene ratios.

Expression plasmid pAM1653 was generated by inserting into vector pRS415 the IS_Pn_Sc coding sequence. Expression plasmid pAM1549 was digested using SapI restriction endonuclease, was treated with Klenow fragment to generated blunt ends, and digested again using NotI restriction endonuclease, and the 2.8 kb DNA fragment comprising the IS_Pn_Sc coding sequence and PGAL sequence was gel purified. Vector pRS415 was digested using NotI and AleI restriction endonucleases, and the 6.0 kb linearized vector backbone was gel purified. The two purified DNA fragments were ligated, yielding expression plasmid pAM1653.

Expression plasmid pAM1734 was generated by eliminating certain restriction sites from the multicloning region of expression plasmid pAM1653. Expression plasmid pAM1653 was digested using XbaI and HindIII restriction endonucleases, treated with Klenow fragment to generate blunt ends, and finally self-ligated, yielding expression plasmid pAM1734.

Expression plasmid pAM1764 (SEQ ID NO: 74) was generated by inserting into expression plasmid pAM1734 the FS_S2D_Ec coding sequence. Expression vector pAM1734 was digested using BamHI and NheI restriction endonucleases, and the approximately 6.9 kb linearized plasmid was gel purified. The FS_S2D_Ec coding sequence was PCR amplified from expression plasmid pAM1421 using primers that overlap with terminal sequences of the linearized pAM1734, and the 1.7 kb PCR product comprising the FS_S2D-Sc coding sequence was gel purified. The two purified DNA fragments were ligated via homologous recombination by transforming strain Y539 with both purified DNA fragments and selecting host cell transformants on CSM-L with 2% glucose as a sole carbon source.

Expression plasmid pAM1668 was generated by deleting from expression plasmid pAM1419 the lad gene. Expression plasmid pAM1419 was digested using EcoRV and SapI restriction endonucleases, the digested plasmid was repaired using the End-It DNA End-Repair Kit (Epicentre, Madison, Wis.) according to manufacturer recommended protocols, and the end-repaired vector was self-ligated, yielding vector pAM1668.

The expression plasmids shown in Table 8 and FIG. 13E were generated by inserting into vector pAM1668 the indicated coding sequences. Vector pAM1668 was digested using BamHI and NdeI restriction endonucleases, and the approximately 2.9 kb linearized vector backbone was gel purified. The coding sequences were PCR amplified using primers that overlap with terminal sequences of the linearized pAM1668, the PCR products were digested using BamHI and NdeI restriction endonucleases, and the digested PCR products comprising the coding sequences were gel purified. Purified linearized vector and digested PCR products were finally ligated, yielding the expression plasmids.

TABLE 8

Construction of pAM1688-derived expression plasmids

| Expression Plasmid | Coding Sequence | Size of Coding Sequence (bp) |
|---|---|---|
| pAM1670 | FS_S2D_Ec (SEQ ID NO: 61) | 1725 |
| pAM2158 | FS_S2D_Sc (SEQ ID NO: 76) | 1725 |
| pAM2157 | FS_Aa_Ec (SEQ ID NO: 62) | 1725 |
| pAM2117 | FS_Aa_Sc (SEQ ID NO: 68) | 1740 |
| pAM2096 | FS_Cj_Ec (SEQ ID NO: 63) | 1686 |
| pAM2097 | FS_Cs_Ec (SEQ ID NO: 66) | 1686 |
| pAM2098 | FS_Pt_Ec (SEQ ID NO: 67) | 1725 |

TABLE 8-continued

Construction of pAM1688-derived expression plasmids

| Expression Plasmid | Coding Sequence | Size of Coding Sequence (bp) |
|---|---|---|
| pAM2101 | PS_S_Ec (SEQ ID NO: 64) | 1014 |
| pAM2104 | TDS_Fs_Ec (SEQ ID NO: 65) | 1125 |

FS_S2D_Ec = β-farnesene synthase gene of Artemisia annua (GenBank accession number AY835398) comprising an amino acid substitution at position 2 from serine to aspartate (S2D) and codon-optimized for expression in *Escherichia coli*

FS_S2D_Sc = β-farnesene synthase gene of Artemisia annua (GenBank accession number AY835398) comprising an amino acid substitution at position 2 from serine to aspartate (S2D) and codon-optimized for expression in *Saccharomyces cerevisiae*

FS_Aa_Sc = β-farnesene synthase gene of Artemisia annua (GenBank accession number AY835398) codon-optimized for expression in *Saccharomyces cerevisiae*

FS_Aa_Ec = β-farnesene synthase gene of Artemisia annua (GenBank accession number AY835398) codon-optimized for expression in *Escherichia coli*

FS_Cj_Ec = β-farnesene synthase of Citrus junos (GenBank Accession No. AAK54279; Maruyama, et al, 2001) codon-optimized for expression in *Escherichia coli*

FS_Cs_Ec = α-farnesene synthase of Cucumis sativus (GenBank Accession No. AAU05951; Mercke, et al, 2004) codon-optimized for expression in *Escherichia coli*

FS_Pt_Ec = α-farnesene synthase of Pinus taeda (GenBank Accession No. AAO61226; Phillips, et al, 2003) codon-optimized for expression in *Escherichia coli*

PS_S_Ec = pentalenene synthase of *Streptomyces* sp. (GenBank Accession No. AAA19131; Cane, et al, 1994) codon-optimized for expression in *Escherichia coli*

TDS_Fs_Ec = trichodiene synthase of *Fusarium sporotrichioides* (GenBank accession number AF364179; Holn, et al, 1989) codon-optimized for expression in *Escherichia coli*

Construct A was generated by PCR amplification as described in Table 9. The construct comprises the upstream region of the NDT80 gene of *Saccharomyces cerevisiae* (NDT80 nucleotide positions −175 to −952), the LEU2 marker of *Saccharomyces cerevisiae* (LEU2 nucleotide positions −661 to +1541), the promoter of the GAL1 gene of *Saccharomyces cerevisiae* (GAL1 nucleotide positions −1 to −667), the FS_Aa_Sc coding sequence, the terminator of the CYC1 gene of *Saccharomyces cerevisiae* (CYC1 nucleotide positions +331 to +521), and the downstream region of the NDT80 gene of *Saccharomyces cerevisiae* (NDT80 nucleotide positions +1685 to +2471). FIG. 1W shows a map and SEQ ID NO: 86 the nucleotide sequence of Construct A.

TABLE 9

PCR reactions performed to generate Construct A

| PCR Round | Template | Primer 1 | Primer 2 | PCR Product |
|---|---|---|---|---|
| 1 | 100 ng of Y002 genomic DNA | PW-091-144-CPK640 (SEQ ID NO: 77) | AM-288-90-CPK1615 (SEQ ID NO: 78) | NDT80$^{-175\ to\ -952}$ |
| | | AM-288-90-CPK1620 (SEQ ID NO: 79) | PW-091-144-CPK649 (SEQ ID NO: 80) | NDT80$^{+1685\ to\ +2471}$ |
| | | AM-288-90-CPK1616 (SEQ ID NO: 81) | AM-288-90-CPK1638 (SEQ ID NO: 82) | GAL1$^{-1\ to\ -667}$ |
| | 10 ng of plasmid pAM404 | AM-288-90-CPK1618 (SEQ ID NO: 83) | AM-288-90-CPK1619 (SEQ ID NO: 84) | FS_Aa_Sc |
| | | AM-288-90-CPK1639 (SEQ ID NO: 85) | AM-288-90-CPK1621 (SEQ ID NO: 75) | CYC1$^{+331\ to\ +521}$ |
| | 10 ng of plasmid pRS415 (Sikorski, et al, 1989) | AM-288-90-CPK1614 (SEQ ID NO: 87) | AM-288-90-CPK1617 (SEQ ID NO: 88) | LEU2$^{-661\ to\ +1541}$ |

TABLE 9-continued

PCR reactions performed to generate Construct A

| PCR Round | Template | Primer 1 | Primer 2 | PCR Product |
|---|---|---|---|---|
| 2 | 25 ng of CYC1$^{+331\ to\ +521}$ and equimolar amounts of each of NDT80$^{-175\ to\ -952}$, LEU2$^{-661\ to\ +1541}$, GAL1$^{-1\ to\ -667}$, FS_Aa_Sc, and NDT80$^{+1685\ to\ +2471}$ gel purified PCR products | PW-091-144-CPK640 (SEQ ID NO: 77) | PW-091-144-CPK649 (SEQ ID NO: 80) | Construct A |

PCR amplifications were done using the Phusion High Fidelity DNA Polymerase System (Finnzyme, Inc., Espoo, Finland). PCR products were gel purified using the E.Z.N.A. ® Gel Extraction Kit (Omega Bio-Tek Inc., Norcross, GA) according to manufacturer's suggested protocols.

Construct B (FIG. 1X) was generated by PCR amplification. The construct comprises the upstream region of the NDT80 gene of *Saccharomyces cerevisiae* (NDT80 nucleotide positions −175 to −952), the LEU2 marker of *Saccharomyces cerevisiae* (LEU2 nucleotide positions −661 to +1541), the promoter of the GAL1 gene of *Saccharomyces cerevisiae* (GAL1 nucleotide positions −1 to −667), the HISG marker, the terminator of the CYC1 gene of *Saccharomyces cerevisiae* (CYC1 nucleotide positions +331 to +521), and the downstream region of the NDT80 gene of *Saccharomyces cerevisiae* (NDT80 nucleotide positions +1685 to +2471).

Construct D was generated by PCR amplification as described in Table 10. The construct comprises the FS_A_5.3 coding sequence flanked by the promoter of the GAL1 gene of *Saccharomyces cerevisiae* (PGAL1; GAL1 nucleotide positions −1 to −455) and the terminator of the PGK1 gene of *Saccharomyces cerevisiae* (TPGK1; PGK1 nucleotide positions +1159 to +1547), and the TDS_Fs_Sc coding sequence flanked by the promoter of the GAL10 gene of *Saccharomyces cerevisiae* (PGAL10; GAL10 nucleotide positions −1 to −202) and the terminator of the ADH1 gene of *Saccharomyces cerevisiae* (TADH1; ADH1 nucleotide positions −1 to −166). FIG. 1Z shows a map and SEQ ID NO: 116 the nucleotide sequence of Construct D.

TABLE 10

PCR reactions performed to generate Construct D

| PCR Round | Template | Primer 1 | Primer 2 | PCR Product |
|---|---|---|---|---|
| 1 | 100 ng of Y002 genomic DNA | AM-288-160-CPK2039 (SEQ ID NO: 123) | AM-288-160-CPK1041 (SEQ ID NO: 125) | TPGK1 |
|   | 10 ng of a plasmid comprising the FS_A_5.3 coding sequences | AM-288-160-CPK2040 (SEQ ID NO: 124) | AM-288-110-CPK1903 (SEQ ID NO: 122) | FS_A_5.3 |
|   | 10 ng of plasmid pAM1948 | AM-288-160-CPK2045 (SEQ ID NO: 129) | AM-288-160-CPK2046 (SEQ ID NO: 130) | PGAL10_TDS_TADH1 |
|   | 10 ng of plasmid comprising spacer | AM-288-160-CPK2042 (SEQ ID NO: 126) | AM-288-160-CPK2044 (SEQ ID NO: 128) | spacer |
|   | 10 ng of plasmid pAM404 | AM-288-110-CPK1849 (SEQ ID NO: 121) | AM-288-160-CPK2043 (SEQ ID NO: 127) | PGAL1 |
| 2 | 25 ng of spacer and equimolar amounts of each of PGAL1, FSA_A_5.3, TPGK1, and PGAL10_TDS_TADH1 gel purified PCR products | AM-288-160-CPK2039 (SEQ ID NO: 123) | AM-288-160-CPK2046 (SEQ ID NO: 130) | Construct D |

PCR amplifications were done using the Phusion High Fidelity DNA Polymerase System (Finnzyme, Inc., Espoo, Finland). PCR products were gel purified using the E.Z.N.A. ® Gel Extraction Kit (Omega Bio-Tek Inc., Norcross, GA) according to manufacturer's suggested protocols.

Expression plasmid pAM2191 was created by in transforming exponentially growing Y 3198 cells with 100 ng of vector pAM552 (SEQ ID NO: 156) digested using FastDigest® BstZ17I restriction enzyme (Fisher Scientific Worldwide, Hampton, N.H.) and 300 ng of Construct D. Host cell transformants were plated on CSM-L agar plates with 2% glucose as a sole carbon source, and the plates were incubated for 3 days at 30° C. until individual colonies were ~1 mm in diameter. DNA was harvested from these colonies using the Zymoprep™ Yeast Plasmid Miniprep Kit II (Zymo Research Corporation, Orange, Calif.), and the harvested DNA was transformed into the chemically competent XL1Blue *Escherichia coli* (Agilent Technologies Inc., Santa Clara, Calif.). Host cell transformants were plated to Lysogeny broth agar media supplemented with carbenicillin, and incubated for 24 hours at 37° C. until individual colonies were visible. Plasmid DNA was harvested from these colonies using the QIAprep Spin Miniprep Kit (QIAGEN Inc, Valencia, Calif.), and the plasmid DNA was sequenced to confirm correct creation of expression plasmid pAM2191.

Example 2

This example describes methods for making yeast strains useful in the generation and characterization of terpene synthases variants.

Strains Y93 (MAT A) and Y94 (MAT alpha) were generated by replacing the promoter of the ERG9 gene of yeast strains Y002 and Y003 (CEN.PK2 background MAT A or MAT alpha, respectively; ura3-52; trp1-289; leu2-3,112; his3Δ1; MAL2-8C; SUC2; van Dijken et al. (2000) Enzyme Microb. Technol. 26:706-714), respectively, with the promoter of the MET3 gene of *Saccharomyces cerevisia*. To this end, exponentially growing Y002 and Y003 cells were transformed with integration construct i8 (SEQ ID NO: 87), which comprised the kanamycin resistance marker (KanMX) flanked by the promoter and terminator of the Tef1 gene of *Kluyveromyces lactis*, the ERG9 coding sequence, a truncated segment of the ERG9 promoter (trunc. PERG9), and the MET3 promoter (PMET3), flanked by ERG9 upstream and downstream sequences (FIG. 1A). Host cell transformants were selected on medium comprising 0.5 ug/mL Geneticin (Invitrogen Corp., Carlsbad, Calif.), and selected clones were confirmed by diagnostic PCR, yielding strains Y93 and Y94.

Strains Y176 (MAT A) and Y177 (MAT alpha) were generated by replacing the coding sequence of the ADE1 gene in strains Y93 and Y94, respectively, with the coding sequence of the LEU2 gene of *Candida glabrata* (CgLEU2). To this end, the 3.5 kb CgLEU2 genomic locus was PCR amplified from *Candida glabrata* genomic DNA (ATCC, Manassas, Va.) using primers 61-67-CPK066-G (SEQ ID NO: 88) and 61-67-CPK067-G (SEQ ID NO: 89), and transforming the PCR product into exponentially growing Y93 and Y94 cells. Host cell transformants were selected on CSM-L, and selected clones were confirmed by diagnostic PCR, yielding strains Y176 and Y177.

Strain Y188 was generated by introducing into strain Y176 an additional copy of the coding sequences of the ERG13, ERG10, and ERG12 genes of *Saccharomyces cerevisia*, and a truncated coding sequence of the HMG1 gene of *Saccharomyces cerevisia*, each under regulatory control of a galactose inducible promoter of the GAL1 or GAL10 gene of *Saccharomyces cerevisia*. To this end, exponentially growing Y176 cells were transformed with 2 μg of expression plasmids pAM491 and pAM495 digested with PmeI restriction endonuclease (New England Biolabs, Beverly, Mass.). Host cell transformants were selected on CSM lacking uracil and histidine (CSM-U-H), and selected clones were confirmed by diagnostic PCR, yielding strain Y188.

Strain Y189 was generated by introducing into strain Y177 an additional copy of the coding sequences of the ERG20, ERGS, and ERG19 genes of *Saccharomyces cerevisia*, and a truncated coding sequence of the HMG1 gene of *Saccharomyces cerevisia*, each under regulatory control of a galactose inducible promoter of the GAL1 or GAL10 gene of *Saccharomyces cerevisia*. To this end, exponentially growing Y188 cells were transformed with 2 ug of expression plasmids pAM489 and pAM497 digested with PmeI restriction endonuclease. Host cell transformants were selected on CSM lacking tryptophan and histidine (CSM-T-H), and selected clones were confirmed by diagnostic PCR, yielding strain Y189.

Strain Y238 was generated by mating strains Y188 and Y189, and by introducing an additional copy of the coding sequence of the IDI1 gene of *Saccharomyces cerevisia* and a truncated coding sequence of the HMG1 gene of *Saccharomyces cerevisia*, each under regulatory control of a galactose inducible promoter of the GAL1 or GAL10 gene of *Saccharomyces cerevisia*. To this end, approximately $1 \times 10^7$ cells of strains Y188 and Y189 were mixed on a YPD medium plate for 6 hours at room temperature, diploid cells were selected on CSM-H-U-T, and exponentially growing diploids were transformed with 2 ug of expression plasmid pAM493 digested with PmeI restriction endonuclease. Host cell transformants were selected on CSM lacking adenine (CSM-A), and selected clones were confirmed by diagnostic PCR, yielding strain Y238.

Strains Y210 (MAT A) and Y211 (MAT alpha) were generated by sporulating strain Y238. The diploid cells were sporulated in 2% potassium acetate and 0.02% raffinose liquid medium, and approximately 200 genetic tetrads were isolated using a Singer Instruments MSM300 series micromanipulator (Singer Instrument Co, LTD. Somerset, UK). Spores were selected on CSM-A-H-U-T, and selected clones were confirmed by diagnostic PCR, yielding strains Y210 (MAT A) and Y211 (MAT alpha).

Strain Y221 was generated by transforming exponentially growing Y211 cells with vector pAM178. Host cell transformants were selected on CSM-L.

Strain Y290 was generated by deleting the coding sequence of the GAL80 gene of strain Y221. To this end, exponentially growing Y221 cells were transformed with integration construct i32 (SEQ ID NO: 90), which comprised the hygromycin B resistance marker (hph) flanked by the promoter and terminator of the Tef1 gene of *Kluyveromyces lactis* flanked by GAL80 upstream and downstream sequences (FIG. 1B). Host cell transformants were selected on medium comprising hygromycin B, and selected clones were confirmed by diagnostic PCR, yielding strain Y290.

Strain Y318 was generated by removing the pAM178 vector from strain Y290 by serial propagation in leucine-rich media, and testing individual colonies for their inability to grow on CSM-L, yielding strain Y318.

Strain Y409 was generated by introducing a heterologous nucleotide sequence encoding a β-farnesene synthase into strain Y318. To this end, exponentially growing Y318 cells were transformed with expression plasmid pAM404. Host cell transformants were selected on CSM-L, yielding strain Y409.

Strain Y419 was generated by rendering the GAL promoters of strain Y409 constitutively active. To this end, exponentially growing Y409 cells were transformed with integration construct i33 (SEQ ID NO: 91), which comprised the nourseothricin resistance marker of *Streptomyces* noursei (NatR) flanked by the promoter and terminator of the Tef1 gene of *Kluyveromyces lactis*, and the coding sequence of the GAL4 gene of *Saccharomyces cerevisiae* under regulatory control of an "operative constitutive" version of its native promoter (PGAL4oc; Griggs & Johnston (1991) *PNAS* 88(19):8597-8601) and the GAL4 terminator (TGAL4) (FIG. 1C), flanked by upstream and downstream sequences of the modified ERG9 promoter and coding sequences. Host cell transformants were selected on medium comprising nourseothricin, and selected clones were confirmed by diagnostic PCR, yielding strain Y419.

Strain Y677 was generated by introducing at the modified GAL80 locus of strain Y419 an additional copy of the coding region of the ERG12 gene of *Saccharomyces cerevisiae* under regulatory control of the promoter of the GAL1 gene of *Saccharomyces cerevisiae*. To this end, exponentially growing Y677 cells were transformed with integration construct i37 (SEQ ID NO: 92), which comprised the kanamycin resistance marker of *Streptomyces* noursei (KanR) flanked by the promoter and terminator of the Tef1 gene of *Kluyveromyces lactis*, and the coding and terminator sequences of the ERG12 gene of *Saccharomyces cerevisiae* flanked by the GAL1 promoter (PGAL1) and the ERG12 terminator (TERG12) (FIG. 1D). Host cell transformants were selected on medium comprising kanamycin, and selected clones were confirmed by diagnostic PCR, yielding strain Y677.

Strain Y1551 was generated from strain Y677 by chemical mutagenesis. Mutated strains were screened for increased production of β-farnesene, yielding strain Y1551.

Strain Y1778 was generated from strain Y1551 by chemical mutagenesis. Mutated strains were screened for increased production of β-farnesene, yielding strain Y1778.

Strain Y1816 was generated by replacing the HXT3 coding sequence of strain Y1778 with two copies of an acetoacetyl-CoA thiolase coding sequence, one being derived from *Saccharomyces cerevisiae* and the other from *C. butylicum*, and one copy of the coding sequence of the HMGS gene of *B. juncea*. To this end, exponentially growing Y1778 cells were transformed with integration construct i301 (SEQ ID NO: 93), which comprised the hygromycin B resistance marker (hyg) flanked by the promoter and terminator of the Tef1 gene of *Kluyveromyces lactis*, the coding sequence of the ERG10 gene of *Saccharomyces cerevisiae* flanked by a truncated TDH3 promoter (tPTDH3) and the AHP1 terminator (TAHP1), the coding sequence of the acetoacetyl-CoA thiolase gene of *C. butylicum* (thiolase) flanked by the YPD1 promoter (PYPD1) and CCW12 terminator (TCCW12), and the coding sequence of the HMGS gene of *B. juncea* (HMGS) preceded by the TUB2 promoter (PTUB2), flanked by upstream and downstream sequences of the HXT3 gene of *Saccharomyces cerevisiae* (FIG. 1E). Host cell transformants were selected on medium comprising hygromycin B, and selected clones were confirmed by diagnostic PCR, yielding strain Y1816.

Strain Y2055 was generated from strain Y1778 by chemical mutagenesis. Mutant strains were screened for increased production of β-farnesene, yielding strain Y2055.

Strain Y2295 was generated from strain Y2055 by chemical mutagenesis. Mutant strains were screened for increased production of β-farnesene, yielding strain Y2295.

Figure 1F:
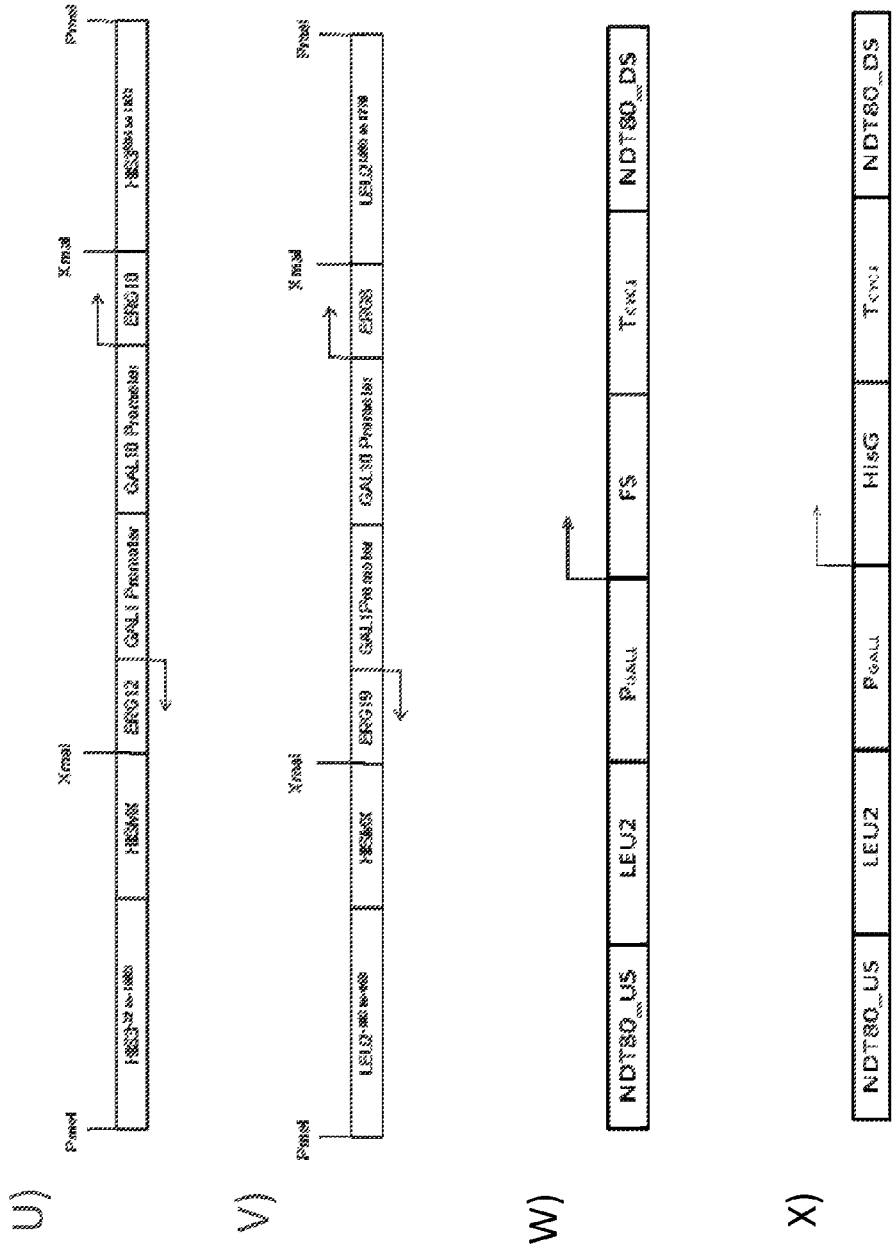

Strain Y3111 was generated by switching the mating type of strain Y2295 from MAT A to MAT alpha. To this end, exponentially growing Y2295 cells were transformed with integration construct i476 (SEQ ID NO: 94), which comprised the MAT alpha mating locus and the hygromycin B resistance marker (hygA) (FIG. 1F). Host cell transformants were selected on medium comprising hygromycin B, and selected clones were confirmed by diagnostic PCR, yielding strain Y3111.

Strain Y2168 was generated from strain Y1816 by chemical mutagenesis. Mutant strains were screened for increased production of β-farnesene, yielding strain Y2168.

Strain Y2446 was generated from strain Y2168 by chemical mutagenesis. Mutant strains were screened for increased production of β-farnesene, yielding strain Y2446.

Figure 1G:
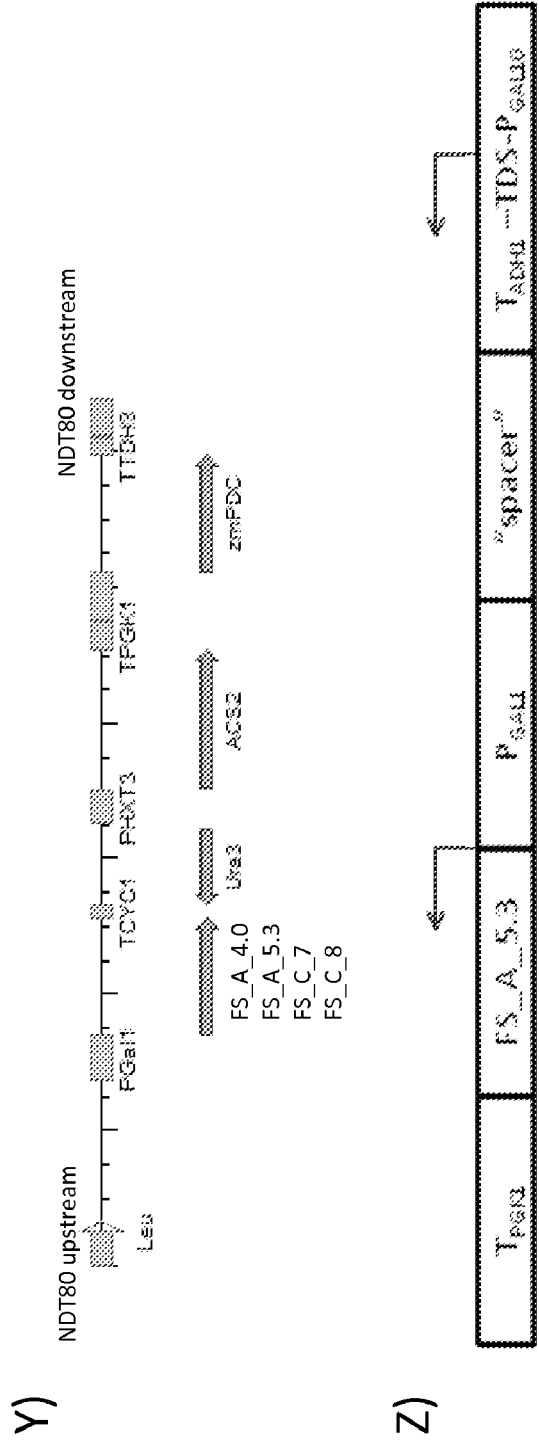

Strain Y3118 was generated by inserting into the native URA3 locus of strain Y2446 the coding sequence, promoter, and terminator of the GAL80 gene of *Saccharomyces cerevisiae*. To this end, exponentially growing Y2446 cells were transformed with integration construct i477 (SEQ ID NO: 95), which comprised the promoter, terminator, and coding sequence of the GAL80 gene of *Saccharomyces cerevisiae* (GAL80) flanked by overlapping URA3 sequences (which enable loop-out excision of the GAL80 gene by homologous recombination and restoration of the original URA3 sequence) (FIG. 1G). Host cell transformants were selected on medium comprising 5-FOA, yielding strain Y3118.

Strain Y3125 was generated from strain Y3118 by removing expression plasmid pAM404. To this end, strain Y3118 was first incubated in 3 mL YPD+0.5% leucine medium with 40 mg/L uracil (YPD+L+U). Cells were diluted by 100-fold in fresh YPD+L+U every 24 hours for up to 5 days to lose expression plasmid pAM404, and were then plated on YPD and incubated at 30° C. for up to 5 days. Small colonies were replica-plated on both YPD and CSM-L, and colonies that could grow on YPD but failed to grow on CSM-L were identified, yielding strain Y3125.

The strains shown in Table 11 were generated by transforming exponentially growing Y3125 cells with the indicated expression plasmids comprising the indicated coding sequences, and selecting host cell transformants on CSM-L.

TABLE 11

| FS and TDS expressing yeast strains | | |
|---|---|---|
| Strain | Plasmid | Coding sequence (promoter) |
| Y3353 | pAM1812 | FS_Aa_Sc ($P_{GAL1}$) |
| | | TDS_Fs_Sc ($P_{GAL10}$) |
| Y3354 | pAM1813 | FS_Aa_Sc ($P_{GAL10}$) |
| | | TDS_Fs_Sc ($P_{GAL1}$) |
| Y3394 | pAM1895 | FS_S2D_Ec ($P_{GAL1}$) |
| | | TDS_Fs_Sc ($P_{GAL10}$) |
| Y3395 | pAM1896 | FS_Ad_Sc ($P_{GAL1}$) |
| | | TDS_Fs_Sc ($P_{GAL10}$) |

Strain Y227 was generated by transforming strain Y211 with expression plasmid pAM426. Host cell transformants were selected on CSM-L.

Strain Y3198 was generated by removing expression plasmid pAM426 from strain Y227. To this end, Y227 cells were propagated in YPD+L for 4 days. Every 24 hours, the culture was inoculated to an OD600 of 0.05 in fresh YPD+L. After 4 days, cells were serial diluted and plated onto YPD solid agar, and the plates were incubated at 30° C. for 4 days. Smaller colonies were replica-plated on both YPD and CSM-L, and colonies that could grow on YPD but failed to grow on CSM-L were identified, yielding strain Y3198.

Strain Y3215 was generated by mating strains Y3111 and Y3118. Approximately $1 \times 10^7$ cells of strains Y3111 and Y3118 were mixed on a YPD medium plate for 6 hours at room temperature to allow for mating, followed by plating on YPD agar plate to isolate single colonies. Diploids were identified by screening by colony PCR for the presence of both the hphA-marked MAT alpha locus and the wild-type MAT A locus.

Strain Y3000 was generated by sporulating strain Y3215 and looping out the GAL80 coding sequence. The diploid cells were sporulated in 2% potassium acetate and 0.02% raffinose liquid medium. Random spores were isolated, plated on YPD agar, grown for 3 days, and then replica-plated to CSM-U to permit growth only of cells lacking GAL80 (i.e., having a functional URA3 gene). Spores were then tested for β-farnesene production, the best producer was identified, and the presence of integration construct i301 was confirmed by diagnostic PCR, yielding strain Y3000.

Strain Y3284 was generated by removing the URA3 marker from strain Y3000. To this end, exponentially growing Y3000 cells were transformed with integration construct i94 (SEQ ID NO: 96), which comprised the hisG coding sequence of Salmonella, and the coding sequence of the ERG13 gene and a truncated coding sequence of the HMG1 gene of Saccharomyces cerevisiae under control of a galactose inducible promoter of the GAL1 or GAL10 gene of Saccharomyces cerevisiae, flanked by upstream and downstream sequences of the URA3 gene of Saccharomyces cerevisiae (FIG. 1H). Host cell transformants were selected on medium comprising 5-FOA, and selected clones were confirmed by diagnostic PCR, yielding strain Y3284.

Strain Y3385 was generated by replacing the NDT80 coding sequence of strain Y3284 with an additional copy of the coding sequence of an acetyl-CoA synthetase gene of Saccharomyces cerevisiae and the coding sequence of the PDC gene of Z. mobilis. To this end, exponentially growing Y3385 cells were transformed with integration construct i467 (SEQ ID NO: 97), which comprised the URA3 marker, the coding sequence of the ACS2 gene of Saccharomyces cerevisiae (ACS2) flanked by the HXT3 promoter (PHXT3) and PGK1 terminator (TPGK1), and the coding sequence of the PDC gene of Z. mobilis (zmPDC) flanked by the GAL7 promoter (PGAL7) and the TDH3 terminator (TTDH3), flanked by upstream and downstream NDT80 sequences (FIG. 1I). Host cell transformants were selected on CSM-U, and selected clones were confirmed by diagnostic PCR, yielding strain Y3385.

Strain Y3547 was generated from strain Y3385 by chemical mutagenesis. Mutated strains were screened for increased production of β-farnesene, yielding strain Y3547.

Strain Y3639 was generated from strain Y3547 by chemical mutagenesis. Mutated strains were screened for increased production of β-farnesene, yielding strain Y3639.

Strain Y3902 was generated by disrupting the URA3 marker at the NDT80 locus of strain Y3639 with an integration of the coding sequence, promoter, and terminator of the GAL80 gene of Saccharomyces cerevisiae. In this instance, a mutant allele of GAL80 called GAL80$^{s-2}$ was used (Nucleic Acids Research (1984) 12(24):9287-9298). Exponentially growing Y3639 cells were transformed with integration construct i601 (SEQ ID NO: 98), which comprised the promoter, terminator, and coding sequence of the GAL80 gene of Saccharomyces cerevisiae (PGAL80, TGAL80, and GAL80, respectively) flanked by overlapping URA3 sequences (which enable loop-out excision of the GAL80 gene by homologous recombination and restoration of the original URA3 sequence), the coding sequences of the ACS2 gene of Saccharomyces cerevisiae (ACS2) flanked by the HXT3 promoter (PHXT3) and the PGK1 terminator (TPGK1), and the PDC coding sequence of Z. mobilis (zmPDC) flanked by the GAL7 promoter (PGAL7) and the TDH3 terminator (TTDH3), flanked by upstream and downstream NDT80 sequences (FIG. 1J). Host cell transformants were selected on medium comprising 5-FOA, and selected clones were confirmed by diagnostic PCR, yielding strain Y3902.

Strain Y4027 was generated from strain Y3902 by removing expression plasmid pAM404 by serial propagation in leucine-rich media, and testing individual colonies for their inability to grow on medium lacking leucine.

Strain Y4909 was generated by replacing the ADH5 coding sequence of strain Y4027 with the FS_D_3.5 coding sequence and the FS_C_7 coding sequence (see Table 17). To this end, exponentially growing Y4909 cells were transformed with integration construct i2125 (SEQ ID NO: 99), which comprised the LEU2 coding sequence (LEU2) and the farnesene synthase variant coding sequences flanked by GAL1 or GAL10 promoter (PGAL1 or PGAL10) and the CYC1 or ADH1 terminator (TCYC1 or TADH1), respectively, flanked by upstream and downstream ADH5 sequences (FIG. 1K). Host cell transformants were selected on CSM-L, and selected clones were confirmed by diagnostic PCR, yielding strain Y4909.

Strain Y4959 was generated by removing from strain Y4909 the coding sequence, promoter, and terminator of the GAL80 gene of Saccharomyces cerevisiae. To this end, Y4909 cells were plated on CSM-U to select for spontaneous GAL80 "loop-out" recombination events, yielding strain Y4959.

Strain Y5444 was generated by inserting at the CANT locus of strain Y4959 the TDS_Fs_Sc coding sequence. To this end, exponentially growing Y4959 cells were transformed with integration construct i2608 (SEQ ID NO: 100), which comprised the TDS_Fs_Sc coding sequence flanked by the GAL1 promoter of Saccharomyces cerevisiae (PGAL1) and the CYC1 terminator of Saccharomyces cerevisiae (TCYC1) (FIG. 1L). Host cell transformants were selected on YNB medium comprising canavanine and lacking arginine, and selected clones were confirmed by diagnostic PCR, yielding strain Y5444.

Strain Y4910 was generated by inserting at the ADH5 locus of Y4027 the FS_A_5.3 coding sequence, the FS_B_5.3 coding sequence, the FS_C_7 coding sequence, and the FS_D_3.5 coding sequence (see Table 17). To this end, exponentially growing Y4909 cells were transformed with integration construct i2127 (SEQ ID NO: 101), which comprised the LEU2 coding sequence (LEU2) and the farnesene synthase variant coding sequences flanked by the GAL1 or GAL 10 promoter (PGAL1 or PGAL10) and the ADH1 or CYC1 terminator (TADH1 or TCYC1), flanked by upstream and downstream ADH5 sequences (FIG. 1M), and which was generated by co-transformation with two overlapping segments of i2127, thereby stimulation homologous recombination between the two overlapping plasmid inserts. Host cell transformants were selected on CSM-L, and selected clones were confirmed by diagnostic PCR, yielding strain Y4910.

Strain Y4960 was generated by removing from strain Y4910 the coding sequence, promoter, and terminator of the GAL80 gene of Saccharomyces cerevisiae. To this end, Y4910 cells were plated on CSM-U to select for spontaneous GAL80 "loop-out" recombination events, yielding strain Y4960.

Strain Y5445 was generated by inserting at the CAN1 locus of strain Y4960 the TDS_Fs_Sc coding sequence. To this end, exponentially growing Y4959 cells were transformed with integration construct i2608 (SEQ ID NO: 100), which comprised the TDS_Fs_Sc coding sequence flanked by the GAL1 promoter of Saccharomyces cerevisiae (PGAL1) and the CYC1 terminator of Saccharomyces cerevisiae (TCYC1) (FIG. 1L). Host cell transformants were selected on YNB medium comprising canavanine and lacking arginine, and selected clones were confirmed by diagnostic PCR, yielding strain Y5445.

Strain Y5064 was generated by removing the URA3 marker from strain Y4960. To this end, exponentially growing Y4960 cells ware transformed with integration construct i569 (SEQ ID NO: 102), which comprised the coding sequence of the ACS2 gene of *Saccharomyces cerevisiae* (ACS2) flanked by the HXT3 promoter (PHXT3) and the PGK1 terminator (TPGK1), and the coding sequence of the PDC gene of *Z. mobilis* (zmPDC) flanked by the GAL7 promoter (PGAL7) and the TDH3 terminator (TTDH3), flanked by upstream and downstream NDT80 sequences (FIG. 1N). Host cell transformants were selected based on their ability to grow on medium containing 5-FO, and selected clones were confirmed by diagnostic PCR, yielding strain Y5064.

Strain Y5065 was generated by inserting at the BIO4 locus of strain Y5064 the FS_A_5.3 coding sequence and the FS_B_5.3 coding sequence (see Table 17). To this end, exponentially growing Y5064 cells were transformed with integration construct i2124 (SEQ ID NO: 103), which comprised the URA3 coding sequence (URA3), and the farnesene synthase variant coding sequences flanked by the GAL1 or GAL10 promoter (PGAL1 or PGAL10) and ADH1 or CYC1 terminator (TADH1 or TCYC1), flanked by upstream and downstream BIO4 sequences (FIG. 1O). Host cell transformants were selected CSM-U, and selected clones were confirmed by diagnostic PCR, yielding strain Y5065.

Strain Y5066 was generated by inserting at the BIO4 locus of strain Y5064 the FS_A_5.3 coding sequence, the FS_B_5.3 coding sequence, the FS_C_7 coding sequence, and the FS_D_3.5 coding sequence (see Table 17). To this end, exponentially growing Y5064 cells were transformed with integration construct i2127 (SEQ ID NO: 101), which comprised the LEU2 coding sequence (LEU2) and the farnesene synthase variant coding sequences flanked by the GAL1 or GAL10 promoter (PGAL1 or PGAL10) and the ADH1 or CYC1 terminator (TADH1 or TCYC1), flanked by upstream and downstream ADH5 sequences (FIG. 1M), and which was generated by co-transformation with two overlapping segments of i2127, thereby stimulation homologous recombination between the two overlapping plasmid inserts. Host cell transformants were selected on CSM-L, and selected clones were confirmed by diagnostic PCR, yielding strain Y5066.

Strain Y5446 was generated by inserting at the CAN1 locus of strain Y5065 the TDS_Fs_Sc coding sequence. To this end, exponentially growing Y4959 cells were transformed with integration construct i2608 (SEQ ID NO: 100), which comprised the TDS_Fs_Sc coding sequence flanked by the promoter of the GAL1 gene of *Saccharomyces cerevisiae* (PGAL1) and the terminator of the CYC1 gene of *Saccharomyces cerevisiae* (TCYC1) (FIG. 1L). Host cell transformants were selected on YNB medium comprising canavanine and lacking arginine, and selected clones were confirmed by diagnostic PCR, yielding strain Y5446.

Strain Y5447 was generated by inserting at the CAN1 locus of strain Y5066 the TDS_Fs_Sc coding sequence. To this end, exponentially growing Y4959 cells were transformed with integration construct i2608 (SEQ ID NO: 100), which comprised the TDS_Fs_Sc coding sequence flanked by the GAL1 promoter of *Saccharomyces cerevisiae* (PGAL1) and the CYC1 terminator of *Saccharomyces cerevisiae* (TCYC1) (FIG. 1L). Host cell transformants were selected on YNB medium comprising canavanine and lacking arginine, and selected clones were confirmed by diagnostic PCR, yielding strain Y5447.

Strain Y224 was generated by introducing into strain Y211 an expression plasmid encoding an amorphadeine synthase (ADS), a cytochrome P450 monooxygenase (AMO, CYP71AV1), and a NADP-cytochrome P450 oxidoreductase (CPR). To this end, exponentially growing Y211 cells were transformed with expression plasmid pAM322, which comprised the coding sequence of the ADS gene of *Artemisia annua* (ADS), the coding sequence of the AMO gene of *Artemisia annua*, and the coding sequence of the CPR gene of *Artemisia annua*, all codon-optimized for expression in *Saccharomyces cerevisiae* and under regulatory control of the promoter of the GAL1 or GAL 10 gene of *Saccharomyces cerevisiae*. Host cell transformants were selected CSM-L, yielding strain Y224.

Strain Y284 was generated by replacing the divergent promoter of the GAL1 and GAL10 genes and the GAL1 coding sequence of strain Y224 with the hygromycin B resistance marker (hphA). To this end, exponentially growing Y224 cells were transformed with integration construct i65 (SEQ ID NO: 104; FIG. 1P). Host cell transformants were selected based on their resistance to hygromycin B, and selected clones were confirmed by diagnostic PCR, yielding strain Y284.

Strain Y301 was generated by putting the ERG9 gene of strain Y284 under regulatory control of the promoter of the CTR3 gene of *Saccharomyces cerevisiae*. To this end, exponentially growing Y284 cells were transformed with integration construct i10 (SEQ ID NO: 105), which comprised the coding sequence of a D-serine deaminase (dsdA) and the CTR3 promoter (PCTR3), flanked by upstream and coding sequences of the ERG9 gene (FIG. 1Q). Host cell transformants were selected based on their ability to grow on D-serine deaminase, and selected clones were confirmed by diagnostic PCR, yielding strain Y301.

Strain Y539 was generated from strain Y301 by removing expression plasmid pAM322. To this end, strain Y301 was propagated in rich Yeast Peptone Dextrose (YPD) medium containing 0.5% leucine (w/v) for 4 days. Every 24 hours, the culture was inoculated to an OD600 of 0.05 in fresh YPD containing 0.5% leucine (w/v). After 4 days, cells were serial diluted and plated onto YPD solid agar, and the plates were incubated at 30° C. for 4 days. Two distinct colony sizes were observed. Smaller colonies (indicating a loss of pAM322) were replica plated onto minimal medium lacking leucine. A clone that was able to grow on YPD solid agar but was unable to grow on medium lacking leucine was selected as strain Y539.

Example 3

This example demonstrates the feasibility of using FPP starvation based selection in *Escherichia coli* to screen for terpene synthases with improved in vivo performance.

DH5α chemical- or electro-competent *Escherichia coli* cells (Invitrogen, Carlsbad, Calif.) were transformed with 5 ng of an expression plasmid selected from the group consisting of expression plasmids pAM1668 (negative control), pAM1670, pAM2096, pAM2097, pAM2098, pAM2101, and pAM2104. Host cell transformants were plated on agar plates comprising carbenicillin, and the plates were incubated at 30° C. for 2-3 days.

As shown in FIG. 2, cells transformed with expression plasmid pAM2097 or pAM2096 produced colonies of similar size as cells transformed with empty vector (pAM1668). However, cells transformed with expression plasmid pAM1670, pAM2098, as well as cells transformed with expression plasmids pAM2104 or pAM2101 (data not shown), produced colonies that were smaller than those produced by the control. The smaller colony sizes were likely due to FPP starvation triggered by the conversion in the host cells of FPP into farnesene mediated by the expression of an active sesquiterpene synthase. The in vivo activities of these sesquiterpene synthases were confirmed by GC analysis of host cells at 72 hours in shake flasks (FIG. 4), showing that FPP starvation based selection in *Escherichia coli* can be used to screen sesquiterpene synthases for in vivo enzyme activity.

Example 4

This example demonstrates the feasibility of using FPP toxicity based growth selection in *Escherichia coli* to screen for sesquiterpene synthases with improved in vivo performance.

DH5α chemical- or electro-competent *Escherichia coli* cells (Invitrogen, Carlsbad, Calif.) were co-transformed with 5 ng of expression plasmid pAM765 (encodes enzymes of the MEV pathway that collectively increase production of FPP in the host cells) and 5 ng of an expression plasmid selected from the group consisting of expression plasmids pAM1668 (negative control), pAM1670, pAM2117, pAM2157, pAM2158, pAM2098, pAM2104, pAM2097, pAM2101, and pAM2096. Host cell transformants were plated on agar plates comprising chloramphenicol and carbenicillin, and the plates were incubated at 30° C. for 2-5 days.

As shown in FIG. 3 and Table 12, cells transformed with empty vector (pAM1668) produced no colonies, likely due to cell death triggered by the accumulation of toxic FPP in the host cells (Withers at al. (2007) *Appl. Environ. Microbiol.* 73:6277-6283). Similarly, cells transformed with expression plasmid pAM2158 or pAM2117 did not form colonies, likely due to the fact that the farnesene synthase coding sequences of these plasmids were not codon-optimized for efficient expression in the *Escherichia coli* host cells. Cells transformed with expression plasmids pAM2096 also did not form colonies, suggesting that the *Citrus junos* farnesene synthase does not possess sufficient activity in *Escherichia coli* host cells. All other transformed cells produced colonies within 1-3 days of culture, presumably due to the conversion of FPP into less toxic sesquiterpenes by the active sesquiterpene synthases encoded by expression plasmids pAM1670, pAM2157, pAM2098, pAM2104, pAM2097, and pAM2101. The in vivo activities of several of these sesquiterpene synthases were confirmed by GC analysis of host cells at 72 hours in shake flasks (FIG. 4), showing that FPP toxicity based growth selection in *Escherichia coli* can be used to screen sesquiterpene synthases for in vivo enzyme activity.

TABLE 12

Growth of *Escherichia coli* Cells Transformed with Plasmids Comprising Various Sesquiterpene Synthase Coding Sequences

| Plasmid | FS coding sequences | Colonies | Incubation Time Until Colonies |
|---|---|---|---|
| pAM1668 | None | None | n/a |
| pAM2096 | FS_Cj_Ec | None | n/a |
| pAM2158 | FS_S2D_Sc | None | n/a |
| pAM2117 | FS_Aa_Sc | None | n/a |
| pAM2104 | TDS_Fs_Ec | Yes | 1 day |
| pAM2101 | PS_S_Ec | Yes | 1 day |
| pAM1670 | FS_S2D_Ec | Yes | 1-2 days |
| pAM2157 | FS_Aa_Ec | Yes | >3 days |
| pAM2098 | FS_Pt_Ec | Yes | >3 days |
| pAM2097 | FS_Cs_Ec | Yes | >3 days |

Example 5

This example demonstrates the feasibility of using FPP toxicity based growth selection in yeast to screen for sesquiterpene synthases with improved in vivo performance.

Strain Y3198 was transformed with 500 ng of Construct A or Construct B, respectively. Host cell transformants were incubated for 6 hours with shaking at 250 rpm in 5 mL YPD medium, and washed twice in 5 mL diH$_2$O. Half of each washed culture was plated to CSM-L agar plates comprising 2% galactose as a sole carbon source (note that growth on galactose induces expression of the MEV pathway enzyme coding sequences engineered into strain Y3198 resulting in increased FPP production in the cells). The remaining half of each washed culture was plated to CSM-L agar plates comprising 2% glucose as a sole carbon source. Plates were incubated for 3 days at 30° C. until individual colonies were approximately 1 mm in diameter.

As shown in FIG. 5, only cells transformed with Construct A were able to grow on CSM-L medium comprising galactose as the sole carbon source, demonstrating the utility of FPP toxicity based growth selection in yeast to screen sesquiterpene synthases for in vivo enzyme activity.

Example 6

This example demonstrates the feasibility of using Nile Red fluorescence to screen for terpene synthases with improved in vivo performance.

To determine relative farnesene titers, 48 colonies of strain Y3198 transformed with Construct A and 48 colonies of strain Y3198 transformed with expression plasmid pAM404 were picked into separate wells of a 96-well plate containing 360 uL of Bird Seed Medium (BSM) with 2% galactose per well (preculture). After 2 days of incubation at 30° C. with 999 rpm agitation, 16 uL of each well was inoculated into a well of a new 96-well plate containing 360 uL of fresh BSM with 2% galactose (production culture). After another 2 days of incubation at 30° C. with 999 rpm agitation, samples were taken for farnesene titer determination by Nile Red fluorescence.

For Nile Red fluorescence analysis, 98 uL of each culture was transferred into a 96-well black polystyrene flat bottom assay plate, and 2 uL of Nile Red (Invitrogen, Carlsbad, Calif.) dissolved at 100 ug/mL in DMSO was added to each well. Fluorescence levels were immediately measured with excitation at 500 nm and emission at 550 nm.

As shown in FIG. 6, the single chromosomally integrated copy of the FS_Aa_Sc coding sequence in strain Y3198 transformed with Construct A produced a Nile Red fluorescence signal that was at 39% of that obtained with strain Y3198 transformed with high-copy expression plasmid pAM404. The approximately 3-fold difference in farnesene titers between the two strains was confirmed by GC analysis (data not shown), demonstrating that there is sufficient difference (delta) in Nile Red fluorescence levels (i.e., farnesene levels) for this system to be a suitable screen for terpene synthases with improved in vivo performance.

Example 7

This example demonstrates the feasibility of using sesquiterpene synthase competition in yeast to rank sesquiterpene synthases according to their in vivo enzyme activity levels.

For each of yeast strains Y3353 and Y3354, eight single colonies of the original transformation of strain Y3125 with expression plasmid pAM1812 or pAM1813, respectively, were incubated in separate wells of a 96-well plate containing 360 uL of Bird Seed Medium (BSM) with 2% sucrose per well (preculture). After 2 days of incubation at 30° C. with 999 rpm agitation, 16 uL of each well was inoculated into a well of a new 96-well plate containing 360 uL of fresh BSM with 4% sucrose (production culture). After another 2 days of incubation at 30° C. with 999 rpm agitation, samples were taken and analyzed for terpene production by gas chromatography (GC) analysis. For each strain, a single colony was also restreaked on CSM-L-M-U agar plates, and eight single colonies from each re-streak were grown as described, and analyzed for terpene production by GC analysis.

For GC analysis, samples were extracted with methanol-heptane (1:1 v/v), and the mixtures were centrifuged to remove cellular material. An aliquot of the methanol-heptane extract was diluted into heptane, and then injected onto a methyl silicone stationary phase using a pulsed split injection. Farnesene and trichodiene were separated by boiling point using GC with flame ionization detection (FID). Trans-β-caryophyllene was used as a retention time marker to monitor successful injection and elution during the specified GC oven profile. The titers of farnesene and trichodiene were used to calculate the farnesene/trichodiene ratios.

As shown in Table 13, terpene titers among independent original transformants varied considerably from well to well, resulting in coefficients of variation (CVs) of up to 29%. CVs were reduced for the eight replicates. The observed CVs show that well-to-well and clone-to-clone variations make it impossible to draw conclusions directly from sesquiterpene titers as to the activities of the sequiterpene synthases that produced the sesquiterpenes. However, as also shown in Table 13, farnesene/trichodiene ratios were rather consistent across samples, producing CVs of no more than 5.7%. Thus, by co-expressing a test sesquiterpene synthase from the same plasmid as a comparison sesquiterpene synthase, and by comparing the activities of the test and comparison sesequiterpene synthases, well-to-well and clone-to-clone variations were greatly reduced, making it possible to benchmark the in vivo catalytic efficiency of a test sesquiterpene synthase (e.g., a farnesene synthase) against that of a comparison sequiterpene synthase (e.g., a TDS).

TABLE 13

β-Farnesene and Trichodiene Titers and Titer Ratios for Yeast Strains Expressing a FS and a TDS from the Same Plasmid

| Strain | Coding Sequences (promoters) | Farnesene (mg/L) (CV %) | Trichodiene (mg/L) (CV %) | Farnesene/ Trichodiene (CV %) |
|---|---|---|---|---|
| Y3353 | FS_Aa_Sc (P$_{GAL1}$) | 953 (5.6%) | 695 (6.3%) | 1.37 (3.0%) |
| Y3353 restreak | TDS_Fs_Sc (P$_{GAL10}$) | 829 (7.1%) | 613 (8.5%) | 1.36 (5.7%) |
| Y3354 | FS_Aa_Sc (P$_{GAL10}$) | 211 (28.9%) | 1033 (29.3%) | 0.21 (4.3%) |
| Y3354 restreak | TDS_Fs_Sc (P$_{GAL1}$) | 200 (11.2%) | 973 (7.9%) | 0.21 (4.8%) |

To further validate sesquiterpene synthase competition as a ranking tool for sesquiterpene synthase activities in yeast, yeast strains Y3353, Y3394, and Y3395 were evaluated as described. As shown in Table 14, absolute farnesene titers again showed significant variations whereas low CVs were observed for the farnesene/trichodiene ratios. As judged by the observed ratios, the tested farnesene synthases could be ranked as follows (from most active to least active): *Actinidia deliciosa* farnesene synthase expressed from the FS_Ad_Sc coding sequence (Y3395)>*Artemisia annua* farnesene synthase expressed from the FS_Aa_Sc coding sequence (Y3353)>S2D mutant *Artemisia annua* farnesene synthase expressed from the FS_S2D_Ec coding sequence (Y3394). This ranking was confirmed by GC analysis using strains that harbored a single copy of the FS_Aa_Sc, FS_S2D_Ec, or FS_Ad_Sc coding sequence (FIG. 7), thus validating the utility of sesquiterpene synthase competition as a means for ranking sesquiterpene synthases according to their in vivo enzyme activity levels in yeast.

TABLE 14

β-Farnesene and Trichodiene Titers and Titer Ratios for Yeast Strains Expressing a FS and a TDS from the Same Plasmid

| Strain | Coding Sequences (promoters) | Farnesene (mg/L) (CV %) | Trichodiene (mg/L) (CV %) | Farnesene/ Trichodiene (CV %) |
|---|---|---|---|---|
| Y3395 | FS_Ad_Sc (P$_{GAL1}$) | 752 | 453 | 1.66 |
|  | TDS_Fs_Sc (P$_{GAL10}$) | (28.3%) | (28.5%) | (3.0%) |
| Y3353 | FS_Aa_Sc (P$_{GAL1}$) | 814 | 616 | 1.32 |
|  | TDS_Fs_Sc (P$_{GAL10}$) | (6.0%) | (5.0%) | (2.6%) |
| Y3394 * | FS_S2D_Ec (P$_{GAL1}$) | 590 | 710 | 0.82 |
|  | TDS_Fs_Sc (P$_{GAL10}$) | (21.5%) | (19.7%) | (6.2%) |

* The S2D mutant *Artemisia annua* farnesene synthase expressed from the FS_S2D_Ec coding sequence was least active likely due to sub-optimal codon usage for the FS_S2D_Ec coding sequence in the yeast host cells.

To yet further validate sesquiterpene synthase competition as a ranking tool for sesquiterpene synthase activities in yeast, yeast strains Y5444, Y5445, Y5446, and Y5447 were evaluated as described with the following exceptions: for each strain four colonies instead of eight colonies were analyzed, cultures were incubated not at 30° C. but at 34° C., the preculture lasted not 2 days but 3 days, and the production culture was a 10-fold dilution of the preculture. As shown in Table 15 and FIG. 8, a linear relationship was observed between the number of integrated farnesene synthase coding sequences and farnesene to trichodiene ratios, confirming the utility of sesquiterpene synthase competition as a means for ranking sesquiterpene synthases according to their in vivo enzyme activity levels in yeast.

TABLE 15

β-Farnesene and Trichodiene Titers and Titer Ratios for Yeast Strains Expressing One Integrated Copy of TDS and Multiple Integrated Copies of FS Coding Sequences

| Strain | Copies of Integrated FS_Aa_Sc Coding Sequence | Farnesene (mg/L) | Trichodiene (mg/L) | Farnesene/ Trichodiene |
|---|---|---|---|---|
| Y5444 | 2 [a] | 2300 ± 62 | 811 ± 20 | 2.8 ± 0.038 |
| Y5445 | 4 [b] | 2721 ± 109 | 516 ± 19 | 5.3 ± 0.057 |
| Y5446 | 6 [c] | 2761 ± 129 | 387 ± 22 | 7.1 ± 0.089 |
| Y5447 | 8 [d] | 2822 ± 53 | 306 ± 9 | 9.2 ± 0.114 |

[a] PGAL1_FS_C_7_TADH1 and pGAL10_FS_D_3.5_TCYC1 integrated at ADH5 locus
[b] = [a] plus pGAL1_FS_B_5.3_TADH1 and pGAL10_FS_A_5.3_TCYC1 integrated at ADH5 locus
[c] = [b] plus pGAL1_FS_B_5.3_TADH1 and pGAL10_FS_A_5.3_TCYC1 integrated at BIO4 locus
[d] = [c] plus pGAL1_FS_C_7_TADH1 and pGAL10_FS_D_3.5_TCYC1 integrated at BIO4 locus Example 8

This example describes methods for generating libraries of sesquiterpene synthases variants.

Several farnesene synthase variant libraries were generated using the FS_S2D_Ec coding sequence as a template. For each library, 250-500 ng of pAM1670 were subjected to error-prone PCR using the GeneMorph® II Random Mutagenesis Kit (Agilent Technologies, Inc., Santa Clara, Calif.) according to manufacturer suggested protocols, and using primers LX-268-139-S2D-F (SEQ ID NO: 106) and LX-268-139-S2D-R (SEQ ID NO: 107) in 25 amplication cycles. The PCR products were gel purified and digested sequentially with FastDigest® NdeI and BamHI restriction endonucleases (Fermentas Inc., Burlington, Ontario). Vector pAM1668 was digested to completion using the same two restriction endonucleases, and the linearized vector DNA fragment was treated with calf intestine alkaline phosphatase (CIP) to remove 5' phosphate groups that would permit recircularization. The purified PCR products and the linearized pAM1688 vector were ligated in an insert to vector ratio of 3:1 using T4 DNA ligase, and 2 uL of the ligation reaction mixture was transformed into XL1-Blue electro-competent *Escherichia coli* cells (Agilent Technologies Inc., Santa Clara, Calif.) according to manufacturer suggested protocols. Host cell transformants were selected on several LB agar plates (100 mm diameter) comprising carbenicillin. To assess the quality of the random mutagenesis library, 48 or 96 single colonies were picked and grown in LB media comprising carbenicillin, plasmid DNA was isolated from each culture using the QIAprep 96 Turbo Miniprep Kit (Qiagen, Valencia, Calif.), and the plasmid DNA was digested using FastDigest® NdeI and BamHI restriction endonucleases (Fermentas Inc., Burlington, Ontario) to determine that approximately 95% of plasmids contained an insert. The plasmids were also sequenced to determine the mutation frequency, which was found to be an estimated average of 2-6 nucleotide changes per FS coding sequence. The remaining colonies were washed off the agar plates and plasmid DNA was isolated using the QIAprep Spin Miniprep Kit (Qiagen, Valencia, Calif.).

Several farnesene synthase variant libraries were also generated using the FS_Aa_Sc coding sequence as a template. Construct C was essentially identical to Construct A except that prior to final assembly the FS_Aa_Sc PCR product was mutagenized by error-prone PCR using the Mutazyme II® Kit (Agilent Technologies, Inc., Santa Clara, Calif.) and primers AM-288-90-CPK1618 (SEQ ID NO: 83) and AM-288-90-CPK1619 (SEQ ID NO: 84) according to manufacturer suggested protocols. Strain Y3198 was transformed with 500 ng of Construct C, and host cell transformants were recovered for 6 hours with shaking at 250 rpm in 5 mL YPD medium before they were plated out on CSM-L with 2% galactose.

Example 9

This example describes methods for screening libraries of sesquiterpene synthase variants by FPP toxicity based growth selection in *Escherichia coli*.

ElectroMAX DH5α-E *Escherichia coli* cells (Invitrogen, Carlsbad, Calif.) were transformed with 5 ng of expression plasmid pAM765 (encoding enzymes of the MEV pathway) and 5 ng of the FS_S2D_Ec based farnesene synthase variant library plasmids of Example 8. More than 40 co-transformation experiments were performed to generate ~2×10$^5$ host cell transformants. Host cell transformants were plated on LB agar plates (100 mm diameter) comprising carbenicillin and chloramphenicol, and incubated at 30° C. for 2 days, after which approximately 400 large colonies and a similar number of small colonies were visible on the agar plates. No colonies were observed when ElectroMAX DH5α-E *Escherichia coli* cells (Invitrogen, Carlsbad, Calif.) were transformed with 5 ng of expression plasmid pAM765 only were plated on LB agar plates comprising carbenicillin and chloramphenicol. Assuming that these colonies all contained farnesene synthase variants that possessed activity equal or greater than the parent farnesene synthase, the hit rate was estimated to be approximately 1%.

Example 10

This example describes methods for screening libraries of terpene synthase variants using Nile Red fluorescence.

The big colonies obtained in the FPP toxicity based growth selection screen of Example 9 were picked individually into 96-well plates containing 5 uL diH$_2$O per well, and heated at 98° C. for 10 minutes. The generated lysates were transformed into XL1-Blue chemical-competent *Escherichia coli* cells (Agilent Technologies Inc., Santa Clara, Calif.), and host cell transformants were plated on LB agar plates comprising carbenicillin. Note that chloramphenicol was omitted from the selective medium so that expression plasmid pAM765 was lost from the cells. Individual colonies were picked and grown in LB media comprising carbenicillin, and plasmid DNA was isolated using the QIAprep 96 Turbo Miniprep Kit (Qiagen, Valencia, Calif.). After the big colonies had been isolated from the selection plates, the small colonies were washed off the plates and their plasmids were isolated as a mixture in a similar fashion.

XL1-Blue chemical-competent *Escherichia coli* cells (Agilent Technologies Inc., Santa Clara, Calif.) were co-transformed with 5 ng of expression plasmid pAM97 (encoding enzymes of the MEV pathway) and 5 ng of the isolated plasmids (obtained from big colonies) or plasmid mixture (obtained from small colonies). Host cell transformants were plated on LB agar plates containing carbenicillin and chlorophenicol, and incubated at 37° C. for 24 hours. Individual colonies were inoculated into 96-well plates containing M9-Hepes media comprising carbenicillin and chlorophenicol, and the cultures were incubated at 30° C. for 24 hours (pre-culture). Then, 50 uL of each culture was used to inoculate a second culture at an initial OD of 0.05. To induce the expression of the MEV pathway enzymes and farnesene synthase, isopropyl β-D-1-thiogalactopyranoside (IPTG) was added to each culture at 1 mM final concentration. The cultures were incubated for at least 20 hours (production culture) before farnesene titers were determined by Nile Red fluorescence. An *Escherichia coli* strain co-transformed with pAM97 and pAM1419 was used as the negative control, and an *Escherichia coli* strain co-transformed with pAM97 and pAM1421 was used as the positive control. To validate the Nile Red fluorescence analysis, farnesene titers were also determined by GC analysis.

As shown in FIG. 9, measured Nile Red fluorescence signals directly correlated with farnesene titers determined by GC analysis, further validating Nile Red fluorescence as a means of measuring farnesene titers.

The top 70 strains derived from cells transformed with plasmids obtained from large colonies that produced the largest farnesene titers as determined by Nile Red fluorescence and GC analysis were replica-plated into new 96-well plates, and their production levels were re-measured as described. As shown in FIG. 10, approximately 50 of these strains produced higher farnesene titers than the control strain comprising the parent FS_S2D_Ec coding sequence, with the best farnesene synthase variant producing 65% more farnesene than the parent farnesene synthase.

The plasmids extracted from the approximately 400 large colonies were combined in equal molar amounts, the FS coding sequences were PCR amplified using primers LX-268-130-3-S2D-F (SEQ ID NO: 110) and LX-268-130-

4-S2D-R (SEQ ID NO: 109), and the PCR products were gel purified. Vector pAM1734 was linearized using FastDigest® BstI 101 restriction endonuclease (Fermentas Inc., Burlington, Ontario), and the linearized vector was cleaned using the Zymo DNA Clean & Concentrator™ Kit (Zymo Research Corp., Orange, Calif.). The purified vector and PCR products were mixed in a ratio of 1:3 (vector:insert), and transformed into either strain Y539 or strain Y3198 for ligation via homologous recombination. Host cell transformants were plated on CSM-L agar plates with 2% glucose (Y539 host) or 2% galactose (Y3198 host) as the sole carbon source. Approximately 2,500 individual colonies were picked and farnesene titers were determined by Nile Red fluorescence as described (using BSM with 2% glucose for the Y539 host and BSM with 2% galactose for the Y3198 host). Clones that produced a fluorescence signal that was greater than the signal obtained for the parent control (pAM1764 (FS_S2D_Ec on CEN.ARS plasmid) in Y539) by three times the standard deviation were re-plated onto CSM-L agar plates to obtain single colonies, and four colonies of each restreak were re-tested by Nile Red fluorescence and GC analysis. As shown in FIGS. 11A and 11B, a number of cells transformed with farnesene synthase variant produced higher titers of farnesene than the parent control strain, and a few produced even higher titers than strain Y539 transformed with expression plasmid pAM1765 (FS_Aa_Ec on high-copy plasmid).

Example 11

This example describes methods for screening libraries of sesquiterpene synthase variants by FPP toxicity based growth selection in yeast.

The washed transformation of strain Y3198 transformed with Construct C of Example 8 was plated to CSM-L agar plates comprising 2% galactose as a sole carbon source. Plates were incubated for 5 days at 30° C. and the colonies were picked, propagated, and analyzed for farnesene titers by Nile Red fluorescence and GC analysis as described. As shown in FIG. 12, approximately 15% of clones grown on galactose as the sole carbon source had at least 15% higher farnesene titers than the average titer obtained with the parent control (strain Y3198 transformed with Construct A). Clones that had at least 15% higher farnesene titers than the parent control were streaked for individual colonies to CSM-L agar plates comprising 2% glucose. For each clone, eight individual colonies were picked and re-tested by GC analysis as described. Clones that maintained >15% higher average farnesene titer than the control through GC assay were promoted for the sesquiterpene competition assay.

Example 12

This example describes methods for screening sesquiterpene synthase variants by sesquiterpene synthase competition in yeast.

Plasmids were isolated from the top farnesene producing yeast strains of Example 10 using the Zymoprep™ Yeast Plasmid Miniprep Kit (Zymo Research Corp., Orange, Calif.). The plasmids were digested using BamHI and NheI restriction endonucleases, and the farnesene synthase variant coding sequences were gel purified and ligated with expression vector pAM1812 digested with the same two restriction endonucleases, thus replacing the FS_Aa_Sc coding sequence of pAM1812 with the variant FS_S2D_Ec or FS_Aa_Sc coding sequences. The new plasmids were transformed into strain Y3125.

Alternatively, and in addition, farnesene synthase variant coding sequences were PCR amplified from isolated plasmids or from cell lysates of top farnesene producing yeast strains of Example 11 using primers AM-288-90-CPK1618 (SEQ ID NO: 83) and AM-288-90-CPK1619 (SEQ ID NO: 84), the PCR products were gel purified using the E.Z.N.A.® Gel Extraction Kit (Omega Bio-Tek Inc., Norcross, Ga.) according to manufacturer suggested protocols, and ligated with expression plasmid pAM1948 digested with FastDigest BamHI restriction endonuclease (Fermentas Inc., Burlington, Ontario) via homologous recombination by transforming strain Y3125 with both purified DNA fragments, thus replacing the IS_Pn_Sc coding sequence of pAM1948 with the variant FS_S2D_Ec coding sequences.

Host cell transformants were plated to CSM-L agar plates with 2% glucose as a sole carbon source, and then replica-plated to CSM-L-U agar plates at 30° C. for at least 72 hours to loop out the GAL80 coding sequence in the host cell transformants. For each clone, eight colonies were picked, propagated, and their terpene titers were determined by GC analysis as described. Farnesene synthase variants that produced a higher farnesene/trichodiene ratio than the ratio obtained for the parent farnesene synthase (strain Y3125 transformed with pAM1812) were re-streaked to CSM-L agar plates. For each re-streak, eight individual colonies were re-tested in a 96-well plate production experiment as described. A total of 11 yeast strains comprising farnesene synthase variant showed improved farnesene/trichodiene ratios, suggesting that these farnesene synthase variants possessed improved in vivo enzyme activity in yeast.

Example 13

This example describes the characterization of sesquiterpene synthase variants that have improved enzyme activity.

To identify possible causal mutations, the improved farnesene synthase variants identified in Example 12, and in other libraries of farnesene synthase variants generated and screened essentially as described, were sequenced by Elim Biopharmaceuticals, Inc. (Hayward, Calif.). The identified mutations are listed in Table 16. Overall, an estimated total of 300,000 clones were screened and evaluated by FPP toxicity based growth selection in *Escherichia coli* and/or yeast, Nile Red fluorescence and/or GC analysis, and sesquiterpene synthase competition in yeast, leading to the identification of 51 farnesene synthase variants with improved enzyme activity. A number of farnesene synthase variants were identified more than once (number of times are indicated in Table 16 in parenthesis next to the variant names), and certain nucleotide and amino acid changes were found in multiple farnesene synthase variants, suggesting causal relationships between the mutations and the increased enzyme activity. In some farnesene synthase variants only silent mutations were uncovered, suggesting that these mutations likely improved expression of the encoded FS.

TABLE 16

Mutations identified in farnesene synthase variants with improved enzyme activity

| Variant FS | Nucleotide change | Amino acid change | Farnesene/trichodiene ratios over parent FS |
|---|---|---|---|
| 1 | 1343 (A → G) | I434T | 163% |
| 2 | 71 (T → A) | V24D | 150% |
|   | 182 (T → A) | L61Q |   |

TABLE 16-continued

Mutations identified in farnesene synthase variants with improved enzyme activity

| Variant FS | Nucleotide change | Amino acid change | Farnesene/trichodiene ratios over parent FS |
|---|---|---|---|
|  | 271 (C → T) | silent |  |
|  | 955 (A → T) | T319S |  |
| 3 | 71 (T → A) | V24D | 136% |
|  | 587 (C → G) | T196S |  |
|  | 1092 (T → C) | silent |  |
|  | 1267 (G → A) | V423I |  |
|  | 1399 (G → A) | V467I |  |
| 4 | 441 (T → C) | silent | 129% |
|  | 807 (A → G) | silent |  |
|  | 839 (T → A) | L280Q |  |
|  | 1301 (T → C) | I434T |  |
|  | 1599 (G → A) | silent |  |
|  | 1629 (T → C) | silent |  |
| 5 | 343 (A → G) | I115V | 129% |
|  | 587 (C → G) | T196S |  |
|  | 955 (A → T) | T319S |  |
| 6 | 429 (T → C) | silent | 126% |
|  | 751 (C → A) | L251M |  |
|  | 861 (G → T) | silent |  |
|  | 863 (A → T) | Y288F |  |
|  | 921 (A → G) | silent |  |
|  | 957 (C → A) | silent |  |
|  | 1325 (G → A) | G442D |  |
| 7 | 168 (A → T) | silent | 122% |
|  | 215 (A → T) | E72V |  |
|  | 431 (T → A) | F144Y |  |
|  | 1325 (G → C) | G442A |  |
|  | 1378 (A → G) | I460V |  |
| 8 | 32 (T → C) | F11S | 181% |
|  | 225 (T → C) | Silent |  |
|  | 345 (A → G) | I115M |  |
|  | 1715 (T → A) | M572K |  |
| 9 | 32 (T → C) | F11S | 180% |
|  | 1015 (T → C) | Silent |  |
|  | 1605 (A → G) | Silent |  |
| 10 | 598 (T → C) | Silent | 156 |
|  | 631 (T → A) | S211T |  |
|  | 1105 (G → C) | V369L |  |
| 11 (7) | 11 (T → C) | L4S | 154% |
| 12 (2) | 8 (C → A) | T3N | 175% |
| 13 (3) | 8 (C → A) | T3N | 188% |
|  | 870 (T → C) | Silent |  |
| 14 | 867 (A → G) | Silent | 124% |
|  | 1587 (C → A) | Silent |  |
| 15 | 867 (A → G) | Silent | 127% |
|  | 1591 (C → T) | P531S |  |
| 16 | 867 (A → G) | Silent | 116% |
| 17 | 17 (T → C) | I6T | 149% |
| 18 | 315 (A → T) | E105D | 124% |
|  | 867 (A → G) | Silent |  |
| 19 | 1337 (C → A) | T446N | 125% |
| 20 | 1667 (C → T) | A556V | 130% |
| 21 | 238 (A → G) | N80D | 154% |
| 22 | 1056 (A → G) | Silent | 163% |
| 23 | 1098 (A → G) | Silent | 156% |
| 24 | 1111 (T → A) | L371M | 156% |
| 25 | 1542 (C → A) | Silent | 158% |
| 26 | 627 (C → T) | Silent | 129% |
| 27 | 1077 (A → T) | E359T | 128% |
| 28 | 1153 (A → G) | T385A | 132% |
|  | 1463 (C → T) | S488F |  |
| 29 | 104 (T → C) | M35T | 125% |
|  | 1584 (T → C) | Silent |  |
| 30 | 1245 (T → C) | Silent | 137% |
|  | 1299 (G → A) | M433I |  |
|  | 1509 (A → T) | Silent |  |
| 31 | 265 (A → G) | I89V | 127% |
|  | 1192 (T → C) | I398v |  |
|  | 1330 (A → C) | I444L |  |
|  | 1371 (T → C) | silent |  |
|  | 1533 (A → G) | Silent |  |
|  | 1636 (T → C) | Silent |  |
|  | 1701 (T → C) | Silent |  |
| 32 | 519 (A → G) | silent | 120% |
| 33 | 1491 (T → C) | silent | 119% |
| 34 | 1514 (A → T) | E505V | 115% |
| 35 | 1576 (A → T) | T526S | 125% |
| 36 | 59 (T → A) | V20E | 128% |
| 37 (3) | 214 (G → A) | E72K | 128% |
| 38 | 26 (T → A) | V9D | 129% |
|  | 39 (A → G) | silent |  |
|  | 113 (A → G) | N38S |  |
|  | 148 (G → A) | D50N |  |
|  | 549 (T → A) | silent |  |
|  | 1723 (T → A) | stop575K |  |
| 39 | 792 (A → G) | silent | 133% |
| 40 | 1100 (A → T) | E357V | 139% |
|  | 1484 (A → G) | E495G |  |
|  | 1542 (C → T) | silent |  |

Example 14

This example describes methods for combining mutations and screening for improved farnesene synthase variants using sesquiterpene synthase competition in yeast.

Various amino acid changes identified in Example 13 were combined by sequence overlap extension (SOE; Ho, et al, 1989), and the combinations were screened by sequiterpene synthase competition as described to identify FS with increased enzyme activity. As shown in Table 17, several farnesene synthase variants showed substantial improvements in their farnesene/trichodiene ratios over that of the wild-type *A. annua* FS. The increased activity of several of these farnesene synthase variants was further confirmed by GC analysis of yeast strains comprising single chromosomally integrated copies of the farnesene synthase variants coding sequences (FIG. 14).

TABLE 17

Variant FS by combination of mutants

| Variant FS | Parent FS coding sequence | Amino Acid mutations relative to wild type *A. annua* FS | Fold increase in enzyme activity over activity of WT FS as measured by farnesene/trichodiene ratios |
|---|---|---|---|
| G6 | FS_A (SEQ ID NO: 118) | F11S, V24D, I115M, V423I, G442A, I460V, V467I | 3 |
| FS_D_3.5 (SEQ ID NO: 108) | FS_D | F11S, V24D, M35T, T196S, Y288F, T319S, I434T, T446N, I460V, V467I | 3.5 |
| FS_A_4A | FS_A (SEQ ID NO: 118) | F11S, V24D, I115M, S211T, V369L, V423I, I434T, G442A, I460V, V467I | 4 |
| FS_A_4B | FS_A (SEQ ID NO: 118) | F11S, V24D, I115M, T196S, T319S, V423I, I434T, G442A, I460V, V467I | 4 |
| FS_A_4.5 | FS_A (SEQ ID NO: 118) | F11S, V24D, I115M, T196S, Y288F, T319S, V423I, I434T, G442A, I460V, V467I | 4.3 |

TABLE 17-continued

Variant FS by combination of mutants

| Variant FS | Parent FS coding sequence | Amino Acid mutations relative to wild type | Fold increase in enzyme activity over activity of WT FS as measured by farnesene/ trichodiene ratios |
|---|---|---|---|
| FS_A_5.3 | FS_A (SEQ ID NO: 118) | F11S, V24D, M35T, I115M, T196S, Y288F, T319S, I434T, T446N, I460V, V467I | 5.3 |
| FS_B_5.3 | FS_B (SEQ ID NO: 119) | F11S, V24D, M35T, T196S, Y288F, T319S, I434T, T446N, I460V, V467I | 5.3 |
| FS_A_6 | FS_A (SEQ ID NO: 118) | F11S, V20E, V24D, M35T, I115M, T196S, Y288F, T319S, T385A, I434T, T446N, I460V, V467I | 6 |
| FS_C_6 | FS_C (SEQ ID NO: 120) | F11S, V24D, S211T, V369L, V423I, I434T, G442A, I460V, V467I | 6 |
| FS_C_7 | FS_C (SEQ ID NO: 120) | F11S, V24D, M35T, T196S, Y288F, T319S, I434T, T446N, I460V, V467I | 7 |
| FS_C_8 | FS_C (SEQ ID NO: 120) | F11S, V24D, L18I, M35T, T196S, Y288F, T319S, R348K, T385A, I434T, T446N, I460V, V467I | 8 |

Example 15

This example describes methods for expressing and purifying wild-type farnesene synthase and farnesene synthase variant proteins.

*Escherichia coli* Rosetta (DE3) cells were transformed with expression plasmids comprising the FS_Aa_Ec, FS_B_5.3_Ec (FS_B_5.3 codon-optimized for expression in *Escherichia coli*), or FS_C_8 coding sequence cloned into the BamHI and NdeI sites of vector pAM1490 (SEQ ID NO: 117). Expression of FS in 1 L cultures of host cell transformants were induced by adding 0.4 mM IPTG, and each culture was incubated at 20° C. for 20 hours. Cell lysates were loaded onto His GraviTrap columns pre-packed with Ni Sepharose™ 6 Fast Flow resin (GE Healthcare, Piscataway, N.J.). The columns were washed with 10 mL (10 column volumes) Binding Buffer (50 mM Tris-HCl, pH 8.0, 500 mM NaCl, 5 mM imidazole, 5% glycerol, 0.5 mM DTT), and fractions were step-wise eluted using 4 ml Elution Buffer (50 mM Tris-HCl, pH 8.0, 500 mM NaCl, 5% glycerol, 0.5 mM DTT) comprising 50 (Fraction 1), 100 (Fraction 2), or 250 mM (Fraction 3) imidazole. All fractions were dialyzed against Binding Buffer, and Fraction 2 was further dialyzed against Protease Digestion Buffer (20 mM Tris-HCl, pH 7.5, 200 mM NaCl, 5% glycerol, 1 mM DTT) in a dialysis cassette. To remove the His$_6$-tags, 120 U of PreScission Protease (GE Healthcare, Piscataway, N.J.) was added directly to each dialysis cassette, and dialysis was allowed to continue overnight before the protease-digested samples were dialyzed against Storage Buffer (20 mM Tris-HCl, pH 7.5, 200 mM NaCl, 20% glycerol, 1 mM DTT) and were removed from the dialysis cassette. To remove the GST-tagged protease, Glutathione Sepharose 4B beads (GE Healthcare, Piscataway, N.J.) pre-washed with the Storage Buffer were added to the protease-digested samples, and the bead mixtures were incubated for one hour with gentle mixing. The FS proteins were finally recovered by passing the mixtures through a Poly-Prep Chromatography Column (Bio-Rad, Hercules, Calif.), and the purified FS proteins were stored at −80° C.

The isolated farnesene synthase variants were assayed for kinetic properties. As shown in Table 18, the increased in vivo activity of the farnesene synthase variants was reflected in an increased $k_{cat}$ of the isolated farnesene synthase variants.

TABLE 18

Steady-state kinetic parameters of wild-type and farnesene synthase variants

| FS coding sequence | $k_{cat}$ (s$^{-1}$) | Relative $k_{cat}$ | $K_m$ (uM) |
|---|---|---|---|
| FS_Aa_Ec | 0.071 ± 0.004 | 1 | 0.58 ± 0.19 |
| FS_B_5.3_Ec | 0.093 ± 0.009 | 1.31 | 1.18 ± 0.44 |
| FS_C_8 | 0.139 ± 0.012 | 1.96 | 1.55 ± 0.76 |

Example 16

This example describes the use of sesquiterpene synthase competition to select suitable promoters to tune farnesene synthase expression to a level that enables FPP toxicity-based growth selection in yeast.

Various promoters were PCR amplified as described in Table 19.

TABLE 19

Templates and primers used to PCR amplify *S. cerevisiae* promoters

| Promoter of Gene | Template | PCR primer 1 | PCR primer 2 |
|---|---|---|---|
| FBA1 | 100 ng of Y002 genomic DNA | AM-288-160-CPK2063 (SEQ ID NO: 141) | AM-288-160-CPK2064 (SEQ ID NO: 142) |
| TPI1 | | AM-288-160-CPK2061 (SEQ ID NO: 139) | AM-288-160-CPK2062 (SEQ ID NO: 140) |
| HSP12 | | AM-288-160-CPK2065 (SEQ ID NO: 143) | AM-288-160-CPK2066 (SEQ ID NO: 144) |
| PET9 | | AM-288-160-CPK2085 (SEQ ID NO: 151) | AM-288-160-CPK2086 (SEQ ID NO: 152) |
| QCR9 | | AM-288-160-CPK2091 (SEQ ID NO: 114) | AM-288-160-CPK2092 (SEQ ID NO: 115) |
| QCR7 | | AM-288-160-CPK2087 (SEQ ID NO: 153) | AM-288-160-CPK2088 (SEQ ID NO: 154) |
| CDC19 | | AM-288-160-CPK2055 (SEQ ID NO: 135) | AM-288-160-CPK2056 (SEQ ID NO: 136) |
| TEF2 | | AM-288-160-CPK2073 (SEQ ID NO: 147) | AM-288-160-CPK2074 (SEQ ID NO: 148) |
| PGK1 | | AM-288-160-CPK2079 (SEQ ID NO: 149) | AM-288-160-CPK2080 (SEQ ID NO: 150) |
| SIP18 | | AM-288-160-CPK2067 (SEQ ID NO: 145) | AM-288-160-CPK2068 (SEQ ID NO: 146) |
| ERG8 | | AM-288-160-CPK2051 (SEQ ID NO: 131) | AM-288-160-CPK2052 (SEQ ID NO: 132) |
| GRE1 | | AM-288-160-CPK2053 (SEQ ID NO: 133) | AM-288-160-CPK2054 (SEQ ID NO: 134) |
| PDC1 | | AM-288-160-CPK2059 (SEQ ID NO: 137) | AM-288-160-CPK2060 (SEQ ID NO: 138) |
| ANB1 | | AM-288-160-CPK2089 (SEQ ID NO: 155) | AM-288-160-CPK2090 (SEQ ID NO: 113) |

PCR amplifications were done using the Phusion High Fidelity DNA Polymerase System (Finnzyme Inc, Espoo, Finland). PCR products were gel purified using the E.Z.N.A. ® Gel Extraction Kit (Omega Bio-Tek Inc., Norcross, GA) according to manufacturer's suggested protocols.

To replace the GAL1 promoter in pAM2191, the expression plasmid was digested using FastDigest® BamHI restriction endonuclease, and 100 ng of this linearized plasmid was co-transformed with 300 ng of each of the promoters PCR products into exponentially growing Y3198 cells. Host cell transformants were plated to CSM-L with 2% glucose as a sole carbon source, and incubated for 3 days at 30° C. until individual colonies were ~1 mm in diameter. Eight colonies from each transformation were picked and grown as described, before their farnesene and trichodiene titers were determined by GC analysis as described (Table 20). Promoters that gave farnesene/trichodiene ratios similar to that of the GAL1 promoter linked to the FS_Aa_Sc coding sequence were selected and further screened by FPP-toxicity based growth selection in Y227 as described. Of the tested promoters, the promoter of the PET9 gene was shown to be suitable for use in FPP toxicity-based selection for improved FS when using the FS_A__5.3 coding sequence as the parent template.

TABLE 20

Farnesene to trichodiene titers obtained using various promoters to drive expression of the FS_A_5.3 coding sequence

| Promoter of Gene | FS coding sequence | Farnesene/ Trichodiene | % Strength of GAL1 promoter |
|---|---|---|---|
| GAL1 | FS_Aa_Sc | 1.06 | 1 |
| FBA1 | FS_A_5.3 | 1.18 | 0.222 |
| TPI1 | | 0.875 | 0.165 |
| HSP12 | | 0.87 | 0.164 |
| PET9 | | 0.71 | 0.133 |
| QCR9 | | 0.6 | 0.113 |
| QCR7 | | 0.525 | 0.099 |
| CDC19 | | 0.19 | 0.035 |
| TEF2 | | 0.19 | 0.035 |
| PGK1 | | 0.19 | 0.035 |
| SIP18 | | 0.16 | 0.030 |
| ERG8 | | 0.137 | 0.025 |
| GRE1 | | 0.093 | 0.017 |
| PDC1 | | 0.085 | 0.016 |
| ANB1 | | 0.072 | 0.013 |

Example 17

This example describes methods for porting beneficial mutations of farnesene synthase, identified through sesquiterpene synthase competition, into a related sesquiterpene synthase.

Various amino acid changes of FS identified in Example 13 were confirmed as causal for improvement in FS activity using saturation mutagenesis, and several of these mutations were ported into a related sesquiterpene synthase, amorphadiene synthase of *Artemisia annua* (ADS), to determine whether a similar improvement in activity could be achieved. The amino acid positions of FS selected for porting were Met 35, Tyr288, Thr 319, Val 369, Ile 434, Thr 446, I460 and V467. Based on multiple sequence alignments, the aligned corresponding amino acids in ADS are Ala13, Cys260, Ala291, Met341, Thr406, Thr418, Phe432 and Gly439. Each of these positions were mutated by substitution with 19 other residues, and each mutant was tested in a amorphadiene: trichodiene competition assay.

The ADS mutants were constructed by using separate PCR reactions to amplify two DNA fragments that overlap at a specific codon in the ADS gene. Each oligonucleotide pair was synthesized with a mismatched degenerate nucleotide sequence in the middle of the oligonucleotide (for example, NNK, wherein K represents mixed G and T bases, and N represents A, T, G and C mixed bases), flanked on both sides by nucleotides that specifically anneal to the target region.

TABLE 21

Primers used in Constructing ADS-TDS 2µ plasmid

| Primer | Sequence (5' to 3') |
|---|---|
| ADS-A13-F | GGAGAAAAAACCCCGGATCCATGGCCTTGACTGAAGAGAAACCTATAAGGCCAATTNNKAATTTCCCACCTTCTATTTG (SEQ ID NO: 157) |
| ADS-C260-F | CATTTGATATTAAGAAAAATGCCCCANNKCTGAGAGATCGTATCGTTGAATGC (SEQ ID NO: 158) |
| ADS-C260-R | CATTTTTCTTAATATCAAATGCCTTCCACC (SEQ ID NO: 159) |
| ADS-A291-F | CAAGAGCTAGAGTTTTTTTCACTAAGNNKGTTGCTGTGATAACACTTATTG (SEQ ID NO: 160) |
| ADS-A291-R | GAAAAAAACTCTAGCTCTTGAATAC (SEQ ID NO: 161) |
| ADS-M341-F | CATGAAGCCTATTTACAAATTATTCNNKGATACCTACACAGAAATG (SEQ ID NO: 162) |
| ADS-M341-R | AATTTGTAAATAGGCTTCATGTATTC (SEQ ID NO: 163) |
| ADS-M406-F | GTTATTATCACTGGTGGTGCAAACTTGCTANNKACTACCTGTTATCTAG (SEQ ID NO: 164) |
| ADS-M406-R | GTTTGCACCACCAGTGATAATAACTACGGG (SEQ ID NO: 165) |
| ADS-M418-F | GTTATCTAGGAATGAGCGATATTTTCNNKAAGGAATCAGTTGAGTGGGC (SEQ ID NO: 166) |
| ADS-M418-R | CGCTCATTCCTAGATAACAGGTAG (SEQ ID NO: 167) |
| ADS-F432-F | GGGCTGTATCTGCTCCGCCTTTANNKCGTTACAGTGGTATTCTG (SEQ ID NO: 168) |
| ADS-F432-R | GGCGGAGCAGATACAGCCCACTCAAC (SEQ ID NO: 169) |
| ADS-G439-F | CTTTATTCCGTTACAGTGGTATTCTGNNKAGGAGATTAAATGACCTGATG (SEQ ID NO: 170) |
| ADS-G439-R | GAATACCACTGTAACGGAATAAAG (SEQ ID NO: 171) |
| ADS-SM-5' | GAAAAAACCCCGGATCCATGGCCTTGACTGAAGAGAAAC (SEQ ID NO: 172) |
| ADS-SM-3' | GGTTAGAGCGGATCTTAGCTAGCTTAGATAGACATAGGGTAAAC (SEQ ID NO: 173) |

TABLE 22

List of PCR reactions for generating ADS saturation mutants

| AA position | Fwd oligo-nucleotide | Rev oligo-nucleotide | Fwd oligo-nucleotide | Rev oligo-nucleotide |
|---|---|---|---|---|
| Ala13 | ADS-A13-F | ADS-SM-3' | | |
| Cys260 | ADS-SM-5' | ADS-C260-R | ADS-C260-F | ADS-SM-3' |
| Ala291 | ADS-SM-5' | ADS-A291-R | ADS-A291-F | ADS-SM-3' |
| Met341 | ADS-SM-5' | ADS-M341-R | ADS-M341-F | ADS-SM-3' |
| Thr406 | ADS-SM-5' | ADS-M406-R | ADS-M406-F | ADS-SM-3' |
| Thr418 | ADS-SM-5' | ADS-M418-R | ADS-M418-F | ADS-SM-3' |
| Phe432 | ADS-SM-5' | ADS-M432-R | ADS-M432-F | ADS-SM-3' |
| Gly439 | ADS-SM-5' | ADS-M439-R | ADS-M439-F | ADS-SM-3' |

To prepare ADS-TDS competition vectors, pAM1948 plasmid was digested with BamHI and NheI to excise the IS_Pn_Sc coding sequence, and gel purified using the Zymoclean Gel purification kit (Zymo Research, Irvine Calif.). Amplification of the ADS open reading frame (orf) containing each saturation mutant was performed by mixing equimolar amounts of a PCR fragment listed in Table 22 and the appropriate ADS-SM-5' and ADS-SM-3' oligos listed in Table 21, with the exception that for mutagenesis of residue Ala13, ADS-A13-F and ADS-SM-3' were used to amplify the orf directly. The amplified PCR products were gap-repaired in linearized pAM1948 and transformed in Y3125. For each site saturation mutant, the fold-improvement was obtained by comparing the ADS/TDS ratio of the mutant to that of the ADS WT.

As shown in FIG. 17, substitution of Ala291 with either a valine (A291V; SEQ ID NO: 174), cysteine (A291C; SEQ ID NO: 175) or a isoleucine (A291I; SEQ ID NO: 176) resulted in improvement of the ADS/TDS ratio by more than 30% compared to the ADS parent (WT).

To confirm the improved activities of ADS A291V, A291C and A291I, amorphadiene titers were determined in cells transformed with expression plasmids for each mutant. The ADS-TDS plasmid containing A291V, A291C and A291I, respectively, was digested using BamHI and NheI and gel extracted. The CEN.ARS plasmid and 2μ Leu2 plasmid were linearized using the same restriction enzyme and gel purified. The digested fragments containing ADS mutants were ligated into linearized CEN.ARS or 2μ Leu2 plasmid using T4 ligase at 16° C. 2 μl of the reaction was transformed into Xl1-Blue cells and plated on LB plates. Colonies containing each ADS mutant either in CEN.ARS plasmid or 2μ Leu2 plasmid were sequence verified.

TABLE 23

List of plasmids encoding ADS variants

| Plasmid No. | Description |
|---|---|
| pAM2507 | *Artemesia Annua* (Aa) ADS mutant A291C on CEN.ARS plasmid using pAM1734 as the backbone |
| pAM2506 | Aa.ADS mutant A291I on CEN.ARS plasmid using pAM1734 as the backbone |
| pAM2505 | Aa.ADS mutant A291V on CEN.ARS plasmid using pAM1734 as the backbone |
| pAM2504 | Aa.ADS WT on CEN.ARS plasmid using pAM1734 as the backbone |
| pAM2503 | PGAL1-Aa.ADS mutant A291C in leu2 2u |
| pAM2502 | PGAL1-Aa.ADS mutant A291I in leu2 2u |
| pAM2501 | PGAL1-Aa.ADS mutant A291V in leu2 2u |
| pAM2419 | Aa.ADS mutant A291I (under pGAL1) and TDS (under PGAL10) in leu2d |
| pAM2418 | Aa.ADS mutant A291C (under pGAL1) and TDS (under PGAL10) in leu2d |
| pAM2417 | *Artemesia Annua* ADS mutant A291V (under pGAL1) and TDS (under PGAL10) in leu2d |
| pAM2414 | Aa. ADS (under pGAL1) and TDS (under PGAL10) in leu2d |

For production, each plasmid was transformed into cured Y227 and plated on CSM-L plates. Eight colonies were picked for each mutant and grown in a 96-well plate containing 360 μl of Bird Seed Media with 4% galactose. After 2 days of incubation at 34° C., 16 μl of each well was inoculated into a new 96-well plate containing fresh Bird Seed Media with 4% galactose for production. After 2 days of incubation at 30° C., production samples were taken for Nile Red and GC analysis.

As shown in FIG. 18, each of ADS A291V, A291C and A291I showed an increase in amorphadiene production compared to parent ADS when expressed on either a 2μ plasmid or CEN.ARS plasmid. The best mutant, Ala291Val, showed up to 58% improvement in amorphadiene titer than that of the parent.

These results demonstrate that beneficial mutations identified in one terpene synthase using the terpene synthase competition assay can be successfully ported into a related terpene synthase to effect improved synthase activity.

Example 18

This example demonstrates the feasibility of using sesquiterpene synthase competition in yeast to rank patchoulol synthases (PS) according to their in vivo enzyme activity levels.

Yeast strains Y9259, Y11136, Y9260 were made by transforming expression plasmids pAM2596, pAM2702, and pAM2597 into yeast strain Y9120 (comprising the MEV pathway), respectively, and confirmed by colony PCR to contain the correct plasmid. Each plasmid contains a different PS isoform on a GAL1 promoter and identical versions of trichodiene synthase (TDS) on the divergent GAL10 promoter. The confirmed colony was re-streaked for single colonies, from which eight colonies were incubated in separate wells of a 96-well plate containing 360 uL Bird Seed Medium (BSM) with 2% sucrose per well (preculture). After 2 days of incubation at 30° C. with 999 rpm agitation, 6.4 uL of each well was inoculated into a well of a new 96-well plate containing 150 uL of fresh BSM with 4% galactose and 3.33% mineral oil and Brij-56 emulsion (production culture). After another 4 days of incubation at 30° C. with 999 rpm agitation, samples were taken and analyzed for terpene production by gas chromatography (GC) analysis.

For GC analysis, samples were extracted with methanol-butoxy ethanol-heptane (100 uL:50 uL:400 uL v/v), and the cell material was allowed to settle by gravity. An aliquot of the heptane extract was further diluted into heptane, and then injected onto a methyl silicone stationary phase using a pulsed split injection. Patchouli alcohol and trichodiene were separated by boiling point using GC with flame ionization detection (FID). Hexadecane was used as a retention time marker to monitor successful injection and elution during the specified GC oven profile. The titers of patchouli alcohol and trichodiene were used to calculate the patchouli oil/trichodiene ratios (patchouli oil is approximately three times the titer of patchouli alcohol).

As shown in Table 24, patchouli oil/trichodiene ratios were fairly consistent across samples, producing CVs of no more than 5.47%. Thus, by co-expressing PS from the same plasmid as a TDS, the tested patchoulol synthases could be ranked as follows (from most active to least active): PS_isoform_3 coding sequence (Y9260)>PS_isoform_2 coding sequence (Y11136)>PS_isoform_1 coding sequence (Y9259).

TABLE 24

Patchouli Oil and Trichodiene Titers and Titer Ratios for Yeast Strains Expressing a PS and a TDS from the Same Plasmid

| Strain | Coding Sequences (promoters) | Patchouli Oil/Trichodiene (CV%) |
|---|---|---|
| Y9259 | PS_isoform_1 ($P_{GAL1}$) TDS_Fs_Sc ($P_{GAL10}$) | 0.17 (2.16%) |
| Y11136 | PS_isoform_2 ($P_{GAL1}$) TDS_Fs_Sc ($P_{GAL10}$) | 0.68 (5.47%) |
| Y9260 | PS_isoform_3 ($P_{GAL1}$) TDS_Fs_Sc ($P_{GAL10}$) | 1.24 (1.82%) |

Example 19

This example demonstrates the feasibility of using monoterpene synthase competition to rank monoterpene synthases according to their in vivo enzymatic activity.

To determine the productivity of synthases for the monoterpene limonene, a competition vector was prepared comprising the coding sequence for myrcene synthase of *Ocimum basilicum*, used here as the comparison terpene synthase, being driven by a pGal10 promoter, and the coding sequence for a query limonene synthase (LS) being driven by pGAL1 on the same plasmid (pAM2645). Eight competition plasmids each encoding a different LS truncation variant or isoform were transformed into yeast strain Y8270 (comprising the MEV pathway), respectively, and transformed strains were confirmed by colony PCR to contain the correct plasmid. Eight single colonies of each strain were incubated in 96-well microtiter plates with 360 μL of Bird Seed Medium containing 2% glucose as a carbon source. After 3 days of growth at 30° C. with shaking at 998 RPM, 6 µL of each culture was inoculated into a well of a 96-well plate containing 75 µL of Bird Seed Medium containing 4% galactose and 75 µL of isopropyl myristate per well. The production plates were sealed with a Velocity 11 heat sealer (Agilent Technologies) and grown at 30° C. with shaking at 998 RPM prior to flash freezing for 2 hours at −20° C. The products were then assayed after quickly adding 300 ml of ethyl acetate containing 0.001% hexadecane internal standard, heat sealing, and shaking for 2 hours at room temperature. Gas chromatogram flame ionization detection (GC-FID) was performed using standard curves of absolute concentrations of myrcene and limonene. In detail, 2 µL of the ethyl acetate extract was injected onto a methyl silicone stationary phase column with a split ratio of 1:50. This injection was analyzed using hexadecane as an internal standard for injection accuracy and retention time adjustment. Oven temperatures were ramped from 25° C.-250° C. over the course of 2.5 minutes, at which point the oven was rapidly cooled for the next sample. The titers of myrcene and the limonene were used to calculate the competition ratio.

As shown in FIG. 18, the terpene synthase competition assay can be used to rank the relative performance of different limonene synthase truncation variants and isoforms.

Various modifications and variations of the present disclosure will be apparent to those skilled in the art without departing from the scope and spirit of the disclosure. Although the disclosure has been described in connection with specific preferred embodiments, it should be understood that the claims should not be unduly limited to such specific embodiments. Indeed, various modifications of the described modes for carrying out the disclosure, which are understood by those skilled in the art are intended to be within the scope of the claims.

What is claimed is:

1. A method of testing a terpene synthase variant for improved in vivo performance, comprising the steps of:
   (a) dividing a population of host cells into a control population and a test population;
   (b) co-expressing in the control population a control terpene synthase ($S_1$) and a comparison terpene synthase ($S_2$), wherein the control terpene synthase can convert a polyprenyl diphosphate to a first terpene ($T_1$) and the comparison terpene synthase can convert the same polyprenyl diphosphate to a different second terpene ($T_2$) and wherein said control terpene synthase and comparison terpene synthase compete for the same pool of polyprenyl diphosphate;
   (c) co-expressing in the test population a test terpene synthase ($S_1'$) and the comparison terpene synthase ($S_2$), wherein the test terpene synthase is a variant of the control terpene synthase that can convert the same polyprenyl diphosphate to the same first terpene ($T_1$) as the control terpene synthase, and wherein the comparison terpene synthase can convert the same polyprenyl diphosphate to a different second terpene ($T_2$) and is expressed at similar levels in the test population and in the control population; and (d) measuring a ratio of the first terpene over the second terpene ($T_1/T_2$) in both the test population and in the control population, wherein the test population is identified as comprising a terpene synthase variant having improved in vivo performance compared to the control terpene synthase by having an increase in the ratio of the first terpene over the second terpene in the test population compared to that in the control population.

2. The method of claim 1, wherein the control terpene synthase, comparison terpene synthase, and the test terpene synthase are sesquiterpene synthases, and the polyprenyl diphosphate is farnesyl diphosphate (FPP).

3. The method of claim 2, wherein the comparison terpene synthase is a trichodiene synthase.

4. The method of claim 2, wherein the control and test terpene synthases are synthases having farnesene synthase activity.

5. The method of claim 1, wherein the control terpene synthase, comparison terpene synthase, and the test terpene synthase are monoterpene synthases, and the polyprenyl diphosphate is geranyl diphosphate (GPP).

6. The method of claim 1, wherein the host cells comprise one or more heterologous enzymes of the mevalonate-dependent (MEV) pathway.

7. The method of claim 6, wherein the one or more heterologous enzymes of the MEV pathway are selected from the group consisting of ERG8, ERG10, ERG12, ERG13, ERG19, and HMG1.

8. The method of claim 1, wherein the test terpene synthase differs from the control terpene synthase by 1 to 10 amino acids.

9. The method of claim 1, wherein the ratio of the first terpene over the second terpene is at least 1.3.

10. The method of claim 1, wherein test terpene synthase is expressed at a similar level in the test population as the control terpene synthase is expressed in the control population.

11. The method of claim 1, wherein the control terpene synthase and the test terpene synthase are identical but are expressed at different levels in the control population and the test population.

12. The method of claim 1, wherein the population of host cells is a population of yeast cells.

13. A composition comprising two cell subpopulations derived from a common population of host cells, wherein:

(a) the first subpopulation comprises a heterologous control terpene synthase ($S_1$) and a heterologous comparison terpene synthase ($S_2$), wherein the control terpene synthase converts a polyprenyl diphosphate to a first terpene ($T_1$), and wherein the comparison terpene synthase converts the same pool of polyprenyl diphosphate to a second, different terpene ($T_2$); and (b) the second subpopulation comprises a heterologous test terpene synthase ($S_1'$) which is a variant of the control terpene synthase ($S_1$) of the first subpopulation, and the same comparison terpene synthase ($S_2$) as in the first subpopulation, wherein the test terpene synthase ($S_1'$) converts the polyprenyl diphosphate to the same first terpene ($T_1$) in the first subpopulation and the comparison terpene synthase ($S_2$) competes for the same of polyprenyl diphosphate as the test terpene synthase ($S_1'$) and converts it to the same second terpene ($T_2$) as in the first subpopulation;

and wherein the comparison terpene synthase ($S_2$) is expressed and present at similar levels in the first subpopulation and in the second subpopulation.

14. The composition of claim 13, wherein the ratio of the first terpene over the second terpene is greater in the second subpopulation compared to that in the first subpopulation.

15. The method of claim 1, wherein the population of host cells is a population of *E. coli* cells.

16. The method of claim 7, wherein the host cells comprise a heterologous isopentyl pyrophosphate (IPP) isomerase.

17. The method of claim 7, wherein the host cells comprise a heterologous farnesyl diphosphate (FPP) synthase.

18. The method of claim 7, wherein the host cells comprise a heterologous geranylgeranyl pyrophosphate (GGPP) synthase.

19. The method of claim 18, wherein the control terpene synthase, comparison terpene synthase, and the test terpene synthase are diterpene synthases, and the polyprenyl diphosphate is geranylgeranyl pyrophosphate (GGPP).

20. The method of claim 2, wherein the sesquiterpene synthase is selected from the group consisting of β-farnesene synthase, α-farnesene synthase, trichodiene synthase, patchoulol synthase, amorphadiene synthase, valencene synthase, farnesol synthase, nerolidol synthase, and nootkatone synthase.

21. The method of claim 1, wherein the control terpene synthase, comparison terpene synthase, and the test terpene synthase are each a sesterterpene synthase, a triterpene synthase, a tetraterpene synthase, or a polyterpene synthase.

22. The method of claim 1, wherein the first terpene or the second terpene is selected from the group consisting of β-farnesene, α-farnesene, trichodiene, patchoulol, amorphadiene, valencene, farnesol, nerolidol, and nootkatone.

23. The method of claim 1, wherein the first terpene or the second terpene is limonene or myrcene.

24. The composition of claim 13, wherein the control terpene synthase, comparison terpene synthase, and the test terpene synthase are sesquiterpene synthases, and the polyprenyl diphosphate is farnesyl diphosphate (FPP).

25. The composition of claim 13, wherein the control and test terpene synthases are synthases having farnesene synthase activity.

26. The composition of claim 13, wherein the comparison terpene synthase is a trichodiene synthase.

27. The composition of claim 13, wherein the host cells comprise one or more heterologous enzymes of the mevalonate-dependent (MEV) pathway.

28. The composition of claim 27, wherein the one or more heterologous enzymes of the MEV pathway are selected from the group consisting of ERGS, ERG10, ERG12, ERG13, ERG19, and HMG1.

29. The composition of claim 13, wherein the host cells comprise a heterologous farnesyl diphosphate (FPP) synthase.

* * * * *

SEQUENCE LISTING

```
<160> NUMBER OF SEQ ID NOS: 176

<210> SEQ ID NO 1
<211> LENGTH: 11741
<212> TYPE: DNA
<213> ORGANISM: Artificial Sequence
<220> FEATURE:
<223> OTHER INFORMATION: Synthetic, Expression plasmid pAM765

<400> SEQUENCE: 1
gaattccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aacccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
```

```
cgaaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttc cgatggcgcg ccgagaggct ttacacttta   1560
tgcttccggc tcgtataatg tgtggaattg tgagcggata caattgaat tcaaaggagg    1620 ccatcctggc catgaagaac tgtgtgattg tttctgcggt ccgcacggcg atcggcagct   1680
ttaacggctc tttagcgagc acctctgcaa tcgatctggg tgcgacggtc attaaggccg   1740
ccattgaacg cgccaaaatc gacagccagc acgttgatga ggtgatcatg ggcaatgtgt   1800
tacaagccgg cctgggtcaa acccagcgc gtcaagcact gttaaaatct ggtctggccg    1860
agaccgtgtg tggcttcacc gtcaataagg tttgcggctc tggcctgaag agcgtggccc   1920
tggcagcaca agcgattcaa gccggtcagg cacaaagcat cgttgcgggt ggcatggaga   1980
acatgtctct ggcgccgtac ttattagatg ccaaagcccg cagcggttat cgcctgggcg   2040
atggtcaggt gtacgacgtc atcttacgcg atggcttaat gtgcgcgacc cacggttacc   2100
acatgggtat tacggccgaa aacgtggcga agaatacgg cattacgcgc gagatgcagg    2160
atgaattagc actgcactct cagcgcaaag cagcagccgc gatcgagtct ggtgcgttta   2220
cggcggaaat cgtgccagtt aacgtggtca cgcgcaagaa gacgttcgtt ttcagccagg   2280
acgagttccc gaaggcaaac agcaccgcgg aggccttagg tgccttacgc ccagcctttg   2340
acaaagcggg cacggtcacc gccggtaatg cgagcggcat caatgatggt gcagcggcac   2400
tggtcatcat ggaagagagc gccgcattag cagcgggtct gaccccatta gcgcgcatta   2460
aatcttatgc cagcggcggc gtcccaccag ccctgatggg catgggtccg gtcccagcca   2520
cgcaaaaagc cctgcaatta gcgggcctgc aactggccga cattgatctg atcgaggcga   2580
acgaggcgtt tgcagcgcag ttcctggcgg tgggtaagaa tctgggcttc gacagcgaga   2640
aagtcaatgt gaacggtggc gcgattgcgt taggccatcc gattggtgca agcggcgcac   2700
gcatcttagt gacgttactg cacgccatgc aggcacgcga caagaccta ggcctggcga    2760 ccttatgtat tggtggcggt caaggtatcg ccatggtgat cgaacgcctg aactgaagat   2820
ctaggaggaa agcaaaatga caataggtat cgacaaaata aacttttacg ttccaaagta   2880
ctatgtagac atggctaaat tagcagaagc acgccaagta gacccaaaca aatttttaat   2940
tggaattggt caaactgaaa tggctgttag tcctgtaaac caagacatcg tttcaatggg   3000
cgctaacgct gctaaggaca ttataacaga cgaagataaa aagaaaattg gtatggtaat   3060
tgtggcaact gaatcagcag ttgatgctgc taaagcagcc gctgttcaaa ttcacaactt   3120
attaggtatt caacctttg cacgttgctt tgaaatgaaa gaagcttgtt atgctgcaac    3180
accagcaatt caattagcta aagattattt agcaactaga ccgaatgaaa agtattagt    3240 tattgctaca gatacagcac gttatggatt gaattcaggc ggcgagccaa cacaaggtgc   3300
tggcgcagtt gcgatggtta ttgcacataa tccaagcatt ttggcattaa atgaagatgc   3360
tgttgcttac actgaagacg tttatgattt ctggcgtcca actggacata aatatccatt   3420
agttgatggt gcattatcta agatgcttta tatccgctca ttccaacaaa gctggaatga   3480
atacgcaaaa cgtcaaggta agtcgctagc tgacttcgca tctctatgct tccatgttcc   3540
atttacaaaa atgggtaaaa aggcattaga gtcaatcatt gataacgctg atgaacaac    3600 tcaagagcgt ttacgttcag gatatgaaga tgctgtagat tataaccgtt atgtcggtaa   3660
tatttatact ggatcattat atttaagcct aatatcatta cttgaaaatc gtgatttaca   3720
```

```
agctggtgaa acaatcggtt tattcagtta tggctcaggt tcagttggtg aattttatag   3780
tgcgacatta gttgaaggct acaaagatca tttagatcaa gctgcacata agcattatt    3840 aaataaccgt actgaagtat ctgttgatgc atatgaaaca ttcttcaaac gttttgatga   3900
cgttgaattt gacgaagaac aagatgctgt tcatgaagat cgtcatattt tctacttatc   3960
aaatattgaa ataacgttc gcgaatatca cagaccagag taactagtag gaggaaaaca    4020
tcatgcaaag tttagataag aatttccgac atttatctcg tcaacaaaag ttacaacaat   4080
tggtagataa gcaatggtta tcagaagatc aattcgacat tttattgaat catccattaa   4140
ttgatgagga agtagcaaat agtttaattg aaaatgtcat cgcgcaaggt gcattacccg   4200
ttggattatt accgaatatc attgtggacg ataaggcata tgttgtacct atgatggtgg   4260
aagagccttc agttgtcgct gcagctagtt atggtgcaaa gctagtgaat cagactggcg   4320
gatttaaaac ggtatcttct gaacgtatta tgataggtca aatcgtcttt gatggcgttg   4380
acgatactga aaaattatca gcagacatta agctttaga aaagcaaatt cataaaattg     4440
cggatgaggc atatccttct attaaagcgc gtggtggtgg ttaccaacgt atagctattg   4500
atacatttcc tgagcaacag ttactatctt taaaagtatt tgttgatacg aaagatgcta   4560
tgggcgctaa tatgcttaat acgattttag aggccataac tgcattttta aaaatgaat    4620 ctccacaaag cgacatttta atgagtattt tatccaatca tgcaacagcg tccgttgtta   4680
aagttcaagg cgaaattgac gttaaagatt tagcaagggg cgagagaact ggagaagagg   4740
ttgccaaacg aatggaacgt gcttctgtat tggcacaagt tgatattcat cgtgctgcaa   4800
cacataataa aggtgttatg aatggcatac atgccgttgt tttagcaaca ggaaatgata   4860
cgcgtggtgc agaagcaagt gcgcatgcat acgcgagtcg tgacgacag tatcgtggta     4920 ttgcaacatg gagatacgat caaaaacgtc aacgtttaat tggtacaata gaagtgccta   4980
tgacattggc aatcgttggc ggtggtacaa aagtattacc aattgctaaa gcttcttag     5040 aattgctaaa tgtagattca gcacaagaat taggtcatgt agttgctgcc gttggtttag   5100
cacagaactt tgcagcatgt cgcgcgctcg tttccgaagg tatccagcaa ggccatatga   5160
gcttgcaata taaatcttta gctattgttg taggtgcaaa aggtgatgaa attgcgcaag   5220
tagctgaagc attgaagcaa gaaccccgtg cgaatacaca agtagctgaa cgcattttac   5280
aagaaattag acaacaatag tctagaagca gcttcgatcc catggtacgc gtgctagagg   5340
catcaaataa aacgaaaggc tcagtcgaaa gactgggcct ttcgttttat ctgttgtttg   5400
tcggtgaacg ctctcctgag taggacaaat ccgccggcga tcgccgagag gctttacact   5460
ttatgcttcc ggctcgtata atgtgtggaa ttgtgagcgg ataacaattg aattcaaagg   5520
aggctcgaga tgacgcgcaa aggctacggt gaatctactg gtaagattat cctgattggc   5580
gagcatgctg taacctttgg cgaacctgcc atcgcagtac cgttcaacgc gggcaaaatc   5640
aaggttctga tcgaagccct ggagtccggc aactattcta gcatcaaatc tgacgtatac   5700
gacggtatgc tgtacgacgc gccggaccac ctgaagagcc tggtgaaccg ttttgttgaa   5760
ctgaacaaca tcactgaacc gctggcgta accattcaga ccaacctgcc gccatctcgc    5820
ggcctgggta gctctgctgc ggttgctgta gcgttcgtac gcgcgtctta tgatttcctg   5880
ggtaagtctc tgaccaaaga agaactgatt gagaaagcga actgggcaga acagattgca   5940
cacggcaaac caagcggcat cgacacccaa actattgtgt ctggcaaacc agtttggttc   6000 caaaaggcc aggcggagac cctgaaaacc ctgagcctgg acggttacat ggttgtaatt    6060
gacactggtg taaaaggcag cacccgccag gcagtagagg atgtgcacaa actgtgcgaa   6120
```

```
gaccctcagt atatgagcca cgtgaagcac atcggtaaac tggtactgcg cgcttctgac    6180
gtgattgaac accacaactt cgaagcactg gcggatatct tcaacgaatg ccatgcggat    6240
ctgaaagcac tgactgtgag ccatgacaaa attgagcagc tgatgaaaat cggcaaagaa    6300
aacggtgcga tcgctggcaa actgactggt gcaggtcgcg gtggctctat gctgctgctg    6360
gctaaagacc tgccgactgc taaaaacatt gttaaggcag tagaaaaggc aggtgctgca    6420
cacacttgga ttgaaaacct gggtggttag gaggcagatc aaatgtcaga gttgagagcc    6480
ttcagtgccc cagggaaagc gttactagct ggtggatatt tagttttaga tacaaaatat    6540
gaagcatttg tagtcggatt atcggcaaga atgcatgctg tagcccatcc ttacggttca    6600
ttgcaagggt ctgataagtt tgaagtgcgt gtgaaaagta acaatttaa agatggggag    6660 tggctgtacc atataagtcc taaaagtggc ttcattcctg tttcgatagg cggatctaag    6720
aaccctttca ttgaaaaagt tatcgctaac gtatttagct actttaaacc taacatggac    6780
gactactgca atagaaactt gttcgttatt gatattttct ctgatgatgc ctaccattct    6840
caggaggata gcgttaccga acatcgtggc aacagaagat tgagttttca ttcgcacaga    6900
attgaagaag ttcccaaaac agggctgggc tcctcggcag gtttagtcac agttttaact    6960
acagctttgg cctcctttt tgtatcggac ctggaaaata atgtagacaa atatagagaa    7020
gttattcata atttagcaca agttgctcat tgtcaagctc agggtaaaat tggaagcggg    7080
tttgatgtag cggcggcagc atatggatct atcagatata gaagattccc accgcatta    7140 atctctaatt tgccagatat tggaagtgct acttacggca gtaaactggc gcatttggtt    7200
gatgaagaag actggaatat tacgattaaa agtaaccatt taccttcggg attaacttta    7260
tggatgggcg atattaagaa tggttcagaa acagtaaaaac tggtccagaa ggtaaaaaat    7320
tggtatgatt cgcatatgcc agaaagcttg aaaatatata cagaactcga tcatgcaaat    7380
tctagattta tggatggact atctaaacta gatcgcttac acgagactca tgacgattac    7440
agcgatcaga tatttgagtc tcttgagagg aatgactgta cctgtcaaaa gtatcctgaa    7500
atcacagaag ttagagatgc agttgccaca attagacgtt cctttagaaa ataactaaa    7560 gaatctggtg ccgatatcga acctcccgta caaactagct tattggatga ttgccagacc    7620
ttaaaaggag ttcttacttg cttaatacct ggtgctggtg gttatgacgc cattgcagtg    7680
attactaagc aagatgttga tcttagggct caaaccgcta atgacaaaag attttctaag    7740
gttcaatggc tggatgtaac tcaggctgac tggggtgtta ggaaagaaaa agatccggaa    7800
acttatcttg ataatagga ggtaatactc atgaccgttt acacagcatc cgttaccgca    7860
cccgtcaaca tcgcaaccct taagtattgg gggaaaaggg acacgaagtt gaatctgccc    7920
accaattcgt ccatatcagt gactttatcg caagatgacc tcagaacgtt gacctctgcg    7980
gctactgcac ctgagtttga acgcgacact ttgtggttaa atggagaacc acacagcatc    8040
gacaatgaaa gaactcaaaa ttgtctgcgc gacctacgcc aattaagaaa ggaaatggaa    8100
tcgaaggacg cctcattgcc cacattatct caatggaaac tccacattgt ctccgaaaat    8160
aactttccta cagcagctgg tttagcttcc tccgctgctg gctttgctgc attggtctct    8220
gcaattgcta agttatacca attaccacag tcaacttcag aaatatctag aatagcaaga    8280 aagggggtctg gttcagcttg tagatcgttg tttggcggat acgtggcctg ggaaatggga    8340
aaagctgaag atggtcatga ttccatggca gtacaaatcg cagacagctc tgactggcct    8400
cagatgaaaa cttgtgtcct agttgtcagc gatattaaaa aggatgtgag ttccactcag    8460
ggtatgcaat tgaccgtggc aacctccgaa ctatttaaag aaagaattga acatgtcgta    8520
```

```
ccaaagagat tgaagtcat gcgtaaagcc attgttgaaa aagatttcgc cacctttgca    8580
aaggaaacaa tgatggattc caactctttc catgccacat gtttggactc tttccctcca    8640
atattctaca tgaatgacac ttccaagcgt atcatcagtt ggtgccacac cattaatcag    8700
ttttacggag aaacaatcgt tgcatacacg tttgatgcag gtccaaatgc tgtgttgtac    8760
tacttagctg aaaatgagtc gaaactcttt gcatttatct ataaattgtt tggctctgtt    8820
cctggatggg acaagaaatt tactactgag cagcttgagg ctttcaacca tcaatttgaa    8880
tcatctaact ttactgcacg tgaattggat cttgagttgc aaaaggatgt tgccagagtg    8940
atttaactc aagtcggttc aggcccacaa gaaacaaacg aatctttgat tgacgcaaag     9000
actggtctac caaaggaata actgcagccc gggaggagga ttactatatg caaacggaac    9060
acgtcatttt attgaatgca cagggagttc ccacgggtac gctggaaaag tatgccgcac    9120
acacggcaga cacccgctta catctcgcgt tctccagttg gctgtttaat gccaaaggac    9180
aattattagt tacccgccgc gcactgagca aaaaagcatg gcctggcgtg tggactaact    9240
cggtttgtgg gcacccacaa ctgggagaaa gcaacgaaga cgcagtgatc cgccgttgcc    9300
gttatgagct tggcgtggaa attacgcctc ctgaatctat ctatcctgac tttcgctacc    9360
gcgccaccga tccgagtggc attgtggaaa atgaagtgtg tccggtattt gccgcacgca    9420
ccactagtgc gttacagatc aatgatgatg aagtgatgga ttatcaatgg tgtgatttag    9480
cagatgtatt acacggtatt gatgccacgc cgtgggcgtt cagtccgtgg atggtgatgc    9540
aggcgacaaa tcgcgaagcc agaaaacgat tatctgcatt tacccagctt aaataacccg    9600
ggggatccac tagttctaga gcggccgcca ccgcggagga ggaatgagta atggactttc    9660
cgcagcaact cgaagcctgc gttaagcagg ccaaccaggc gctgagccgt tttatcgccc    9720
cactgccctt tcagaacact cccgtggtcg aaaccatgca gtatggcgca ttattaggtg    9780
gtaagcgcct gcgaccttc ctggtttatg ccaccggtca tatgttcggc gttagcacaa    9840
acacgctgga cgcacccgct gccgccgttg agtgtatcca cgcttactca ttaattcatg    9900
atgatttacc ggcaatggat gatgacgatc tgcgtcgcgg tttgccaacc tgccatgtga    9960
agtttggcga agcaaacgcg attctcgctg gcgacgcttt acaaacgctg gcgttctcga   10020
ttttaagcga tgccgatatg ccggaagtgt cggaccgcga cagaatttcg atgatttctg   10080
aactggcgag cgccagtggt attgccggaa tgtgcggtgg tcaggcatta gatttagacg   10140
cggaaggcaa acacgtacct ctggacgcgc ttgagcgtat tcatcgtcat aaaaccggcg   10200
cattgattcg cgccgccgtt cgccttggtg cattaagcgc cggagataaa ggacgtcgtg   10260
ctctgccggt actcgacaag tatgcagaga gcatcggcct tgccttccag gttcaggatg   10320
acatcctgga tgtggtggga gatactgcaa cgttgggaaa acgccagggt gccgaccagc   10380
aacttggtaa aagtacctac cctgcacttc tgggtcttga gcaagcccgg aagaagccc    10440
gggatctgat cgacgatgcc cgtcagtcgc tgaaacaact ggctgaacag tcactcgata   10500
cctcggcact ggaagcgcta gcggactaca tcatccagcg taataaataa gagctccaat   10560
tcgccctata gtgagacgcg tgctagaggc atcaaataaa acgaaaggct cagtcgaaag   10620
actgggcctt tcgttttatc tgttgtttgt cggtgaacgc tctcctgagt taattaactc   10680
caggccggcc tacgcgttta aacttccggt taacgccatg agcggcctca tttcttattc   10740
tgagttacaa cagtccgcac cgctgccggt agctccttcc ggtgggcgcg gggcatgact   10800
atcgtcgccg cacttatgac tgtcttcttt atcatgcaac tcgtaggaca ggtgccggca   10860
gcgcccaaca gtccccggc cacggggcct gccaccatac ccacgccgaa acaagcgccc   10920
```

| | |
|---|---|
| tgcaccatta tgttccggat ctgcatcgca ggatgctgct ggctaccctg tggaacacct | 10980 |
| acatctgtat taacgaagcg ctaaccgttt ttatcaggct ctgggaggca gaataaatga | 11040 |
| tcatatcgtc aattattacc tccacgggga gagcctgagc aaactggcct caggcatttg | 11100 |
| agaagcacac ggtcacactg cttccggtag tcaataaacc ggtaaaccag caatagacat | 11160 |
| aagcggctat ttaacgaccc tgccctgaac cgacgaccgg gtcgaatttg ctttcgaatt | 11220 |
| tctgccattc atccgcttat tatcacttat tcaggcgtag caccaggcgt ttaagggcac | 11280 |
| caataactgc cttaaaaaaa ttacgccccg ccctgccact catcgcagta ctgttgtaat | 11340 |
| tcattaagca ttctgccgac atggaagcca tcacagacgg catgatgaac ctgaatcgcc | 11400 |
| agcggcatca gcaccttgtc gccttgcgta taatatttgc ccatggtgaa aacgggggcg | 11460 |
| aagaagttgt ccatattggc cacgtttaaa tcaaaactgg tgaaactcac ccagggattg | 11520 |
| gctgagacga aaaacatatt ctcaataaac cctttaggga ataggccag gttttcaccg | 11580 |
| taacacgcca catcttgcga atatatgtgt agaaactgcc ggaaatcgtc gtggtattca | 11640 |
| ctccagagcg atgaaaacgt ttcagtttgc tcatggaaaa cggtgtaaca agggtgaaca | 11700 |
| ctatcccata tcaccagctc accgtctttc attgccatac g | 11741 |

<210> SEQ ID NO 2
<211> LENGTH: 5050
<212> TYPE: DNA
<213> ORGANISM: Artificial Sequence
<220> FEATURE:
<223> OTHER INFORMATION: Synthetic, TRP1_PGAL10-ERG20_PGAL1-tHMGR_TRP
      insert of expression plasmid pAM489

<400> SEQUENCE: 2

| | |
|---|---|
| gtttaaacta ctattagctg aattgccact gctatcgttg ttagtggcgt tagtgcttgc | 60 |
| attcaaagac atggagggcg ttattacgcc ggagctcctc gacagcagat ctgatgactg | 120 |
| gtcaatatat ttttgcattg aggctctgtt tggaattata ttttgagatg acccatctaa | 180 |
| tgtactggta tcaccagatt tcatgtcgtt ttttaaagcg gctgcttgag tcttagcaat | 240 |
| agcgtcacca tctggtgaat cctttgaagg aaccactgac gaaggtttgg acagtgacga | 300 |
| agaggatctt tcctgctttg aattagtcgc gctgggagca gatgacgagt tggtggagct | 360 |
| gggggcagga ttgctggccg tcgtgggtcc tgaatgggtc cttggctggt ccatctctat | 420 |
| tctgaaaacg gaagaggagt agggaatatt actggctgaa aataagtctt gaatgaacgt | 480 |
| atacgcgtat atttctacca atctctcaac actgagtaat ggtagttata agaaagagac | 540 |
| cgagttaggg acagttagag gcggtggaga tattccttat ggcatgtctg gcgatgataa | 600 |
| aacttttcaa acggcagccc cgatctaaaa gagctgacac ccgggagtta tgacaattac | 660 |
| aacaacagaa ttctttctat atatgcacga acttgtaata tggaagaaat tatgacgtac | 720 |
| aaactataaa gtaaatattt tacgtaacac atggtgctgt tgtgcttctt tttcaagaga | 780 |
| ataccaatga cgtatgacta agtttaggat ttaatgcagg tgacggaccc atctttcaaa | 840 |
| cgatttatat cagtggcgtc caaattgtta ggttttgttg gttcagcagg tttcctgttg | 900 |
| tgggtcatat gactttgaac caaatggccg gctgctaggg cagcacataa ggataattca | 960 |
| cctgccaaga cggcacaggc aactattctt gctaattgac gtgcgttggt accaggagcg | 1020 |
| gtagcatgtg ggcctcttac acctaataag tccaacatgg caccttgtgg ttctagaaca | 1080 |
| gtaccaccac cgatggtacc tacttcgatg gatggcatgg atacgaaaat tctcaaatca | 1140 |
| ccgtccactt ctttcatcaa tgttatacag ttggaacttt cgacattttg tgcaggatct | 1200 |

```
tgtcctaatg ccaagaaaac agctgtcact aaattagctg catgtgcgtt aaatccacca   1260
acagacccag ccattgcaga tccaaccaaa ttcttagcaa tgttcaactc aaccaatgcg   1320
gaaacatcac ttttttaacac ttttctgaca acatcaccag gaatagtagc ttctgcgacg   1380
acactcttac cacgaccttc gatccagttg atggcagctg ttttttgtc ggtacagtag    1440 ttaccagaaa cggagacaac ctccatatct tcccagccat actcttctac catttgcttt   1500
aatgagtatt cgacacccctt agaaatcata ttcatacccca ttgcgtcacc agtagttgtt 1560
ctaaatctca tgaagagtaa atcctcctgct agacaagttt gaatatgttg cagacgtgca  1620
aatcttgatg tagagttaaa agcttttta attgcgtttt gtccctcttc tgagtctaac    1680
catatcttac aggcaccaga tcttttcaaa gttgggaaac ggactactgg gcctcttgtc   1740
ataccatcct tagttaaaac agttgttgca ccaccgccag cattgattgc cttacagcca   1800
cgcatggcag aagctaccaa acaaccctct gtagttgcca ttggtatatg ataagatgta   1860
ccatcgataa ccaaggggcc tataacacca acgggcaaag gcatgtaacc tataacattt   1920
tcacaacaag cgccaaatac gcggtcgtag tcataatttt tatatggtaa acgatcagat   1980
gctaatacag gagcttctgc caaaattgaa agagccttcc tacgtaccgc aaccgctctc   2040
gtagtatcac ctaatttttt ctccaaagcg tacaaaggta acttaccgtg aataaccaag   2100
gcagcgacct ctttgttctt caattgtttt gtatttccac tacttaataa tgcttctaat   2160
tcttctaaag gacgtatttt cttatccaag ctttcaatat cgcgggaatc atcttcctca   2220
ctagatgatg aaggtcctga tgagctcgat tgcgcagatg ataaacttttt gactttcgat  2280 ccagaaatga ctgttttatt ggttaaaact ggtgtagaag ccttttgtac aggagcagta   2340
aaagacttct tggtgacttc agtcttcacc aattggtctg cagccattat agtttttttct 2400 ccttgacgtt aaagtataga ggtatattaa caattttttg ttgatacttt tatgacattt   2460
gaataagaag taatacaaac cgaaaatgtt gaaagtatta gttaaagtgg ttatgcagct   2520
tttgcattta tatatctgtt aatagatcaa aaatcatcgc ttcgctgatt aattacccca   2580
gaaataaggc taaaaaacta atcgcattat tatcctatgg ttgttaattt gattcgttga   2640
tttgaaggtt tgtggggcca ggttactgcc aattttttcct cttcataacc ataaaagcta   2700
gtattgtaga atctttattg ttcggagcag tgcggcgcga ggcacatctg cgtttcagga   2760
acgcgaccgg tgaagaccag gacgcacgga ggagagtctt ccgtcggagg gctgtcgccc   2820
gctcggcggc ttctaatccg tacttcaata tagcaatgag cagttaagcg tattactgaa   2880
agttccaaag agaaggtttt tttaggctaa gataatgggg ctctttacat ttccacaaca   2940
tataagtaag attagatatg gatatgtata tggtggtatt gccatgtaat atgattatta   3000
aacttctttg cgtccatcca aaaaaaaagt aagaattttt gaaaattcaa tataaatggc   3060
ttcagaaaaa gaaattagga gagagagatt cttgaacgtt ttccctaaat tagtagagga   3120
attgaacgca tcgcttttgg cttacggtat gcctaaggaa gcatgtgact ggtatgccca   3180
ctcattgaac tacaacactc caggcggtaa gctaaataga ggtttgtccg ttgtggacac   3240
gtatgctatt ctctccaaca agaccgttga acaattgggg caagaagaat acgaaaaggt   3300
tgccattcta ggttggtgca ttgagttgtt gcaggcttac ttcttggtcg ccgatgatat   3360
gatggacaag tccattacca gaagaggcca accatgttgg tacaaggttc ctgaagttgg   3420
ggaaattgcc atcaatgacg cattcatgtt agaggctgct atctacaagc ttttgaaatc   3480
tcacttcaga aacgaaaaat actacataga tatcaccgaa ttgttccatg aggtcacctt   3540
ccaaaccgaa ttgggccaat tgatggactt aatcactgca cctgaagaca aagtcgactt   3600
```

-continued

```
gagtaagttc tccctaaaga agcactcctt catagttact ttcaagactg cttactattc    3660
tttctacttg cctgtcgcat tggccatgta cgttgccggt atcacggatg aaaaggattt    3720
gaaacaagcc agagatgtct tgattccatt gggtgaatac ttccaaattc aagatgacta    3780
cttagactgc ttcggtaccc cagaacagat cggtaagatc ggtacagata tccaagataa    3840
caaatgttct tgggtaatca acaaggcatt ggaacttgct tccgcagaac aaagaaagac    3900
tttagacgaa aattacggta agaaggactc agtcgcagaa gccaaatgca aaagatttt     3960 caatgacttg aaaattgaac agctatacca cgaatatgaa gagtctattg ccaaggattt    4020
gaaggccaaa atttctcagg tcgatgagtc tcgtggcttc aaagctgatg tcttaactgc    4080
gttcttgaac aaagtttaca agagaagcaa atagaactaa cgctaatcga taaaacatta    4140
gatttcaaac tagataagga ccatgtataa gaactatata cttccaatat aatatagtat    4200
aagctttaag atagtatctc tcgatctacc gttccacgtg actagtccaa ggattttttt    4260
taacccggga tatatgtgta cttttgcagtt atgacgccag atggcagtag tggaagatat    4320
tctttattga aaaatagctt gtcaccttac gtacaatctt gatccggagc ttttctttt    4380 ttgccgatta agaattcggt cgaaaaaaga aaaggagagg gccaagaggg agggcattgg    4440
tgactattga gcacgtgagt atacgtgatt aagcacacaa aggcagcttg gagtatgtct    4500
gttattaatt tcacaggtag ttctggtcca ttggtgaaag tttgcggctt gcagagcaca    4560
gaggccgcag aatgtgctct agattccgat gctgacttgc tgggtattat atgtgtgccc    4620
aatagaaaga gaacaattga cccggttatt gcaaggaaaa tttcaagtct tgtaaaagca    4680
tataaaaata gttcaggcac tccgaaatac ttggttggcg tgtttcgtaa tcaacctaag    4740
gaggatgttt tggctctggt caatgattac ggcattgata tcgtccaact gcatggagat    4800
gagtcgtggc aagaatacca agagttcctc ggtttgccag ttattaaaag actcgtattt    4860
ccaaaagact gcaacatact actcagtgca gcttcacaga aacctcattc gtttattccc    4920
ttgtttgatt cagaagcagg tgggacaggt gaacttttgg attggaactc gatttctgac    4980
tgggttggaa ggcaagagag ccccgaaagc ttacatttta tgttagctgg tggactgacg    5040
ccgtttaaac                                                            5050
```

<210> SEQ ID NO 3
<211> LENGTH: 30
<212> TYPE: DNA
<213> ORGANISM: Artificial Sequence
<220> FEATURE:
<223> OTHER INFORMATION: Synthetic, Primer 61-67-CPK001-G

<400> SEQUENCE: 3

```
gtttaaacta ctattagctg aattgccact                                        30
```

<210> SEQ ID NO 4
<211> LENGTH: 46
<212> TYPE: DNA
<213> ORGANISM: Artificial Sequence
<220> FEATURE:
<223> OTHER INFORMATION: Synthetic, Primer 61-67-CPK002-G

<400> SEQUENCE: 4

```
actgcaaagt acacatatat cccgggtgtc agctcttta gatcgg                     46
```

<210> SEQ ID NO 5
<211> LENGTH: 46
<212> TYPE: DNA
<213> ORGANISM: Artificial Sequence
<220> FEATURE:

-continued

<223> OTHER INFORMATION: Synthetic, Primer 61-67-CPK003-G

<400> SEQUENCE: 5
ccgatctaaa agagctgaca cccgggatat atgtgtactt tgcagt               46

<210> SEQ ID NO 6
<211> LENGTH: 30
<212> TYPE: DNA
<213> ORGANISM: Artificial Sequence
<220> FEATURE:
<223> OTHER INFORMATION: Synthetic, Primer 61-67-CPK004-G

<400> SEQUENCE: 6
gtttaaacgg cgtcagtcca ccagctaaca                                30

<210> SEQ ID NO 7
<211> LENGTH: 35
<212> TYPE: DNA
<213> ORGANISM: Artificial Sequence
<220> FEATURE:
<223> OTHER INFORMATION: Synthetic, Primer 61-67-CPK025-G

<400> SEQUENCE: 7 tcccccggg ttaaaaaaaa tccttggact agtca                           35

<210> SEQ ID NO 8
<211> LENGTH: 47
<212> TYPE: DNA
<213> ORGANISM: Artificial Sequence
<220> FEATURE:
<223> OTHER INFORMATION: Synthetic, Primer 61-67-CPK050-G

<400> SEQUENCE: 8 aattttttgaa aattcaatat aaatggcttc agaaaaagaa attagga            47

<210> SEQ ID NO 9
<211> LENGTH: 47
<212> TYPE: DNA
<213> ORGANISM: Artificial Sequence
<220> FEATURE:
<223> OTHER INFORMATION: Synthetic, Primer 61-67-CPK051-G

<400> SEQUENCE: 9
tcctaatttc tttttctgaa gccatttata ttgaattttc aaaaatt             47

<210> SEQ ID NO 10
<211> LENGTH: 51
<212> TYPE: DNA
<213> ORGANISM: Artificial Sequence
<220> FEATURE:
<223> OTHER INFORMATION: Synthetic, Primer 61-67-CPK052-G

<400> SEQUENCE: 10
agttttcacc aattggtctg cagccattat agtttttttct ccttgacgtt a       51

<210> SEQ ID NO 11
<211> LENGTH: 51
<212> TYPE: DNA
<213> ORGANISM: Artificial Sequence
<220> FEATURE:
<223> OTHER INFORMATION: Synthetic, Primer 61-67-CPK053-G

<400> SEQUENCE: 11
taacgtcaag gagaaaaaac tataatggct gcagaccaat tggtgaaaac t        51

<210> SEQ ID NO 12

```
<211> LENGTH: 35
<212> TYPE: DNA
<213> ORGANISM: Artificial Sequence
<220> FEATURE:
<223> OTHER INFORMATION: Synthetic, Primer 61-67-CPK031-G

<400> SEQUENCE: 12
tcccccgggg agttatgaca attacaacaa cagaa                                35

<210> SEQ ID NO 13
<211> LENGTH: 5488
<212> TYPE: DNA
<213> ORGANISM: Artificial Sequence
<220> FEATURE:
<223> OTHER INFORMATION: Synthetic, URA3_PGAL10-ERG13_PGAL1-tHMGR_URA3
      insert of expression plasmid pAM491

<400> SEQUENCE: 13
gtttaaactt gctaaattcg agtgaaacac aggaagacca gaaatcctc atttcatcca        60 tattaacaat aatttcaaat gtttatttgc attatttgaa actagggaag acaagcaacg      120
aaacgttttt gaaattttg agtattttca ataaatttgt agaggactca gatattgaaa       180
aaaagctaca gcaattaata cttgataaga agagtattga gaagggcaac ggttcatcat      240
ctcatggatc tgcacatgaa caaacaccag agtcaaacga cgttgaaatt gaggctactg      300
cgccaattga tgacaataca gacgatgata acaaaccgaa gttatctgat gtagaaaagg      360
attaaagatg ctaagagata gtgatgatat tcataaata atgtaattct atatatgtta       420
attccttttt ttgcgaggca tatttatggt gaaggataag ttttgaccat caaagaaggt      480
taatgtggct gtggtttcag ggtccatacc cgggagttat gacaattaca acaacagaat      540
tctttctata tatgcacgaa cttgtaatat ggaagaaatt atgacgtaca aactataaag      600
taaatatttt acgtaacaca tggtgctgtt gtgcttcttt ttcaagagaa taccaatgac      660
gtatgactaa gttaggatt taatgcaggt gacggaccca tctttcaaac gatttatatc       720
agtggcgtcc aaattgttag gttttgttgg ttcagcaggt ttcctgttgt gggtcatatg      780
actttgaacc aaatggccgg ctgctagggc agcacataag gataattcac ctgccaagac      840
ggcacaggca actattcttg ctaattgacg tgcgttggta ccaggagcgg tagcatgtgg      900
gcctcttaca cctaataagt ccaacatggc accttgtggt tctagaacag taccaccacc      960
gatggtacct acttcgatgg atggcatgga tacggaaatt ctcaaatcac cgtccacttc     1020
tttcatcaat gttatacagt tggaactttc gacattttgt gcaggatctt gtcctaatgc     1080
caagaaaaca gctgtcacta aattagctgc atgtgcgtta aatccaccaa cagacccagc     1140
cattgcagat ccaaccaaat tcttagcaat gttcaactca accatgcgg aaacatcact      1200 ttttaacact tttctgacaa catcaccagg aatagtagct tctgcgacga cactcttacc     1260
acgaccttcg atccagttga tggcagctgg tttttgtcg gtacagtagt taccagaaac      1320
ggagacaacc tccatatctt cccagccata ctcttctacc atttgcttta atgagtattc     1380
gacaccctta gaaatcatat tcatacccat tgcgtcacca gtagttgttc taaatctcat     1440
gaagagtaaa tctcctgcta gacaagtttg aatatgttgc agacgtgcaa atcttgatgt     1500
agagttaaaa gctttttaa ttgcgttttg tccctcttct gagtctaacc atatcttaca      1560
ggcaccagat ctttttcaaag ttgggaaacg gactactggg cctcttgtca taccatcctt    1620
agttaaaaca gttgttgcac caccgccagc attgattgcc ttacagccac gcatggcaga    1680
agctaccaaa caacccctctg tagttgccat tggtatatga taagatgtac catcgataac    1740
caaggggcct ataacaccaa cgggcaaagg catgtaacct ataacatttt cacaacaagc    1800
```

```
gccaaatacg cggtcgtagt cataattttt atatggtaaa cgatcagatg ctaatacagg    1860
agcttctgcc aaaattgaaa gagccttcct acgtaccgca accgctctcg tagtatcacc    1920 taatttttc tccaaagcgt acaaaggtaa cttaccgtga ataaccaagg cagcgacctc    1980
tttgttcttc aattgttttg tatttccact acttaataat gcttctaatt cttctaaagg    2040
acgtattttc ttatccaagc tttcaatatc gcgggaatca tcttcctcac tagatgatga    2100
aggtcctgat gagctcgatt gcgcagatga taaacttttg actttcgatc cagaaatgac    2160
tgttttattg gttaaaactg gtgtagaagc cttttgtaca ggagcagtaa aagacttctt    2220
ggtgacttca gtcttcacca attggtctgc agccattata gttttttctc cttgacgtta    2280
aagtatagag gtatattaac aattttttgt tgatactttt atgacatttg aataagaagt    2340
aatacaaacc gaaaatgttg aaagtattag ttaaagtggt tatgcagctt ttgcatttat    2400
atatctgtta atagatcaaa aatcatcgct tcgctgatta attacccag aaataaggct    2460 aaaaaactaa tcgcattatt atcctatggt tgttaatttg attcgttgat ttgaaggttt    2520
gtggggccag ttactgcca attttcctc ttcataacca taaaagctag tattgtagaa    2580
tctttattgt tcggagcagt gcggcgcgag gcacatctgc gtttcaggaa cgcgaccggt    2640
gaagaccagg acgcacggag gagagtcttc cgtcggaggg ctgtcgcccg ctcggcggct    2700
tctaatccgt acttcaatat agcaatgagc agttaagcgt attactgaaa gttccaaaga    2760 gaaggtttt ttaggctaag ataatggggc tctttacatt tccacaacat ataagtaaga    2820
ttagatatgg atatgtatat ggtggtattg ccatgtaata tgattattaa acttctttgc    2880
gtccatccaa aaaaaagta agaattttg aaaattcaat ataaatgaaa ctctcaacta    2940
aactttgttg gtgtggtatt aaaggaagac ttaggccgca aaagcaacaa caattacaca    3000
atacaaactt gcaaatgact gaactaaaaa acaaaagac cgctgaacaa aaaaccagac    3060
ctcaaaatgt cggtattaaa ggtatccaaa tttacatccc aactcaatgt gtcaaccaat    3120
ctgagctaga gaaatttgat ggcgtttctc aaggtaaata cacaattggt ctgggccaaa    3180
ccaacatgtc ttttgtcaat gacagagaag atatctactc gatgtcccta actgttttgt    3240
ctaagttgat caagagttac aacatcgaca ccaacaaaat tggtagatta gaagtcggta    3300
ctgaaactct gattgacaag tccaagtctg tcaagtctgt cttgatgcaa ttgtttggtg    3360
aaaacactga cgtcgaaggt attgacacgc ttaatgcctg ttacggtggt accaacgcgt    3420
tgttcaactc tttgaactgg attgaatcta acgcatggga tggtagagac gccattgtag    3480
tttgcggtga tattgccatc tacgataagg gtgccgcaag accaaccggt ggtgccggta    3540
ctgttgctat gtggatcggt cctgatgctc caattgtatt tgactctgta agagcttctt    3600
acatggaaca cgcctacgat ttttacaagc cagatttcac cagcgaatat ccttacgtcg    3660
atggtcattt ttcattaact tgttacgtca aggctcttga tcaagtttac aagagttatt    3720
ccaagaaggc tatttctaaa gggttggtta gcgatcccgc tggttcggat gctttgaacg    3780
ttttgaaata tttcgactac aacgttttcc atgttccaac ctgtaaattg gtcacaaaat    3840
catacggtag attactatat aacgatttca gagccaatcc tcaattgttc ccagaagttg    3900
acgccgaatt agctactcgc gattatgacg aatctttaac cgataagaac attgaaaaaa    3960
cttttgttaa tgttgctaag ccattccaca agagagagt tgcccaatct ttgattgttc    4020
caacaaacac aggtaacatg tacaccgcat ctgtttatgc cgcctttgca tctctattaa    4080
actatgttgg atctgacgac ttacaaggca agcgtgttgg tttattttct tacggttccg    4140
gtttagctgc atctctatat tcttgcaaaa ttgttggtga cgtccaacat attatcaagg    4200
```

```
aattagatat tactaacaaa ttagccaaga gaatcaccga aactccaaag gattacgaag    4260
ctgccatcga attgagagaa atgcccatt tgaagaagaa cttcaaacct caaggttcca    4320
ttgagcattt gcaaagtggt gtttactact tgaccaacat cgatgacaaa tttagaagat    4380
cttacgatgt taaaaaataa tcttcccca tcgattgcat cttgctgaac ccccttcata    4440
aatgctttat ttttttggca gcctgctttt tttagctctc atttaataga gtagtttttt    4500
aatctatata ctaggaaaac tctttattta ataacaatga tatatatata cccgggaagc    4560
ttttcaattc atcttttttt tttttgttct ttttttgat tccggtttct ttgaaattt    4620 tttgattcgg taatctccga gcagaaggaa gaacgaagga aggagcacag acttagattg    4680
gtatatatac gcatatgtgg tgttgaagaa acatgaaatt gcccagtatt cttaacccaa    4740
ctgcacagaa caaaaacctg caggaaacga agataaatca tgtcgaaagc tacatataag    4800
gaacgtgctg ctactcatcc tagtcctgtt gctgccaagc tatttaatat catgcacgaa    4860
aagcaaacaa acttgtgtgc ttcattggat gttcgtacca ccaaggaatt actggagtta    4920
gttgaagcat taggtcccaa aatttgttta ctaaaaacac atgtggatat cttgactgat    4980
ttttccatgg agggcacagt taagccgcta aaggcattat ccgccaagta caatttttta    5040
ctcttcgaag acagaaaatt tgctgacatt ggtaatacag tcaaattgca gtactctgcg    5100
ggtgtataca gaatagcaga atgggcagac attacgaatg cacacggtgt ggtgggccca    5160
ggtattgtta gcggtttgaa gcaggcggcg gaagaagtaa caaggaacc tagaggcctt    5220 ttgatgttag cagaattgtc atgcaagggc tccctagcta ctggagaata tactaagggt    5280
actgttgaca ttgcgaagag cgacaaagat tttgttatcg gctttattgc tcaaagagac    5340
atgggtggaa gagatgaagg ttacgattgg ttgattatga cacccggtgt gggtttagat    5400
gacaagggag acgcattggg tcaacagtat agaaccgtgg atgatgtggt ctctacagga    5460
tctgacatta ttattgttgg gtttaaac                                        5488

<210> SEQ ID NO 14
<211> LENGTH: 30
<212> TYPE: DNA
<213> ORGANISM: Artificial Sequence
<220> FEATURE:
<223> OTHER INFORMATION: Synthetic, Primer 61-67-CPK005-G

<400> SEQUENCE: 14
gtttaaactt gctaaattcg agtgaaacac                                       30

<210> SEQ ID NO 15
<211> LENGTH: 46
<212> TYPE: DNA
<213> ORGANISM: Artificial Sequence
<220> FEATURE:
<223> OTHER INFORMATION: Synthetic, Primer 61-67-CPK006-G

<400> SEQUENCE: 15
aaagatgaat tgaaaagctt cccgggtatg gaccctgaaa ccacag                     46

<210> SEQ ID NO 16
<211> LENGTH: 46
<212> TYPE: DNA
<213> ORGANISM: Artificial Sequence
<220> FEATURE:
<223> OTHER INFORMATION: Synthetic, Primer 61-67-CPK007-G

<400> SEQUENCE: 16
ctgtggtttc agggtccata cccgggaagc ttttcaattc atcttt                     46
```

```
<210> SEQ ID NO 17
<211> LENGTH: 30
<212> TYPE: DNA
<213> ORGANISM: Artificial Sequence
<220> FEATURE:
<223> OTHER INFORMATION: Synthetic, Primer 61-67-CPK008-G

<400> SEQUENCE: 17
gtttaaaccc aacaataata atgtcagatc                                    30

<210> SEQ ID NO 18
<211> LENGTH: 30
<212> TYPE: DNA
<213> ORGANISM: Artificial Sequence
<220> FEATURE:
<223> OTHER INFORMATION: Synthetic, Primer 61-67-CPK032-G

<400> SEQUENCE: 18 tcccccggg tatatatata tcattgttat                                     30

<210> SEQ ID NO 19
<211> LENGTH: 47
<212> TYPE: DNA
<213> ORGANISM: Artificial Sequence
<220> FEATURE:
<223> OTHER INFORMATION: Synthetic, Primer 61-67-CPK054-G

<400> SEQUENCE: 19
aatttttgaa aattcaatat aaatgaaact ctcaactaaa ctttgtt                 47

<210> SEQ ID NO 20
<211> LENGTH: 51
<212> TYPE: DNA
<213> ORGANISM: Artificial Sequence
<220> FEATURE:
<223> OTHER INFORMATION: Synthetic, Primer 61-67-CPK052-G

<400> SEQUENCE: 20
agttttcacc aattggtctg cagccattat agttttttct ccttgacgtt a            51

<210> SEQ ID NO 21
<211> LENGTH: 47
<212> TYPE: DNA
<213> ORGANISM: Artificial Sequence
<220> FEATURE:
<223> OTHER INFORMATION: Synthetic, Primer 61-67-CPK055-G

<400> SEQUENCE: 21
aacaaagttt agttgagagt ttcatttata ttgaattttc aaaaatt                 47

<210> SEQ ID NO 22
<211> LENGTH: 35
<212> TYPE: DNA
<213> ORGANISM: Artificial Sequence
<220> FEATURE:
<223> OTHER INFORMATION: Synthetic, Primer 61-67-CPK031-G

<400> SEQUENCE: 22 tcccccggg agttatgaca attacaacaa cagaa                               35

<210> SEQ ID NO 23
<211> LENGTH: 51
<212> TYPE: DNA
<213> ORGANISM: Artificial Sequence
<220> FEATURE:
<223> OTHER INFORMATION: Synthetic, Primer 61-67-CPK053-G
```

<400> SEQUENCE: 23

```
taacgtcaag gagaaaaaac tataatggct gcagaccaat tggtgaaaac t          51
```

<210> SEQ ID NO 24
<211> LENGTH: 4933
<212> TYPE: DNA
<213> ORGANISM: Artificial Sequence
<220> FEATURE:
<223> OTHER INFORMATION: Synthetic, ADE1_PGAL10-IDI1_PGAL1-tHMGR_ADE1
      insert of expression plasmid pAM493

<400> SEQUENCE: 24

```
gtttaaacta ctcagtatat taagtttcga attgaagggc gaactcttat tcgaagtcgg    60
agtcaccaca acacttccgc ccatactctc cgaatcctcg tttcctaaag taagtttact   120
tccacttgta ggcctattat taatgatatc tgaataatcc tctattaggg ttggatcatt   180
cagtagcgcg tgcgattgaa aggagtccat gcccgacgtc gacgtgatta gcgaaggcgc   240
gtaaccattg tcatgtctag cagctataga actaacctcc ttgacaccac ttgcggaagt   300
ctcatcaaca tgctcttcct tattactcat tctcttacca agcagagaat gttatctaaa   360
aactacgtgt atttcacctc tttctcgact tgaacacgtc caactcctta agtactacca   420
cagccaggaa agaatggatc cagttctaca cgatagcaaa gcagaaaaca caaccagcgt   480
accctgtag aagcttcttt gtttacagca cttgatccat gtagccatac tcgaaatttc   540
aactcatctg aaacttttcc tgaaggttga aaaagaatgc cataagggtc acccgaagct   600
tattcacgcc cgggagttat gacaattaca acaacagaat tctttctata tatgcacgaa   660
cttgtaatat ggaagaaatt atgacgtaca aactataaag taaatatttt acgtaacaca   720
tggtgctgtt gtgcttcttt ttcaagagaa taccaatgac gtatgactaa gtttaggatt   780
taatgcaggt gacggaccca tctttcaaac gatttatatc agtggcgtcc aaattgttag   840
gttttgttgg ttcagcaggt ttcctgttgt gggtcatatg actttgaacc aaatggccgg   900
ctgctagggc agcacataag gataattcac ctgccaagac ggcacaggca actattcttg   960
ctaattgacg tgcgttggta ccaggagcgg tagcatgtgg gcctcttaca cctaataagt  1020
ccaacatggc accttgtggt tctagaacag taccaccacc gatggtacct acttcgatgg  1080
atggcatgga tacggaaatt ctcaaatcac cgtccacttc tttcatcaat gttatacagt  1140
tggaactttc gacattttgt gcaggatctt gtcctaatgc caagaaaaca gctgtcacta  1200
aattagctgc atgtgcgtta aatccaccaa cagacccagc cattgcagat ccaaccaaat  1260
tcttagcaat gttcaactca accaatgcgg aaacatcact ttttaacact tttctgacaa  1320
catcaccagg aatagtagct tctgcgacga cactcttacc acgaccttcg atccagttga  1380
tggcagctgg ttttttgtcg gtacagtagt taccagaaac ggagacaacc tccatatctt  1440
cccagccata ctcttctacc atttgcttta atgagtattc gacaccctta gaaatcatat  1500
tcatacccat tgcgtcacca gtagttgttc taaatctcat gaagagtaaa tctcctgcta  1560
gacaagtttg aatatgttgc agacgtgcaa atcttgatgt agagttaaaa gcttttttaa  1620
ttgcgttttg tccctcttct gagtctaacc atatcttaca ggcaccagat cttttcaaag  1680
ttgggaaacg gactactggg cctcttgtca taccatcctt agttaaaaca gttgttgcac  1740
caccgccagc attgattgcc ttacagccac gcatggcaga agctaccaaa caaccctctg  1800
tagttgccat tggtatatga taagatgtac catcgataac caaggggcct ataacaccaa  1860
cgggcaaagg catgtaacct ataacatttt cacaacaagc gccaaatacg cggtcgtagt  1920
```

```
cataatttttt atatggtaaa cgatcagatg ctaatacagg agcttctgcc aaaattgaaa    1980
gagccttcct acgtaccgca accgctctcg tagtatcacc taattttttc tccaaagcgt    2040
acaaaggtaa cttaccgtga ataaccaagg cagcgacctc tttgttcttc aattgttttg    2100
tatttccact acttaataat gcttctaatt cttctaaagg acgtattttc ttatccaagc    2160
tttcaatatc gcgggaatca tcttcctcac tagatgatga aggtcctgat gagctcgatt    2220
gcgcagatga taaacttttg actttcgatc cagaaatgac tgttttattg gttaaaactg    2280
gtgtagaagc cttttgtaca ggagcagtaa aagacttctt ggtgacttca gttttcacca    2340
attggtctgc agccattata gttttttctc cttgacgtta aagtatagag gtatattaac    2400
aattttttgt tgatactttt atgacatttg aataagaagt aatacaaacc gaaaatgttg    2460
aaagtattag ttaaagtggt tatgcagctt ttgcatttat atatctgtta atagatcaaa    2520
aatcatcgct tcgctgatta attaccccag aaataaggct aaaaaactaa tcgcattatt    2580
atcctatggt tgttaatttg attcgttgat ttgaaggttt gtggggccag ttactgcca    2640 atttttcctc ttcataacca taaaagctag tattgtagaa tctttattgt tcggagcagt    2700
gcggcgcgag gcacatctgc gtttcaggaa cgcgaccggt gaagaccagg acgcacggag    2760
gagagtcttc cgtcggaggg ctgtcgcccg ctcggcggct tctaatccgt acttcaatat    2820
agcaatgagc agttaagcgt attactgaaa gttccaaaga aaggtttttt ttaggctaag    2880 ataatgggc tctttacatt tccacaacat ataagtaaga ttagatatgg atatgtatat     2940
ggtggtattg ccatgtaata tgattattaa acttctttgc gtccatccaa aaaaaaagta    3000 agaattttg aaaattcaat ataaatgact gccgacaaca atagtatgcc ccatggtgca     3060
gtatctagtt acgccaaatt agtgcaaaac caaacacctg aagacatttt ggaagagttt    3120
cctgaaatta ttccattaca acaaagacct aatacccgat ctagtgagac gtcaaatgac    3180
gaaagcggag aaacatgttt ttctggtcat gatgaggagc aaattaagtt aatgaatgaa    3240
aattgtattg ttttggattg ggacgataat gctattggtg ccggtaccaa gaaagtttgt    3300
catttaatgg aaaatattga aaagggttta ctacatcgtg cattctccgt ctttattttc    3360
aatgaacaag gtgaattact tttacaacaa agagccactg aaaaaataac tttccctgat    3420
ctttggacta acacatgctg ctctcatcca ctatgtattg atgacgaatt aggtttgaag    3480
ggtaagctag acgataagat taagggcgct attactgcgg cggtgagaaa actagatcat    3540
gaattaggta ttccagaaga tgaaactaag acaaggggta agtttcactt tttaaacaga    3600
atccattaca tggcaccaag caatgaacca tggggtgaac atgaaattga ttacatccta    3660
ttttataaga tcaacgctaa agaaaacttg actgtcaacc caaacgtcaa tgaagttaga    3720
gacttcaaat gggtttcacc aaatgatttg aaaactatgt ttgctgaccc aagttacaag    3780
tttacgcctt ggtttaagat tatttgcgag aattacttat tcaactggtg ggagcaatta    3840
gatgaccttt ctgaagtgga aaatgacagg caaattcata gaatgctata caacgcgtc    3900 aataatatag gctacataaa aatcataata actttgttat catagcaaaa tgtgatataa    3960
aacgtttcat ttcacctgaa aaatagtaaa aataggcgac aaaaatcctt agtaatatgt    4020
aaactttatt ttctttatttt acccgggagt cagtctgact cttgcgagag atgaggatgt    4080
aataatacta atctcgaaga tgccatctaa tacatataga catacatata tatatatata    4140
cattctatat attcttaccc agattctttg aggtaagacg gttgggtttt atcttttgca    4200
gttggtacta ttaagaacaa tcgaatcata agcattgctt acaaagaata cacatacgaa    4260
atattaacga taatgtcaat tacgaagact gaactggacg gtatattgcc attggtggcc    4320
```

-continued

```
agaggtaaag ttagagacat atatgaggta gacgctggta cgttgctgtt tgttgctacg    4380
gatcgtatct ctgcatatga cgttattatg gaaaacagca ttcctgaaaa ggggatccta    4440
ttgaccaaac tgtcagagtt ctggttcaag ttcctgtcca acgatgttcg taatcatttg    4500
gtcgacatcg ccccaggtaa gactattttc gattatctac ctgcaaaatt gagcgaacca    4560
aagtacaaaa cgcaactaga agaccgctct ctattggttc acaaacataa actaattcca    4620
ttggaagtaa ttgtcagagg ctacatcacc ggatctgctt ggaaagagta cgtaaaaaca    4680
ggtactgtgc atggtttgaa acaacctcaa ggacttaaag aatctcaaga gttcccagaa    4740
ccaatcttca ccccatcgac caaggctgaa caaggtgaac atgacgaaaa catctctcct    4800
gcccaggccg ctgagctggt gggtgaagat ttgtcacgta gagtggcaga actggctgta    4860
aaactgtact ccaagtgcaa agattatgct aaggagaagg gcatcatcat cgcagacact    4920
aaattgttta aac                                                      4933
```

<210> SEQ ID NO 25
<211> LENGTH: 30
<212> TYPE: DNA
<213> ORGANISM: Artificial Sequence
<220> FEATURE:
<223> OTHER INFORMATION: Synthetic, Primer 61-67-CPK009-G

<400> SEQUENCE: 25

```
gtttaaacta ctcagtatat taagtttcga                                      30
```

<210> SEQ ID NO 26
<211> LENGTH: 70
<212> TYPE: DNA
<213> ORGANISM: Artificial Sequence
<220> FEATURE:
<223> OTHER INFORMATION: Synthetic, Primer 61-67-CPK010-G

<400> SEQUENCE: 26

```
atctctcgca agagtcagac tgactcccgg gcgtgaataa gcttcgggtg acccttatgg    60
cattcttttt                                                           70
```

<210> SEQ ID NO 27
<211> LENGTH: 70
<212> TYPE: DNA
<213> ORGANISM: Artificial Sequence
<220> FEATURE:
<223> OTHER INFORMATION: Synthetic, Primer 61-67-CPK011-G

<400> SEQUENCE: 27

```
aaaaagaatg ccataagggt cacccgaagc ttattcacgc ccgggagtca gtctgactct    60
tgcgagagat                                                           70
```

<210> SEQ ID NO 28
<211> LENGTH: 30
<212> TYPE: DNA
<213> ORGANISM: Artificial Sequence
<220> FEATURE:
<223> OTHER INFORMATION: Synthetic, Primer 61-67-CPK012-G

<400> SEQUENCE: 28

```
gtttaaacaa tttagtgtct gcgatgatga                                      30
```

<210> SEQ ID NO 29
<211> LENGTH: 30
<212> TYPE: DNA
<213> ORGANISM: Artificial Sequence
<220> FEATURE:

```
<223> OTHER INFORMATION: Synthetic, Primer 61-67-CPK047-G

<400> SEQUENCE: 29 tcccccggg taaataaaga aaataaagtt                                      30

<210> SEQ ID NO 30
<211> LENGTH: 47
<212> TYPE: DNA
<213> ORGANISM: Artificial Sequence
<220> FEATURE:
<223> OTHER INFORMATION: Synthetic, Primer 61-67-CPK064-G

<400> SEQUENCE: 30 aattttgaa aattcaatat aaatgactgc cgacaacaat agtatgc                   47

<210> SEQ ID NO 31
<211> LENGTH: 51
<212> TYPE: DNA
<213> ORGANISM: Artificial Sequence
<220> FEATURE:
<223> OTHER INFORMATION: Synthetic, Primer 61-67-CPK052-G

<400> SEQUENCE: 31
agttttcacc aattggtctg cagccattat agttttttct ccttgacgtt a             51

<210> SEQ ID NO 32
<211> LENGTH: 47
<212> TYPE: DNA
<213> ORGANISM: Artificial Sequence
<220> FEATURE:
<223> OTHER INFORMATION: Synthetic, Primer 61-67-CPK065-G

<400> SEQUENCE: 32
gcatactatt gttgtcggca gtcatttata ttgaattttc aaaaatt                  47

<210> SEQ ID NO 33
<211> LENGTH: 51
<212> TYPE: DNA
<213> ORGANISM: Artificial Sequence
<220> FEATURE:
<223> OTHER INFORMATION: Synthetic, Primer 61-67-CPK053-G

<400> SEQUENCE: 33
taacgtcaag gagaaaaaac tataatggct gcagaccaat tggtgaaaac t             51

<210> SEQ ID NO 34
<211> LENGTH: 6408
<212> TYPE: DNA
<213> ORGANISM: Artificial Sequence
<220> FEATURE:
<223> OTHER INFORMATION: Synthetic, HIS3_PGAL10-ERG10_PGAL1-ERG12_HIS3
      insert of expression plasmid pAM495

<400> SEQUENCE: 34
gtttaaacta ttgtgagggt cagttatttc atccagatat aacccgagag gaaacttctt    60
agcgtctgtt ttcgtaccat aaggcagttc atgaggtata ttttcgttat tgaagcccag   120
ctcgtgaatg cttaatgctg ctgaactggt gtccatgtcg cctaggtacg caatctccac   180
aggctgcaaa ggttttgtct caagagcaat gttattgtgc accccgtaat tggtcaacaa   240
gtttaatctg tgcttgtcca ccagctctgt cgtaaccttc agttcatcga ctatctgaag   300
aaatttacta ggaatagtgc catggtacag caaccgagaa tggcaatttc tactcgggtt   360
cagcaacgct gcataaacgc tgttggtgcc gtagacatat cgaagatag gattatcatt   420 cataagtttc agagcaatgt ccttattctg gaacttggat ttatggctct tttggtttaa   480
```

-continued

```
tttcgcctga ttcttgatct cctttagctt ctcgacgtgg gccttttct tgccatatgg    540 atccgctgca cggtcctgtt ccctagcatg tacgtgagcg tatttccttt taaaccacga    600
cgctttgtct tcattcaacg tttcccattg ttttttttcta ctattgcttt gctgtgggaa   660
aaacttatcg aaagatgacg acttttctt aattctcgtt ttaagagctt ggtgagcgct    720
aggagtcact gccaggtatc gtttgaacac ggcattagtc agggaagtca taacacagtc    780 cttcccgca attttctttt tctattactc ttggcctcct ctagtacact ctatattttt    840
ttatgcctcg gtaatgattt tcattttttt tttttccacc tagcggatga ctctttttt     900 ttcttagcga ttggcattat cacataatga attatacatt atataaagta atgtgatttc    960
ttcgaagaat atactaaagt ttagcttgcc tcgtccccgc cgggtcaccc ggccagcgac   1020
atggaggccc agaatacccct ccttgacagt cttgacgtgc gcagctcagg ggcatgatgt  1080
gactgtcgcc cgtacattta gcccatacat ccccatgtat aatcatttgc atccatacat   1140
tttgatggcc gcacggcgcg aagcaaaaat tacggctcct cgctgcagac ctgcgagcag   1200
ggaaacgctc ccctcacaga cgcgttgaat tgtccccacg ccgcgcccct gtagagaaat   1260 ataaaggtt aggatttgcc actgaggttc ttctttcata tacttccttt taaaatcttg    1320
ctaggataca gttctcacat cacatccgaa cataaacaac catggcagaa ccagcccaaa   1380
aaaagcaaaa acaaactgtt caggagcgca aggcgtttat ctcccgtatc actaatgaaa   1440
ctaaaattca aatcgctatt tcgctgaatg gtggttatat tcaaataaaa gattcgattc   1500
ttcctgcaaa gaaggatgac gatgtagctt cccaagctac tcagtcacag gtcatcgata   1560
ttcacacagg tgttggcttt ttggatcata tgatccatgc gttggcaaaa cactctggtt   1620
ggtctcttat tgttgaatgt attggtgacc tgcacattga cgatcaccat actaccgaag   1680
attgcggtat cgcattaggg caagcgttca agaagcaat gggtgctgtc cgtggtgtaa    1740
aaagattcgg tactgggttc gcaccattgg atgaggcgct atcacgtgcc gtagtcgatt    1800
tatctagtag accatttgct gtaatcgacc ttggattgaa gagagagatg attggtgatt    1860
tatccactga aatgattcca cacttttttgg aaagtttcgc ggaggcggcc agaattactt   1920
tgcatgttga ttgtctgaga ggtttcaacg atcaccacag aagtgagagt gcgttcaagg   1980
ctttggctgt tgccataaga gaagctattt ctagcaatgg caccaatgac gttccctcaa    2040
ccaaaggtgt tttgatgtga agtactgaca ataaaaagat tcttgttttc aagaacttgt   2100
catttgtata gttttttttat attgtagttg ttctatttta atcaaatgtt agcgtgatttt  2160 atattttttt tcgcctcgac atcatctgcc cagatgcgaa gttaagtgcg cagaaagtaa   2220
tatcatgcgt caatcgtatg tgaatgctgg tcgctatact gctgtcgatt cgatactaac   2280
gccgccatcc acccgggatg gtctgcttaa atttcattct gtcttcgaaa gctgaattga   2340
tactacgaaa aatttttttt tgtttctctt tctatcttta ttacataaaa cttcatacac   2400
agttaagatt aaaaacaact aataaataat gcctatcgca aattagctta tgaagtccat   2460
ggtaaattcg tgtttcctgg caataataga tcgtcaattt gttgctttgt ggtagtttta    2520
ttttcaaata attggaatac tagggatttg attttaagat cttattcaa attttttgcg    2580 cttaacaaac agcagccagt cccacccaag tctgtttcaa atgtctcgta actaaaatca   2640
tcttgcaatt tcttttgaa actgtcaatt tgctcttgag taatgtctct tcgtaacaaa     2700
gtcaaagagc aaccgccgcc accagcaccg gtaagttttg tggagccaat tctcaaatca   2760
tcgctcagat ttttaataag ttctaatcca ggatgagaaa caccgattga gacaagcagt    2820
ccatgattta ttcttatcaa ttccaatagt tgttcataca gttcattatt agtttctaca    2880
```

-continued

```
gcctcgtcat cggtgccttt acatttactt aacttagtca tgatctctaa gccttgtagg    2940
gcacattcac ccatggcatc tagaattggc ttcataactt caggaaattt ctcggtgacc    3000
aacacacgaa cgcgagcaac aagatctttt gtagaccttg gaattctagt ataggttagg    3060
atcattggaa tggctgggaa atcatctaag aacttaaaat tgtttgtgtt tattgttcca    3120
ttatgtgagt cttttcaaa tagcagggca ttaccataag tggccacagc gttatctatt     3180
cctgaagggg taccgtgaat acacttttca cctatgaagg cccattgatt cactatatgc    3240
ttatcgtttt ctgacagctt ttccaagtca ttagatccta ttaaccccc caagtaggcc     3300
atagctaagg ccagtgatac agaaatagag gcgcttgagc ccacccagc accgatgggt     3360
aaagtagact ttaaagaaaa cttaatattc ttggcatggg ggcataggca aacaaacata    3420
tacaggaaac aaaacgctgc atggtagtgg aaggattcgg atagttgagc taacaacgga    3480
tccaaaagac taacgagttc ctgagacaag ccatcggtgg cttgttgagc cttggccaat    3540
ttttgggagt ttacttgatc ctcggtgatg gcattgaaat cattgatgga ccacttatga    3600
ttaaagctaa tgtccgggaa gtccaattca atagtatctg gtgcagatga ctcgcttatt    3660
agcaggtagg ttctcaacgc agacacacta gcagcgacgg caggcttgtt gtacacagca    3720
gagtgttcac caaaaataat aacctttccc ggtgcagaag ttaagaacgg taatgacatt    3780
atagttttt ctccttgacg ttaaagtata gaggtatatt aacaattttt tgttgatact     3840
tttatgacat ttgaataaga agtaatacaa accgaaaatg ttgaaagtat tagttaaagt    3900
ggttatgcag cttttgcatt tatatatctg ttaatagatc aaaaatcatc gcttcgctga    3960
ttaattaccc cagaaataag gctaaaaaac taatcgcatt attatcctat ggttgttaat    4020
ttgattcgtt gatttgaagg tttgtggggc caggttactg ccaatttttc ctcttcataa    4080
ccataaaagc tagtattgta gaatctttat tgttcggagc agtgcggcgc gaggcacatc    4140
tgcgtttcag gaacgcgacc ggtgaagacc aggacgcacg gaggagagtc ttccgtcgga    4200
gggctgtcgc ccgctcggcg gcttctaatc cgtacttcaa tatagcaatg agcagttaag    4260
cgtattactg aaagttccaa agagaaggtt ttttaggct aagataatgg ggctctttac     4320
atttccacaa catataagta agattagata tggatatgta tatggtggta ttgccatgta    4380
atatgattat taaacttctt tgcgtccatc caaaaaaaa gtaagaattt ttgaaaattc     4440
aatataaatg tctcagaacg tttacattgt atcgactgcc agaaccccaa ttggttcatt    4500
ccagggttct ctatcctcca agacagcagt ggaattgggt gctgttgctt taaaaggcgc    4560
cttggctaag gttccagaat tggatgcatc caaggatttt gacgaaatta tttttggtaa    4620
cgttctttct gccaatttgg gccaagctcc ggccagacaa gttgctttgg ctgccggttt    4680
gagtaatcat atcgttgcaa gcacagttaa caaggtctgt gcatccgcta tgaaggcaat    4740
cattttgggt gctcaatcca tcaaatgtgg taatgctgat gttgtcgtag ctggtggttg    4800
tgaatctatg actaacgcac catactacat gccagcagcc cgtgcgggtg ccaaatttgg    4860
ccaaactgtt cttgttgatg gtgtcgaaag agatgggttg aacgatgcgt acgatggtct    4920
agccatgggt gtacacgcag aaaagtgtgc ccgtgattgg gatattacta gagaacaaca    4980
agacaatttt gccatcgaat cctaccaaaa atctcaaaaa tctcaaaagg aagtaaatt     5040
cgacaatgaa attgtacctg ttaccattaa gggatttaga ggtaagcctg atactcaagt    5100
cacgaaggac gaggaacctg ctagattaca cgttgaaaaa ttgagatctg caaggactgt    5160
tttccaaaaa gaaaacggta ctgttactgc cgctaacgct tctccaatca acgatggtgc    5220
tgcagccgtc atcttggttt ccgaaaaagt tttgaaggaa aagaatttga agcctttggc    5280
```

```
tattatcaaa ggttggggtg aggccgctca tcaaccagct gattttacat gggctccatc    5340
tcttgcagtt ccaaaggctt tgaaacatgc tggcatcgaa gacatcaatt ctgttgatta    5400
ctttgaattc aatgaagcct tttcggttgt cggtttggtg aacactaaga ttttgaagct    5460
agacccatct aaggttaatg tatatggtgg tgctgttgct ctaggtcacc cattgggttg    5520
ttctggtgct agagtggttg ttacactgct atccatctta cagcaagaag gaggtaagat    5580
cggtgttgcc gccatttgta atggtggtgg tggtgcttcc tctattgtca ttgaaaagat    5640
atgattacgt tctgcgattt tctcatgatc ttttttcataa aatacataaa tatataaatg    5700
gctttatgta taacaggcat aatttaaagt tttatttgcg attcatcgtt tttcaggtac    5760
tcaaacgctg aggtgtgcct tttgacttac ttttcccggg agaggctagc agaattaccc    5820
tccacgttga ttgtctgcga ggcaagaatg atcatcaccg tagtgagagt gcgttcaagg    5880
ctcttgcggt tgccataaga gaagccacct cgcccaatgg taccaacgat gttccctcca    5940 ccaaggtgt tcttatgtag tgacaccgat tatttaaagc tgcagcatac gatatatata    6000
catgtgtata tatgtatacc tatgaatgtc agtaagtatg tatacgaaca gtatgatact    6060
gaagatgaca aggtaatgca tcattctata cgtgtcattc tgaacgaggc gcgctttcct    6120
tttttctttt tgcttttttct ttttttttct cttgaactcg agaaaaaaaa tataaaagag    6180
atggaggaac gggaaaaagt tagttgtggt gataggtggc aagtggtatt ccgtaagaac    6240
aacaagaaaa gcatttcata ttatggctga actgagcgaa caagtgcaaa atttaagcat    6300
caacgacaac aacgagaatg gttatgttcc tcctcactta agaggaaaac caagaagtgc    6360
cagaaataac agtagcaact acaataacaa caacggcggc gtttaaac              6408

<210> SEQ ID NO 35
<211> LENGTH: 30
<212> TYPE: DNA
<213> ORGANISM: Artificial Sequence
<220> FEATURE:
<223> OTHER INFORMATION: Synthetic, Primer 61-67-CPK013-G

<400> SEQUENCE: 35
gtttaaacta ttgtgagggt cagttatttc                                      30

<210> SEQ ID NO 36
<211> LENGTH: 44
<212> TYPE: DNA
<213> ORGANISM: Artificial Sequence
<220> FEATURE:
<223> OTHER INFORMATION: Synthetic, Primer 61-67-CPK014alt-G

<400> SEQUENCE: 36
gcggggacga ggcaagctaa actttagtat attcttcgaa gaaa                      44

<210> SEQ ID NO 37
<211> LENGTH: 60
<212> TYPE: DNA
<213> ORGANISM: Artificial Sequence
<220> FEATURE:
<223> OTHER INFORMATION: Synthetic, Primer 61-67-CPK017-G

<400> SEQUENCE: 37
cgatactaac gccgccatcc acccgggaga ggctagcaga attaccctcc acgttgattg     60

<210> SEQ ID NO 38
<211> LENGTH: 30
<212> TYPE: DNA
<213> ORGANISM: Artificial Sequence
```

```
<220> FEATURE:
<223> OTHER INFORMATION: Synthetic, Primer 61-67-CPK018-G

<400> SEQUENCE: 38
gtttaaacgc cgccgttgtt gttattgtag                              30

<210> SEQ ID NO 39
<211> LENGTH: 30
<212> TYPE: DNA
<213> ORGANISM: Artificial Sequence
<220> FEATURE:
<223> OTHER INFORMATION: Synthetic, Primer 61-67-CPK035-G

<400> SEQUENCE: 39
tccccccggg aaaagtaagt caaaaggcac                              30

<210> SEQ ID NO 40
<211> LENGTH: 47
<212> TYPE: DNA
<213> ORGANISM: Artificial Sequence
<220> FEATURE:
<223> OTHER INFORMATION: Synthetic, Primer 61-67-CPK056-G

<400> SEQUENCE: 40
aatttttgaa aattcaatat aaatgtctca gaacgtttac attgtat           47

<210> SEQ ID NO 41
<211> LENGTH: 47
<212> TYPE: DNA
<213> ORGANISM: Artificial Sequence
<220> FEATURE:
<223> OTHER INFORMATION: Synthetic, Primer 61-67-CPK057-G

<400> SEQUENCE: 41
atacaatgta aacgttctga gacatttata ttgaattttc aaaaatt           47

<210> SEQ ID NO 42
<211> LENGTH: 51
<212> TYPE: DNA
<213> ORGANISM: Artificial Sequence
<220> FEATURE:
<223> OTHER INFORMATION: Synthetic, Primer 61-67-CPK058-G

<400> SEQUENCE: 42
tgcagaagtt aagaacggta atgacattat agttttttct ccttgacgtt a      51

<210> SEQ ID NO 43
<211> LENGTH: 30
<212> TYPE: DNA
<213> ORGANISM: Artificial Sequence
<220> FEATURE:
<223> OTHER INFORMATION: Synthetic, Primer 61-67-CPK040-G

<400> SEQUENCE: 43
tccccccggg atggtctgct taaatttcat                              30

<210> SEQ ID NO 44
<211> LENGTH: 51
<212> TYPE: DNA
<213> ORGANISM: Artificial Sequence
<220> FEATURE:
<223> OTHER INFORMATION: Synthetic, Primer 61-67-CPK059-G

<400> SEQUENCE: 44
taacgtcaag gagaaaaaac tataatgtca ttaccgttct taacttctgc a      51
```

```
<210> SEQ ID NO 45
<211> LENGTH: 44
<212> TYPE: DNA
<213> ORGANISM: Artificial Sequence
<220> FEATURE:
<223> OTHER INFORMATION: Synthetic, Primer 61-67-CPK015alt-G

<400> SEQUENCE: 45
tttcttcgaa gaatatacta aagtttagct tgcctcgtcc ccgc                44

<210> SEQ ID NO 46
<211> LENGTH: 60
<212> TYPE: DNA
<213> ORGANISM: Artificial Sequence
<220> FEATURE:
<223> OTHER INFORMATION: Synthetic, Primer 61-67-CPK016-G

<400> SEQUENCE: 46
caatcaacgt ggagggtaat tctgctagcc tctcccgggt ggatggcggc gttagtatcg    60

<210> SEQ ID NO 47
<211> LENGTH: 6087
<212> TYPE: DNA
<213> ORGANISM: Artificial Sequence
<220> FEATURE:
<223> OTHER INFORMATION: Synthetic, LEU2_PGAL10-ERG8_PGAL1-ERG19_LEU2
      insert of expression plasmid pAM497

<400> SEQUENCE: 47
gtttaaactt ttccaatagg tggttagcaa tcgtcttact ttctaacttt tcttaccttt    60
tacatttcag caatatatat atatatattt caaggatata ccattctaat gtctgcccct   120
aagaagatcg tcgttttgcc aggtgaccac gttggtcaag aaatcacagc cgaagccatt   180
aaggttctta aagctatttc tgatgttcgt tccaatgtca agttcgattt cgaaaatcat   240
ttaattggtg gtgctgctat cgatgctaca ggtgttccac ttccagatga ggcgctggaa   300
gcctccaaga aggctgatgc cgttttgtta ggtgctgtgg gtggtcctaa atgggggtacc   360 ggtagtgtta gacctgaaca aggttttacta aaaatccgta agaacttca attgtacgcc   420 aacttaagac catgtaactt tgcatccgac tctcttttag acttatctcc aatcaagcca   480
caatttgcta aagtactga cttcgttgtt gtcagagaat tagtgggagg tatttacttt   540
ggtaagagaa aggaagacgt ttagcttgcc tcgtccccgc cgggtcaccc ggccagcgac   600
atggaggccc agaataccct ccttgacagt cttgacgtgc gcagctcagg ggcatgatgt   660
gactgtcgcc cgtacattta gcccatacat ccccatgtat aatcatttgc atccatacat   720
tttgatggcc gcacggcgcg aagcaaaaat tacggctcct cgctgcagac ctgcgagcag   780
ggaaacgctc ccctcacaga cgcgttgaat tgtccccacg ccgcgcccct gtagagaaat   840
ataaaaggtt aggatttgcc actgaggttc ttctttcata tacttccttt taaaatcttg   900
ctaggataca gttctcacat cacatccgaa cataaacaac catggcagaa ccagcccaaa   960 aaagcaaaa acaaactgtt caggagcgca aggcgtttat ctcccgtatc actaatgaaa  1020
ctaaaattca aatcgctatt tcgctgaatg gtgttatat caaataaaa gattcgattc  1080 ttcctgcaaa gaaggatgac gatgtagctt cccaagctac tcagtcacag gtcatcgata  1140
ttcacacagg tgttggcttt ttggatcata tgatccatgc gttggcaaaa cactctggtt  1200
ggtctcttat tgttgaatgt attggtgacc tgcacattga cgatcaccat actaccgaag  1260
attgcggtat cgcattaggg caagcgttca aagaagcaat gggtgctgtc cgtggtgtaa  1320
aaagattcgg tactgggttc gcaccattgg atgaggcgct atcacgtgcc gtagtcgatt  1380
```

```
tatctagtag accatttgct gtaatcgacc ttggattgaa gagagagatg attggtgatt    1440
tatccactga aatgattcca cactttttgg aaagtttcgc ggaggcggcc agaattactt    1500
tgcatgttga ttgtctgaga ggtttcaacg atcaccacag aagtgagagt gcgttcaagg    1560
ctttggctgt tgccataaga gaagctattt ctagcaatgg caccaatgac gttccctcaa    1620
ccaaaggtgt tttgatgtga agtactgaca ataaaaagat tcttgttttc aagaacttgt    1680
catttgtata gttttttat attgtagttg ttctatttta atcaaatgtt agcgtgattt     1740
atattttttt tcgcctcgac atcatctgcc cagatgcgaa gttaagtgcg cagaaagtaa    1800
tatcatgcgt caatcgtatg tgaatgctgg tcgctatact gctgtcgatt cgatactaac    1860
gccgccatcc acccgggttt ctcattcaag tggtaactgc tgttaaaatt aagatattta    1920
taaattgaag cttggtcgtt ccgaccaata ccgtagggaa acgtaaatta gctattgtaa    1980
aaaaaggaaa agaaaagaaa agaaaaatgt tacatatcga attgatctta ttcctttggt    2040
agaccagtct ttgcgtcaat caaagattcg tttgtttctt gtgggcctga accgacttga    2100
gttaaaatca ctctggcaac atccttttgc aactcaagat ccaattcacg tgcagtaaag    2160
ttagatgatt caaattgatg gttgaaagcc tcaagctgct cagtagtaaa tttcttgtcc    2220
catccaggaa cagagccaaa caatttatag ataaatgcaa agagtttcga ctcattttca    2280
gctaagtagt acaacacagc atttggacct gcatcaaacg tgtatgcaac gattgtttct    2340
ccgtaaaact gattaatggt gtggcaccaa ctgatgatac gcttggaagt gtcattcatg    2400
tagaatattg gagggaaaga gtccaaacat gtggcatgga aagagttgga atccatcatt    2460
gtttcctttg caaaggtggc gaaatctttt tcaacaatgg ctttacgcat gacttcaaat    2520
ctctttggta cgacatgttc aattctttct ttaaatagtt cggaggttgc cacggtcaat    2580
tgcataccct gagtggaact cacatccttt ttaatatcgc tgacaactag gacacaagct    2640
ttcatctgag gccagtcaga gctgtctgcg atttgtactg ccatggaatc atgaccatct    2700
tcagcttttc ccatttccca ggccacgtat ccgccaaaca acgatctaca agctgaacca    2760
gaccccttc ttgctattct agatatttct gaagttgact gtggtaattg gtataactta     2820
gcaattgcag agaccaatgc agcaaagcca gcagcggagg aagctaaacc agctgctgta    2880
ggaaagttat tttcggagac aatgtggagt ttccattgag ataatgtggg caatgaggcg    2940
tccttcgatt ccatttcctt tcttaattgg cgtaggtcgc gcagacaatt ttgagttctt    3000
tcattgtcga tgctgtgtgg ttctccattt aaccacaaag tgtcgcgttc aaactcaggt    3060
gcagtagccg cagaggtcaa cgttctgagg tcatcttgcg ataaagtcac tgatatggac    3120
gaattggtgg gcagattcaa cttcgtgtcc cttttccccc aatacttaag ggttgcgatg    3180
ttgacgggtg cggtaacgga tgctgtgtaa acggtcatta tagttttttc tccttgacgt    3240
taaagtatag aggtatatta acaattttt gttgatactt ttatgacatt tgaataagaa     3300
gtaatacaaa ccgaaaatgt tgaaagtatt agttaaagtg gttatgcagc ttttgcattt    3360
atatatctgt taatagatca aaaatcatcg cttcgctgat taattacccc agaaataagg    3420
ctaaaaaact aatcgcatta ttatcctatg gttgttaatt tgattcgttg atttgaaggt    3480
ttgtggggcc aggttactgc caattttttcc tcttcataac cataaaagct agtattgtag   3540
aatctttatt gttcggagca gtgcggcgcg aggcacatct gcgtttcagg aacgcgaccg    3600
gtgaagacca ggacgcacgg aggagagtct tccgtcggag ggctgtcgcc cgctcggcgg    3660
cttctaatcc gtacttcaat atagcaatga gcagttaagc gtattactga aagttccaaa    3720
gagaaggttt ttttaggcta agataatggg gctctttaca tttccacaac atataagtaa    3780
```

```
gattagatat ggatatgtat atggtggtat tgccatgtaa tatgattatt aaacttcttt      3840
gcgtccatcc aaaaaaaaag taagaatttt tgaaaattca atataaatgt cagagttgag      3900
agccttcagt gccccaggga aagcgttact agctggtgga tatttagttt tagatccgaa      3960
atatgaagca tttgtagtcg gattatcggc aagaatgcat gctgtagccc atccttacgg      4020
ttcattgcaa gagtctgata agtttgaagt gcgtgtgaaa agtaaacaat ttaaagatgg      4080
ggagtggctg taccatataa gtcctaaaac tggcttcatt cctgtttcga taggcggatc      4140 taagaacccct ttcattgaaa aagttatcgc taacgtattt agctacttta agcctaacat    4200
ggacgactac tgcaatagaa acttgttcgt tattgatatt ttctctgatg atgcctacca     4260
ttctcaggag gacagcgtta ccgaacatcg tggcaacaga agattgagtt ttcattcgca     4320
cagaattgaa gaagttccca aaacagggct gggctcctcg gcaggtttag tcacagtttt    4380
aactacagct ttggcctcct tttttgtatc ggacctggaa aataatgtag acaaatatag    4440
agaagttatt cataatttat cacaagttgc tcattgtcaa gctcagggta aaattggaag    4500
cgggtttgat gtagcggcgg cagcatatgg atctatcaga tatagaagat tcccacccgc    4560
attaatctct aatttgccag atattggaag tgctacttac ggcagtaaac tggcgcattt    4620
ggttaatgaa gaagactgga atataacgat taaaagtaac catttacctt cgggattaac    4680
tttatggatg ggcgatatta agaatggttc agaaacagta aaactggtcc agaaggtaaa    4740
aaattggtat gattcgcata tgccggaaag cttgaaaata tatacagaac tcgatcatgc    4800
aaattctaga tttatggatg gactatctaa actagatcgc ttacacgaga ctcatgacga    4860
ttacagcgat cagatatttg agtctcttga gaggaatgac tgtacctgtc aaaagtatcc    4920
tgagatcaca gaagttagag atgcagttgc cacaattaga cgttcctta gaaaaataac    4980 taagaatct ggtgccgata tcgaacctcc cgtacaaact agcttattgg atgattgcca     5040
gaccttaaaa ggagttctta cttgcttaat acctggtgct ggtggttatg acgccattgc    5100
agtgattgct aagcaagatg ttgatcttag ggctcaaacc gctgatgaca aaagattttc    5160
taaggttcaa tggctggatg taactcaggc tgactggggt gttaggaaag aaaaagatcc    5220
ggaaacttat cttgataaat aacttaaggt agataatagt ggtccatgtg acatctttat    5280
aaatgtgaag tttgaagtga ccgcgcttaa catctaacca ttcatcttcc gatagtactt    5340
gaaattgttc ctttcggcgg catgataaaa ttctttaat gggtacaagc tacccgggcc    5400
cgggaaagat tctctttttt tatgatattt gtacataaac tttataaatg aaattcataa    5460
tagaaacgac acgaaattac aaaatggaat atgttcatag ggtagacgaa actatatacg    5520
caatctacat acatttatca agaaggagaa aaaggaggat gtaaaggaat acaggtaagc    5580 aaaattgatac taatggctca acgtgataag gaaaaagaat tgcactttaa cattaatatt    5640
gacaaggagg agggcaccac acaaaaagtt aggtgtaaca gaaaatcatg aaactatgat    5700
tcctaattta tatattggag gattttctct aaaaaaaaaa aaatacaaca aataaaaaac    5760
actcaatgac ctgaccattt gatggagttt aagtcaatac cttcttgaac catttcccat    5820
aatggtgaaa gttccctcaa gaattttact ctgtcagaaa cggccttaac gacgtagtcg    5880
acctcctctt cagtactaaa tctaccaata ccaaatctga tggaagaatg ggctaatgca    5940
tcatccttac ccagcgcatg taaaacataa gaaggttcta gggaagcaga tgtacaggct    6000
gaacccgagg ataatgcgat atcccttagt gccatcaata aagattctcc ttccacgtag    6060
gcgaaagaaa cgttaacacg tttaaac                                        6087
```

<210> SEQ ID NO 48

```
<211> LENGTH: 30
<212> TYPE: DNA
<213> ORGANISM: Artificial Sequence
<220> FEATURE:
<223> OTHER INFORMATION: Synthetic, Primer 61-67-CPK019-G

<400> SEQUENCE: 48
gtttaaactt ttccaatagg tggttagcaa                              30

<210> SEQ ID NO 49
<211> LENGTH: 55
<212> TYPE: DNA
<213> ORGANISM: Artificial Sequence
<220> FEATURE:
<223> OTHER INFORMATION: Synthetic, Primer 61-67-CPK020-G

<400> SEQUENCE: 49
gggtgacccg gcggggacga ggcaagctaa acgtcttcct ttctcttacc aaagt   55

<210> SEQ ID NO 50
<211> LENGTH: 62
<212> TYPE: DNA
<213> ORGANISM: Artificial Sequence
<220> FEATURE:
<223> OTHER INFORMATION: Synthetic, Primer 61-67-CPK023-G

<400> SEQUENCE: 50
gctgtcgatt cgatactaac gccgccatcc acccgggaaa gattctcttt ttttatgata  60
tt                                                                62

<210> SEQ ID NO 51
<211> LENGTH: 45
<212> TYPE: DNA
<213> ORGANISM: Artificial Sequence
<220> FEATURE:
<223> OTHER INFORMATION: Synthetic, Primer 61-67-CPK024-G

<400> SEQUENCE: 51
gtttaaacgt gttaacgttt ctttcgccta cgtggaagga gaatc              45

<210> SEQ ID NO 52
<211> LENGTH: 55
<212> TYPE: DNA
<213> ORGANISM: Artificial Sequence
<220> FEATURE:
<223> OTHER INFORMATION: Synthetic, Primer 61-67-CPK021-G

<400> SEQUENCE: 52
actttggtaa gagaaaggaa gacgtttagc ttgcctcgtc cccgccgggt caccc   55

<210> SEQ ID NO 53
<211> LENGTH: 62
<212> TYPE: DNA
<213> ORGANISM: Artificial Sequence
<220> FEATURE:
<223> OTHER INFORMATION: Synthetic, Primer 61-67-CPK022-G

<400> SEQUENCE: 53
aatatcataa aaaaagagaa tctttcccgg gtggatggcg gcgttagtat cgaatcgaca  60
gc                                                                62

<210> SEQ ID NO 54
<211> LENGTH: 45
<212> TYPE: DNA
<213> ORGANISM: Artificial Sequence
<220> FEATURE:
```

<223> OTHER INFORMATION: Synthetic, Primer 61-67-CPK041-G

<400> SEQUENCE: 54 tcccccggg tagcttgtac ccattaaaag aattttatca tgccg        45

<210> SEQ ID NO 55
<211> LENGTH: 47
<212> TYPE: DNA
<213> ORGANISM: Artificial Sequence
<220> FEATURE:
<223> OTHER INFORMATION: Synthetic, Primer 61-67-CPK060-G

<400> SEQUENCE: 55 aattttgaa aattcaatat aaatgtcaga gttgagagcc ttcagtg        47

<210> SEQ ID NO 56
<211> LENGTH: 47
<212> TYPE: DNA
<213> ORGANISM: Artificial Sequence
<220> FEATURE:
<223> OTHER INFORMATION: Synthetic, Primer 61-67-CPK061-G

<400> SEQUENCE: 56
cactgaaggc tctcaactct gacatttata ttgaattttc aaaaatt        47

<210> SEQ ID NO 57
<211> LENGTH: 51
<212> TYPE: DNA
<213> ORGANISM: Artificial Sequence
<220> FEATURE:
<223> OTHER INFORMATION: Synthetic, Primer 61-67-CPK062-G

<400> SEQUENCE: 57
ggtaacggat gctgtgtaaa cggtcattat agttttttct ccttgacgtt a        51

<210> SEQ ID NO 58
<211> LENGTH: 30
<212> TYPE: DNA
<213> ORGANISM: Artificial Sequence
<220> FEATURE:
<223> OTHER INFORMATION: Synthetic, Primer 61-67-CPK046-G

<400> SEQUENCE: 58 tcccccggg tttctcattc aagtggtaac        30

<210> SEQ ID NO 59
<211> LENGTH: 51
<212> TYPE: DNA
<213> ORGANISM: Artificial Sequence
<220> FEATURE:
<223> OTHER INFORMATION: Synthetic, Primer 61-67-CPK063-G

<400> SEQUENCE: 59
taacgtcaag gagaaaaaac tataatgacc gtttacacag catccgttac c        51

<210> SEQ ID NO 60
<211> LENGTH: 4178
<212> TYPE: DNA
<213> ORGANISM: Artificial Sequence
<220> FEATURE:
<223> OTHER INFORMATION: Synthetic, Expression plasmid pAM1419

<400> SEQUENCE: 60
gtttgacagc ttatcatcga ctgcacggtg caccaatgct tctggcgtca ggcagccatc        60
ggaagctgtg gtatggctgt gcaggtcgta aatcactgca taattcgtgt cgctcaaggc        120

```
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagacatatg gaattcgag ctcggtaccc ggggatcctc     300
tagagtcgac ctgcaggcat gcaagcttgg ctgttttggc ggatgagaga agattttcag    360
cctgatacag attaaatcag aacgcagaag cggtctgata aaacagaatt tgcctggcgg    420
cagtagcgcg gtggtcccac ctgaccccat gccgaactca gaagtgaaac gccgtagcgc    480
cgatggtagt gtggggtctc cccatgcgag agtagggaac tgccaggcat caaataaaac    540
gaaaggctca gtcgaaagac tgggcctttc gttttatctg ttgtttgtcg gtgaacgctc    600
tcctgagtag gacaaatccg ccgggagcgg atttgaacgt tgcgaagcaa cggcccggag    660
ggtggcgggc aggacgcccg ccataaactg ccaggcatca aattaagcag aaggccatcc    720
tgacggatgg cctttttgcg tttctacaaa ctcttttgt ttattttct aaatacattc      780 aaatatgtat ccgctcatga gacaataacc ctgataaatg cttcaataat attgaaaaag    840
gaagagtatg agtattcaac atttccgtgt cgcccttatt cccttttttg cggcattttg    900
ccttcctgtt tttgctcacc cagaaacgct ggtgaaagta aaagatgctg aagatcagtt    960
gggtgcacga gtgggttaca tcgaactgga tctcaacagc ggtaagatcc ttgagagttt   1020
tcgccccgaa gaacgttttc caatgatgag cacttttaaa gttctgctat gtggcgcggt   1080
attatcccgt gttgacgccg ggcaagagca actcggtcgc cgcatacact attctcagaa   1140
tgacttggtt gagtactcac cagtcacaga aaagcatctt acggatggca tgacagtaag   1200
agaattatgc agtgctgcca taaccatgag tgataacact gcggccaact tacttctgac   1260
aacgatcgga ggaccgaagg agctaaccgc ttttttgcac aacatggggg atcatgtaac   1320
tcgccttgat cgttgggaac cggagctgaa tgaagccata ccaaacgacg agcgtgacac   1380
cacgatgcct acagcaatgg caacaacgtt gcgcaaacta ttaactggcg aactacttac   1440
tctagcttcc cggcaacaat taatagactg gatggaggcg gataaagttg caggaccact   1500
tctgcgctcg gcccttccgg ctggctggtt tattgctgat aaatctggag ccggtgagcg   1560
tgggtctcgc ggtatcattg cagcactggg gccagatggt aagccctccc gtatcgtagt   1620
tatctacacg acggggagtc aggcaactat ggatgaacga aatagacaga tcgctgagat   1680
aggtgcctca ctgattaagc attggtaact gtcagaccaa gtttactcat atatacttta   1740
gattgattta aaacttcatt tttaatttaa aaggatctag gtgaagatcc ttttgataa    1800 tctcatgacc aaaatccctt aacgtgagtt ttcgttccac tgagcgtcag accccgtaga   1860
aaagatcaaa ggatcttctt gagatccttt ttttctgcgc gtaatctgct gcttgcaaac   1920
aaaaaaacca ccgctaccag cggtggtttg tttgccggat caagagctac caactctttt   1980
tccgaaggta actggcttca gcagagcgca gataccaaat actgtccttc tagtgtagcc   2040
gtagttaggc caccacttca agaactctgt agcaccgcct acatacctcg ctctgctaat   2100
cctgttacca gtggctgctg ccagtggcga taagtcgtgt cttaccgggt tggactcaag   2160
acgatagtta ccggataagg cgcagcggtc gggctgaacg gggggttcgt gcacacagcc   2220
cagcttggag cgaacgacct acaccgaact gagatacta cagcgtgagc tatgagaaag   2280
cgccacgctt cccgaaggga gaaaggcgga caggtatccg gtaagcggca gggtcggaac   2340
aggagagcgc acgagggagc ttccagggg aaacgcctgg tatctttata gtcctgtcgg    2400
gtttcgccac ctctgacttg agcgtcgatt tttgtgatgc tcgtcagggg gcggagccta   2460
atggaaaaac gccagcaacg cggccttttt acggttcctg gccttttgct ggccttttgc   2520
```

```
tcacatgttc tttcctgcgt tatcccctga ttctgtggat aaccgtatta ccgcctttga    2580
gtgagctgat accgctcgcc gcagccgaac gaccgagcgc agcgagtcag tgagcgagga    2640
agcggaagag cgcctgatgc ggtattttct ccttacgcat ctgtgcggta tttcacaccg    2700
cacatggtgc actctcagta caatctgctc tgatgccgca tagttaagcc agtatacact    2760
ccgctatcgc tacgtgactg ggtcatggct gcgccccgac acccgccaac acccgctgac    2820
gcgccctgac gggcttgtct gctcccggca tccgcttaca gacaagctgt gaccgtctcc    2880
gggagctgca tgtgtcagag gttttcaccg tcatcaccga aacgcgcgag gcagcagatc    2940
aattcgcgcg cgaaggcgaa gcggcatgca tttacgttga caccatcgaa tggtgcaaaa    3000
cctttcgcgg tatggcatga tagcgcccgg aagagagtca attcagggtg gtgaatgtga    3060
aaccagtaac gttatacgat gtcgcagagt atgccggtgt ctcttatcag accgtttccc    3120
gcgtggtgaa ccaggccagc cacgtttctg cgaaaacgcg ggaaaaagtg gaagcggcga    3180
tggcggagct gaattacatt cccaaccgcg tggcacaaca actggcgggc aaacagtcgt    3240
tgctgattgg cgttgccacc tccagtctgg ccctgcacgc gccgtcgcaa attgtcgcgg    3300
cgattaaatc tcgcgccgat caactgggtg ccagcgtggt ggtgtcgatg gtagaacgaa    3360
gcggcgtcga agcctgtaaa gcggcggtgc acaatcttct cgcgcaacgc gtcagtgggc    3420
tgatcattaa ctatccgctg gatgaccagg atgccattgc tgtggaagct gcctgcacta    3480
atgttccggc gttatttctt gatgtctctg accagacacc catcaacagt attattttct    3540
cccatgaaga cggtacgcga ctgggcgtgg agcatctggt cgcattgggt caccagcaaa    3600
tcgcgctgtt agcgggccca ttaagttctg tctcggcgcg tctgcgtctg gctggctggc    3660
ataaatatct cactcgcaat caaattcagc cgatagcgga acgggaaggc gactggagtg    3720
ccatgtccgg ttttcaacaa accatgcaaa tgctgaatga gggcatcgtt cccactgcga    3780
tgctggttgc caacgatcag atggcgctgg gcgcaatgcg cgccattacc gagtccgggc    3840
tgcgcgttgg tgcggatatc tcggtagtgg gatacgacga taccgaagac agctcatgtt    3900
atatcccgcc gtcaaccacc atcaaacagg attttcgcct gctggggcaa accagcgtgg    3960
accgcttgct gcaactctct cagggccagg cggtgaaggg caatcagctg ttgcccgtct    4020
cactggtgaa aagaaaaacc accctggcgc ccaatacgca aaccgcctct ccccgcgcgt    4080
tggccgattc attaatgcag ctggcacgac aggtttcccg actggaaagc gggcagtgag    4140
cgcaacgcaa ttaatgtgag ttagcgcgaa ttgatctg                           4178
```

<210> SEQ ID NO 61
<211> LENGTH: 1725
<212> TYPE: DNA
<213> ORGANISM: Artificial Sequence
<220> FEATURE:
<223> OTHER INFORMATION: Synthetic, FS_S2D_Ec coding sequence

<400> SEQUENCE: 61

```
atggacactc tgccgatctc ttccgtaagc ttttcttcct ctacttcccc gctggtagtc      60
gatgacaagg tttctaccaa acctgatgta attcgtcaca ctatgaactt caacgcatct     120
atctggggcg atcagttcct gacttatgat gaaccggaag atctggtaat gaaaaagcaa     180
ctggtagaag aactgaaaga agaagttaaa aaggaactga tcaccattaa gggtagcaac     240
gaaccgatgc agcacgtgaa actgattgaa ctgatcgatg cggttcagcg tctgggtatt     300
gcttatcatt ttgaagagga aatcgaggaa gctctgcaac acatccacgt aacctacggc     360
gaacaatggg tggataaaga gaatctgcag tctatcagcc tgtggttccg cctgctgcgt     420
```

```
cagcaaggtt tcaatgtctc ttctggcgtt ttcaaagact tcatggatga aagggcaaa      480 ttcaaggaat ccctgtgtaa cgatgcgcaa ggtatcctgg cactgtacga agcggccttc      540
atgcgtgtgg aagacgaaac cattctggac aacgcgctgg aattcactaa agtgcatctg      600
gacatcatcg cgaaagatcc gtcctgcgac tcctctctgc gtactcagat ccatcaagcg      660
ctgaaacagc cgctgcgtcg tcgcctggca cgtattgagg ctctgcacta tgccgatt       720 taccagcagg aaacctctca cgacgaagtc ctgctgaaac tggctaaact ggacttcagc      780
gttctgcaat ctatgcacaa gaaagaactg tcccacatct gcaaatggtg aaagatctg      840 gatctgcaaa acaaactgcc gtacgttcgt gaccgtgttg ttgagggcta ttttggatt      900 ctgtccatct actatgaacc acagcacgcg cgtactcgca tgtttctgat gaaaacctgc      960
atgtggctgt tgtcctgga cgacccttt gacaactatg gtacgtacga agaactggaa       1020
atcttcaccc aggccgtgga acgttggtct atttcctgcc tggatatgct gccggaatac      1080
atgaaactga tctatcaaga actggttaac ctgcacgtgg aaatggaaga gtctctggag      1140
aaagaaggta aaacttacca gatccactac gtcaaggaga tggcgaaaga actggtccgt      1200
aactatctgg tcgaggcgcg ttggctgaaa gagggctata tgccgactct ggaagaatac      1260
atgagcgtat ccatggttac cggcacctac ggcctgatga ttgcgcgttc ctacgtcggc      1320
cgtggtgata ttgttaccga agataccttt aagtgggttt cttcctaccc gccgatcatc      1380
aaagcgtctt gtgtcatcgt tcgcctgatg gacgacatcg tttctcacaa agaggagcaa      1440
gaacgtggtc acgtagcatc tagcatcgaa tgctactcca agaatccggg cgcgtccgaa      1500
gaagaagctt gcgaatacat cagccgtaaa gttgaagatg cctggaaagt tatcaaccgc      1560
gaaagcctgc gtccgacggc ggtcccgttt ccgctgctga tgccggcaat caacctggca      1620
cgcatgtgtg aggttctgta cagcgtgaac gatggtttta ctcacgcgga aggtgacatg      1680
aagagctata tgaagagctt cttcgtacac cctatggtcg tatga                      1725
```

<210> SEQ ID NO 62
<211> LENGTH: 1725
<212> TYPE: DNA
<213> ORGANISM: Artificial Sequence
<220> FEATURE:
<223> OTHER INFORMATION: Synthetic, FS_Aa_Ec coding sequence

<400> SEQUENCE: 62

```
atgtctactc tgccgatctc ttccgtaagc ttttcttcct ctacttcccc gctggtagtc       60
gatgacaagg tttctaccaa acctgatgta attcgtcaca ctatgaactt caacgcatct      120
atctggggcg atcagttcct gacttatgat gaaccggaag atctggtaat gaaaaagcaa      180
ctggtagaag aactgaaaga agaagttaaa aggaactga tcaccattaa gggtagcaac       240
gaaccgatgc agcacgtgaa actgattgaa ctgatcgatg cggttcagcg tctgggtatt      300
gcttatcatt ttgaagagga aatcgaggaa gctctgcaac acatccacgt aacctacggc      360
gaacaatggg tggataaaga gaatctgcag tctatcagcc tgtggttccg cctgctgcgt      420
cagcaaggtt tcaatgtctc ttctggcgtt ttcaaagact tcatggatga aagggcaaa      480 ttcaaggaat ccctgtgtaa cgatgcgcaa ggtatcctgg cactgtacga agcggccttc      540
atgcgtgtgg aagacgaaac cattctggac aacgcgctgg aattcactaa agtgcatctg      600
gacatcatcg cgaaagatcc gtcctgcgac tcctctctgc gtactcagat ccatcaagcg      660
ctgaaacagc cgctgcgtcg tcgcctggca cgtattgagg ctctgcacta tgccgatt       720 taccagcagg aaacctctca cgacgaagtc ctgctgaaac tggctaaact ggacttcagc      780
```

```
gttctgcaat ctatgcacaa gaaagaactg tcccacatct gcaaatggtg gaaagatctg    840
gatctgcaaa acaaactgcc gtacgttcgt gaccgtgttg ttgagggcta tttttggatt    900
ctgtccatct actatgaacc acagcacgcg cgtactcgca tgtttctgat gaaaacctgc    960
atgtggctgg ttgtcctgga cgacaccttt gacaactatg gtacgtacga agaactggaa   1020
atcttcaccc aggccgtgga acgttggtct atttcctgcc tggatatgct gccggaatac   1080
atgaaactga tctatcaaga actggttaac ctgcacgtgg aaatggaaga gtctctggag   1140
aaagaaggta aaacttacca gatccactac gtcaaggaga tggcgaaaga actggtccgt   1200
aactatctgg tcgaggcgcg ttggctgaaa gagggctata tgccgactct ggaagaatac   1260
atgagcgtat ccatggttac cggcacctac ggcctgatga ttgcgcgttc ctacgtcggc   1320
cgtggtgata ttgttaccga agatacccttt aagtgggttt cttcctaccc gccgatcatc   1380
aaagcgtctt gtgtcatcgt tcgcctgatg gacgacatcg tttctcacaa agaggagcaa   1440
gaacgtggtc acgtagcatc tagcatcgaa tgctactcca agaatccgg cgcgtccgaa    1500 gaagaagctt gcgaatacat cagccgtaaa gttgaagatg cctggaaagt tatcaaccgc   1560
gaaagcctgc gtccgacggc ggtcccgttt ccgctgctga tgccggcaat caacctggca   1620
cgcatgtgtg aggttctgta cagcgtgaac gatggttta ctcacgcgga aggtgacatg    1680
aagagctata tgaagagctt cttcgtacac cctatggtcg tatga                   1725
```

```
<210> SEQ ID NO 63
<211> LENGTH: 1683
<212> TYPE: DNA
<213> ORGANISM: Artificial Sequence
<220> FEATURE:
<223> OTHER INFORMATION: Synthetic, FS_Cj_Ec coding sequence

<400> SEQUENCE: 63
```

```
atgaaagata tgagcatccc gctgttagcc gcggtttcta gctctaccga ggagacggtc     60
cgtccgatcg cggatttcca tccgacgctg tggggcaacc atttcctgaa gtctgcggca    120
gatgttgaga cgattgatgc ggcaacgcaa gagcagcacg cggcactgaa acaagaggtt    180
cgccgcatga ttaccaccac ggcgaataag ctggcgcaga aactgcacat gattgacgcc    240
gtccagcgct taggtgtggc gtaccacttc gagaaggaga ttgaagacga actgggcaaa    300
gttagccatg acctggactc tgacgatctg tatgtggtca gcctgcgttt tcgtctgttt    360
cgtcaacagg gcgtcaagat tagctgcgat gtgttcgaca agttcaagga cgacgagggc    420
aaattcaaag agagcctgat taacgacatc cgtggcatgt tatctttata cgaggcggcc    480
tatctggcaa ttcgcggtga ggatatctta gacgaggcaa ttgtcttcac cacgacccat    540
ctaaagagcg tcatcagcat tagcgaccat tctcatgcga atagcaatct ggcggagcag    600
atccgtcata gcctgcaaat tccactgcgc aaagccgccg cccgtctgga ggcccgctac    660
ttcctggaca tctattctcg tgacgacctg catgacgaga ccttactgaa attcgccaaa    720
ctggacttca acatcttaca agccgcgcac caaaaggagg caagcatcat gacccgctgg    780
tggaatgacc tgggcttccc aaaaaaggtg ccgtacgcgc gcgaccgcat tattgagacc    840
tacatttgga tgctgctggg cgtgagctac gagccaaacc tggcctttgg ccgtatcttc    900
gcgagcaaag tggtctgcat gatcacgacg atcgacgata ccttcgacgc gtacggtacg    960
ttcgaggaac tgacccttgt tacggaggcg gtgacgcgct gggacatcgg cctgatcgac   1020
acgctgccgg agtacatgaa gttcatcgtc aaggccctgc tggacattta ccgtgaagcg   1080
gaggaggaat tagcgaagga aggccgcagc tatggtatcc cgtacgcgaa gcagatgatg   1140
```

| | |
|---|---:|
| caggagctga tcatcctgta ctttaccgaa gcgaaatggc tgtacaaggg ctacgtgccg | 1200 |
| acgttcgacg agtacaaaag cgttgccctg cgcagcattg gtctgcgcac gctggccgtt | 1260 |
| gcaagcattg tggacctggg cgacttcatt gcgaccaagg acaacttcga gtgcatcctg | 1320 |
| aagaacgcca gagcctgaa agccacggag accatcggcc gtctgatgga tgatatcgcg | 1380 |
| ggctacaagt tcgagcagaa acgcggccat aacccatctg cggtggagtg ttacaagaat | 1440 |
| cagcacggcg tcagcgaaga ggaggcggtt aaagagctgc tgctggaggt ggcgaacagc | 1500 |
| tggaaggaca tcaatgagga gctgttaaac ccgaccaccg tcccactgcc gatgctgcag | 1560 |
| cgtctgctgt acttcgcacg cagcggtcat ttcatttacg acgacggcca tgatcgctac | 1620 |
| acccacagcc tgatgatgaa gcgccaggtc gcgttactgt taacggaacc actggcgatc | 1680 |
| taa | 1683 |

<210> SEQ ID NO 64
<211> LENGTH: 1014
<212> TYPE: DNA
<213> ORGANISM: Artificial Sequence
<220> FEATURE:
<223> OTHER INFORMATION: Synthetic, PS_S_Ec coding sequence

<400> SEQUENCE: 64

| | |
|---|---:|
| atgccgcagg acgtcgactt ccatattccg ctgccaggcc gtcagtcacc ggaccatgcc | 60 |
| cgcgctgaag cggagcaatt agcgtggccg cgcagcttgg gcctgattcg ttccgatgct | 120 |
| gcggcagagc gtcatctccg tggtggttac gcagatctgg caagccgctt ttatccgcat | 180 |
| gcgaccggcg cagaccttga tttaggggtg gacctgatga gctggttttt cctctttgat | 240 |
| gacctgttcg atggcccgcg cggtgaaaac ccggaggata ccaaacagct gaccgaccaa | 300 |
| gtggctgcag cactggatgg cccgctcccc gataccgccc ccccatcgc tcacggtttt | 360 |
| gcagatattt ggcgccgtac gtgtgaaggt atgacgccgg cgtggtgcgc ccgtagcgcg | 420 |
| cgccattggc gtaattattt tgatggctac gtagatgaag ccgagagccg cttttggaac | 480 |
| gctccatgcg attcggccgc ccaatacctg gcgatgcgcc gtcacacgat cggtgtacaa | 540 |
| cctaccgtcg atttggcgga gcgtgcgggc cgtttcgaag tgccacaccg tgtgttcgat | 600 |
| tctgcagtga tgtctgcaat gctgcagatt gcggtagacg tgaacctgct gctgaacgac | 660 |
| atcgccagcc tggaaaaaga ggaagcccgt ggtgagcaaa acaatatggt catgatcctg | 720 |
| cgtcgcgaac acggctggtc aaagagccgc agcgtcagcc acatgcaaaa tgaagttcgc | 780 |
| gcccgccttg aacagtattt gttactgaaa gctgtctcc cgaaagtcgg cgaaatttat | 840 |
| cagctggata ccgcagaacg cgaggcactg aacgttatc gtacggatgc tgtccgtacc | 900 |
| gttatccgtg gttcctatga ctggcatcgc agcagtgggc gctatgacgc cgagttcgct | 960 |
| ctggcggcag gtgcacaggg atacctggaa gaactgggct ccagcgccca ttaa | 1014 |

<210> SEQ ID NO 65
<211> LENGTH: 1125
<212> TYPE: DNA
<213> ORGANISM: Artificial Sequence
<220> FEATURE:
<223> OTHER INFORMATION: Synthetic, TDS_Fs_Ec coding sequence

<400> SEQUENCE: 65

| | |
|---|---:|
| atggaaaatt ttcctacgga atacttcctg aataccacgg tccgcttgct ggaatacatt | 60 |
| cgctaccgtg attctaatta tacgcgcgag gagcgtatcg aaaacctcca ttatgcgtac | 120 |
| aacaaagcgg ctcatcattt tgcacagccg cgtcagcaac aactcctgaa agtggaccct | 180 |

```
aaacgtctcc aggcaagcct gcaaactatt gttggcatgg tggtttatag ctgggccaaa    240
gtttcaaaag agtgcatggc ggatctgagt atccattata cgtatacgct ggtgttagat    300
gactcaaaag atgacccgta cccaactatg gtgaattact ttgacgactt gcaagcgggc    360
cgtgaacagg cacatccgtg gtgggctctg gtgaacgaac atttccgaa tgttcttcgc     420 catttcggcc cgttttgctc gttaaattta atccgtagca ccctggattt cttttgaagga   480 tgctggatcg aacagtataa ttttggcggt tttccaggga gccacgacta cccgcagttt    540
ctgcgccgca tgaatggtct tggacattgt gttggtgcct cgttatggcc gaaggaacag    600
tttaatgaac gcagcctgtt cctggaaatc acctctgcca ttgcacagat ggaaaattgg    660
atggtatggg tcaacgatct gatgtccttc tataaagagt tcgatgatga acgcgaccag    720
atttcgttag tcaaaaatta tgtcgtgtca gatgaaatct ccttcacga agccctggag     780 aagttgacgc aggacaccct gcactccagt aaacaaatgg tagccgtttt ttctgacaaa    840
gatccgcaag taatggacac catcgagtgt ttcatgcatg ggtatgtgac ctggcatttg    900
tgcgaccgtc gttatcgtct gtccgaaatt tacgaaaaag ttaaggagga gaaaaccgaa    960
gacgcacaaa aattctgcaa attttacgaa caggccgcga atgtaggcgc tgtcagccct   1020
tccgaatggg catatccgcc tgtggcccag ctggcgaacg ttcgttcaaa agatgtgaaa   1080
gaagtccaga accgtttcct gagctctatt gaattagtcg agtaa                   1125

<210> SEQ ID NO 66
<211> LENGTH: 1686
<212> TYPE: DNA
<213> ORGANISM: Artificial Sequence
<220> FEATURE:
<223> OTHER INFORMATION: Synthetic, FS_Cs_Ec coding sequence

<400> SEQUENCE: 66
atgagctcta acgtgagcgc catcccaaac tcttttgaac tgattcgccg ctctgcgcaa     60
ttccaggcaa gcgtctgggg cgattatttc ctgagctacc acagcctgcc accggagaag   120
ggcaacaagg tgatggaaaa acaaacggag gagctgaagg aggagatcaa aatggagctg   180
gtgtctacca ccaaggacga gccggagaaa ttacgcctga ttgatctgat ccaacgttta   240
ggcgtgtgct accacttcga gaacgaaatc aacaatatcc tgcagcagct gcatcacatc   300
acgattacca gcgagaaaaa tggcgacgac aatccataca acatgacgct gtgctttcgt   360
ttactgcgtc agcagggcta caacgtgtct tctgagccgt ttgaccgctt ccgcggcaag   420
tgggagagca gctacgacaa caatgtgaa gaactgctga gcctgtatga agcaagccaa    480
ctgcgcatgc aaggcgagga ggccctggat gaggcgtttt gcttcgccac cgcgcaactg   540
gaagcgatcg tgcaagaccc gaccaccgat ccgatggtcg ccgcggagat tcgtcaggcc   600
ttaaaatggc caatgtacaa gaatttaccg cgtctgaaag cccgtcacca cattggtctg   660
tattctgaga aaccgtggcg taacgagagc ttactgaact ttgcgaagat ggacttcaac   720
aagctgcaaa acctgcatca gaccgagatc gcatacatct ctaagtggtg ggacgattat   780
ggctttgcgg agaaactgtc ttttgcccgt aatcgcattg tggaaggtta tttctttgcc   840
ctgggtatct tcttcgaacc gcaattatta accgcacgcc tgatcatgac gaaagttatt   900
gcgattggta gcatgctgga tgacatctac gacgtctacg gtacgtttga ggaactgaag   960
ctgttaacgt tagcgttaga acgctgggac aagagcgaaa cgaagcaatt accgaactac  1020
atgaaaatgt actacgaggc cctgctggac gtgtttgaag agattgagca ggaaatgtct  1080
caaaaagaga cggaaacgac cccgtattgc attcatcaca tgaaagaagc cacgaaggaa  1140
```

| | |
|---|---|
| ttaggtcgtg ttttcttagt cgaggcgacc tggtgtaagg agggttatac cccgaaggtc | 1200 |
| gaagaatatc tggacattgc gctgatcagc ttcggccaca agctgctgat ggttacggca | 1260 |
| ctgctgggta tgggttctca catggccacg cagcagattg tccagtggat cacgagcatg | 1320 |
| ccgaatatcc tgaaggcaag cgccgttatt tgtcgcctga tgaacgatat cgtctctcac | 1380 |
| aagtttgagc aggaacgcgg ccacgttgcg agcgcgatcg agtgctacat ggagcaaaat | 1440 |
| cacttatctg agtacgaggc actgatcgcc ttacgtaagc agatcgatga tctgtggaaa | 1500 |
| gacatggtcg aaaactactg tgcggtgatc acggaggacg aggttccgcg cggcgtcctg | 1560 |
| atgcgcgtgt taaatttaac ccgtttattt aacgtgattt acaaagatgg cgatggctat | 1620 |
| acgcagtctc atggtagcac gaaggcacat attaagagcc tgttagttga ctctgttcca | 1680 |
| ttataa | 1686 |

<210> SEQ ID NO 67
<211> LENGTH: 1725
<212> TYPE: DNA
<213> ORGANISM: Artificial Sequence
<220> FEATURE:
<223> OTHER INFORMATION: Synthetic, FS_Pt_Ec coding sequence

<400> SEQUENCE: 67

| | |
|---|---|
| atgagctctt tagcggttga tgacgccgaa cgccgtgtgg gcgactacca cccgaactta | 60 |
| tgggacgacg cactgatcca gagcttaagc acgccatacg gcgcaagccc gtatcgcgat | 120 |
| gttgccgaga agctgatcgg cgagatcaag gagatgtttg cgagcatctc tatcgaggat | 180 |
| ggcgatgacg agatctgcta cttcctgcag cgcctgtgga tgattgacaa cgtcgagcgc | 240 |
| ctgggcatta gccgtcattt cgaaaatgag attaaggcgg cgatggagga cgtgtattct | 300 |
| cgtcattgga gcgacaaagg catcgcgtgt ggccgccaca gcgtggttgc agacctgaac | 360 |
| tctaccgcac tggcgttccg cacccctgcg ctgcacggct acagcgtttg cagcgacgtg | 420 |
| ttcaagattt tccaagatca gaaaggtgag ttcgcatgtt ctgcggatca gaccgagggt | 480 |
| gagattaaag gcattctgaa cctgttacgc gccagcctga tcgcctttcc gggcgagcgt | 540 |
| atcctgcagg aggccgagat ctttgcgacg acctatctga agaggccttt accgaagatc | 600 |
| cagggcagcc gcttatctca ggaaattgaa tacgtgctgg agtacggctg gctgaccgat | 660 |
| ctgccgcgcc tggagacgcg taactacatc gaggtcctgg ccgaggagat cacgccgtac | 720 |
| ttcaagaagc cgtgcatggc cgtcgagaaa ctgctgaaac tggcgaaaat cgagttcaac | 780 |
| ctgtttcaca gcctgcagca aaccgagctg aagcacctgt ctcgctggtg aaggacagc | 840 |
| ggttttgcgc agctgacgtt cacgcgtcac cgccatgttg aattttatac cctggccagc | 900 |
| tgcatcgcca tggagccgaa gcactctgcg ttccgcctgg gcttcgccaa actgtgctat | 960 |
| ctgggcatcg tgctggacga tatctatgac acctacggca agatggagga gctggagctg | 1020 |
| ttcaccgcgc caatcaaacg ttgggatacg agcacgacgg agtgcctgcc ggagtacatg | 1080 |
| aagggcgttt acatggcgtt ttatgactgt gtcaacgaga tggcccgcca agcagagaag | 1140 |
| acccaaggct gggacaccct ggactacgcg cgcaagacct gggaggccct gatcgacgca | 1200 |
| ttcatggagg aggcgaagtg gatcagctct ggctacgtcc caaccttcca gaagtacctg | 1260 |
| gacaacggca aggtcagctt cggttaccgt gcagcgacgc tgcagccaat cttaacgctg | 1320 |
| gacatcccgc tgccgctgca catcctgcaa gagattgact cccgagcag cttcaacgac | 1380 |
| ctggcgagct ctattctgcg cttacgtggc gacatttgcg gttatcaggc cgaacgttct | 1440 |
| cgtggtgagc aggcgtctag catcagctgc tacatgaagg ataacccggg tagcacggaa | 1500 |

-continued

| | |
|---|---|
| gaggatgccc tgagccacgt caacgccatg atcggcgaca agatcccgga gttcaattgg | 1560 |
| gagttcatga aaccaagcaa ggccccgatt agcagcaaaa agtacgcctt cgacatcctg | 1620 |
| cgcgcattct accacctgta caagtaccgc gatggcttca gcatcgccaa gatcgagacc | 1680 |
| aaaaaactgg tgatgcgcac ggtcctggac ccggtcccaa tgtaa | 1725 |

<210> SEQ ID NO 68
<211> LENGTH: 1725
<212> TYPE: DNA
<213> ORGANISM: Artificial Sequence
<220> FEATURE:
<223> OTHER INFORMATION: Synthetic, FS_Aa_Sc coding sequence

<400> SEQUENCE: 68

| | |
|---|---|
| atgtcaactt tgcctatttc ttctgtgtca ttttcctctt ctacatcacc attagtcgtg | 60 |
| gacgacaaag tctcaaccaa gcccgacgtt atcagacata caatgaattt caatgcttct | 120 |
| atttggggag atcaattctt gacctatgat gagcctgaag atttagttat gaagaaacaa | 180 |
| ttagtggagg aattaaaaga ggaagttaag aaggaattga taactatcaa aggttcaaat | 240 |
| gagcccatgc agcatgtgaa attgattgaa ttaattgatg ctgttcaacg tttaggtata | 300 |
| gcttaccatt ttgaagaaga gatcgaggaa gctttgcaac atatacatgt tacctatggt | 360 |
| gaacagtggg tggataagga aaatttacag agtatttcat tgtggttcag gttgttgcgt | 420 |
| caacagggct ttaacgtctc ctctggcgtt ttcaaagact ttatggacga aaaaggtaaa | 480 |
| ttcaaagagt ctttatgcaa tgatgcacaa ggaatattag ccttatatga agctgcattt | 540 |
| atgagggttg aagatgaaac catcttagac aatgctttgg aattcacaaa agttcattta | 600 |
| gatatcatag caaagaccc atcttgcgat tcttcattgc gtacacaaat ccatcaagcc | 660 |
| ttaaaacaac ctttaagaag gagattagca aggattgaag cattacatta catgccaatc | 720 |
| taccaacagg aaacatctca tgatgaagta ttgttgaaat tagccaagtt ggatttcagt | 780 |
| gttttgcagt ctatgcataa aaaggaattg tcacatatct gtaagtggtg aaagatttta | 840 |
| gatttacaaa ataagttacc ttatgtacgt gatcgtgttg tcgaaggcta cttctggata | 900 |
| ttgtccatat actatgagcc acaacacgct agaacaagaa tgttttgat gaaaacatgc | 960 |
| atgtggttag tagttttgga cgatacttt gataattatg gaacatacga agaattggag | 1020 |
| attttttactc aagccgtcga gagatggtct atctcatgct tagatatgtt gcccgaatat | 1080 |
| atgaaattaa tctaccaaga attagtcaat ttgcatgtgg aaatggaaga atctttggaa | 1140 |
| aaggagggaa agacctatca gattcattac gttaaggaga tggctaaaga attagttcgt | 1200 |
| aattacttag tagaagcaag atggttgaag gaaggttata tgcctacttt agaagaatac | 1260 |
| atgtctgttt ctatggttac tggtacttat ggtttgatga ttgcaaggtc ctatgttggc | 1320 |
| agaggagaca ttgttactga agacacattc aaatggggttt ctagttaccc acctattatt | 1380 |
| aaagcttcct gtgtaatagt aagattaatg gacgatattg tatctcacaa ggaagaacaa | 1440 |
| gaaagaggac atgtggcttc atctatagaa tgttactcta agaatcagg tgcttctgaa | 1500 |
| gaggaagcat gtgaatatat tagtaggaaa gttgaggatg cctggaaagt aatcaataga | 1560 |
| gaatctttgc gtccaacagc cgttcccttc cctttgttaa tgccagcaat aaacttagct | 1620 |
| agaatgtgtg aggtcttgta ctctgttaat gatggttttta ctcatgctga gggtgacatg | 1680 |
| aaatcttata tgaagtcctt cttcgttcat cctatggtcg tttga | 1725 |

<210> SEQ ID NO 69
<211> LENGTH: 7348
<212> TYPE: DNA

<213> ORGANISM: Artificial Sequence
<220> FEATURE:
<223> OTHER INFORMATION: Synthetic, Expression plasmid pAM178

<400> SEQUENCE: 69

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatcga ctacgtcgta aggccgtttc tgacagagta aaattcttga gggaactttc   240
accattatgg gaaatgcttc aagaaggtat tgacttaaac tccatcaaat ggtcaggtca   300
ttgagtgttt tttatttgtt gtatttttt tttttagag aaaatcctcc aatatcaaat     360
taggaatcgt agtttcatga ttttctgtta cacctaactt tttgtgtggt gccctcctcc   420
ttgtcaatat taatgttaaa gtgcaattct ttttccttat cacgttgagc cattagtatc   480
aatttgctta cctgtattcc tttactatcc tcctttttct ccttcttgat aaatgtatgt   540
agattgcgta tatagtttcg tctaccctat gaacatattc cattttgtaa tttcgtgtcg   600
tttctattat gaatttcatt tataaagttt atgtacaaat atcataaaaa aagagaatct   660
ttttaagcaa ggatttttctt aacttcttcg gcgacagcat caccgacttc ggtggtactg   720
ttggaaccac ctaaatcacc agttctgata cctgcatcca aaaccttttt aactgcatct   780
tcaatggcct taccttcttc aggcaagttc aatgacaatt tcaacatcat tgcagcagac   840
aagatagtgg cgatagggtc aaccttattc tttggcaaat ctggagcaga accgtggcat   900
ggttcgtaca aaccaaatgc ggtgttcttg tctggcaaag aggccaagga cgcagatggc   960
aacaaaccca aggaacctgg gataacggag gcttcatcgg agatgatatc accaaacatg  1020
ttgctggtga ttataatacc atttaggtgg gttgggttct taactaggat catggcggca  1080
gaatcaatca attgatgttg aaccttcaat gtagggaatt cgttcttgat ggtttcctcc  1140
acagtttttc tccataatct tgaagaggcc aaaagattag ctttatccaa ggaccaaata  1200
ggcaatggtg gctcatgttg tagggccatg aaagcggcca ttcttgtgat tctttgcact  1260
tctggaacgg tgtattgttc actatcccaa gcgacaccat caccatcgtc ttcctttctc  1320
ttaccaaagt aaatacctcc cactaattct ctgacaacaa cgaagtcagt acctttagca  1380
aattgtggct tgattggaga taagtctaaa agagagtcgg atgcaaagtt acatggtctt  1440
aagttggcgt acaattgaag ttctttacgg attttagta aaccttgttc aggtctaaca   1500
ctaccggtac cccatttagg accagccaca gcacctaaca aaacggcatc aaccttcttg  1560
gaggcttcca gcgcctcatc tggaagtgga acacctgtag catcgatagc agcaccacca  1620
attaaatgat tttcgaaatc gaacttgaca ttggaacgaa catcagaaat agctttaaga  1680
accttaatgg cttcggctgt gatttcttga ccaacgtggt cacctggcaa acgacgatc   1740
ttcttagggg cagacattac aatggtatat ccttgaaata tatataaaaa aaggcgcctt  1800
agaccgctcg gccaaacaac caattacttg ttgagaaata gagtataatt atcctataaa  1860
tataacgttt tgaacacac atgaacaagg aagtacagga caattgattt tgaagagaat   1920
gtggattttg atgtaattgt tgggattcca ttttttaataa ggcaataata ttaggtatgt  1980
ggatatacta gaagttctcc tcgaccgtcg atatgcggtg tgaaataccg cacagatgcg  2040
taaggagaaa ataccgcatc aggaaattgt aaacgttaat attttgttaa aattcgcgtt  2100
aaattttgt taaatcagct catttttta ccaataggcc gaaatcggca aaatccctta   2160
taaatcaaaa gaatagaccg agataggttt gagtgttgtt ccagtttgga acaagagtcc  2220
```

```
actattaaag aacgtggact ccaacgtcaa agggcgaaaa accgtctatc agggcgatgg    2280
cccactacgt gaaccatcac cctaatcaag ttttttgggg tcgaggtgcc gtaaagcact    2340
aaatcggaac cctaaaggga gcccccgatt tagagcttga cggggaaagc cggcgaacgt    2400
ggcgagaaag gaagggaaga aagcgaaagg agcgggcgct agggcgctgg caagtgtagc    2460
ggtcacgctg cgcgtaacca ccacacccgc cgcgcttaat gcgccgctac agggcgcgtc    2520
gcgccattcg ccattcaggc tgcgcaactg ttgggaaggg cgatcggtgc gggcctcttc    2580
gctattacgc cagctgaatt ggagcgacct catgctatac ctgagaaagc aacctgacct    2640
acaggaaaga gttactcaag aataagaatt ttcgttttaa aacctaagag tcactttaaa    2700
atttgtatac acttattttt tttataactt atttaataat aaaaatcata aatcataaga    2760
aattcgctta tttagaagtg tcaacaacgt atctaccaac gatttgaccc ttttccatct    2820
tttcgtaaat ttctggcaag gtagacaagc cgacaacctt gattggagac ttgaccaaac    2880
ctctggcgaa gaattgttaa ttaagagctc agatcttatc gtcgtcatcc ttgtaatcca    2940
tcgatactag tgcggccgcc ctttagtgag ggttgaattc gaattttcaa aaattcttac    3000 ttttttttg gatggacgca aagaagttta ataatcatat tacatggcat taccaccata    3060
tacatatcca tatacatatc catatctaat cttacttata tgttgtggaa atgtaaagag    3120
ccccattatc ttagcctaaa aaaaccttct ctttggaact ttcagtaata cgcttaactg    3180
ctcattgcta tattgaagta cggattagaa gccgccgagc gggtgacagc cctccgaagg    3240
aagactctcc tccgtgcgtc ctcgtcttca ccggtcgcgt tcctgaaacg cagatgtgcc    3300
tcgcgccgca ctgctccgaa caataaagat tctacaatac tagctttat ggttatgaag    3360 aggaaaaatt ggcagtaacc tggccccaca aaccttcaaa tgaacgaatc aaattaacaa    3420
ccataggatg ataatgcgat tagttttta gccttatttc tggggtaatt aatcagcgaa    3480
gcgatgattt ttgatctatt aacagatata taaatgcaaa aactgcataa ccactttaac    3540
taatactttc aacattttcg gtttgtatta cttcttattc aaatgtaata aaagtatcaa    3600
caaaaaattg ttaatatacc tctatacttt aacgtcaagg agaaaaaacc ccggatccgt    3660
aatacgactc actatagggc ccgggcgtcg acatggaaca gaagttgatt tccgaagaag    3720
acctcgagta agcttggtac cgcggctagc taagatccgc tctaaccgaa aaggaaggag    3780
ttagacaacc tgaagtctag gtccctattt attttttat agttatgtta gtattaagaa    3840
cgttatttat atttcaaatt tttctttttt ttctgtacag acgcgtgtac gcatgtaaca    3900
ttatactgaa aaccttgctt gagaaggttt tgggacgctc gaagatccag ctgcattaat    3960
gaatcggcca acgcgcgggg agaggcggtt tgcgtattgg gcgctcttcc gcttcctcgc    4020
tcactgactc gctgcgctcg tcgttcggc tgcggcgagc ggtatcagct cactcaaagg    4080
cggtaatacg gttatccaca gaatcagggg ataacgcagg aaagaacatg tgagcaaaag    4140
gccagcaaaa ggccaggaac cgtaaaaagg ccgcgttgct ggcgtttttc cataggctcc    4200
gcccccctga cgagcatcac aaaaatcgac gctcaagtca gaggtggcga aacccgacag    4260
gactataaag ataccaggcg tttccccctg gaagctccct cgtgcgctct cctgttccga    4320
ccctgccgct taccggatac ctgtccgcct ttctcccttc gggaagcgtg cgctttctc    4380 atagctcacg ctgtaggtat ctcagttcgg tgtaggtcgt tcgctccaag ctgggctgtg    4440
tgcacgaacc ccccgttcag cccgaccgct gcgccttatc cggtaactat cgtcttgagt    4500
ccaacccggt aagacacgac ttatcgccac tggcagcagc cactggtaac aggattagca    4560
gagcgaggta tgtaggcggt gctacagagt tcttgaagtg gtggcctaac tacggctaca    4620
```

```
ctagaaggac agtatttggt atctgcgctc tgctgaagcc agttaccttc ggaaaaagag    4680
ttggtagctc ttgatccggc aaacaaacca ccgctggtag cggtggtttt tttgtttgca    4740
agcagcagat tacgcgcaga aaaaaggat ctcaagaaga tcctttgatc ttttctacgg     4800
ggtctgacgc tcagtggaac gaaaactcac gttaagggat tttggtcatg agattatcaa    4860
aaaggatctt cacctagatc cttttaaatt aaaaatgaag ttttaaatca atctaaagta    4920
tatatgagta aacttggtct gacagttacc aatgcttaat cagtgaggca cctatctcag    4980
cgatctgtct atttcgttca tccatagttg cctgactccc cgtcgtgtag ataactacga    5040
tacgggaggg cttaccatct ggccccagtg ctgcaatgat accgcgagac ccacgctcac    5100
cggctccaga tttatcagca ataaaccagc cagccggaag ggccgagcgc agaagtggtc    5160
ctgcaacttt atccgcctcc atccagtcta ttaattgttg ccgggaagct agagtaagta    5220
gttcgccagt taatagtttg cgcaacgttg ttgccattgc tacaggcatc gtggtgtcac    5280
gctcgtcgtt tggtatggct tcattcagct ccggttccca acgatcaagg cgagttacat    5340 gatccccat gttgtgcaaa aaagcggtta gctccttcgg tcctccgatc gttgtcagaa     5400
gtaagttggc cgcagtgtta tcactcatgg ttatggcagc actgcataat tctcttactg    5460
tcatgccatc cgtaagatgc ttttctgtga ctggtgagta ctcaaccaag tcattctgag    5520
aatagtgtat gcggcgaccg agttgctctt gcccggcgtc aatacgggat aataccgcgc    5580
cacatagcag aactttaaaa gtgctcatca ttggaaaacg ttcttcgggg cgaaaactct    5640
caaggatctt accgctgttg agatccagtt cgatgtaacc cactcgtgca cccaactgat    5700
cttcagcatc ttttactttc accagcgttt ctgggtgagc aaaaacagga aggcaaaatg    5760
ccgcaaaaaa gggaataagg gcgacacgga aatgttgaat actcatactc ttcctttttc    5820
aatattattg aagcatttat cagggttatt gtctcatgag cggatacata tttgaatgta    5880
tttagaaaaa taaacaaata ggggttccgc gcacatttcc ccgaaaagtg ccacctgaac    5940
gaagcatctg tgcttcattt tgtagaacaa aaatgcaacg cgagagcgct aatttttcaa    6000
acaaagaatc tgagctgcat ttttacagaa cagaaatgca acgcgaaagc gctattttac    6060
caacgaagaa tctgtgcttc attttgtaa aacaaaatg caacgcgaga gcgctaatt    6120 ttcaaacaaa gaatctgagc tgcatttta cagaacagaa atgcaacgcg agagcgctat    6180
tttaccaaca aagaatctat acttcttttt tgttctacaa aaatgcatcc cgagagcgct    6240 attttttctaa caaagcatct tagattactt ttttttctcct tgtgcgctc tataatgcag    6300 tctcttgata acttttttgca ctgtaggtcc gttaaggtta gaagaaggct actttggtgt    6360
ctatttctct ttccataaaa aaagcctgac tccacttccc gcgtttactg attactagcg    6420
aagctgcggg tgcattttt caagataaag gcatccccga ttatattcta taccgatgtg    6480
gattgcgcat actttgtgaa cagaaagtga tagcgttgat gattcttcat tggtcagaaa    6540
attatgaacg gtttcttcta ttttgtctct atatactacg tataggaaat gtttacattt    6600
tcgtattgtt ttcgattcac tctatgaata gttcttacta caatttttttt gtctaaagag    6660 taatactaga gataaacata aaaaatgtag aggtcgagtt tagatgcaag ttcaaggagc    6720
gaaaggtgga tgggtaggtt atatagggat atagcacaga gatatatagc aaagagatac    6780
ttttgagcaa tgtttgtgga agcggtattc gcaatatttt agtagctcgt tacagtccgg    6840
tgcgtttttg gttttttgaa agtgcgtctt cagagcgctt ttggttttca aaagcgctct    6900
gaagttccta ctttctag agaataggaa cttcggaata ggaacttcaa agcgtttccg    6960
aaaacgagcg cttccgaaaa tgcaacgcga gctgcgcaca tacagctcac tgttcacgtc    7020
```

<210> SEQ ID NO 70
<211> LENGTH: 1125
<212> TYPE: DNA
<213> ORGANISM: Artificial Sequence
<220> FEATURE:
<223> OTHER INFORMATION: Synthetic, TDS_Fs_Sc coding sequence

<400> SEQUENCE: 70

```
gcacctatat ctgcgtgttg cctgtatata tatatacatg agaagaacgg catagtgcgt    7080
gtttatgctt aaatgcgtac ttatatgcgt ctatttatgt aggatgaaag gtagtctagt    7140
acctcctgtg atattatccc attccatgcg gggtatcgta tgcttccttc agcactaccc    7200
tttagctgtt ctatatgctg ccactcctca attggattag tctcatcctt caatgctatc    7260
atttcctttg atattggatc atactaagaa accattatta tcatgacatt aacctataaa    7320
aataggcgta tcacgaggcc ctttcgtc                                       7348
```

<210> SEQ ID NO 70
<211> LENGTH: 1125
<212> TYPE: DNA
<213> ORGANISM: Artificial Sequence
<220> FEATURE:
<223> OTHER INFORMATION: Synthetic, TDS_Fs_Sc coding sequence

<400> SEQUENCE: 70

```
atggaaaact ttccaaccga gtacttcttg aacaccaccg tcaggttgtt ggagtacatt      60
aggtacaggg actcaaacta taccagggag gagaggattg agaacttaca ctacgcctac     120
aacaaagccg cccaccactt cgcccagcca agacagcagc agttgttgaa ggtcgaccct     180
aagagattgc aagcttcatt gcagaccatt gtcggtatgg ttgtatattc atgggccaag     240
gtatctaaag agtgtatggc agacttgtca atccactata cctacacctt ggtattggac     300
gattcaaaag acgacccata ccctactatg gtaaactact tcgatgactt acaagcaggt     360
agagaacagg ctcatccttg gtgggcttta gtaaacgagc acttccaaa cgtattgagg     420
cattttggtc cttttttgctc attgaacttg atcaggtcta ccttagactt cttcgagggt     480
tgctggatag aacaatacaa ttttggagga ttcccaggtt ctcacgacta cccacagttc     540
ttgagaagaa tgaacggttt aggacactgc gtcggtgcct ctttgtggcc aaaggagcag     600
ttcaatgaaa gatcattgtt tttggagatc acttcagcca tagctcaaat ggaaaattgg     660
atggtctggg ttaatgattt gatgtcattt tacaaggagt cgacgacga gagggatcag     720
atctctttgg taaagaacta cgttgtttct gacgagatat cattcacga ggccttagaa     780
aaattgaccc aggataccct gcactcttca agcaaatgg ttgcagtttt ctcagacaag     840
gaccctcaag taatggacac catagagtgc ttcatgcatg gttatgtcac atggcattta     900
tgcgacagga ggtacaggtt gtctgaaatc tacgagaaag tcaaggagga aaagactgag     960
gatgcccaaa aattttgcaa gttctacgag caagctgcca atgtaggagc cgtttcacct    1020
tctgagtggg cctatccacc agtcgcccag ttagctaacg taagatcaaa ggacgtcaaa    1080
gaggtccaga accattttt atcatctata gaattagttg aataa                     1125
```

<210> SEQ ID NO 71
<211> LENGTH: 1788
<212> TYPE: DNA
<213> ORGANISM: Artificial Sequence
<220> FEATURE:
<223> OTHER INFORMATION: Synthetic, IS_Pn_Sc coding sequence

<400> SEQUENCE: 71

```
atggctaccg agttgttgtg cttgcacagg ccaatatctt tgacccacaa attgttcagg      60
aatccattgc caaaagtcat acaagcaaca ccattgacct tgaagttaag gtgctctgta     120
tcaaccgaga acgtttcatt cacagagaca gaaacagaaa caaggaggtc agctaattac     180
gagccaaact catgggatta tgactacttg ttgtcttctg acaccgacga gtctattgag     240
gtatataaag acaaggcaaa gaagttggag gctgaagtca ggagggagat caacaacgaa     300
```

```
aaggcagagt tcttgacttt gccagagttg attgacaacg tacagaggtt gggattgggt    360
tataggtttg agtcagacat aagaagggct ttggacaggt tgtatcttc aggtggattc     420 gacgcagtta ctaagacctc attgcatgct accgctttat cttttaggtt attgagacag    480
catggtttcg aagtatcaca ggaggcattc tcaggattca aagaccagaa cggaaacttt    540
ttgaagaact tgaaggagga cataaaagcc atcttgtctt tatacgaagc ctcattttg     600 gccttagagg gtgagaatat tttagacgag gctaaggtct tcgccatatc tcacttgaag    660
gagttgtctg aggagaaaat aggaaaggac ttagccgaac aagtaaacca cgcattggaa    720
ttaccattgc ataggagaac tcaaaggtta gaagcagtct ggtctatcga ggcctacagg    780
aagaaagagg atgctgatca ggttttattg gagttggcca tcttagacta caacatgatc    840
cagtcagtct atcagagaga cttgagagaa acttctaggt ggtggagaag agtcggatta    900
gccactaaat tgcacttcgc tagggatagg ttaatagagt cattctattg ggctgttgga    960
gtagcttttg aaccacaata ctcagattgt aggaactcag tagccaagat gttctcattc   1020
gtcaccataa tcgatgacat ctacgacgta tacggaactt tggatgaatt ggaattattc   1080
actgatgcag tcgagagatg ggacgtaaat gccattgatg acttgcctga ttacatgaag   1140
ttgtgcttct tagctttgta caacaccata aacgagatcg catacgacaa cttgaaggac   1200
aagggtgaaa atatattgcc ttacttaacc aaggcctggg ctgatttgtg taacgcattc   1260
ttacaggaag caaaatggtt gtataacaaa tcaacaccta ctttcgacga gtattttggt   1320
aacgcttgga agtcttcatc tggaccttta caattggtat ttgcttactt cgccgtcgta   1380
caaaacatta agaaagagga gattgataac ttgcaaaagt accacgatat catctcaaga   1440
ccatcacaca tttttcaggtt atgtaacgac ttggcctctg cttcagctga aatagctaga   1500
ggagagactg caaattcagt ttcatgttac atgaggacca agggtatatc agaagaatta   1560
gcaaccgaat ctgtcatgaa tttaatcgac gagacctgga agaagatgaa caaggaaaag   1620
ttgggaggtt ctttattcgc aaaacctttt gtcgaaacag ccatcaattt agccaggcag   1680
tcacactgta catatcacaa tggtgatgcc cacacctcac ctgacgagtt gaccaggaaa   1740
agagttttgt cagttattac tgaacctata ttacctttg agaggtga                 1788
```

<210> SEQ ID NO 72
<211> LENGTH: 9905
<212> TYPE: DNA
<213> ORGANISM: Artificial Sequence
<220> FEATURE:
<223> OTHER INFORMATION: Synthetic, Expression plasmid pAM1812

<400> SEQUENCE: 72

```
gacgaaaggg cctcgtgata cgcctatttt tataggttaa tgtcatgata ataatggttt     60
cttagtatga tccaatatca aaggaaatga tagcattgaa ggatgagact aatccaattg    120
aggagtggca gcatatagaa cagctaaagg gtagtgctga aggaagcata cgatacccccg   180 catggaatgg gataatatca caggaggtac tagactacct ttcatcctac ataaatagac    240
gcatataagt acgcatttaa gcataaacac gcactatgcc gttcttctca tgtatatata    300
tatacaggca acacgcagat ataggtgcga cgtgaacagt gagctgtatg tgcgcagctc    360
gcgttgcatt ttcggaagcg ctcgttttcg gaaacgcttt gaagttccta ttccgaagtt    420
cctattctct agaaagtata ggaacttcag agcgcttttg aaaaccaaaa gcgctctgaa    480
gacgcacttt caaaaaacca aaaacgcacc ggactgtaac gagctactaa atatattgcga   540 ataccgcttc cacaaacatt gctcaaaagt atctctttgc tatatatctc tgtgctatat    600
```

```
ccctatataa cctacccatc cacctttcgc tccttgaact tgcatctaaa ctcgacctct    660
acatttttta tgtttatctc tagtattact ctttagacaa aaaaattgta gtaagaacta    720
ttcatagagt gaatcgaaaa caatacgaaa atgtaaacat ttcctatacg tagtatatag    780
agacaaaata gaagaaaccg ttcataattt tctgaccaat gaagaatcat caacgctatc    840
actttctgtt cacaaagtat gcgcaatcca catcggtata gaatataatc ggggatgcct    900
ttatcttgaa aaaatgcacc cgcagcttcg ctagtaatca gtaaacgcgg gaagtggagt    960
caggcttttt ttatggaaga gaaaatagac accaaagtag ccttcttcta accttaacgg   1020
acctacagtg caaaaagtta tcaagagact gcattataga gcgcacaaag gagaaaaaaa   1080
gtaatctaag atgctttgtt agaaaaatag cgctctcggg atgcatttt gtagaacaaa    1140 aaagaagtat agattctttg ttggtaaaat agcgctctcg cgttgcattt ctgttctgta   1200
aaaatgcagc tcagattctt tgtttgaaaa attagcgctc tcgcgttgca ttttttgtttt   1260 acaaaaatga agcacagatt cttcgttggt aaaatagcgc tttcgcgttg catttctgtt   1320
ctgtaaaaat gcagctcaga ttctttgttt gaaaaattag cgctctcgcg ttgcattttt   1380
gttctacaaa atgaagcaca gatgcttcgt tcaggtggca cttttcgggg aaatgtgcgc   1440 ggaacccta tttgtttatt tttctaaata cattcaaata tgtatccgct catgagacaa    1500
taaccctgat aaatgcttca ataatattga aaaggaaga gtatgagtat tcaacatttc    1560
cgtgtcgccc ttattccctt ttttgcggca ttttgccttc ctgttttgc tcacccagaa     1620 acgctggtga agtaaaaga tgctgaagat cagttgggtg cacgagtggg ttacatcgaa    1680
ctggatctca acagcggtaa gatccttgag agttttcgcc ccgaagaacg ttttccaatg   1740
atgagcactt ttaaagttct gctatgtggc gcggtattat cccgtattga cgccgggcaa   1800
gagcaactcg gtcgccgcat acactattct cagaatgact tggttgagta ctcaccagtc   1860
acagaaaagc atcttacgga tggcatgaca gtaagagaat tatgcagtgc tgccataacc   1920
atgagtgata acactgcggc caacttactt ctgacaacga tcggaggacc gaaggagcta   1980
accgcttttt tgcacaacat gggggatcat gtaactcgcc ttgatcgttg gaaccggag    2040 ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcatttttaa    2460
tttaaaagga tctaggtgaa gatcctttt gataatctca tgaccaaaat cccttaacgt    2520
gagttttcgt tccactgagc gtcagacccc gtagaaaaga tcaaaggatc ttcttgagat   2580
cctttttttc tgcgcgtaat ctgctgcttg caaacaaaaa aaccaccgct accagcggtg   2640
gtttgtttgc cggatcaaga gctaccaact cttttttccga aggtaactgg cttcagcaga   2700
gcgcagatac caaatactgt ccttctagtg tagccgtagt taggccacca cttcaagaac   2760
tctgtagcac cgcctacata cctcgctctg ctaatcctgt taccagtggc tgctgccagt   2820
ggcgataagt cgtgtcttac cgggttggac tcaagacgat agttaccgga taaggcgcag   2880
cggtcgggct gaacgggggg ttcgtgcaca gcccagct tggagcgaac gacctacacc     2940
gaactgagat acctacagcg tgagctatga gaaagcgcca cgcttcccga agggagaaag   3000
```

```
                                         -continued gcggacaggt atccggtaag cggcagggtc ggaacaggag agcgcacgag ggagcttcca      3060
gggggaaacg cctggtatct ttatagtcct gtcgggtttc gccacctctg acttgagcgt      3120 cgattttgt gatgctcgtc agggggcgg agcctatgga aaaacgccag caacgcggcc        3180
tttttacggt tcctggcctt tgctggcct tttgctcaca tgttctttcc tgcgttatcc       3240
cctgattctg tggataaccg tattaccgcc tttgagtgag ctgataccgc tcgccgcagc      3300
cgaacgaccg agcgcagcga gtcagtgagc gaggaagcgg aagagcgccc aatacgcaaa      3360
ccgcctctcc ccgcgcgttg gccgattcat taatgcagct ggatcttcga gcgtcccaaa      3420
accttctcaa gcaaggtttt cagtataatg ttacatgcgt acacgcgtct gtacagaaaa      3480 aaagaaaaa tttgaaatat aaataacgtt cttaatacta ataactat aaaaaaataa         3540 atagggaccta agacttcagg ttgtctaact ccttcctttt cggttagagc ggatcttagc     3600
tagctcaaac gaccatagga tgaacgaaga aggacttcat ataagatttc atgtcaccct      3660
cagcatgagt aaaaccatca ttaacagagt acaagacctc acacattcta gctaagttta     3720
ttgctggcat taacaaaggg aagggaacgg ctgttggacg caaagattct ctattgatta     3780 cttttccaggc atcctcaact ttcctactaa tatattcaca tgcttcctct tcagaagcac    3840
ctgattcttt agagtaacat tctatagatg aagccacatg tcctcttct tgttcttcct     3900 tgtgagatac aatatcgtcc attaatctta ctattacaca ggaagcttta ataataggtg    3960
ggtaactaga aacccatttg aatgtgtctt cagtaacaat gtctcctctg ccaacatagg     4020
accttgcaat catcaaacca taagtaccag taaccataga aacagacatg tattcttcta    4080
aagtaggcat ataaccttcc ttcaaccatc ttgcttctac taagtaatta cgaactaatt    4140
ctttagccat ctccttaacg taatgaatct gataggtctt tccctccttt tccaaagatt    4200
cttccatttc cacatgcaaa ttgactaatt cttggtagat taatttcata tattcgggca   4260
acatatctaa gcatgagata gaccatctct cgacggcttg agtaaaaatc tccaattctt    4320
cgtatgttcc ataattatca aaagtatcgt ccaaaactac taaccacatg catgttttca    4380
tcaaaaacat tcttgttcta gcgtgttgtg gctcatagta tatggacaat atccagaagt    4440
agccttcgac aacacgatca cgtacataag gtaacttatt ttgtaaatct aaatcttttcc   4500 accacttaca gatatgtgac aattcctttt tatgcataga ctgcaaaaca ctgaaatcca    4560
acttggctaa tttcaacaat acttcatcat gagatgtttc ctgttggtag attggcatgt   4620
aatgtaatgc ttcaatcctt gctaatctcc ttcttaaagg ttgttttaag gcttgatgga   4680
tttgtgtacg caatgaagaa tcgcaagatg ggtcttttgc tatgatatct aaatgaactt    4740
ttgtgaattc caaagcattg tctaagatgg tttcatcttc aaccctcata aatgcagctt    4800
catataaggc taatattcct tgtgcatcat tgcataaaga ctctttgaat ttacctttt     4860 cgtccataaa gtctttgaaa acgccagagg agacgttaaa gccctgttga cgcaacaacc    4920
tgaaccacaa tgaaatactc tgtaaatttt ccttatccac ccactgttca ccataggtaa    4980
catgtatatg ttgcaaagct tcctcgatct cttcttcaaa atggtaagct ataactaaac    5040
gttgaacagc atcaattaat tcaatcaatt tcacatgctg catgggctca tttgaacctt    5100
tgatagttat caattccttc ttaacttcct cttttaattc ctccactaat tgtttcttca   5160
taactaaatc ttcaggctca tcataggtca agaattgatc tccccaaata gaagcattga    5220
aattcattgt atgtctgata acgtcgggct tggttgagac tttgtcgtcc acgactaatg   5280
gtgatgtaga agaggaaaat gacacagaag aaataggcaa agttgacatg gatccggggt   5340
tttttctcct tgacgttaaa gtatagaggt atattaacaa ttttttgttg atacttttat    5400
```

```
tacatttgaa taagaagtaa tacaaaccga aaatgttgaa agtattagtt aaagtggtta    5460
tgcagttttt gcatttatat atctgttaat agatcaaaaa tcatcgcttc gctgattaat    5520
taccccagaa ataaggctaa aaaactaatc gcattatcat cctatggttg ttaatttgat    5580
tcgttcattt gaaggtttgt ggggccaggt tactgccaat ttttcctctt cataaccata    5640
aaagctagta ttgtagaatc tttattgttc ggagcagtgc ggcgcgaggc acatctgcgt    5700
ttcaggaacg cgaccggtga agacgaggac gcacggagga gagtcttcct tcggagggct    5760
gtcacccgct cggcggcttc taatccgtac ttcaatatag caatgagcag ttaagcgtat    5820
tactgaaagt tccaaagaga aggtttttt aggctaagat aatggggctc tttacatttc    5880
cacaacatat aagtaagatt agatatggat atgtatatgg atatgtatat ggtggtaatg    5940
ccatgtaata tgattattaa acttctttgc gtccatccaa aaaaaaagta agaattttg    6000
aaaattcgaa ttcatggaaa actttccaac cgagtacttc ttgaacacca ccgtcaggtt    6060
gttggagtac attaggtaca gggactcaaa ctataccagg gaggagagga ttgagaactt    6120
acactacgcc tacaacaaag ccgcccacca cttcgcccag ccaagacagc agcagttgtt    6180
gaaggtcgac cctaagagat tgcaagcttc attgcagacc attgtcggta tggttgtata    6240
ttcatgggcc aaggtatcta aagagtgtat ggcagacttg tcaatccact atacctacac    6300
cttggtattg gacgattcaa aagacgaccc ataccctact atggtaaact acttcgatga    6360
cttacaagca ggtagagaac aggctcatcc ttggtgggct ttagtaaacg agcactttcc    6420
aaacgtattg aggcattttg gtcctttttg ctcattgaac ttgatcaggt ctaccttaga    6480
cttcttcgag ggttgctgga tagaacaata caattttgga ggattcccag gttctcacga    6540
ctacccacag ttcttgagaa gaatgaacgg tttaggacac tgcgtcggtg cctcttgtg    6600
gccaaaggag cagttcaatg aaagatcatt gttttggag atcacttcag ccatagctca    6660
aatgaaaat tggatggtct gggttaatga tttgatgtca ttttacaagg agttcgacga    6720
cgagagggat cagatctctt tggtaaagaa ctacgttgtt tctgacgaga tatcattaca    6780
cgaggcctta gaaaaattga cccaggatac cttgcactct tcaaagcaaa tggttgcagt    6840
tttctcagac aaggaccctc aagtaatgga caccatagag tgcttcatgc atggttatgt    6900
cacatggcat ttatgcgaca ggaggtacag gttgtctgaa atctacgaga aagtcaagga    6960
ggaaaagact gaggatgccc aaaaattttg caagttctac gagcaagctg ccaatgtagg    7020
agccgtttca ccttctgagt gggcctatcc accagtcgcc cagttagcta acgtaagatc    7080
aaaggacgtc aaagaggtcc agaaaccatt tttatcatct atagaattag ttgaataagc    7140
gaatttctta tgatttatga ttttattat taaataagtt ataaaaaaaa taagtgtata    7200
caaattttaa agtgactctt aggttttaaa acgaaaattc ttattcttga gtaactcttt    7260
cctgtaggtc aggttgcttt ctcaggtata gcatgaggtc gctccaattc agctggcgta    7320
atagcgaaga ggcccgcacc gatcgcccct cccaacagtt gcgcagcctg aatggcgaat    7380
ggcgcgacgc gccctgtagc ggcgcattaa gcgcggcggg tgtggtggtt acgcgcagcg    7440
tgaccgctac acttgccagc gccctagcgc ccgctccttt cgctttcttc ccttcctttc    7500
tcgccacgtt cgccggcttt ccccgtcaag ctctaaatcg ggggctccct ttagggttcc    7560
gatttagtgc tttacggcac ctcgacccca aaaaacttga ttagggtgat ggttcacgta    7620
gtgggccatc gccctgatag acggtttttc gccctttgac gttggagtcc acgttcttta    7680
atagtggact cttgttccaa actggaacaa cactcaaccc tatctcggtc tattcttttg    7740
atttataagg gattttgccg atttcggcct attggttaaa aaatgagctg atttaacaaa    7800
```

-continued

```
aatttaacgc gaattttaac aaaatattaa cgtttacaat ttcctgatgc ggtattttct    7860
ccttacgcat ctgtgcggta tttcacaccg catatcgacg gtcgaggaga acttctagta    7920
tatccacata cctaatatta ttgccttatt aaaaatggaa tcccaacaat tacatcaaaa    7980
tccacattct cttcaaaatc aattgtcctg tacttccttg ttcatgtgtg ttcaaaaacg    8040
ttatatttat aggataatta tactctattt ctcaacaagt aattggttgt ttggccgagc    8100
ggtctaaggc gccttttttt atatatattt caaggatata ccattgtaat gtctgcccct    8160
aagaagatcg tcgttttgcc aggtgaccac gttggtcaag aaatcacagc cgaagccatt    8220
aaggttctta aagctatttc tgatgttcgt tccaatgtca agttcgattt cgaaaatcat    8280
ttaattggtg gtgctgctat cgatgctaca ggtgttccac ttccagatga ggcgctggaa    8340
gcctccaaga aggttgatgc cgttttgtta ggtgctgtgg ctggtcctaa atggggtacc    8400
ggtagtgtta gacctgaaca aggtttacta aaaatccgta aagaacttca attgtacgcc    8460
aacttaagac catgtaactt tgcatccgac tctcttttag acttatctcc aatcaagcca    8520
caatttgcta aaggtactga cttcgttgtt gtcagagaat tagtgggagg tatttacttt    8580
ggtaagagaa aggaagacga tggtgatggt gtcgcttggg atagtgaaca atacaccgtt    8640
ccagaagtgc aaagaatcac aagaatggcc gctttcatgg ccctacaaca tgagccacca    8700
ttgcctattt ggtccttgga taaagctaat cttttggcct cttcaagatt atggagaaaa    8760
actgtggagg aaaccatcaa gaacgaattc cctacattga aggttcaaca tcaattgatt    8820
gattctgccg ccatgatcct agttaagaac ccaacccacc taaatggtat tataatcacc    8880
agcaacatgt ttggtgatat catctccgat gaagcctccg ttatcccagg ttccttgggt    8940
ttgttgccat ctgcgtcctt ggcctctttg ccagacaaga acaccgcatt tggttttgtac   9000
gaaccatgcc acggttctgc tccagatttg ccaaagaata aggttgaccc tatcgccact    9060
atcttgtctg ctgcaatgat gttgaaattg tcattgaact tgcctgaaga aggtaaggcc    9120
attgaagatg cagttaaaaa ggttttggat gcaggtatca gaactggtga tttaggtggt    9180
tccaacagta ccaccgaagt cggtgatgct gtcgccgaag aagttaagaa aatccttgct    9240
taaaaagatt ctcttttttt atgatatttg tacataaact ttataaatga aattcataat    9300
agaaacgaca cgaaattaca aaatggaata tgttcatagg gtagacgaaa ctatatacgc    9360
aatctacata catttatcaa gaaggagaaa aaggaggata gtaaaggaat acaggtaagc    9420
aaattgatac taatggctca acgtgataag gaaaaagaat tgcactttaa cattaatatt    9480
gacaaggagg agggcaccac acaaaaagtt aggtgtaaca gaaaatcatg aaactacgat    9540
tcctaatttg atattggagg attttctcta aaaaaaaaaa aatacaacaa ataaaaaaca    9600
ctcaatgacc tgaccatttg atggagttta agtcaatacc ttcttgaagc atttcccata    9660
atggtgaaag ttccctcaag aattttactc tgtcagaaac ggccttacga cgtagtcgat    9720
atggtgcact ctcagtacaa tctgctctga tgccgcatag ttaagccagc ccgacacccc    9780
gccaacaccc gctgacgcgc cctgacgggc ttgtctgctc ccggcatccg cttacagaca    9840
agctgtgacc gtctccggga gctgcatgtg tcagaggttt tcaccgtcat caccgaaacg    9900
cgcga                                                               9905
```

<210> SEQ ID NO 73
<211> LENGTH: 2307
<212> TYPE: DNA
<213> ORGANISM: Artificial Sequence
<220> FEATURE:
<223> OTHER INFORMATION: Synthetic, FS_Ad_Sc coding sequence

```
<400> SEQUENCE: 73
atggaacctc tgctattctc aatccaaaca ctagtgcatc aagtgaaaca ggaaattttc      60
tcatctactt ttgatttgta tagctttgta agcccatctg cctatgatac agcatggtta     120
gccatgattc cccatccaaa acaaaactct tgccctaaat ttaaaggctg tttggattgg     180
atcttagata accaaaagga agcaggatac tggggtgaat gtgatcacga tggattacca     240
actatagata gcctgcccgc aactctagcc tgtatggtag cttcgaagac gtggggtgtg     300
tcagagaagc atataaataa aggacttgct tttattcacg caaactcaac cacattgttg     360
aaagaaaaat acgaccattt gccaaggtgg tttgtcatag ttttcccgc gatggtcgaa      420
gtcgctcaag ccgccggcct aaaagttttg tttagtaacg gattagaaga ggtggttctt     480
aatatttctc tggaaagaga aaaaatacta gaaagagaag agttcgtcga taaatatcat     540
tacccacctc ttgcatctta tttagaagcc ctgcctccaa gttataccat agacagaaag     600
gatataacta tgaacctatc aggcgatggc tcctgctttc agtccccgtc agctactgct     660
tgcgcctttt tggcaaccgg aaatcaaaaa tgcatggctt acctggaatc tttggtacag     720
aagagacccg gtggtgtgcc gaccatgtat ccgatggatg gagaattggt gagcctttgc     780
ttagtaaatc aaattcaaag attgggttta gcggagcatt tcacagaaga aattgaggag     840
aatttaaaat tgatatatga aaattataag aaccaagaat cacgtgaaat gaaagattca     900
tatttggtgc caactaagat ttataaggat agtttagcct tcagattgct acgtatgcac     960
ggttataatg ttacgcccag acgtttctgt tggtttttat accaagaaga tatacgtgtc    1020
cacatagaga aaaattacga gtgttttaca tcagcgctgt acaatgtcta ccgtgccaca    1080
gacttaatgt tttctggtga atatgaattg gaagaagcca gggtcttctc taggaaattg    1140
ctggagaaat caatgaaatt gaagtcttta acgataatt tggttaattt tccatctttc    1200
aggtcagtta ttgatcatga gttgtctgtg ccttggatcg cccgtttgga gcatcttgat    1260
catagaatgt ggattgaaga aaataaggtg gatacacttt ggatcggtaa agcctctttt    1320
tatcgtctgc gtgcgcttaa cgataagtta atgacattag ctgtggagtc atataagttt    1380
agacaatctt tttatagaaa cgaacttgaa gaattgaaaa gatggagtaa ggactgggt     1440
ttgacagatt taggattcgg tagaaaaaaa acgacatatt gttattatgc aattgctgct    1500
tcctctagtt taccacacaa ttctatggtc agattgattg tggcaaaatc cgcattactt    1560
gtgaccattg cagatgattt ctttgatatg aagggtccc tagaggattt acaaagtttg     1620
acacaggcta tacaaagatg ggatggcaac agtttgtccg gtcacggtaa ataatattc     1680
tgcgcattag acaacttggt tagtgatatc gccaaccccc atttacacct agaagggtca    1740
catgtagccg agaatgtcaa aaacatgtgg tctgaaacta tcgccagctg gttgactgag    1800
actacctgga gtcacacagg ttacgtccct agtctggatg aatacctaca gacaggtaag    1860
atttctgttg cttctcagtt gatgaccgtc ccagctttat gttttttatc tccaaacgtt    1920
caccctatct gtaagcttga agctaatcac tatcaaatta taactaagtt gttgatggtc    1980
tctacaagat tgcttaacga tactcaaaca tacgaaaagg agttaaaaga cggtaaaaga    2040
aattttgtta tccttcattc taagggtca ccacagacag gaatcgagaa atcagttgct    2100
tttgttaagg aaattttgga tcaaatagaa aaagagttct tagaacatac tttgatggac    2160
ggtcataacg atctacctaa gccttgtaag catttacatt tgtctatatt aagagcattt    2220
cacatgttct ataactcagg agacttattc gatagcgata caggattgct tcatgatatc    2280
aataaggcgt tttatgtccc cttgtaa                                        2307
```

<210> SEQ ID NO 74
<211> LENGTH: 8671
<212> TYPE: DNA
<213> ORGANISM: Artificial Sequence
<220> FEATURE:
<223> OTHER INFORMATION: Synthetic, Expression plasmid pAM1764

<400> SEQUENCE: 74

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatcga | ctacgtcgta | aggccgtttc | tgacagagta | aaattcttga | gggaactttc | 240 |
| accattatgg | gaaatggttc | aagaaggtat | tgacttaaac | tccatcaaat | ggtcaggtca | 300 |
| ttgagtgttt | tttatttgtt | gtattttttt | tttttagag | aaaatcctcc | aatatcaaat | 360 |
| taggaatcgt | agtttcatga | ttttctgtta | cacctaactt | tttgtgtggt | gccctcctcc | 420 |
| ttgtcaatat | taatgttaaa | gtgcaattct | ttttccttat | cacgttgagc | cattagtatc | 480 |
| aatttgctta | cctgtattcc | tttactatcc | tccttttct | ccttcttgat | aaatgtatgt | 540 |
| agattgcgta | tatagtttcg | tctaccctat | gaacatattc | cattttgtaa | tttcgtgtcg | 600 |
| tttctattat | gaatttcatt | tataaagttt | atgtacaaat | atcataaaaa | aagagaatct | 660 |
| ttttaagcaa | ggattttctt | aacttcttcg | gcgacagcat | caccgacttc | ggtggtactg | 720 |
| ttggaaccac | ctaaatcacc | agttctgata | cctgcatcca | aaaccttttt | aactgcatct | 780 |
| tcaatggcct | taccttcttc | aggcaagttc | aatgacaatt | tcaacatcat | tgcagcagac | 840 |
| aagatagtgg | cgatagggtc | aaccttattc | tttggcaaat | ctggagcaga | accgtggcat | 900 |
| ggttcgtaca | aaccaaatgc | ggtgttcttg | tctggcaaag | aggccaagga | cgcagatggc | 960 |
| aacaaaccca | aggaacctgg | gataacggag | gcttcatcgg | agatgatatc | accaaacatg | 1020 |
| ttgctggtga | ttataatacc | atttaggtgg | gttgggttct | taactaggat | catggcggca | 1080 |
| gaatcaatca | attgatgttg | aaccttcaat | gtagggaatt | cgttcttgat | ggtttcctcc | 1140 |
| acagtttttc | tccataatct | tgaagaggcc | aaaacattag | ctttatccaa | ggaccaaata | 1200 |
| ggcaatggtg | gctcatgttg | tagggccatg | aaagcggcca | ttcttgtgat | tctttgcact | 1260 |
| tctggaacgg | tgtattgttc | actatcccaa | gcgacaccat | caccatcgtc | ttcctttctc | 1320 |
| ttaccaaagt | aaatacctcc | cactaattct | ctgacaacaa | cgaagtcagt | acctttagca | 1380 |
| aattgtggct | tgattggaga | taagtctaaa | agagagtcgg | atgcaaagtt | acatggtctt | 1440 |
| aagttggcgt | acaattgaag | ttcttttacgg | attttttagta | aaccttgttc | aggtctaaca | 1500 |
| ctaccggtac | cccatttagg | accacccaca | gcacctaaca | aaacggcatc | aaccttcttg | 1560 |
| gaggcttcca | gcgcctcatc | tggaagtggg | acacctgtag | catcgatagc | agcaccacca | 1620 |
| attaaatgat | tttcgaaatc | gaacttgaca | ttggaacgaa | catcagaaat | agctttaaga | 1680 |
| accttaatgg | cttcggctgt | gatttcttga | ccaacgtggt | cacctggcaa | aacgacgatc | 1740 |
| ttcttagggg | cagacatagg | ggcagacatt | agaatggtat | atccttgaaa | tatatatata | 1800 |
| tattgctgaa | atgtaaaagg | taagaaaagt | tagaaagtaa | gacgattgct | aaccaccat | 1860 |
| tggaaaaaac | aataggtcct | taaataatat | tgtcaacttc | aagtattgtg | atgcaagcat | 1920 |
| ttagtcatga | acgcttctct | attctatatg | aaaagccggt | tccggcctct | cacctttcct | 1980 |
| ttttctccca | ttttttcagt | tgaaaaaggt | atatgcgtca | ggcgacctct | gaaattaaca | 2040 |
| aaaaatttcc | agtcatcgaa | tttgattctg | tgcgatagcg | cccctgtgtg | ttctcgttat | 2100 |

```
gttgaggaaa aaaataatgg ttgctaagag attcgaactc ttgcatctta cgatacctga    2160
gtattcccac agttaactgc ggtcaagata tttcttgaat caggcgcctt agaccgctcg    2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca ttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttgt    2520
taaatcagct cattttttaa ccaataggcc gaaatcggca aaatcccta taaatcaaaa    2580
gaatagaccg atagggttg gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag tttttgggg tcgaggtgcc gtaaagcact aaatcggaac    2760
cctaaaggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggatg tgctgcaagg cgattaagtt gggtaacgcc agggttttcc    3060
cagtcacgac gttgtaaaac gacggccagt gagcgcgcgt aatacgactc actatagggc    3120
gaattgggta ccgggccccc cctcgaggtc gacggtatcg ataagctcta gagcggccgc    3180
cctttagtga gggttgaatt cgaattttca aaaattctta cttttttttt ggatggacgc    3240
aaagaagttt aataatcata ttacatggca ttaccaccat atacatatcc atatacatat    3300
ccatatctaa tcttacttat atgttgtgga aatgtaaaga gccccattat cttagcctaa    3360
aaaaaccttc tctttggaac tttcagtaat acgcttaact gctcattgct atattgaagt    3420
acggattaga agccgccgag cgggtgacag ccctccgaag gaagactctc ctccgtgcgt    3480
cctcgtcttc accggtcgcg ttcctgaaac gcagatgtgc ctcgcgccgc actgctccga    3540
acaataaaga ttctacaata ctagctttta tggttatgaa gaggaaaaat tggcagtaac    3600
ctggccccac aaaccttcaa atgaacgaat caaattaaca accataggat gataatgcga    3660
ttagtttttt agccttattt ctggggtaat taatcagcga agcgatgatt tttgatctat    3720
taacagatat ataaatgcaa aaactgcata accactttaa ctaatacttt caacattttc    3780
ggtttgtatt acttcttatt caatgtaat aaaagtatca acaaaaaatt gttaatatac    3840
ctctatactt taacgtcaag gagaaaaac cccggatcca tggatacttt gcctatttct    3900
tctgtgtcat tttcctcttc tacatcacca ttagtcgtgg acgacaaagt ctcaaccaag    3960
cccgacgtta tcagacatac aatgaatttc aatgcttcta tttggggaga tcaattcttg    4020
acctatgatg agcctgaaga tttagttatg aagaaacaat tagtggagga attaaaagag    4080
gaagttaaga aggaattgat aactatcaaa ggttcaaatg agcccatgca gcatgtgaaa    4140
ttgattgaat taattgatgc tgttcaacgt ttaggtatag cttaccattt tgaagaagag    4200
atcgaggaag ctttgcaaca tatacatgtt acctatggtg aacagtgggt ggataaggaa    4260
aatttacaga gtatttcatt gtggttcagg ttgttcgtc aacagggctt taacgtctcc    4320
tctggcgttt tcaaagactt tatggacgaa aaaggtaaat tcaaagagtc tttatgcaat    4380
gatgcacaag gaatattagc cttatatgaa gctgcattta tgagggttga agatgaaacc    4440
atcttagaca atgctttgga attcacaaaa gttcatttag atatcatagc aaaagaccca    4500
```

```
tcttgcgatt cttcattgcg tacacaaatc catcaagcct taaaacaacc tttaagaagg    4560
agattagcaa ggattgaagc attacattac atgccaatct accaacagga aacatctcat    4620
gatgaagtat tgttgaaatt agccaagttg gatttcagtg ttttgcagtc tatgcataaa    4680
aaggaattgt cacatatctg taagtggtgg aaagatttag atttacaaaa taagttacct    4740
tatgtacgtg atcgtgttgt cgaaggctac ttctggatat tgtccatata ctatgagcca    4800
caacacgcta gaacaagaat gttttttgatg aaaacatgca tgtggttagt agttttggac   4860
gatactttg ataattatgg aacatacgaa gaattggaga ttttttactca agccgtcgag    4920
agatggtcta tctcatgctt agatatgttg cccgaatata tgaaattaat ctaccaagaa    4980
ttagtcaatt tgcatgtgga aatggaagaa tctttggaaa aggagggaaa gacctatcag    5040
attcattacg ttaaggagat ggctaaagaa ttagttcgta attacttagt agaagcaaga    5100
tggttgaagg aaggttatat gcctacttta gaagaataca tgtctgtttc tatggttact    5160
ggtacttatg gtttgatgat tgcaaggtcc tatgttggca gaggagacat tgttactgaa    5220
gacacattca aatgggtttc tagttaccca cctattatta aagcttcctg tgtaatagta    5280
agattaatgg acgatattgt atctcacaag gaagaacaag aaagaggaca tgtggcttca    5340
tctatagaat gttactctaa agaatcaggt gcttctgaag aggaagcatg tgaatatatt    5400
agtaggaaag ttgaggatgc ctggaaagta atcaatagag aatctttgcg tccaacagcc    5460
gttcccttcc ctttgttaat gccagcaata aacttagcta gaatgtgtga ggtcttgtac    5520
tctgttaatg atggttttac tcatgctgag ggtgacatga atcttatat gaagtccttc    5580
ttcgttcatc ctatggtcgt tgagctagc taagatccgc tctaaccgaa aaggaaggag    5640
ttagacaacc tgaagtctag gtccctattt attttttat agttatgtta gtattaagaa    5700
cgttatttat atttcaaatt tttctttttt ttctgtacag acgcgtgtac gcatgtaaca    5760
ttatactgaa aaccttgctt gagaaggttt tgggacgctc gaagatccag ctgcattaat    5820
gaatcggcca acgcgcgggg agaggcggtt tgcgtattgg gcgctcttcc gcttcctcg    5880
gctccagctt tgttccctt tagtgagggt taattgcgcg cttggcgtaa tcatggtcat    5940
agctgttttcc tgtgtgaaat tgttatccgc tcacaattcc acacaacata ggagccggaa    6000
gcataaagtg taaagcctgg ggtgcctaat gagtgaggta actcacatta attgcgttgc    6060
gctcactgcc cgctttccag tcgggaaacc tgtcgtgcca gctgcattaa tgaatcggcc    6120
aacgcgcggg gagaggcggt ttgcgtattg ggcgctcttc cgcttcctcg ctcactgact    6180
cgctgcgctc ggtcgttcgg ctgcggcgag cggtatcagc tcactcaaag gcggtaatac    6240
ggttatccac agaatcaggg gataacgcag gaaagaacat gtgagcaaaa ggccagcaaa    6300
aggccaggaa ccgtaaaaag gccgcgttgc tggcgttttt ccataggctc cgcccccctg    6360
acgagcatca caaaaatcga cgctcaagtc agaggtggcg aaacccgaca ggactataaa    6420
gataccaggc gtttccccct ggaagctccc tcgtgcgctc tcctgttccg accctgccgc    6480
ttaccggata cctgtccgcc tttctccctt cgggaagcgt ggcgctttct catagctcac    6540
gctgtaggta tctcagttcg gtgtaggtcg ttcgctccaa gctgggctgt gtgcacgaac    6600
cccccgttca gcccgaccgc tgcgccttat ccggtaacta tcgtcttgag tccaacccgg    6660
taagacacga cttatcgcca ctggcagcag ccactggtaa caggattagc agagcgaggt    6720
atgtaggcgg tgctacagag ttcttgaagt ggtggcctaa ctacggctac actagaagga    6780
cagtatttgg tatctgcgct ctgctgaagc cagttacctt cggaaaaaga gttggtagct    6840
cttgatccgg caaacaaacc accgctggta gcggtggttt ttttgtttgc aagcagcaga    6900
```

```
ttacgcgcag aaaaaaagga tctcaagaag atcctttgat cttttctacg gggtctgacg    6960
ctcagtggaa cgaaaactca cgttaaggga ttttggtcat gagattatca aaaggatct    7020 tcacctagat cctttaaat taaaaatgaa gttttaaatc aatctaaagt atatatgagt     7080
aaacttggtc tgacagttac caatgcttaa tcagtgaggc acctatctca gcgatctgtc    7140
tatttcgttc atccatagtt gcctgactcc ccgtcgtgta gataactacg atacgggagg    7200
gcttaccatc tggccccagt gctgcaatga taccgcgaga cccacgctca ccggctccag    7260
atttatcagc aataaaccag ccagccggaa gggccgagcg cagaagtggt cctgcaactt    7320
tatccgcctc catccagtct attaattgtt gccgggaagc tagagtaagt agttcgccag    7380
ttaatagttt gcgcaacgtt gttgccattg ctacaggcat cgtggtgtca cgctcgtcgt    7440
ttggtatggc ttcattcagc tccggttccc aacgatcaag gcgagttaca tgatccccca    7500
tgttgtgcaa aaaagcggtt agctccttcg gtcctccgat cgttgtcaga agtaagttgg    7560
ccgcagtgtt atcactcatg gttatggcag cactgcataa ttctcttact gtcatgccat    7620
ccgtaagatg cttttctgtg actggtgagt actcaaccaa gtcattctga aatagtgta    7680 tgcggcgacc gagttgctct tgcccggcgt caatacggga taataccgcg ccacatagca    7740
gaactttaaa agtgctcatc attggaaaac gttcttcggg gcgaaaactc tcaaggatct    7800
taccgctgtt gagatccagt tcgatgtaac ccactcgtgc acccaactga tcttcagcat    7860
cttttacttt caccagcgtt tctgggtgag caaaaacagg aaggcaaaat gccgcaaaaa    7920
agggaataag ggcgacacgg aaatgttgaa tactcatact cttccttttt caatattatt    7980
gaagcattta tcagggttat tgtctcatga gcggatacat atttgaatgt atttagaaaa    8040
ataaacaaat aggggttccg cgcacatttc cccgaaaagt gccacctggg tccttttcat    8100
cacgtgctat aaaaataatt ataatttaaa tttttttaata taaatatata aattaaaaat    8160
agaaagtaaa aaaagaaatt aaagaaaaaa tagtttttgt tttccgaaga tgtaaaagac    8220
tctaggggga tcgccaacaa atactacctt ttatcttgct cttcctgctc tcaggtatta    8280
atgccgaatt gtttcatctt gtctgtgtag aagaccacac acgaaaatcc tgtgatttta    8340
cattttactt atcgttaatc gaatgtatat ctatttaatc tgcttttctt gtctaataaa    8400
tatatatgta aagtacgctt tttgttgaaa ttttttaaac ctttgtttat ttttttttct    8460
tcattccgta actcttctac cttctttatt tactttctaa aatccaaata caaacataa    8520 aaataaataa acacagagta aattcccaaa ttattccatc attaaaagat acgaggcgcg    8580
tgtaagttac aggcaagcga tccgtcctaa gaaaccatta ttatcatgac attaacctat    8640 aaaaatagggc gtatcacgag gccctttcgt c                                  8671
```

<210> SEQ ID NO 75
<211> LENGTH: 44
<212> TYPE: DNA
<213> ORGANISM: Artificial Sequence
<220> FEATURE:
<223> OTHER INFORMATION: Synthetic, Primer AM-288-90-CPK1621

<400> SEQUENCE: 75

```
cttggcacat cctcttccgt agcttcgagc gtcccaaaac cttc                      44
```

<210> SEQ ID NO 76
<211> LENGTH: 1725
<212> TYPE: DNA
<213> ORGANISM: Artificial Sequence
<220> FEATURE:
<223> OTHER INFORMATION: Synthetic, FS_S2D_Sc coding sequence

<400> SEQUENCE: 76

```
atggatactt tgcctatttc ttctgtgtca ttttcctctt ctacatcacc attagtcgtg    60
gacgacaaag tctcaaccaa gcccgacgtt atcagacata caatgaattt caatgcttct   120
atttggggag atcaattctt gacctatgat gagcctgaag atttagttat gaagaaacaa   180
ttagtggagg aattaaaaga ggaagttaag aaggaattga taactatcaa aggttcaaat   240
gagcccatgc agcatgtgaa attgattgaa ttaattgatg ctgttcaacg tttaggtata   300
gcttaccatt ttgaagaaga gatcgaggaa gctttgcaac atatacatgt tacctatggt   360
gaacagtggg tggataagga aaatttacag agtatttcat tgtggttcag gttgttgcgt   420
caacagggct ttaacgtctc ctctggcgtt ttcaaagact ttatggacga aaaaggtaaa   480
ttcaaagagt ctttatgcaa tgatgcacaa ggaatattag ccttatatga agctgcattt   540
atgagggttg aagatgaaac catcttagac aatgctttgg aattcacaaa agttcattta   600
gatatcatag caaagacccc atcttgcgat tcttcattgc gtacacaaat ccatcaagcc   660
ttaaaacaac ctttaagaag gagattagca aggattgaag cattacatta catgccaatc   720
taccaacagg aaacatctca tgatgaagta ttgttgaaat tagccaagtt ggatttcagt   780
gttttgcagt ctatgcataa aaaggaattg tcacatatct gtaagtggtg aaagatttta   840
gatttacaaa ataagttacc ttatgtacgt gatcgtgttg tcgaaggcta cttctggata   900
ttgtccatat actatgagcc acaacacgct agaacaagaa tgtttttgat gaaaacatgc   960
atgtggttag tagttttgga cgatactttt gataattatg gaacatacga gaattggag  1020
atttttactc aagccgtcga gagatggtct atctcatgct tagatatgtt gcccgaatat  1080
atgaaattaa tctaccaaga attagtcaat ttgcatgtgg aaatgaaaga atctttggaa  1140
aaggagggaa agacctatca gattcattac gttaaggaga tggctaaaga attagttcgt  1200
aattacttag tagaagcaag atggttgaag aaggttata tgcctacttt agaagaatac  1260
atgtctgttt ctatggttac tggtacttat ggtttgatga ttgcaaggtc ctatgttggc  1320
agaggagaca ttgttactga agacacattc aaatgggttt ctagttaccc acctattatt  1380
aaagcttcct gtgtaatagt aagattaatg gacgatattg tatctcacaa ggaagaacaa  1440
gaaagaggac atgtggcttc atctatagaa tgttactcta agaatcagg tgcttctgaa  1500
gaggaagcat gtgaatatat tagtaggaaa gttgaggatg cctggaaagt aatcaataga  1560
gaatctttgc gtccaacagc cgttcccttc cctttgttaa tgccagcaat aaacttagct  1620
agaatgtgtg aggtcttgta ctctgttaat gatggttta ctcatgctga gggtgacatg  1680
aaatcttata tgaagtcctt cttcgttcat cctatggtcg tttga              1725
```

<210> SEQ ID NO 77
<211> LENGTH: 29
<212> TYPE: DNA
<213> ORGANISM: Artificial Sequence
<220> FEATURE:
<223> OTHER INFORMATION: Synthetic, Primer PW-091-144-CPK640

<400> SEQUENCE: 77

```
gtttaaactg cgaaaagaaa cgtggataa                                      29
```

<210> SEQ ID NO 78
<211> LENGTH: 44
<212> TYPE: DNA
<213> ORGANISM: Artificial Sequence
<220> FEATURE:
<223> OTHER INFORMATION: Synthetic, Primer AM-288-90-CPK1615

```
<400> SEQUENCE: 78
aagttccctc aagaatttta ctgacaggcc tcgagatatt tgag           44

<210> SEQ ID NO 79
<211> LENGTH: 44
<212> TYPE: DNA
<213> ORGANISM: Artificial Sequence
<220> FEATURE:
<223> OTHER INFORMATION: Synthetic, Primer AM-288-90-CPK1620

<400> SEQUENCE: 79
gaaggttttg ggacgctcga agctacggaa gaggatgtgc caag           44

<210> SEQ ID NO 80
<211> LENGTH: 28
<212> TYPE: DNA
<213> ORGANISM: Artificial Sequence
<220> FEATURE:
<223> OTHER INFORMATION: Synthetic, Primer PW-091-144-CPK649

<400> SEQUENCE: 80
gtttaaaccg tttaagtgtc actgtgct                              28

<210> SEQ ID NO 81
<211> LENGTH: 41
<212> TYPE: DNA
<213> ORGANISM: Artificial Sequence
<220> FEATURE:
<223> OTHER INFORMATION: Synthetic, Primer AM-288-90-CPK1616

<400> SEQUENCE: 81
actagaagtt ctcctcgacc gttttcaaaa attcttactt t               41

<210> SEQ ID NO 82
<211> LENGTH: 20
<212> TYPE: DNA
<213> ORGANISM: Artificial Sequence
<220> FEATURE:
<223> OTHER INFORMATION: Synthetic, Primer AM-288-90-CPK1638

<400> SEQUENCE: 82
gtatagaggt atattaacaa                                       20

<210> SEQ ID NO 83
<211> LENGTH: 51
<212> TYPE: DNA
<213> ORGANISM: Artificial Sequence
<220> FEATURE:
<223> OTHER INFORMATION: Synthetic, Primer AM-288-90-CPK1618

<400> SEQUENCE: 83
ttgttaatat acctctatac tttaacgtca aggagaaaaa accccggatc c    51

<210> SEQ ID NO 84
<211> LENGTH: 47
<212> TYPE: DNA
<213> ORGANISM: Artificial Sequence
<220> FEATURE:
<223> OTHER INFORMATION: Synthetic, Primer AM-288-90-CPK1619

<400> SEQUENCE: 84
aggttgtctg actccttcct tttcggttag agcggatctt agctagc         47

<210> SEQ ID NO 85
<211> LENGTH: 20
<212> TYPE: DNA
```

<213> ORGANISM: Artificial Sequence
<220> FEATURE:
<223> OTHER INFORMATION: Synthetic, Primer AM-288-90-CPK1639

<400> SEQUENCE: 85

| gaaaaggaag gagtcagaca | 20 |

<210> SEQ ID NO 86
<211> LENGTH: 6365
<212> TYPE: DNA
<213> ORGANISM: Artificial Sequence
<220> FEATURE:
<223> OTHER INFORMATION: Synthetic, Construct A

<400> SEQUENCE: 86

| ctgcgaaaag aaacgtggat aagtattata gaaacagcac ttcttcggcc aacaatatca | 60 |
| cgcaaattga gcaagatagt gctataaaag gtcttttgcc cttttttgcc tattatgcaa | 120 |
| gcattgcttt actagtgtgg atgcaaccaa gctttattac actctctttc atcctttccg | 180 |
| ttggtttcac gggagcattt accgtcggaa gaataatcgt ttgccattta actaagcaga | 240 |
| gctttcccat gttcaatgca cccatgttaa ttcctttgtg ccagatagta ttgtacaaaa | 300 |
| tatgtctatc cctttgggga attgagtcta ataaaatcgt ctttgcccta tcttggcttg | 360 |
| ggttcggtct ctcactaggt gttcacatta tgtttatgaa tgacattatc catgaattta | 420 |
| ctgagtacct ggacgtttat gctttatcca tcaagcgctc caagctgaca taaatcgcac | 480 |
| tttgtatcta cttttttttta ttcgaaaaca aggcacaaca atgaatctat cgccctgtga | 540 |
| gattttcaat ctcaagtttg tgtaatagat agcgttatat tatagaacta taaaggtcct | 600 |
| tgaatataca tagtgtttca ttcctattac tgtatatgtg actttacatt gttacttccg | 660 |
| cggctatttg acgttttctg cttcaggtgc ggcttggagg gcaaagtgtc agaaaatcgg | 720 |
| ccaggccgta tgacacaaaa gagtagaaaa cgagatctca aatatctcga ggcctgtcag | 780 |
| taaaattctt gagggaactt tcaccattat gggaaatggt tcaagaaggt attgacttaa | 840 |
| actccatcaa atggtcaggt cattgagtgt ttttttattg ttgtatttt ttttttttag | 900 |
| agaaaatcct ccaatatcaa attaggaatc gtagtttcat gattttctgt tacacctaac | 960 |
| tttttgtgtg gtgccctcct ccttgtcaat attaatgtta aagtgcaatt ctttttcctt | 1020 |
| atcacgttga gccattagta tcaatttgct tacctgtatt cctttactat cctccttttt | 1080 |
| ctccttcttg ataaatgtat gtagattgcg tatatagttt cgtctaccct atgaacatat | 1140 |
| tccattttgt aatttcgtgt cgtttctatt atgaatttca tttataaagt ttatgtacaa | 1200 |
| atatcataaa aaagagaat cttttttaagc aaggattttc ttaacttctt cggcgacagc | 1260 |
| atcaccgact tcggtggtac tgttggaacc acctaaatca ccagttctga tacctgcatc | 1320 |
| caaaaccttt ttaactgcat cttcaatggc cttaccttct tcaggcaagt tcaatgacaa | 1380 |
| tttcaacatc attgcagcag acaagatagt ggcgataggg tcaaccttat tctttggcaa | 1440 |
| atctggagca gaaccgtggc atggttcgta caaaccaaat gcggtgttct tgtctggcaa | 1500 |
| agaggccaag gacgcagatg gcaacaaacc caaggaacct gggataacgg aggcttcatc | 1560 |
| ggagatgata tcaccaaaca tgttgctggt gattataata ccatttaggt gggttgggtt | 1620 |
| cttaactagg atcatggcgg cagaatcaat caattgatgt tgaaccttca atgtagggaa | 1680 |
| ttcgttcttg atggtttcct ccacagtttt tctccataat cttgaagagg ccaaaacatt | 1740 |
| agctttatcc aaggaccaaa taggcaatgg tggctcatgt tgtagggcca tgaaagcggc | 1800 |
| cattcttgtg attcttgca cttctggaac ggtgtattgt tcactatccc aagcgacacc | 1860 |

```
atcaccatcg tcttcctttc tcttaccaaa gtaaatacct cccactaatt ctctgacaac    1920
aacgaagtca gtacctttag caaattgtgg cttgattgga gataagtcta aaagagagtc    1980
ggatgcaaag ttacatggtc ttaagttggc gtacaattga agttctttac ggattttag     2040 taaaccttgt tcaggtctaa cactaccggt accccattta ggaccaccca cagcacctaa    2100
caaaacggca tcaaccttct tggaggcttc cagcgcctca tctggaagtg ggacacctgt    2160
agcatcgata gcagcaccac caattaaatg attttcgaaa tcgaacttga cattggaacg    2220
aacatcagaa atagctttaa gaaccttaat ggcttcggct gtgatttctt gaccaacgtg    2280
gtcacctggc aaaacgacga tcttcttagg ggcagacata ggggcagaca ttagaatggt    2340
atatccttga aatatatata tatattgctg aaatgtaaaa ggtaagaaaa gttagaaagt    2400
aagacgattg ctaaccacct attggaaaaa acaataggtc cttaaataat attgtcaact    2460
tcaagtattg tgatgcaagc atttagtcat gaacgcttct ctattctata tgaaaagccg    2520
gttccggcct ctcacctttc ctttttctcc caatttttca gttgaaaaag gtatatgcgt    2580
caggcgacct ctgaaattaa caaaaaattt ccagtcatcg aatttgattc tgtgcgatag    2640
cgcccctgtg tgttctcgtt atgttgagga aaaaaataat ggttgctaag agattcgaac    2700
tcttgcatct tacgatacct gagtattccc acagttaact gcggtcaaga tatttcttga    2760
atcaggcgcc ttagaccgct cggccaaaca accaattact tgttgagaaa tagagtataa    2820
ttatcctata aatataacgt ttttgaacac acatgaacaa ggaagtacag gacaattgat    2880
tttgaagaga atgtggattt tgatgtaatt gttgggattc catttttaat aaggcaataa    2940
tattaggtat gtggatatac tagaagttct cctcgaccgt tttcaaaaat tcttactttt    3000
tttttggatg gacgcaaaga agtttaataa tcatattaca tggcattacc accatataca    3060
tatccatata catatccata tctaatctta cttatatgtt gtggaaatgt aaagagcccc    3120
attatcttag cctaaaaaaa ccttctcttt ggaactttca gtaatacgct taactgctca    3180
ttgctatatt gaagtacgga ttagaagccg ccgagcgggt gacagccctc cgaaggaaga    3240
ctctcctccg tgcgtcctcg tcttcaccgg tcgcgttcct gaaacgcaga tgtgcctcgc    3300
gccgcactgc tccgaacaat aaagattcta caatactagc ttttatggtt atgaagagga    3360
aaaattggca gtaacctggc cccacaaacc ttcaaatgaa cgaatcaaat taacaaccat    3420
aggatgataa tgcgattagt ttttagcct tatttctggg gtaattaatc agcgaagcga    3480
tgatttttga tctattaaca gatatataaa tgcaaaaact gcataaccac tttaactaat    3540
actttcaaca ttttcggttt gtattacttc ttattcaaat gtaataaaag tatcaacaaa    3600
aaattgttaa tatacctcta tactttaacg tcaaggagaa aaaccccggg atccatgtca    3660
actttgccta tttcttctgt gtcatttcc tcttctacat caccattagt cgtgacgac     3720 aaagtctcaa ccaagcccga cgttatcaga catacaatga atttcaatgc ttctatttgg    3780
ggagatcaat tcttgaccta tgatgagcct gaagatttag ttatgaagaa acaattagtg    3840
gaggaattaa aagaggaagt taagaaggaa ttgataacta tcaaaggttc aaatgagccc    3900
atgcagcatg tgaaattgat tgaattaatt gatgctgttc aacgtttagg tatagcttac    3960
cattttgaag aagagatcga ggaagctttg caacatatac atgttaccta tggtgaacag    4020
tgggtggata aggaaaattt acagagtatt tcattgtggt tcaggttgtt gcgtcaacag    4080
ggctttaacg tctcctctgg cgttttcaaa gactttatgg acgaaaaagg taaattcaaa    4140
gagtctttat gcaatgatgc acaaggaata ttagccttat atgaagctgc atttatgagg    4200
gttgaagatg aaaccatctt agacaatgct ttggaattca caaaagttca tttagatatc    4260
```

```
atagcaaaag acccatcttg cgattcttca ttgcgtacac aaatccatca agccttaaaa    4320
caacctttaa gaaggagatt agcaaggatt gaagcattac attacatgcc aatctaccaa    4380
caggaaacat ctcatgatga agtattgttg aaattagcca agttggattt cagtgttttg    4440
cagtctatgc ataaaaagga attgtcacat atctgtaagt ggtggaaaga tttagattta    4500
caaaataagt taccttatgt acgtgatcgt gttgtcgaag gctacttctg gatattgtcc    4560
atatactatg agccacaaca cgctagaaca agaatgtttt tgatgaaaac atgcatgtgg    4620
ttagtagttt tggacgatac ttttgataat tatggaacat acgaagaatt ggagattttt    4680
actcaagccg tcgagagatg gtctatctca tgcttagata tgttgcccga atatatgaaa    4740
ttaatctacc aagaattagt caatttgcat gtggaaatgg aagaatcttt ggaaaaggag    4800
ggaaagacct atcagattca ttacgttaag gagatggcta agaattagt tcgtaattac     4860
ttagtagaag caagatggtt gaaggaaggt tatatgccta ctttagaaga atacatgtct    4920
gtttctatgg ttactggtac ttatggtttg atgattgcaa ggtcctatgt tggcagagga    4980
gacattgtta ctgaagacac attcaaatgg gtttctagtt acccacctat tattaaagct    5040
tcctgtgtaa tagtaagatt aatggacgat attgtatctc acaaggaaga acaagaaaga    5100
ggacatgtgg cttcatctat agaatgttac tctaaagaat caggtgcttc tgaagaggaa    5160
gcatgtgaat atattagtag gaaagttgag gatgcctgga aagtaatcaa tagagaatct    5220
ttgcgtccaa cagccgttcc cttccctttg ttaatgccag caataaactt agctagaatg    5280
tgtgaggtct tgtactctgt taatgatggt tttactcatg ctgagggtga catgaaatct    5340
tatatgaagt ccttcttcgt tcatcctatg gtcgtttgag ctagctaaga tccgctctaa    5400
ccgaaaagga aggagtcaga caacctgaag tctaggtccc tatttatttt tttatagtta    5460
tgttagtatt aagaacgtta tttatatttc aaatttttct tttttttctg tacagacgcg    5520
tgtacgcatg taacattata ctgaaaacct tgcttgagaa ggttttggga cgctcgaagc    5580
tacggaagag gatgtgccaa ggacattttc aagaatatta gaaacaggtt cgtttcaaaa    5640
ttattatcaa aaaatggatg cagaaaatgc agatagggta tattcgaaag gggtcaagtt    5700
gattgcaagc ggtactctac catctggtat atttaatagg gaagaattgt ttgaggaaga    5760
tagtttctat aagtattaaa taaactaatg attttaaatc gttaaaaaaa tatgcgaatt    5820
ctgtggatcg aacacaggac ctccagataa cttgaccgaa gttttttctt cagtctggcg    5880
ctctcccaac tgagctaaat ccgcttacta tttgttatca gttcccttca tatctacata    5940
gaataggtta agtattttat tagttgccag aagaactact gatagttggg aatatttggt    6000
gaataatgaa gattgggtga ataatttgat aattttgaga ttcaattgtt aatcaatgtt    6060
acaatattat gtatacagag tatactgaaa gttctcttcg gagatcttga agttcacaaa    6120
agggaatcga tatttctaca taatattatc attacttctt ccccatctta tatttgtcat    6180
tcattattga ttatgatcaa tgcaataatg attggtagtt gccaaacatt taatacgatc    6240
ctctgtaata tttctatgaa taattatcac agcaacgttc aattatcttc aattcggctt    6300
cagtactgta tgaaatactc gctaacattt tctttattct ataatagcac agtgacactt    6360
aaacg                                                                6365
```

<210> SEQ ID NO 87
<211> LENGTH: 5251
<212> TYPE: DNA
<213> ORGANISM: Artificial Sequence
<220> FEATURE:
<223> OTHER INFORMATION: Synthetic, Integration construct i8

<400> SEQUENCE: 87

```
ttgcctatgc tttgtttgct ttgaacactt gtttccgctc tccttttact tattggctac    60
taaaactacg tgtaaaagat cgcccagcgc aaaaaggtcc ggcggtttca ataatctcg    120
aactattcct ataatatgca aaatagtagg taggaacaag tcgactctag gcagataagg    180
aagatgtccg gtaaatggag actagtgctg accgggatag gcaatccaga gcctcagtac    240
gctggtaccc gtcacaatgt agggctatat atgctggagc tgctacgaaa gcggcttggt    300
ctgcaggga  gaacttattc ccctgtgcct aatacgggcg gcaaagtgca ttatatagaa    360
gacgaacatt gtacgatact aagatcggat ggccagtaca tgaatctaag tggagaacag    420
gtgtgcaagg tctgggcccg gtacgccaag taccaagccc gacacgtagt tattcatgac    480
gagttaagtg tggcgtgtgg aaaagtgcag ctcagagccc ccagcaccag tattagaggt    540
cataatgggc tgcgaagcct gctaaaatgc agtggaggcc gtgtacccct tgccaaattg    600
gctattggaa tcggcagaga acctgggtcc cgttctagag accctgcgag cgtgtcccgg    660
tgggttctgg gagctctaac tccgcaggaa ctacaaacct tgcttacaca gagtgaacct    720
gctgcctggc gtgctctgac tcagtacatt tcatagtgga tggcggcgtt agtatcgaat    780
cgacagcagt atagcgacca gcattcacat acgattgacg catgatatta ctttctgcgc    840
acttaacttc gcatctgggc agatgatgtc gaggcgaaaa aaaatataaa tcacgctaac    900
atttgattaa aatagaacaa ctacaatata aaaaaactat acaaatgaca agttcttgaa    960
aacaagaatc tttttattgt cagtactgat tagaaaaact catcgagcat caaatgaaac   1020
tgcaatttat tcatatcagg attatcaata ccatattttt gaaaaagccg tttctgtaat   1080
gaaggagaaa actcaccgag gcagttccat aggatggcaa gatcctggta tcggtctgcg   1140
attccgactc gtccaacatc aatacaacct attaatttcc cctcgtcaaa aataaggtta   1200
tcaagtgaga atcaccatg  agtgacgact gaatccggtg agaatggcaa aagcttatgc   1260
atttcttttcc agacttgttc aacaggccag ccattacgct cgtcatcaaa atcactcgca   1320
tcaaccaaac cgttattcat tcgtgattgc gcctgagcga gacgaaatac gcgatcgctg   1380
ttaaaaggac aattacaaac aggaatcgaa tgcaaccggc gcaggaacac tgccagcgca   1440
tcaacaatat tttcacctga atcaggatat tcttctaata cctggaatgc tgttttgccg   1500
gggatcgcag tggtgagtaa ccatgcatca tcaggagtac ggataaaatg cttgatggtc   1560
ggaagaggca taaattccgt cagccagttt agtctgacca tctcatctgt aacatcattg   1620
gcaacgctac ctttgccatg tttcagaaac aactctggcg catcgggctt cccatacaat   1680
cgatagattg tcgcacctga ttgcccgaca ttatcgcgag cccatttata cccatataaa   1740
tcagcatcca tgttggaatt taatcgcggc ctcgaaacgt gagtcttttc cttacccatg   1800
gttgtttatg ttcggatgtg atgtgagaac tgtatcctag caagatttta aaggaagta    1860
tatgaaagaa gaacctcagt ggcaaatcct aaccttttat atttctctac aggggcgcgg   1920
cgtgggaca  attcaacgcg tctgtgaggg gagcgtttcc ctgctcgcag gtctgcagcg   1980
aggagccgta atttttgctt cgcgccgtgc ggccatcaaa atgtatggat gcaaatgatt   2040
atacatgggg atgtatgggc taaatgtacg ggcgacagtc acatcatgcc cctgagctgc   2100
gcacgtcaag actgtcaagg agggtattct gggcctccat gtcgctggcc gggtgacccg   2160
gcggggacga ggcaagctaa acagatctga tcttgaaact gagtaagatg ctcagaatac   2220
ccgtcaagat aagagtataa tgtagagtaa tataccaagt attcagcata ttctcctctt   2280
cttttgtata aatcacggaa gggatgattt ataagaaaaa tgaatactat tacacttcat   2340
```

```
ttaccaccct ctgatctaga ttttccaacg atatgtacgt agtggtataa ggtgaggggg    2400
tccacagata taacatcgtt taatttagta ctaacagaga cttttgtcac aactacatat    2460
aagtgtacaa atatagtaca gatatgacac acttgtagcg ccaacgcgca tcctacggat    2520
tgctgacaga aaaaaggtc acgtgaccag aaaagtcacg tgtaattttg taactcaccg    2580
cattctagcg gtccctgtcg tgcacactgc actcaacacc ataaaccta gcaacctcca    2640 aaggaaatca ccgtataaca aagccacagt tttacaactt agtctcttat gaagttactt    2700
accaatgaga aatagaggct ctttctcgag aaatatgaat atggatatat atatatatat    2760
atatatatat atatatatat gtaaacttgg ttcttttttta gcttgtgatc tctagcttgg    2820
gtctctctct gtcgtaacag ttgtgatatc ggaagaagag aaaagacgaa gagcagaagc    2880
ggaaaacgta tacacgtcac atatcacaca cacacaatgg gaaagctatt acaattggca    2940
ttgcatccgg tcgagatgaa ggcagctttg aagctgaagt tttgcagaac accgctattc    3000
tccatctatg atcagtccac gtctccatat ctcttgcact gtttcgaact gttgaacttg    3060
acctccagat cgtttgctgc tgtgatcaga gagctgcatc cagaattgag aaactgtgtt    3120
actctctttt atttgatttt aagggctttg gataccatcg aagacgatat gtccatcgaa    3180
cacgatttga aaattgactt gttgcgtcac ttccacgaga aattgttgtt aactaaatgg    3240
agtttcgacg gaaatgcccc cgatgtgaag gacagagccg ttttgacaga tttcgaatcg    3300
attcttattg aattccacaa attgaaacca gaatatcaag aagtcatcaa ggagatcacc    3360
gagaaaatgg gtaatggtat ggccgactac atcttagatg aaaattacaa cttgaatggg    3420
ttgcaaaccg tccacgacta cgacgtgtac tgtcactacg tagctggttt ggtcggtgat    3480
ggtttgaccc gtttgattgt cattgccaag tttgccaacg aatctttgta ttctaatgag    3540
caattgtatg aaagcatggg tctttttccta caaaaaacca acatcatcag agattacaat    3600
gaagatttgg tcgatggtag atccttctgg cccaaggaaa tctggtcaca atacgctcct    3660
cagttgaagg acttcatgaa acctgaaaac gaacaactgg ggttggactg tataaaccac    3720
ctcgtcttaa acgcattgag tcatgttatc gatgtgttga cttatttggc cggtatccac    3780
gagcaatcca cttttccaatt ttgtgccatt ccccaagtta tggccattgc aaccttggct    3840
ttggtattca acaaccgtga agtgctacat ggcaatgtaa agattcgtaa gggtactacc    3900
tgctatttaa ttttgaaatc aaggactttg cgtggctgtg tcgagatttt tgactattac    3960
ttacgtgata tcaaatctaa attggctgtg caagatccaa atttcttaaa attgaacatt    4020
caaatctcca agatcgaaca gtttatggaa gaaatgtacc aggataaatt acctcctaac    4080
gtgaagccaa atgaaactcc aattttcttg aaagttaaag aaagatccag atacgatgat    4140
gaattggttc caacccaaca agaagaagag tacaagttca atatggtttt atctatcatc    4200
ttgtccgttc ttcttgggtt ttattatata tacactttac acagagcgtg aagtctgcgc    4260
caaataacat aaacaaacaa ctccgaacaa taactaagta cttacataat aggtagaggc    4320
ctatccttaa agataacctt atatttcatt acatcaacta attcgacctt attatctttc    4380
gaattgaaat gcattatacc catcggtacg tctagctttg tcaccttccc cagtaaacgc    4440
tgtttcttgc cgacaaacaa tgtggccctc tctccgtcaa tctgtaacga cccaaatcgt    4500
attaaagttt cgccgtcctg ttcactgaac cttccctcat ttggagaatc tctcctcgcc    4560
agcgacgcaa agtccttagg caactctagt tcaccttgaa tctccagcat catcatccca    4620
agcggtgtta tcaccgtggt ctgcttttct cttgactgtg tcaacttctg ccattgacta    4680
gcatctatat ctacactagg cattcttttc agctgtttat tgggctgaat gatagtgata    4740
```

```
attctttttt ctatcactcc tttggctata ttagtggtta gcttactaaa aaagattaaa      4800
ggaaaaatga aattcaagat gctaacgttg acatgtatat tttaagaaaa caaaaatcat      4860
acaaagagga gatcggatat aaaagaataa cataaatatg tttagtgcat taggtaaatg      4920
ggtccgaggc tctcgcaatg ataaggactt tgtgacgaag tataccgcag atttatcaca      4980
aataacttca cagatccatc aattagatgt cgcgttaaag aaaagccaat ccatcttgag      5040
tcaatggcaa tcaaatctga ccttttatgg tattgcgtta acggtattgg ccctgagcta      5100
cacatattgg gagtaccatg gttatcgacc ataccttgtg gtgactgcgc tactatgcat      5160
aggctcgcta atcttgttca aatgggcatt aaccaaactc tatgcatttt ataacaacaa      5220
taggttacgc aagttggcaa aactccgtgc a                                    5251
```

<210> SEQ ID NO 88
<211> LENGTH: 70
<212> TYPE: DNA
<213> ORGANISM: Artificial Sequence
<220> FEATURE:
<223> OTHER INFORMATION: Synthetic, Primer 61-67-CPK066-G

<400> SEQUENCE: 88

```
ggtaagacgg ttgggtttta tcttttgcag ttggtactat taagaacaat cacaggaaac      60
agctatgacc                                                            70
```

<210> SEQ ID NO 89
<211> LENGTH: 70
<212> TYPE: DNA
<213> ORGANISM: Artificial Sequence
<220> FEATURE:
<223> OTHER INFORMATION: Synthetic, Primer 61-67-CPK067-G

<400> SEQUENCE: 89

```
ttgcgttttg tactttggtt cgctcaattt tgcaggtaga taatcgaaaa gttgtaaaac      60
gacggccagt                                                            70
```

<210> SEQ ID NO 90
<211> LENGTH: 4162
<212> TYPE: DNA
<213> ORGANISM: Artificial Sequence
<220> FEATURE:
<223> OTHER INFORMATION: Synthetic, Integration construct i32

<400> SEQUENCE: 90

```
gcctgtctac aggataaaga cgggtcggat acctgcacaa gcaatttggc acctgcatac      60
cccatttccc cagtagataa cttcaacaca cacatcaatg tccctcacca gtttatttcc      120
aaaagagacg cttttacta cctgactaga ttttcatttt gtttcttttg gattgcgctt      180
gcctttgtag gtgtgtcgtt tatcctttac gttttgactt ggtgctcgaa gatgctttca      240
gagatggtgc ttatcctcat gtcttttggg tttgtcttca atacggcagc cgttgtcttg      300
caaacggccg cctctgccat ggcaaagaat gctttccatg acgatcatcg tagtgcccaa      360
ttgggtgcct ctatgatggg tatggcttgg gcaagtgtct ttttatgtat cgtggaattt      420
atcctgctgg tcttctggtc tgttagggca aggttggcct ctacttactc catcgacaat      480
tcaagataca gaacctcctc cagatggaat cccttccata gagagaagga gcaagcaact      540
gacccaatat tgactgccac tggacctgaa gacatgcaac aaagtgcaag catagtgggg      600
ccttcttcca atgctaatcc ggtcactgcc actgctgcta cggaaaacca acctaaaggt      660
attaacttct tcactataag aaaatcacac gagcgcccgg acgatgtctc tgtttaaatg      720
```

```
gcgcaagttt tccgctttgt aatatatatt tataccccct tcttctctcc cctgcaatat    780
aatagtttaa ttctaatatt aataatatcc tatattttct tcatttaccg gcgcactctc    840
gcccgaacga cctcaaaatg tctgctacat tcataataac caaaagctca taacttttt     900
ttttgaacct gaatatatat acatcacata tcactgctgg tccttgccga ccagcgtata    960
caatctcgat agttggtttc ccgttctttc cactcccgtc cacaggaaac agctatgacc   1020
atgattacgc caagctattt aggtgacact atagaatact caagctatgc atcaagcttg   1080
gtaccgagct cggatccact agtaacggcc gccagtgtgc tggaattcgc cctgtcgaca   1140
ctagtaatac acatcatcgt cctacaagtt catcaaagtg ttggacagac aactatacca   1200
gcatggatct cttgtatcgg ttcttttctc ccgctctctc gcaataacaa tgaacactgg   1260
gtcaatcata gcctacacag gtgaacagag tagcgtttat acagggttta tacggtgatt   1320
cctacggcaa aaattttttca tttctaaaaa aaaaagaaa aattttttctt tccaacgcta   1380
gaaggaaaag aaaaatctaa ttaaattgat ttggtgattt tctgagagtt cccttttttca   1440
tatatcgaat tttgaatata aaaggagatc gaaaaaattt ttctattcaa tctgttttct   1500
ggttttattt gatagttttt ttgtgtatta ttattatgga ttagtactgg tttatatggg   1560
tttttctgta taacttcttt ttattttagt ttgtttaatc ttattttgag ttacattata   1620
gttccctaac tgcaagagaa gtaacattaa aaatgaaaaa gcctgaactc accgcgacgt   1680
ctgtcgagaa gtttctgatc gaaaagttcg acagcgtctc cgacctgatg cagctctcgg   1740
agggcgaaga atctcgtgct ttcagcttcg atgtaggagg gcgtggatat gtcctgcggg   1800
taaatagctg cgccgatggt ttctacaaag atcgttatgt ttatcggcac tttgcatcgg   1860
ccgcgctccc gattccggaa gtgcttgaca ttggggaatt cagcgagagc ctgacctatt   1920
gcatctcccg ccgtgcacag ggtgtcacgt tgcaagacct gcctgaaacc gaactgcccg   1980
ctgttctgca gccggtcgcg gaggccatgg atgcgatcgc tgcggccgat cttagccaga   2040
cgagcgggtt cggcccattc ggaccgcaag gaatcggtca atacactaca tggcgtgatt   2100
tcatatgcgc gattgctgat ccccatgtgt atcactggca aactgtgatg gacgacaccg   2160
tcagtgcgtc cgtcgcgcag gctctcgatg agctgatgct ttgggccgag gactgccccg   2220
aagtccggca cctcgtgcac gcggatttcg gctccaacaa tgtcctgacg gacaatggcc   2280
gcataacagc ggtcattgac tggagcgagg cgatgttcgg ggattcccaa tacgaggtcg   2340
ccaacatctt cttctggagg ccgtggttgg cttgtatgga gcagcagacg cgctacttcg   2400
agcggaggca tccggagctt gcaggatcgc cgcggctccg ggcgtatatg ctccgcattg   2460
gtcttgacca actctatcag agcttggttg acggcaattt cgatgatgca gcttgggcgc   2520
agggtcgatg cgacgcaatc gtccgatccg gagccgggac tgtcgggcgt acacaaatcg   2580
cccgcagaag cgcggccgtc tggaccgatg gctgtgtaga agtactcgcc gatagtggaa   2640
accgacgccc cagcactcgt ccgagggcaa aggaataggg ttaacttgat actactagat   2700
ttttctctt catttataaa attttggtt ataattgaag ctttagaagt atgaaaaaat   2760
ccttttttt cattctttgc aaccaaaata agaagcttct tttattcatt gaatgatga   2820
atataaacct aacaaaagaa aaagactcga atatcaaaca ttaaaaaaaa ataaaagagg   2880
ttatctgttt tcccatttag ttggagtttg cattttctaa tagatagaac tctcaattaa   2940
tgtggattta gtttctctgt tcgttttttt ttgttttgtt ctcactgtat ttacatttct   3000
atttagtatt tagttattca tataatctta acttctcgag gagctctaag ggcgaattct   3060
gcagatatcc atcacactgg cggccgctcg agcatgcatc tagagggccc aattcgccct   3120
```

-continued

```
atagtgagtc gtattacaat tcactggccg tcgttttaca acaagcatct tgccctgtgc    3180 ttggcccca gtgcagcgaa cgttataaaa acgaatactg agtatatatc tatgtaaaac      3240
aaccatatca tttcttgttc tgaactttgt ttacctaact agttttaaat ttccctttt      3300 cgtgcatgcg ggtgttctta tttattagca tactacattt gaaatatcaa atttccttag    3360
tagaaaagtg agagaaggtg cactgacaca aaaaataaaa tgctacgtat aactgtcaaa    3420
actttgcagc agcgggcatc cttccatcat agcttcaaac atattagcgt tcctgatctt    3480
catacccgtg ctcaaaatga tcaaacaaac tgttattgcc aagaaataaa cgcaaggctg    3540
ccttcaaaaa ctgatccatt agatcctcat atcaagcttc ctcatagaac gcccaattac    3600
aataagcatg ttttgctgtt atcaccgggt gataggtttg ctcaaccatg gaaggtagca    3660
tggaatcata atttggatac taatacaaat cggccatata atgccattag taaattgcgc    3720
tcccatttag gtggttctcc aggaatacta ataaatgcgg tgcatttgca aaatgaattt    3780
attccaaggc caaacaaca cgatgaatgg ctttattttt ttgttattcc tgacatgaag      3840
ctttatgtaa ttaaggaaac ggacatcgag gaatttgcat cttttttaga tgaaggagct    3900
attcaagcac caaagctatc cttccaggat tatttaagcg gtaaggccaa ggcttcccaa    3960
caggttcatg aagtgcatca tagaaaagctt acaaggtttc agggtgaaac ttttctaaga    4020
gattggaact tagtctgtgg gcattataag agagatgcta agtgtggaga atgggaccc     4080 gacataattg cagcatttca agatgaaaag ctttttcctg agaataatct agccttaatt    4140
tctcatattg ggggtcatat tt                                              4162
```

<210> SEQ ID NO 91
<211> LENGTH: 7879
<212> TYPE: DNA
<213> ORGANISM: Artificial Sequence
<220> FEATURE:
<223> OTHER INFORMATION: Synthetic, Integration construct i33
<220> FEATURE:
<221> NAME/KEY: misc_feature
<222> LOCATION: (270)..(270)
<223> OTHER INFORMATION: n is a, c, g, or t

<400> SEQUENCE: 91

```
atgaattggc cagttttttc caattatgga acgcctgttc ctgatccacg gcctgcactt    60
gcgaccacaa ttccacacct gaggcgcctg cctcttttcc agcatgtggc aactgtcccc    120
acgacagggc atcccagaat cctctggtaa atcttaaatg aaactgacgc gtggcagtag    180
attccaacaa tggtgggatg gcccgtggga aagtcgtgta gtgctcatac gcatcatatg    240
acatggatga tacggccggg tcaaacggtn cgattgcagt tggaatgcaa atgagagtag    300
cagatcattg ttgggcagcg gcttcaacac cagtgcttcg tcgtacggat accataaact    360
gtcatttata ccaatctgcg acaccgtgtc ttctgcgaac acacccagca gtagagtgcc    420
cagcatgaaa taggccagtg tgaggatcat cgtcgtcttg cctatgcttt gtttgctttg    480
aacacttgtt tccgctctcc ttttacttat tggctactaa aactacgtgt aaaagatcgc    540
ccagcgcaaa aaggtccggc ggtttcaaat aatctcgaac tattcctata atatgcaaaa    600
tagtaggtag gaacaagtca actctaggca gataacgaag atgtccggta aatggagact    660
agtgctgact gggataggca atccagagcc tcagtacgct ggcacccgtc acaatgtagg    720
gctatatatg ctggagctgc tacgaaagcg gcttggtctg caggggagaa cttattcccc    780
tgtgcctaat acgggcggca aagtgcatta tatagaagac gaacattgta cgatactaag    840
atcggatggc cagtacatga atctaagtgg agaacaggtg tgcaaggtct gggcccggta    900
```

```
cgccaagtac caagcccgac acgttgttat tcatgacgag ttaagtgtgg cgtgtggaaa      960
agtgcagctc agagccccca gcaccagtat tagaggtcat aatgggctgc gaagcctgct     1020
aaaatgcagt ggaggccgtg tacccttttgc caaattggct attggaatcg gcagagaacc    1080
tgggtcccgt tctagagacc ctgcgagcgt gtcccggtgg gttctgggag ctctaactcc     1140
gcaggaacta caaaccttgc ttacacagag tgaacctgct gcctggcgtg tctgactca     1200 gtacatttca taggacagca ttcgcccagt attttttttta ttctacaaac cttctataat    1260
ttcaaagtat ttacataatt ctgtatcagt ttaatcacca taatatcgtt ttctttgttt     1320
agtgcaatta atttttccta ttgttacttc gggccttttt ctgttttatg agctattttt     1380
tccgtcatcc ttccggatcc agattttcag cttcatctcc agattgtgtc tacgtaatgc     1440
acgccatcat tttaagagag gacagagaag caagcctcct gaaagatgaa gctactgtct     1500
tctatcgaac aagcatgcga tatttgccga cttaaaaagc tcaagtgctc caagaaaaa     1560 ccgaagtgcg ccaagtgtct gaagaacaac tgggagtgtc gctactctcc caaaaccaaa    1620
aggtctccgc tgactagggc acatctgaca gaagtggaat caaggctaga aagactggaa    1680
cagctatttc tactgatttt tcctcgagaa gaccttgaca tgattttgaa aatggattct    1740
ttacaggata taaaagcatt gttaacagga ttatttgtac aagataatgt gaataaagat    1800
gccgtcacag atagattggc ttcagtggag actgatatgc ctctaacatt gagacagcat    1860
agaataagtg cgacatcatc atcggaagag agtagtaaca aaggtcaaag acagttgact    1920
gtatcgattg actcggcagc tcatcatgat aactccacaa ttccgttgga ttttatgccc    1980
agggatgctc ttcatggatt tgattggtct gaagaggatg acatgtcgga tggcttgccc    2040
ttcctgaaaa cggaccccaa caataatggg ttctttggcg acggttctct cttatgtatt    2100
cttcgatcta ttggctttaa accggaaaat tacacgaact ctaacgttaa caggctcccg    2160
accatgatta cggatagata cacgttggct tctagatcca caacatcccg tttacttcaa    2220
agttatctca ataattttca cccctactgc cctatcgtgc actcaccgac gctaatgatg    2280
ttgtataata accagattga aatcgcgtcg aaggatcaat ggcaaatcct tttaactgc    2340 atattagcca ttggagcctg gtgtatagag ggggaatcta ctgatataga tgttttttac    2400
tatcaaaatg ctaaatctca tttgacgagc aaggtcttcg agtcaggttc cataattttg    2460
gtgacagccc tacatcttct gtcgcgatat acacagtgga ggcagaaaac aaatactagc    2520
tataattttc acagcttttc cataagaatg gccatatcat tgggcttgaa tagggacctc    2580
ccctcgtcct tcagtgatag cagcattctg gaacaaagac gccgaatttg gtggtctgtc    2640
tactcttggg agatccaatt gtccctgctt tatggtcgat ccatccagct ttctcagaat    2700
acaatctcct tcccttcttc tgtcgacgat gtgcagcgta ccacaacagg tcccaccata    2760
tatcatggca tcattgaaac agcaaggctc ttacaagttt tcacaaaaat ctatgaacta    2820
gacaaaacag taactgcaga aaaagtcct atatgtgcaa aaaatgctt gatgatttgt     2880 aatgagattg aggaggtttc gagacaggca ccaaagtttt tacaaatgga tatttccacc    2940
accgctctaa ccaatttgtt gaaggaacac ccttggctat cctttacaag attcgaactg    3000
aagtggaaac agttgtctct tatcatttat gtattaagag attttttcac taatttttacc   3060 cagaaaaagt cacaactaga acaggatcaa aatgatcatc aaagttatga agttaaacga    3120
tgctccatca tgttaagcga tgcagcacaa agaactgtta tgtctgtaag tagctatatg    3180
gacaatcata atgtcacccc atattttgcc tggaattgtt cttattactt gttcaatgca    3240
gtcctagtac ccataaagac tctactctca aactcaaaat cgaatgctga gaataacgag    3300
```

```
accgcacaat tattacaaca aattaacact gttctgatgc tattaaaaaa actggccact    3360
tttaaaatcc agacttgtga aaaatacatt caagtactgg aagaggtatg tgcgccgttt    3420
ctgttatcac agtgtgcaat cccattaccg catatcagtt ataacaatag taatggtagc    3480
gccattaaaa atattgtcgg ttctgcaact atcgcccaat accctactct tccggaggaa    3540
aatgtcaaca atatcagtgt taaatatgtt tctcctggct cagtagggcc ttcacctgtg    3600
ccattgaaat caggagcaag tttcagtgat ctagtcaagc tgttatctaa ccgtccaccc    3660
tctcgtaact ctccagtgac aataccaaga agcacacctt cgcatcgctc agtcacgcct    3720
tttctagggc aacagcaaca gctgcaatca ttagtgccac tgaccccgtc tgctttgttt    3780
ggtggcgcca atttaatca aagtgggaat attgctgata gctcattgtc cttcactttc    3840
actaacagta gcaacggtcc gaacctcata acaactcaaa caaattctca agcgctttca    3900
caaccaattg cctcctctaa cgttcatgat aacttcatga ataatgaaat cacggctagt    3960
aaaattgatg atggtaataa ttcaaaacca ctgtcacctg gttggacgga ccaaactgcg    4020
tataacgcgt ttggaatcac tacagggatg tttaatacca ctacaatgga tgatgtatat    4080
aactatctat tcgatgatga agataccccca ccaaacccaa aaaaagagta aaatgaatcg    4140
tagatactga aaaccccgc aagttcactt caactgtgca tcgtgcacca tctcaatttc    4200
tttcatttat acatcgtttt gccttctttt atgtaactat actcctctaa gtttcaatct    4260
tggccatgta acctctgatc tatagaattt tttaaatgac tagaattaat gcccatcttt    4320
tttttggacc taaattcttc atgaaaatat attacgaggg cttattcaga agcttcgctc    4380
agtcgacact agtaatacac atcatcgtcc tacaagttca tcaaagtgtt ggacagacaa    4440
ctataccagc atggatctct tgtatcggtt ctttttctccc gctctctcgc aataacaatg    4500
aacactgggt caatcatagc ctacacaggt gaacagagta gcgtttatac agggtttata    4560
cggtgattcc tacggcaaaa atttttcatt tctaaaaaaa aaagaaaaa ttttttcttcc    4620 caacgctaga aggaaaagaa aaatctaatt aaattgattt ggtgattttc tgagagttcc    4680 cttttttcata tatcgaattt tgaatataaa aggagatcga aaaaatttttt ctattcaatc    4740 tgttttctgg ttttatttga tagttttttt gtgtattatt attatggatt agtactggtt    4800
tatatgggtt tttctgtata acttcttttt attttagttt gtttaatctt attttgagtt    4860
acattatagt tccctaactg caagagaagt aacattaaaa atgaccactc ttgacgacac    4920
ggcttaccgg taccgcacca gtgtcccggg ggacgccgag gccatcgagg cactggatgg    4980
gtccttcacc accgacaccg tcttccgcgt caccgccacc ggggacggct tcaccctgcg    5040
ggaggtgccg gtggacccgc ccctgaccaa ggtgttcccc gacgacgaat cggacgacga    5100
atcggacgcc ggggaggacg gcgacccgga ctcccgacg ttcgtcgcgt acggggacga    5160
cggcgacctg gcgggcttcg tggtcgtctc gtactccggc tggaaccgcc ggctgaccgt    5220
cgaggacatc gaggtcgccc cggagcaccg ggggcacggg gtcgggcgcg cgttgatggg    5280
gctcgcgacg gagttcgccc gcgagcgggg cgccgggcac ctctggctgg aggtcaccaa    5340
cgtcaacgca ccggcgatcc acgcgtaccg gcggatgggg ttcacccctct gcggcctgga    5400 caccgccctg tacgacggca ccgcctcgga cggcgagcag gcgctctaca tgagcatgcc    5460 ctgccctctga gttaacttg atactactag atttttttctc ttcatttata aaatttttgg    5520
ttataattga agctttagaa gtatgaaaaa atcctttttt ttcattcttt gcaaccaaaa    5580
taagaagctt cttttattca ttgaaatgat gaatataaac ctaacaaaag aaaaagactc    5640
gaatatcaaa cattaaaaaa aaataaaaga ggttatctgt tttcccattt agttggagtt    5700
```

```
tgcattttct aatagataga actctcaatt aatgtggatt tagtttctct gttcgttttt    5760
ttttgttttg ttctcactgt atttacattt ctatttagta tttagttatt catataatct    5820
taacttctcg aggagctcga tcttgaaact gagtaagatg ctcagaatac ccgtcaagat    5880
aagagtataa tgtagagtaa tataccaagt attcagcata ttctcctctt cttttgtata    5940
aatcacggaa gggatgattt ataagaaaaa tgaatactat tacacttcat ttaccaccct    6000
ctgatctaga ttttccaacg atatgtacgt agtggtataa ggtgaggggg tccacagata    6060
taacatcgtt taatttagta ctaacagaga cttttgtcac aactacatat aagtgtacaa    6120
atatagtaca gatatgacac acttgtagcg ccaacgcgca tcctacggat tgctgacaga    6180
aaaaaaggtc acgtgaccag aaaagtcacg tgtaattttg taactcaccg cattctagcg    6240
gtccctgtcg tgcacactgc actcaacacc ataaaccttta gcaacctcca aaggaaatca    6300
ccgtataaca aagccacagt tttacaactt agtctcttat gaagtgtctc tctctgtcgt    6360
aacagttgtg atatcggaag aagagaaaag acgaagagca gaagcggaaa acgtatacac    6420
gtcacatatc acacacacac aatgggaaag ctattacaat tggcattgca tccggtcgag    6480
atgaaggcag cttttgaagct gaagttttgc agaacaccgc tattctccat ctatgatcag    6540
tccacgtctc catatctctt gcactgtttc gaactgttga acttgacctc cagatcgttt    6600
gctgctgtga tcagagagct gcatccagaa ttgagaaact gtgttactct cttttatttg    6660
attttaaggg ctttggatac catcgaagac gatatgtcca tcgaacacga tttgaaaatt    6720
gacttgttgc gtcacttcca cgagaaattg ttgttaacta aatggagttt cgacggaaat    6780
gcccccgatg tgaaggacag agccgttttg acagatttcg aatcgattct tattgaattc    6840
cacaaattga aaccagaata tcaagaagtc atcaaggaga tcaccgagaa aatgggtaat    6900
ggtatggccg actacatctt ggatgaaaat tacaacttga atgggttgca aaccgtccac    6960
gactacgacg tgtactgtca ctacgtagct ggtttggtcg gtgatggttt gacccgtttg    7020
attgtcattg ccaagtttgc caacgaatct ttgtattcta atgagcaatt gtatgaaagc    7080
atgggtcttt tcctacaaaa aaccaacatc atcagagact acaatgaaga tttggtcgat    7140
ggtagatcct tctggcccaa ggaaatctgg tcacaatacg ctcctcagtt gaaggacttc    7200
atgaaacctg aaaacgaaca actggggttg gactgtataa accacctcgt cttaaacgca    7260
ttgagtcatg ttatcgatgt gttgacttat ttggccagta tccacgagca atccactttc    7320
caattttgtg ccattcccca agttatggcc attgcaacct tggctttggt attcaacaac    7380
cgtgaagtgc tacatggcaa tgtaaagatt cgtaagggta ctacctgcta tttaattttg    7440
aaatcaagga ctttgcgtgg ctgtgtcgag attttttgact attacttacg tgatatcaaa    7500
tctaaattgg ctgtgcaaga tccaaatttc ttaaaattga acattcaaat ctccaagatc    7560
gaacaattca tggaagaaat gtaccaggat aaattacctc ctaacgtgaa gccaaatgaa    7620
actccaattt tcttgaaagt taaagaaaga tccagatacg atgatgaatt ggtcccaacc    7680
caacaagaag aagagtacaa gttcaatatg gttttatcta tcatcttgtc cgttcttctt    7740
gggttttatt atatatacac tttacacaga gcgtgaagtc tgcgccaaat aacataaaca    7800
aacaactccg aacaataact aagtacttac ataataggta gaggcctatc cttaaagata    7860
accttatatt tcattacat                                                  7879

<210> SEQ ID NO 92
<211> LENGTH: 5714
<212> TYPE: DNA
<213> ORGANISM: Artificial Sequence
<220> FEATURE:
```

<223> OTHER INFORMATION: Synthetic, Integration construct i37

<400> SEQUENCE: 92

```
gcctgtctac aggataaaga cgggtcggat acctgcacaa gcaatttggc acctgcatac      60
cccatttccc cagtagataa cttcaacaca cacatcaatg tccctcacca gtttatttcc     120
aaaagagacg cttttactac cctgactaga ttttcatttt gtttcttttg gattgcgctt     180
gcctttgtag gtgtgtcgtt tatcctttac gttttgactt ggtgctcgaa gatgctttca     240
gagatggtgc ttatcctcat gtcttttggg tttgtcttca atacggcagc cgttgtcttg     300
caaacggccg cctctgccat ggcaaagaat gctttccatg acgatcatcg tagtgcccaa     360
ttgggtgcct ctatgatggg tttaaacgta tggcttgggc aagtgtcttt ttatgtatcg     420
tggaatttat cctgctggtc ttctggtctg ttagggcaag gttggcctct acttactcca     480
tcgacaattc aagatacaga acctcctcca gatggaatcc cttccataga gagaaggagc     540
aagcaactga cccaatattg actgccactg gacctgaaga catgcaacaa agtgcaagca     600
tagtggggcc ttcttccaat gctaatccgg tcactgccac tgctgctacg gaaaaccaac     660
ctaaaggtat taacttcttc actataagaa aatcacacga gcgcccggac gatgtctctg     720
tttaaatggc gcaagttttc cgctttgtaa tatatattta tacccctttc ttctctcccc     780
tgcaatataa tagtttaatt ctaatattaa taatatccta tattttcttc atttaccggc     840
gcactctcgc ccgaacgacc tcaaaatgtc tgctacattc ataataacca aaagctcata     900
acttttttt ttgaacctga atatatatac atcacatatc actgctggtc ctgagaagtt     960
aagattatat gaataactaa atactaaata gaaatgtaaa tacagtgaga acaaaacaaa    1020
aaaaaacgaa cagagaaact aaatccacat taattgagag ttctatctat tagaaaatgc    1080
aaactccaac taaatgggaa aacagataac ctcttttatt ttttttttaat gtttgatatt    1140
cgagtctttt tcttttgtta ggtttatatt catcatttca atgaataaaa gaagcttctt    1200
attttggttg caaagaatga aaaaaaagga tttttcata cttctaaagc ttcaattata    1260
accaaaaatt ttataaatga agagaaaaaa tctagtagta tcaagttaaa cttagaaaaa    1320
ctcatcgagc atcaaatgaa actgcaattt attcatatca ggattatcaa taccatattt    1380
ttgaaaaagc cgtttctgta atgaaggaga aaactcaccg aggcagttcc ataggatggc    1440
aagatcctgg tatcggtctg cgattccgac tcgtccaaca tcaatacaac ctattaattt    1500
cccctcgtca aaataaggt tatcaagtga gaaatcacca tgagtgacga ctgaatccgg    1560
tgagaatggc aaaagcttat gcatttcttt ccagacttgt tcaacaggcc agccattacg    1620
ctcgtcatca aaatcactcg catcaaccaa accgttattc attcgtgatt gcgcctgagc    1680
gagacgaaat acgcgatcgc tgttaaaagg acaattacaa acaggaatcg aatgcaaccg    1740
gcgcaggaac actgccagcg catcaacaat attttcacct gaatcaggat attcttctaa    1800
tacctggaat gctgttttgc cggggatcgc agtggtgagt aaccatgcat catcaggagt    1860
acggataaaa tgcttgatgg tcggaagagg cataaattcc gtcagccagt ttagtctgac    1920
catctcatct gtaacatcat tggcaacgct acctttgcca tgtttcagaa caactctgg    1980
cgcatcgggc ttcccataca atcgatagat tgtcgcacct gattgcccga cattatcgcg    2040
agcccattta tacccatata atcagcatc catgttggaa tttaatcgcg gcctcgaaac    2100
gtgagtcttt tccttaccca ttttaatgt tacttctctt gcagttaggg aactataatg    2160
taactcaaaa taagattaaa caaactaaaa taaaagaag ttatacagaa aaacccatat    2220
aaaccagtac taatccataa taataataca caaaaaact atcaaataaa accagaaaac    2280
```

```
agattgaata gaaaaatttt ttcgatctcc ttttatattc aaaattcgat atatgaaaaa    2340
gggaactctc agaaaatcac caaatcaatt taattagatt tttcttttcc ttctagcgtt    2400
ggaaagaaaa attttctttt ttttttttag aaatgaaaaa ttttttgccgt aggaatcacc   2460 gtataaaccc tgtataaacg ctactctgtt cacctgtgta ggctatgatt gacccagtgt    2520
tcattgttat tgcgagagag cgggagaaaa gaaccgatac aagagatcca tgctggtata    2580
gttgtctgtc caacactttg atgaacttgt aggacgatga tgtgtattac tagtgtcgac    2640
accatataca tatccatatc taatcttact tatatgttgt ggaaatgtaa agagccccat    2700
tatcttagcc taaaaaaacc ttctctttgg aactttcagt aatacgctta actgctcatt    2760
gctatattga agtacggatt agaagccgcc gagcgggcga cagccctccg acggaagact    2820
ctcctccgtg cgtcctggtc ttcaccggtc gcgttcctga aacgcagatg tgcctcgcgc    2880
cgcactgctc cgaacaataa agattctaca atactagctt ttatggttat gaagaggaaa    2940
aattggcagt aacctggccc cacaaacctt caaatcaacg aatcaaatta caaaccatag    3000
gataataatg cgattagttt tttagcctta tttctggggt aattaatcag cgaagcgatg    3060
atttttgatc tattaacaga tatataaatg caaaagctgc ataaccactt taactaatac    3120
tttcaacatt ttcggtttgt attacttctt attcaaatgt cataaaagta tcaacaaaaa    3180
attgttaata tacctctata ctttaacgtc aaggagaaaa aactataatg tcattaccgt    3240
tcttaacttc tgcaccggga aaggttatta tttttggtga acactctgct gtgtacaaca    3300
agcctgccgt cgctgctagt gtgtctgcgt tgagaaccta cctgctaata agcgagtcat    3360
ctgcaccaga tactattgaa ttggacttcc cggacattag ctttaatcat aagtggtcca    3420
tcaatgattt caatgccatc accgaggatc aagtaaactc ccaaaaattg gccaaggctc    3480
aacaagccac cgatggcttg tctcaggaac tcgttagtct tttggatccg ttgttagctc    3540
aactatccga atccttccac taccatgcag cgttttgttt cctgtatatg tttgtttgcc    3600
tatgccccca tgccaagaat attaagtttt ctttaaagtc tactttaccc atcggtgctg    3660
ggttgggctc aagcgcctct atttctgtat cactggcctt agctatggcc tacttggggg   3720
ggttaatagg atctaatgac ttggaaaagc tgtcagaaaa cgataagcat atagtgaatc    3780
aatgggcctt cataggtgaa aagtgtattc acggtacccc ttcaggaata gataacgctg    3840
tggccactta tggtaatgcc ctgctatttg aaaaagactc acataatgga acaataaaca    3900
caaacaattt taagttctta gatgatttcc cagccattcc aatgatccta acctatacta    3960
gaattccaag gtctacaaaa gatcttgttg ctcgcgttcg tgtgttggtc accgagaaat    4020
ttcctgaagt tatgaagcca attctagatg ccatgggtga atgtgcccta caaggcttag    4080
agatcatgac taagttaagt aaatgtaaag gcaccgatga cgaggctgta gaaactaata    4140
atgaactgta tgaacaacta ttggaattga taagaataaa tcatggactg cttgtctcaa    4200
tcggtgtttc tcatcctgga ttagaactta ttaaaaatct gagcgatgat ttgagaattg    4260
gctccacaaa acttaccggt gctggtggcg gcggttgctc tttgactttg ttacgaagag    4320
acattactca agagcaaatt gacagtttca aaagaaatt gcaagatgat tttagttacg    4380
agacatttga aacagacttg ggtgggactg gctgctgttt gttaagcgca aaaaatttga    4440
ataaagatct taaatcaaa tccctagtat tccaattatt tgaaaataaa actaccacaa     4500
agcaacaaat tgacgatcta ttattgccag gaaacacgaa tttaccatgg acttcataag    4560
ctaatttgcg ataggcatta tttattagtt gttttaatc ttaactgtgt atgaagtttt     4620
atgtaataaa gatagaaaga gaaacaaaaa aaaattttc gtagtatcaa ttcagctttc    4680
```

-continued

| | |
|---|---|
| gaagacagaa tgaaatttaa gcagaccatc atcttgccct gtgcttggcc cccagtgcag | 4740 |
| cgaacgttat aaaaacgaat actgagtata tatctatgta aaacaaccat atcatttctt | 4800 |
| gttctgaact ttgtttacct aactagtttt aaatttccct ttttcgtgca tgcgggtgtt | 4860 |
| cttatttatt agcatactac atttgaaata tcaaatttcc ttagtagaaa agtgagagaa | 4920 |
| ggtgcactga cacaaaaaat aaaatgctac gtataactgt caaaactttg cagcagcggg | 4980 |
| catccttcca tcatagcttc aaacatatta gcgttcctga tcttcatacc cgtgctcaaa | 5040 |
| atgatcaaac aaactgttat tgccaagaaa taaacgcaag gctgccttca aaaactgatc | 5100 |
| cattagatcc tcatatcaag cttcctcata gaacgcccaa ttacaataag catgttttgc | 5160 |
| tgttatcacc gggtgatagg tttgctcaac catggaaggt agcatggaat cataatttgg | 5220 |
| atactaatac aaatcggcca tataatgcca ttagtaaatt gcgctcccat ttaggtggtt | 5280 |
| ctccaggcaa atttgaatac taataaatgc ggtgcatttg caaaatgaat ttattccaag | 5340 |
| gccaaaacaa cacgatgaat ggctttattt ttttgttatt cctgacatga agctttatgt | 5400 |
| aattaaggaa acggacatcg aggaatttgc atcttttta gatgaaggag ctattcaagc | 5460 |
| accaaagcta tccttccagg attatttaag cggtaaggcc aaggcttccc aacaggttca | 5520 |
| tgaagtgcat catagaaagc ttacaaggtt tcagggtgaa acttttctaa gagattggaa | 5580 |
| cttagtctgt gggcattata agagagatgc taagtgtgga gaaatgggac ccgacataat | 5640 |
| tgcagcattt caagatgaaa agcttttccc tgagaataat ctagccttaa tttctcatat | 5700 |
| tgggggtcat attt | 5714 |

<210> SEQ ID NO 93
<211> LENGTH: 7688
<212> TYPE: DNA
<213> ORGANISM: Artificial Sequence
<220> FEATURE:
<223> OTHER INFORMATION: Synthetic, Integration construct i301

<400> SEQUENCE: 93

| | |
|---|---|
| gacggcacgg ccacgcgttt aaaccgccga gctattcgcg gaacattcta gctcgtttgc | 60 |
| atcttcttgc atttggtagg ttttcaatag ttcggtaata ttaacggata cctactatta | 120 |
| tcccctagta ggctcttttc acggagaaat tcgggagtgt ttttttttccg tgcgcatttt | 180 |
| cttagctata ttcttccagc ttcgcctgct gcccggtcat cgttcctgtc acgtagtttt | 240 |
| tccggattcg tccggctcat ataataccgc aataaacacg gaatatctcg ttccgcggat | 300 |
| tcggttaaac tctcggtcgc ggattatcac agagaaagct tcgtggagaa ttttccaga | 360 |
| ttttccgctt tccccgatgt tggtatttcc ggaggtcatt atactgaccg ccattataat | 420 |
| gactgtacaa cgaccttctg gagaaagaaa caactcaata acgatgtggg acattggggg | 480 |
| cccactcaaa aaatctgggg actatatccc cagagaattt ctccagaaga gaagaaaagt | 540 |
| caaagttttt tttcgcttgg gggttgcata taaagctcac acgcggccag ggggagccat | 600 |
| gaaaaagcct gaactcaccg cgacgtctgt cgagaagttt ctgatcgaaa agttcgacag | 660 |
| cgtctccgac ctgatgcagc tctcggaggg cgaagaatct cgtgctttca gcttcgatgt | 720 |
| aggagggcgt ggatatgtcc tgcgggtaaa tagctgcgcc gatggtttct acaaagatcg | 780 |
| ttatgtttat cggcactttg catcggccgc gctcccgatt ccggaagtgc ttgacattgg | 840 |
| ggaattcagc gagagcctga cctattgcat ctcccgccgt gcacagggtg tcacgttgca | 900 |
| agacctgcct gaaaccgaac tgcccgctgt tctgcagccg gtcgcggagg ccatggatgc | 960 |
| gatcgctgcg gccgatctta gccagacgag cgggttcggc ccattcggac cgcaaggaat | 1020 |

```
cggtcaatac actacatggc gtgatttcat atgcgcgatt gctgatcccc atgtgtatca    1080
ctggcaaact gtgatggacg acaccgtcag tgcgtccgtc gcgcaggctc tcgatgagct    1140
gatgctttgg gccgaggact gccccgaagt ccggcacctc gtgcacgcgg atttcggctc    1200
caacaatgtc ctgacggaca atggccgcat aacagcggtc attgactgga gcgaggcgat    1260
gttcggggat tcccaatacg aggtcgccaa catcttcttc tggaggccgt ggttggcttg    1320
tatggagcag cagacgcgct acttcgagcg gaggcatccg gagcttgcag gatcgccgcg    1380
gctccgggcg tatatgctcc gcattggtct tgaccaactc tatcagagct tggttgacgg    1440
caatttcgat gatgcagctt gggcgcaggg tcgatgcgac gcaatcgtcc gatccggagc    1500
cgggactgtc gggcgtacac aaatcgcccg cagaagcgcg gccgtctgga ccgatggctg    1560
tgtagaagta ctcgccgata gtggaaaccg acgcccagc actcgtccga gggcaaagga    1620
atagcgctcg tccaacgccg gcggacctcg ctcgtccaac gccggcggac ctcttttaat    1680
tctgctgtaa cccgtacatg cccaaaatag ggggcgggtt acacagaata tataacatcg    1740
taggtgtctg ggtgaacagt ttattcctgg catccactaa atataatgga gcccgctttt    1800
taagctggca tccagaaaaa aaagaatcc cagcaccaaa atattgtttt cttcaccaac    1860
catcagttca taggtccatt ctcttagcgc aactacagag aacaggggca caaacaggca    1920
aaaaacgggc acaacctcaa tggagtgatg caacctgcct ggagtaaatg atgacacaag    1980
gcaattgacc cacgcatgta tctatctcat tttcttacac cttctattac cttctgctct    2040
ctctgatttg gaaaaagctg aaaaaaaagg ttgaaaccag ttccctgaaa ttattcccct    2100
acttgactaa taagtatata aagacggtag gtattgattg taattctgta aatctatttc    2160
ttaaacttct taaattctac ttttatagtt agtctttttt ttagttttaa aacaccaaga    2220
acttagtttc gatccccgcg tgcttggccg gccgtatccc cgcgtgcttg gccggccgta    2280
tgtctcagaa cgtttacatt gtatcgactg ccagaacccc aattggttca ttccagggtt    2340
ctctatcctc caagacagca gtggaattgg gtgctgttgc tttaaaaggc gccttggcta    2400
aggttccaga attggatgca tccaaggatt ttgacgaaat tatttttggt aacgttcttt    2460
ctgccaattt gggccaagct ccggccagac aagttgcttt ggctgccggt ttgagtaatc    2520
atatcgttgc aagcacagtt aacaaggtct gtgcatccgc tatgaaggca atcattttgg    2580
gtgctcaatc catcaaatgt ggtaatgctg atgttgtcgt agctggtggt tgtgaatcta    2640
tgactaacgc accatactac atgccagcag cccgtgcggg tgccaaattt ggccaaactg    2700
ttcttgttga tggtgtcgaa agagatgggt tgaacgatgc gtacgatggt ctagccatgg    2760
gtgtacacgc agaaaagtgt gcccgtgatt gggatattac tagagaacaa caagacaatt    2820
ttgccatcga atcctaccaa aaatctcaaa aatctcaaaa ggaaggtaaa ttcgacaatg    2880
aaattgtacc tgttaccatt aagggattta gaggtaagcc tgatactcaa gtcacgaagg    2940
acgaggaacc tgctagatta cacgttgaaa aattgagatc tgcaaggact gttttccaaa    3000
aagaaaacgg tactgttact gccgctaacg cttctccaat caacgatggt gctgcagccg    3060
tcatcttggt ttccgaaaaa gttttgaagg aaaagaattt gaagcctttg gctattatca    3120
aaggttgggg tgaggccgct catcaaccag ctgattttac atgggctcca tctcttgcag    3180
ttccaaaggc tttgaaacat gctggcatcg aagacatcaa ttctgttgat actttgaat    3240 tcaatgaagc cttttcggtt gtcggtttgg tgaacactaa gatttgaag ctagacccat    3300 ctaaggttaa tgtatatggt ggtgctgttg ctctaggtca cccattgggt tgttctggtg    3360
ctagagtggt tgttacactg ctatccatct tacagcaaga aggaggtaag atcggtgttg    3420
```

```
ccgccatttg taatggtggt ggtggtgctt cctctattgt cattgaaaag atatgattac   3480
gttctgcgat tttctcatga tcttttcat aaaatacata aatatataaa tggctttatg    3540
tataacaggc ataatttaaa gttttatttg cgattcatcg tttttcaggt actcaaacgc   3600
tgaggtgtgc cttttgactt acttttccgc cttggcaagc tggccgggtg atacttgcac   3660
aagttccact aattactgac atttgtggta ttaactcgtt tgactgctct acaattgtag   3720
gatgttaatc aatgtcttgg ctgcctaacc tgcaggccgc gagcgccgat atgctatgta   3780
atagacaata aaaccatgtt tatataaaaa aaattcaaaa tagaaaacga ttctgtacaa   3840
ggagtatttt tttttgttc tagtgtgttt atattatcct tggctaagag gcactgcgta    3900
tacttcaagg taccctgtg ttttgaaaaa aaacaacagt aaaataggaa ctccgcgagg    3960
ttcaggaacc tgaaacaaaa tcaataaaaa cattatatgc gtttcgaaca aaattaaaga   4020 aaagaataa atatagatta aaaaaaaaa gaagaaatta aaagaatttc tactaaatcc     4080
caattgttat atatttgtta aatgccaaaa aagtttataa aaaatttaga atgtataaat   4140
aataataaac taagtaacgc gatcgccgac gccgccgata tctccctcgc cagcggccgc   4200
cttatggcta agaatgttgg aatttttggcc atggacatct acttcccacc aacttgtgtt   4260
cagcaggagg ctttagaagc acatgacgga gcctcaaagg gtaagtacac aatcggatta   4320
ggacaggatt gcttagcatt ctgcactgaa ttggaggacg tcatctcaat gtcttttcaac  4380 gccgtcacct cattgttaga gaagtacaaa atcgacccaa accagatcgg aaggttggaa   4440
gtcggttctg aaaccgtcat cgacaagtct aaatcaatca agactttcgt tatgcagttg   4500
ttcgaaaagt gcggtaatac tgacgtcgag ggtgtagact ctactaacgc ttgttatggt   4560
ggtaccgcag cttattgaa ctgcgtaaac tgggttgagt caaactcatg ggatggtagg    4620
tacggattag tcatttgcac cgattctgcc gtctacgccg agggtccagc aaggccaacc   4680
ggtggagctg cagctattgc tatgttaatc ggaccagatg cccctatagt cttcgagtct   4740
aagttgaggg gttcacacat ccctaacgtc tacgacttct acaagccaaa cttggcctca   4800
gagtatccag ttgtcgacgg aaagttatct cagacatgct acttgatggc cttagattca   4860
tgttacaagc acttatgcaa caagttcgaa aagttggagg gaaggagtt ctcaattaac    4920 gacgccgact acttcgtttt tcactctcca tacaacaaat tggtccagaa gtcattcgcc   4980
aggttattgt acaacgattt tttgagaaac gcatcatcta tcgatgaggc cgccaaggag   5040
aaattcaccc catattcttc tttgtcattg gacgagtctt accagtctag ggacttggag   5100
aaggtatcac agcaattggc taaaaccttc tatgacgcca agttcagcc aaccaccttg    5160 gtccctaaac aggtcggaaa tatgtatact gcatctttgt atgccgcctt tgcctctttg   5220
atccacaaca agcacaacga tttagtcgga aaaaggggtg tcatgttttc ttacggtgcc   5280
ggatctactg ccactatgtt ctcattgagg ttatgcgaaa accagtcacc attttcattg   5340
tctaacatcg cctcagtcat ggacgtaggt gtctcacctg agaagttcgt agaaaccatg   5400
aagttgatgg agcacagata cggtgccaaa gaattcgtca cttcaaaaga gggaatcttg   5460
gatttgttgg ccccaggaac ctactatttg aaggaggtcg actcttttgta cagaaggttc   5520 tatggaaaga agggagacga cggatctgtc gcaaacggtc agtaaatcgg cggcgtcggc   5580
gatcgcgtta aggcggccgc tgcgaggga gatatttcaa cctgggccta acagtaaaga    5640
tatcctcctc aaaactggtg cacttaatcg ctgaatttgt tctggcttct cttctttttc   5700
tttattcccc ccatgggcca aaaaaatag tactatcagg aattggcgc cgggtcacga    5760 tatacgtgta cagtgaccta ggcgacgcca caaggaaaaa ggaaaaaaac agaaaaaaca   5820
```

-continued

| | |
|---|---|
| acaaaaacta aaacaaacac gaaaacttta atagatctaa gtgaagtagt ggtgaggcaa | 5880 |
| ttggagtgac atagcagcta ctacaactac aaaaaaggcg cgccacggtc gtgcggatat | 5940 |
| gaaagaggtc gttatagctt ctgccgtcag gaccgccatc ggatcttacg gtaagtcatt | 6000 |
| aaaggacgtc cctgccgttg atttaggagc caccgcaatt aaagaggccg ttaaaaaggc | 6060 |
| aggtataaag ccagaggacg tcaacgaggt catcttggga aatgtcttac aagccggatt | 6120 |
| aggtcaaaac ccagcaagac aagcatcatt caaagccggt ttacctgtcg agatacctgc | 6180 |
| aatgaccatc aacaaggttt gcggttcagg attaaggacc gtttctttag cagcacagat | 6240 |
| cattaaggct ggagatgcag acgttatcat tgctggtggt atggaaaaca tgtcaagagc | 6300 |
| cccatacttg gctaataacg ccaggtgggg atataggatg ggaaacgcca gtttgtcga | 6360 |
| cgaaatgatt actgacggat tgtgggacgc cttcaatgac tatcacatgg gtataaccgc | 6420 |
| agaaaacatt gccgagaggt ggaatatctc aagagaagaa caggatgagt ttgcattggc | 6480 |
| ctcacagaaa aaagcagagg aggcaataaa gtcaggtcag tttaaggatg aaatcgtccc | 6540 |
| agtcgtcatc aagggaagaa agggtgagac agttgtcgac accgacgaac accctagatt | 6600 |
| tggttcaacc atcgagggat tagcaaagtt gaagccagcc ttcaagaaag acggaaccgt | 6660 |
| aaccgccggt aatgcatctg gattgaacga ttgcgcagca gttttggtca taatgtcagc | 6720 |
| cgagaaagct aaggagttgg gtgtcaagcc attggcaaaa attgtttcat acggatcagc | 6780 |
| cggtgtcgac cctgccatca tgggttacgg accttttac gccaccaagg ctgcaatcga | 6840 |
| aaaggccggt tggaccgtag atgaattgga tttgatcgag tcaaacgagg cctttgccgc | 6900 |
| ccaatcattg gctgtcgcca aggacttgaa gttcgacatg aacaaggtca acgtcaacgg | 6960 |
| tggtgccatc gcattgggtc accctatcgg agcctctggt gccaggatct tggttacctt | 7020 |
| ggtccacgcc atgcagaaga gggacgcaaa gaagggtttg gccaccttgt gcatcggtgg | 7080 |
| aggtcaggga acagctatct tgttagagaa atgcagcccc tcagccccc tagcgtcgaa | 7140 |
| taaaagacat tggtacatga tatcaaacag aattttaaca tttcttgatc cagtttgtaa | 7200 |
| acaaacaaa caattttct accatttaac ttcataccat cggcgagagc cgaacaggaa | 7260 |
| aaaaagaag tctccggtta tcgtaagcag tatcaaataa taagaatgta tgtgtgtgca | 7320 |
| atttgttata cccacgaaga agtgcgcagt agagttagaa aaccaactga gtaatctta | 7380 |
| ctcccgacaa tcgtccaata atcctcttgt tgctaggaac gtgatgatgg atttcgtttg | 7440 |
| aaatccggac ggaaaactca aaagaagtcc aaccaccaac cattttcgag cctcaagaat | 7500 |
| ctctaagcag gtttctttac taaggggatg gcctttctgt cctggacatt ttttccttcc | 7560 |
| ttttttcatt tccttgaaag gaacagattt tttttgactt tgccacaca gctgcactat | 7620 |
| ctcaacccct tttacatttt aagttttcgg gttgaatggc cggtgtttaa accccagcgc | 7680 |
| ctggcggg | 7688 |

<210> SEQ ID NO 94
<211> LENGTH: 5025
<212> TYPE: DNA
<213> ORGANISM: Artificial Sequence
<220> FEATURE:
<223> OTHER INFORMATION: Synthetic, Integration construct i476

<400> SEQUENCE: 94

| | |
|---|---|
| caggatccga cggcacggcc acgcgtttaa accgcctggg ataggatagt agcaactctt | 60 |
| ggaggagagc attgtcagtt gtccagtctc tgaagttaag tagtaagttt gcggagtcaa | 120 |
| aggggatgg cttttgccat ttgtgagagt tgtgcggcag catcttattc aaatagagct | 180 |

```
gtattctgaa gacctcttgt agaacatcat ccatactaaa aagtaaatcg tcctgtccca    240
ttacgagctg tattagtgct gtgaccctct gtatatttac gttgccatga agaaggtaat    300
gggcgatatt ttgatacaat tcctgagttg catgttggat tgagtttacg aagggtcgcc    360
agacggccag aaacctccag gcggagttaa caactagtaa tacggcatcc atgtttgcat    420
cagcgccgag cctataccag tcactgagta gacgttttct tgctcttttt atgtcctgac    480
ttcttttgac gaggggggcat tctctagaga cacaggcagt tgcttccagc aactgccgta    540
cggccgttct catgctgtcg aggattttt ttgggacgat attgtcatta tagggcagtg    600
tgtgacttat gaattgttgt agaaggacgt ctgtgatgtt ggagatatgt attttgttaa    660
ctcttcttga gacgatttgg ccctggatag cgaagcgtgc ggttacaaat aggtcgtctt    720
gttcaagaag gtaggcgagg acattatcta tcagtacaaa catcttagta gtgtctgagg    780
agagggttga ttgtttatgt attttttgcga aatatatata tatatattct acacagatat    840
atacatattt gttttcggg ctcattcttt cttctttgcc agaggctcac cgctcaagag    900
gtccgctaat tctggagcga ttgttattgt ttttcttt cttcttctat tcgaaaccca    960
gtttttgatt tgaatgcgag ataaactggt attcttcatt agattctcta ggcccttggt   1020
atctagatat gggttctcga tgttctttgc aaaccaactt tctagtattc ggacattttc   1080
ttttgtaaac cggtgtcctc tgtaaggttt agtacttttg tttatcatat cttgagttac   1140
cacattaaat accaacccat ccgccgattt attttctgt gtaagttgat aattacttct   1200
atcgttttct atgctgcgca tttctttgag taatacagta atggtagtag tgagttgaga   1260
tgttgtttgc aacaacttct tctcctcatc actaatctta cggttttgt tggccctaga   1320 taagaatcct aatatatccc ttaattcaac ttcttcttct gttgttacac tctctggtaa   1380
cttaggtaaa ttacagcaaa tagaaaagag cttttatt atgtctagta tgctggattt   1440
aaactcatct gtgatttgtg gatttaaaag gtctttaatg ggtatttat tcattttttc   1500 ttgcttatct tcctttttt cttgcccact tctaagctga tttcaatctc tcctttatat   1560
atatttttaa gttccaacat tttatgtttc aaaacattaa tgatgtctgg gttttgtttg   1620
ggatgcaatt tattgcttcc caatgtagaa aagtacatca tatgaaacaa cttaaactct   1680
taactacttc ttttaacctt cactttttat gaaatgtatc aaccatatat aataacttaa   1740
tagacgacat tcacaatatg tttacttcga agcctgcttt caaaattaag aacaaagcat   1800
ccaaatcata cagaaacaca gcggtttcaa aaaagctgaa agaaaaacgt ctagctgagc   1860
atgtgaggcc aagctgcttc aatattattc gaccactcaa gaaagatatc cagattcctg   1920
ttccttcctc tcgattttta aataaaatcc aaattcacag gatagcgtct ggaagtcaaa   1980
atactcagtt tcgacagttc aataagacat ctataaaatc ttcaaagaaa tatttaaact   2040
catttatggc ttttagagca tattactcac agtttggctc cggtgtaaaa caaaatgtct   2100
tgtcttctct gctcgctgaa gaatggcacg cggacaaaat gcagcacgga atatgggact   2160
acttcgcgca acagtataat tttataaacc ctggttttgg ttttgtagag tggttgacga   2220
ataattatgc tgaagtacgt ggtgacggat attgggaaga tgtgtttgta catttggcct   2280
tatagagtgt ggtcgtggcg gaggttgttt atctttcgag tactgaatgt tgtcagtata   2340
gctatcctat ttgaaactcc ccatcgtctt gctcttgttc ccaatgtttg tttatacact   2400
catatggcta tacccttatc tacttgcctc ttttgtttat gtctatgtat ttgtataaaa   2460
tatgatatta ctcagactca agcaaacaat caatgctcac acgcggccag ggggagcctc   2520
gacactagta atacacatca tcgtcctaca agttcatcaa agtgttggac agacaactat   2580
```

```
accagcatgg atctcttgta tcggttcttt tctcccgctc tctcgcaata acaatgaaca    2640
ctgggtcaat catagcctac acaggtgaac agagtagcgt ttatacaggg tttatacggt    2700
gattcctacg gcaaaaattt ttcatttcta aaaaaaaaaa gaaaaatttt tctttccaac    2760
gctagaagga aaagaaaaat ctaattaaat tgatttggtg attttctgag agttcccttt    2820
ttcatatatc gaattttgaa tataaaagga gatcgaaaaa attttttctat tcaatctgtt    2880
ttctggtttt atttgatagt ttttttgtgt attattatta tggattagta ctggtttata    2940
tgggttttc tgtataactt cttttttattt tagtttgttt aatcttattt tgagttacat     3000
tatagttccc taactgcaag agaagtaaca ttaaaaatga aaaagcctga actcaccgcg    3060
acgtctgtcg agaagtttct gatcgaaaag ttcgacagcg tctccgacct gatgcagctc    3120
tcggagggcg aagaatctcg tgctttcagc ttcgatgtag gagggcgtgg atatgtcctg    3180
cgggtaaata gctgcgccga tggtttctac aaagatcgtt atgtttatcg gcactttgca    3240
tcggccgcgc tcccgattcc ggaagtgctt gacattgggg aattcagcga gagcctgacc    3300
tattgcatct cccgccgtgc acagggtgtc acgttgcaag acctgcctga aaccgaactg    3360
cccgctgttc tgcagccggt cgcggaggcc atggatgcga tcgctgcggc cgatcttagc    3420
cagacgagcg ggttcggccc attcggaccg caaggaatcg gtcaatacac tacatggcgt    3480
gatttcatat gcgcgattgc tgatccccat gtgtatcact ggcaaactgt gatggacgac    3540
accgtcagtg cgtccgtcgc gcaggctctc gatgagctga tgctttgggc cgaggactgc    3600
cccgaagtcc ggcacctcgt gcacgcggat tccggctcca acaatgtcct gacggacaat    3660
ggccgcataa cagcggtcat tgactggagc gaggcgatgt tcgggattc ccaatacgag      3720
gtcgccaaca tcttcttctg gaggccgtgg ttggcttgta tggagcagca gacgcgctac    3780
ttcgagcgga ggcatccgga gcttgcagga tcgccgcggc tccgggcgta tatgctccgc    3840
attggtcttg accaactcta tcagagcttg gttgacggca atttcgatga tgcagcttgg    3900
gcgcagggtc gatgcgacgc aatcgtccga tccggagccg gactgtcgg gcgtacacaa       3960
atcgcccgca gaagcgcggc cgtctggacc gatggctgtg tagaagtact cgccgatagt    4020
ggaaaccgac gccccagcac tcgtccgagg gcaaggaat aggtttaact tgatactact       4080
agatttttc tcttcattta taaaattttt ggttataatt gaagctttag aagtatgaaa      4140
aaatcctttt ttttcattct ttgcaaccaa aataagaagc ttcttttatt cattgaaatg    4200
atgaatataa acctaacaaa agaaaaagac tcgaatatca acattaaaa aaaaataaaa       4260
gaggttatct gttttcccat ttagttggag tttgcatttt ctaatagata gaactctcaa    4320
ttaatgtgga tttagtttct ctgttcgttt ttttttgttt tgttctcact gtatttacat    4380
ttctatttag tatttagtta ttcatataat cttaacttct cgaggagctc cgctcgtcca    4440
acgccggcgg acctcggagg ttgtttatct ttcgagtact gaatgttgtc agtatagcta    4500
tcctatttga aactccccat cgtcttgctc ttgttcccaa tgtttgttta tacactcata    4560
tggctatacc cttatctact tgcctctttt gtttatgtct atgtatttgt ataaaatatg    4620
atattactca gactcaagca aacaatcaat tcttagcatc attctttgtt cttatcttaa    4680
ccataaacga tcttgatgtg acttttgtaa tttgaacgaa ttggctatac gggacggatg    4740
acaaatgcac cattactcta ggttgttgtt ggatcttaac aaaccgtaaa ggtaaactgc    4800
ccatgcggtt cacatgactt ttgactttcc tttgtttgct agttaccttc ggcttcacaa    4860
tttgtttttc cacttttcta acaggttat caccttcaa acttatcttt atcttattcg      4920
ccttcttggg tgcctccaca gtagaggtta cttccttttt aatatgtact tttaggatac    4980
```
tttcacgctt tataacacgg tgtttaaacc ccagcgcctg gcggg 5025

<210> SEQ ID NO 95
<211> LENGTH: 3665
<212> TYPE: DNA
<213> ORGANISM: Artificial Sequence
<220> FEATURE:
<223> OTHER INFORMATION: Synthetic, Integration construct i477

<400> SEQUENCE: 95

| | | |
|---|---|---|
| agctcgagga cggcacggcc acgcgtttaa accgccaagc ttttcaattc atctttttt | 60 |
| tttttgttct ttttttgat tccggtttct ttgaaatttt tttgattcgg taatctccga | 120 |
| gcagaaggaa gaacgaagga aggagcacag acttagattg gtatatatac gcatatgtgg | 180 |
| tgttgaagaa acatgaaatt gcccagtatt cttaacccaa ctgcacagaa caaaaacctg | 240 |
| caggaaacga agataaatca tgtcgaaagc tacatataag gaacgtgctg ctactcatcc | 300 |
| tagtcctgtt gctgccaagc tatttaatat catgcacgaa aagcaaacaa acttgtgtgc | 360 |
| ttcattggat gttcgtacca ccaaggaatt actggagtta gttgaagcat taggtcccaa | 420 |
| aatttgttta ctaaaaacac atgtggatat cttgactgat ttttccatgg agggcacagt | 480 |
| taagccgcta aaggcattat ccgccaagta caattttta ctcttcgaag acagaaaatt | 540 |
| tgctgacatt ggtaatacag tcaaattgca gtactctgcg ggtgtataca gaatagcaga | 600 |
| atgggcagac attacgaatg cacacggtgt ggtgggccca ggtattgtta gcggtttgaa | 660 |
| gcaggcggca gaagaagtaa caaaggaacc tagaggcctt ttgatgttag cagaattgtc | 720 |
| atgcaagggc tccctatcta ctggagaata tactaagggt actgttgaca ttgcgaagag | 780 |
| tgacaaagat tttgttatcg gctttattgc tcaaagagac atgggtggaa gagatgaagg | 840 |
| ttacgattgg ttgattatga cacccggtgt gggtttagat gacaagggag acgcattggg | 900 |
| tcaacagtat agaaccgtgg atgatgtggt ctctacagga tctgacatta ttattgttgg | 960 |
| aagcgctcgt ccaacgccgg cggacctatg gcgcaagttt ccgctttgt aatatatatt | 1020 |
| tataccccctt tcttctctcc cctgcaatat aatagtttaa ttctaatatt aataatatcc | 1080 |
| tatattttct tcatttaccg gcgcactctc gcccgaacga cctcaaaatg tctgctacat | 1140 |
| tcataataac caaaagctca aactttttt ttttgaacct gaatatatat acatcacata | 1200 |
| tcactgctgg tccttgccga ccagcgtata caatctcgat agttggtttc cgttctttc | 1260 |
| cactcccgtc atggactaca acaagagatc ttcggtctca accgtgccta atgcagctcc | 1320 |
| cataagagtc ggattcgtcg gtctcaacgc agccaaagga tgggcaatca agacacatta | 1380 |
| ccccgccata ctgcaactat cgtcacaatt tcaaatcact gccttataca gtccaaaaat | 1440 |
| tgagacttct attgccacca tccagcgtct aaaattgagt aatgccactg cttttcccac | 1500 |
| tttagagtca tttgcatcat cttccactat agatatgata gtgatagcta tccaagtggc | 1560 |
| cagtcattat gacgttgtta tgcctctctt ggaattctcc aaaaataatc cgaacctcaa | 1620 |
| gtatcttttc gtagaatggg cccttgcatg ttcactagat caagccgaat ccatttataa | 1680 |
| ggctgctgct gaacgtgggg ttcaaaccat catctcttta caaggtcgta atcaccata | 1740 |
| tattttgaga gcaaaagaat taatatctca aggctatatc ggcgacatta ttctatcga | 1800 |
| gattgctgga atggcggtt ggtacggcta cgaaaggcct gttaaatcac caaaatacat | 1860 |
| ctatgaaatc gggaacggtg tagatctggt aaccacaaca tttggtcaca caatcgatat | 1920 |
| tttacaatac atgacaagtt cgtacttttc caggataaat gcaatggttt tcaataatat | 1980 |
| tccagagcaa gagctgatag atgagcgtgg taaccgattg ggccagcgag tcccaaagac | 2040 |

```
agtaccggat catctttat tccaaggcac attgttaaat ggcaatgttc cagtgtcatg   2100
cagtttcaaa ggtggcaaac ctaccaaaaa atttaccaaa aatttggtca ttgatattca   2160
cggtaccaag ggagatttga aacttgaagg cgatgccgga ttcgcagaaa tttcaaatct   2220
ggtcctttac tacagtggaa ctagagcaaa cgacttcccg ctagctaatg acaacaagc   2280 tcctttagac ccggggtatg atgcaggtaa agaaatcatg gaagtatatc atttacgaaa   2340
ttataatgcc attgtcggta atattcatcg actgtatcaa tctatctctg acttccactt   2400
caatacaaag aaaattcctg aattaccctc acaatttgta atgcaaggtt tcgatttcga   2460
aggctttccc accttgatgg atgctctgat attacacagg ttaatcgaga gcgtttataa   2520
aagtaacatg atgggctcca cattaaacgt tagcaatatc tcgcattata gtttataaaa   2580
gcatcttgcc ctgtgcttgg cccccagtgc agcgaacgtt ataaaaacga atactgagta   2640
tatatctatg taaaacaacc atatcatttc ttgttctgaa ctttgtttac ctaactagtt   2700
ttaaatttcc cttttcgtg catgcgggtg ttcttattta ttagcatact acatttgaaa   2760
tatcaaattt ccttagtaga aaagtgagag aaggtgcact gacacaaaaa ataaaatccc   2820
cgcgtgcttg gccggccgtc ttcattggat gttcgtacca ccaaggaatt actggagtta   2880
gttgaagcat taggtcccaa aatttgttta ctaaaaacac atgtggatat cttgactgat   2940
ttttccatgg agggcacagt taagccgcta aaggcattat ccgccaagta caattttta   3000 ctcttcgaag acagaaaatt tgctgacatt ggtaatacag tcaaattgca gtactctgcg   3060
ggtgtataca gaatagcaga atgggcagac attacgaatg cacacggtgt ggtgggccca   3120
ggtattgtta gcggtttgaa gcaggcggca gaagaagtaa caaaggaacc tagaggcctt   3180
ttgatgttag cagaattgtc atgcaagggc tccctatcta ctggagaata tactaagggt   3240
actgttgaca ttgcgaagag tgacaaagat tttgttatcg gctttattgc tcaaagagac   3300
atgggtggaa gagatgaagg ttacgattgg ttgattatga cacccggtgt gggtttagat   3360
gacaagggag acgcattggg tcaacagtat agaaccgtgg atgatgtggt ctctacagga   3420
tctgacatta ttattgttgg aagaggacta tttgcaaagg gaagggatgc taaggtagag   3480
ggtgaacgtt acagaaaagc aggctgggaa gcatatttga agaatgcgg ccagcaaaac   3540 taaaaaactg tattataagt aaatgcatgt atactaaact cacaaattag agcttcaatt   3600
taattatatc agttattacc cgggaatctc ggtgtttaaa ccccagcgcc tggcgggtct   3660
agatc                                                             3665
```

<210> SEQ ID NO 96
<211> LENGTH: 10623
<212> TYPE: DNA
<213> ORGANISM: Artificial Sequence
<220> FEATURE:
<223> OTHER INFORMATION: Synthetic, Integration construct i94

<400> SEQUENCE: 96

```
atgagtgata gggaattcgt cacggtagat cccgtcacta tcataatcaa agaatgcatt     60
aatttatcga cagcgatgcg gaaatactct aaatttacct ctcaatctgg agtggccgct    120
ttgctggggg gaggaagtga aatatttagc aatcaagatg actacttggc tcacacattc    180
aacaatttga ataccaacaa gcacaatgat ccatttttat ctggattcat tcagttaaga    240
cttatgttga ataaactgaa aaatctagat aatatagatt cactaaccat attgcagcca    300
tttttattaa ttgtgagtac aagttccatt tctggttaca tcacttccct ggccctggac    360
tctttgcaga aattctttac cttgaatatc atcaatgaat catcgcaaaa ctatattggt    420
```

```
gcacacaggg cgacggtaaa tgctctaaca cattgtaggt ttgaaggatc tcaacaactt      480
tctgatgatt cagttctttt gaaagtcgtg tttttactgc gttcaatcgt cgactcacct      540
tacggagatt tattatcaaa ctctatcata tatgacgtat tgcaaacgat tctttcattg      600
gcttgtaata acagaaggag cgaagtcctt aggaatgctg cacaatcaac aatgatagcc      660
gttaccgtaa agattttctc aaaactaaag actattgagc ctgttaatgt gaatcaaata      720
tacatcaatg atgaaagtta cacaaatgat gtattgaagg ccgatacaat tggcacaaat      780
gtagaatcca agaagaagg aagtcaagaa gatcccatcg gcatgaaagt gaataatgag       840
gaagctatta gcgaggacga tggcattgaa gaagagcata ttcattcaga gaagagcaca      900
aatggcgccg aacaactaga tattgtgcaa aaaacaacaa gatcaaattc caggatccaa      960
gcgtatgctg atgataacta tggattgccc gtggttaggc aatatttaaa cttattacta     1020
tcattgattg cgccagaaaa tgaattaaaa cattcatact ccactagaat atttggccta     1080
gagttaattc aaacggcatt agaaatttca ggtgatcgat tgcagctata cccacggctt     1140
tttacactga tatcagatcc tattttcaaa agcattttgt ttatcataca gaacactaca     1200
aaattatcac tacttcaagc tacattgcag ctatttacta ctctagttgt tatattgggc     1260
aacaacttac aattacagat cgagctcact ctaacaagaa tattttctat tcttttagat     1320
gatggtaccg caaataactc gagttctgaa aataagaaca agccatcaat aataaaggaa     1380
cttctaattg agcaaatatc catcttatgg actaggtcgc catcttttt tacttctact      1440
tttatcaatt tcgattgtaa tctcgatagg gcagacgttt ccataaactt tttgaaggct     1500
ttgactaaat tggccttacc agaatccgcc ttaactacca cagaaagtgt accacccatt     1560
tgccttgagg gattggtctc cctagtcgat gatatgttcg atcacatgaa ggacattgac     1620
agagaagaat ttggcaggca aaagaatgaa atggaaatct taaaaagag ggaccgtaaa       1680
acagagttta ttgaatgtac caatgcattc aatgaaaagc ccaaaaggg tattccgatg       1740
ttaatagaaa aaggtttcat tgcttccgac tccgataaag atattgcgga gtttctttc      1800
aataataaca accgtatgaa taaaaaaaca atcggtttgc tactttgcca tccggacaaa     1860
gtaagcttgt tgaatgaata tattcgtttg tttgattttt cagggttaag ggtcgatgaa     1920
gctattagaa ttttgttgac gaaatttagg ttgcctggtg aatcgcaaca aattgaaaga     1980
atcatcgaag ccttctcgtc tgcgtattgt gaaaatcaag attacgatcc atccaaaatc     2040
agtgacaacg cggaggatga catttctact gttcaaccag acgctgattc tgttttcatt     2100
ttaagttatt caattattat gttgaacact gacctacata cccctcaagt gaaggaacac     2160
atgtcatttg aagattactc tggtaactta aagggatgct gtaatcacaa agacttccca     2220
ttctggtatt tggatagaat ttactgttca atcagagata aagaaattgt tatgcctgaa     2280
gagcaccacg gcaacgaaaa gtggtttgaa gatgcttgga ataacttgat atcttcaact     2340
actgttataa ctgaaataaa aaaagacaca caatctgtca tggataaatt aacacccttg     2400
gagcttttga actttgatag agcaattttt aaacaagttg gcccaagtat tgtcagtact     2460
ttattcaaca tttacgtagt tgcatctgat gaccatatat ctaccagaat gataacaagt     2520
ttggacaaat gttcctatat ttccgcattt tttgacttca agatctctct taatgatata     2580
ctaaactcca ttgctaaggg cactactttg attaattcaa gccatgacga tgaactttca     2640
actttagctt ttgaatatgg cccaatgcca ctggtgcaaa ttaaattcga agacactaac     2700
actgagatcc cggttagtac agatgctgtt agatttggta gatcatttaa gggtcaacta     2760
aatacagttg ttttttttccg gattattcgc aggaacaaag atcctaaaat tttctccaag    2820
```

```
gaattatggt taaacattgt taatattata ctaacattgt acgaagactt gattttgtct    2880
cctgatattt tccctgattt acaaaaaaga ctgaaattaa gcaacttgcc taagccatct    2940
cctgaaattt ctattaacaa gagcaaagaa agcaaaggtc tcttatcaac atttgcttct    3000
tatttaaaag gtgatgaaga acccacgaaa gaggaaatca aatcctcaaa aaaagcgatg    3060
gagtgcataa agtcgagtaa tattgccgcc tctgtctttg gaaatgaatc aaatataaca    3120
gcggatttaa taaaaacttt actagactcc gccaaaactg agaaaaacgc agataattcc    3180
aggtattttg aagcagaact tttatttatc atcgaattga ctattgcatt atttctattt    3240
tgcaaagagg agaagaatt aggaaagttc atacttcaaa aagttttcca actttctcac    3300
acgaaaggcc tcacgaaaag gactgttcgt agaatgctaa catacaaaat tttgttaatt    3360
tcgttatgtg cggatcagac ggagtacttg tccaaattaa taaacgatga gctgttaaaa    3420 aaggggata ttttttaccca aaaattttt gcaactaatc aaggtaagga attttgaag    3480 agactatttt cattgaccga atcagagttt tatagaggat ttttactagg aaatgagaat    3540
ttttggaaat ttttaagaaa agttacagca atgaaagagc agagcgagag catttttgaa    3600
tatttaaatg aatcgatcaa gacagacagc aatattttga caaatgagaa cttcatgtgg    3660
gtcctaggac tattagatga aatttcatca atgggtgccg ttggaaatca ctgggaaata    3720
gaatacaaga aattgacaga aagtggtcat aaaattgata aggagaatcc atacaagaaa    3780
tcgatcgaat tatcattgaa atccattcaa ctaacatcac acttgctgga agataataac    3840
gatctgcgta aaaacgagat attcgctatt attcaagctt tggcacatca atgcatcaat    3900
ccgtgtaagc agataagtga atttgcagtg gtaacgctag agcagacgct catcaataaa    3960
atcgaaattc caactaatga gatgaatcg gtagaagaat taattgaggg cggattacta    4020
ccgttgctaa attcgagtga aacacaggaa gaccagaaaa tcctcatttc atccatatta    4080
acaataattt caaatgttta tttgcattat ttgaaactag ggaagacaag caacgaaacg    4140
tttttgaaaa ttttgagtat tttcaataaa tttgtagagg actcagatat tgaaaaaaag    4200
ctacagcaat taatacttga taagaagagt attgagaagg gcaacggttc atcatctcat    4260
ggatctgcac atgaacaaac accagagtca acgacgttg aaattgaggc tactgcgcca    4320
attgatgaca atacagacga tgataacaaa ccgaagttat ctgatgtaga aaaggattaa    4380
agatgctaag agatagtgat gatatttcat aaataatgta attctatata tgttaattac    4440 ctttttgcg aggcatattt atggtgaagg ataagttttg accatcaaag aaggttaatg    4500
tggctgtggt ttcagggtcc atacccggga gttatgacaa ttacaacaac agaattcttt    4560
ctatatatgc acgaacttgt aatatggaag aaattatgac gtacaaacta taaagtaaat    4620
attttacgta acacatggtg ctgttgtgct tcttttcaa gagaatacca atgacgtatg    4680
actaagttta ggatttaatg caggtgacgg acccatcttt caaacgattt atatcagtgg    4740
cgtccaaatt gttaggtttt gttggttcag caggtttcct gttgtgggtc atatgacttt    4800
gaaccaaatg gccggctgct agggcagcac ataaggataa ttcacctgcc aagacggcac    4860
aggcaactat tcttgctaat tgacgtgcgt tggtaccagg agcggtagca tgtgggcctc    4920
ttacacctaa taagtccaac atggcacctt gtggttctag aacagtacca ccaccgatgg    4980
tacctacttc gatggatggc atggatacgg aaattctcaa atcaccgtcc acttctttca    5040
tcaatgttat acagttggaa ctttcgacat tttgtgcagg atcttgtcct aatgccaaga    5100
aaacagctgt cactaaatta gctgcatgtg cgttaaatcc accaacagac ccagccattg    5160
cagatccaac caaattctta gcaatgttca actcaaccaa tgcggaaaca tcactttta    5220
```

```
acacttttct gacaacatca ccaggaatag tagcttctgc gacgacactc ttaccacgac    5280
cttcgatcca gttgatggca gctggttttt tgtcggtaca gtagttacca gaaacggaga    5340
caacctccat atcttcccag ccatactctt ctaccatttg ctttaatgag tattcgacac    5400
ccttagaaat catattcata cccattgcgt caccagtagt tgttctaaat ctcatgaaga    5460
gtaaatctcc tgctagacaa gtttgaatat gttgcagacg tgcaaatctt gatgtagagt    5520
taaaagcttt tttaattgcg ttttgtccct cttctgagtc taaccatatc ttacaggcac    5580
cagatctttt caaagttggg aaacggacta ctgggcctct tgtcatacca tccttagtta    5640
aaacagttgt tgcaccaccg ccagcattga ttgccttaca gccacgcatg gcagaagcta    5700
ccaaacaacc ctctgtagtt gccattggta tatgataaga tgtaccatcg ataaccaagg    5760
ggcctataac accaacgggc aaaggcatgt aacctataac attttcacaa caagcgccaa    5820
atacgcggtc gtagtcataa tttttatatg gtaaacgatc agatgctaat acaggagctt    5880
ctgccaaaat tgaaagagcc ttcctacgta ccgcaaccgc tctcgtagta tcacctaatt    5940
ttttctccaa agcgtacaaa ggtaacttac cgtgaataac caaggcagcg acctctttgt    6000
tcttcaattg ttttgtattt ccactactta ataatgcttc taattcttct aaaggacgta    6060
ttttcttatc caagctttca atatcgcggg aatcatcttc ctcactagat gatgaaggtc    6120
ctgatgagct cgattgcgca gatgataaac ttttgacttt cgatccagaa atgactgttt    6180
tattggttaa aactggtgta gaagcctttt gtacaggagc agtaaaagac ttcttggtga    6240
cttcagtctt caccaattgg tctgcagcca ttatagtttt ttctccttga cgttaaagta    6300
tagaggtata ttaacaattt tttgttgata cttttatgac atttgaataa gaagtaatac    6360
aaaccgaaaa tgttgaaagt attagttaaa gtggttatgc agcttttgca tttatatatc    6420
tgttaataga tcaaaaatca tcgcttcgct gattaattac cccagaaata aggctaaaaa    6480
actaatcgca ttattatcct atggttgtta atttgattcg ttgatttgaa ggtttgtggg    6540
gccaggttac tgccaatttt tcctcttcat aaccataaaa gctagtattg tagaatcttc    6600
attgttcgga gcagtgcggc gcgaggcaca tctgcgtttc aggaacgcga ccggtgaaga    6660
ccaggacgca cggaggagag tcttccgtcg gagggctgtc gcccgctcgg cggcttctaa    6720
tccgtacttc aatatagcaa tgagcagtta agcgtattac tgaaagttcc aaagagaagg    6780 ttttttttagg ctaagataat ggggctcttt acatttccac aacatataag taagattaga    6840
tatggatatg tatatggtgg tattgccatg taatatgatt attaaacttc tttgcgtcca    6900
tccaaaaaaa aagtaagaat ttttgaaaat tcaatataaa tgaaactctc aactaaactt    6960
tgttggtgtg gtattaaagg aagacttagg ccgcaaaagc aacaacaatt acacaataca    7020
aacttgcaaa tgactgaact aaaaaaacaa aagaccgctg aacaaaaaac cagacctcaa    7080
aatgtcggta ttaaaggtat ccaaatttac atcccaactc aatgtgtcaa ccaatctgag    7140
ctagagaaat ttgatggcgt ttctcaaggt aaatacacaa ttggtctggg ccaaaccaac    7200
atgtcttttg tcaatgacag agaagatatc tactcgatgt ccctaactgt tttgtctaag    7260
ttgatcaaga gttacaacat cgacaccaac aaaattggta gattagaagt cggtactgaa    7320
actctgattg acaagtccaa gtctgtcaag tctgtcttga tgcaattgtt tggtgaaaac    7380
actgacgtcg aaggtattga cacgcttaat gcctgttacg gtggtaccaa cgcgttgttc    7440
aactctttga actggattga atctaacgca tgggatggta gagacgccat tgtagtttgc    7500
ggtgatattg ccatctacga taagggtgcc gcaagaccaa ccggtggtgc cggtactgtt    7560
gctatgtgga tcggtcctga tgctccaatt gtatttgact ctgtaagagc ttcttacatg    7620
```

```
gaacacgcct acgatttta caagccagat ttcaccagcg aatatcctta cgtcgatggt    7680 cattttcat taacttgtta cgtcaaggct cttgatcaag tttacaagag ttattccaag    7740
aaggctattt ctaaagggtt ggttagcgat cccgctggtt cggatgcttt gaacgttttg    7800
aaatatttcg actacaacgt tttccatgtt ccaacctgta aattggtcac aaaatcatac    7860
ggtagattac tatataacga tttcagagcc aatcctcaat tgttcccaga agttgacgcc    7920
gaattagcta ctcgcgatta tgacgaatct ttaaccgata agaacattga aaaaactttt    7980
gttaatgttg ctaagccatt ccacaaagag agagttgccc aatctttgat tgttccaaca    8040
aacacaggta acatgtacac cgcatctgtt tatgccgcct ttgcatctct attaaactat    8100
gttggatctg acgacttaca aggcaagcgt gttggtttat tttcttacgg ttccggttta    8160
gctgcatctc tatattcttg caaaattgtt ggtgacgtcc aacatattat caaggaatta    8220
gatattacta acaaattagc caagagaatc accgaaactc caaggattta cgaagctgcc    8280
atcgaattga gagaaaatgc ccatttgaag aagaacttca aacctcaagg ttccattgag    8340
catttgcaaa gtggtgttta ctacttgacc aacatcgatg acaaatttag aagatcttac    8400
gatgttaaaa aataatcttc ccccatcgat tgcatcttgc tgaaccccct tcataaatgc    8460 tttattttt tggcagcctg ctttttttag ctctcattta atagagtagt tttttaatct    8520
atatactagg aaaactcttt atttaataac aatgatatat atatattcca gtggtgcatg    8580
aacgcatgag aaagcccccg gaagatcatc ttccgggggc tttttttttg gcgcgcgata    8640
cagaccggtt cagacaggat aaagaggaac gcagaatgtt agacaacacc cgcttacgca    8700
tagctattca gaaatcaggc cgtttaagcg atgattcacg agaattgctg gcccgctgcg    8760
gcataaaaat taatttacac actcagcgcc tgattgcgat ggcggaaaac atgccgattg    8820
atatcctgcg cgtgcgtgat gatgacattc cgggtctggt aatggatggc gtggtcgatc    8880
tcggtattat cggcgaaaac gtgctggaag aagagctact caaccgccgc gcacagggcg    8940
aagatccacg ctatttaacc ctgcgccgtc ttgacttcgg cggctgccgt ttatcgctgg    9000
caacaccggt tgacgaagcc tgggacggcc cggccgcgct ggacggtaaa cgtatcgcta    9060
cctcatatcc gcacctcctc aaacgctacc tcgaccagaa aggcgtctct tttaaatcgt    9120
gtctgttaaa tggttctgtc gaagtcgcgc cgcgcgcggg gctggccgac gctatctgcg    9180
atttggtctc taccggcgcg acgcttgaag ctaacggcct gcgtgaagtc gaagttatct    9240
accgctctaa agcctgtctg attcagcgcg acggtgagat ggcacagagc aagcaagagc    9300
tgatcgataa attgctgacc cgtattcagg gcgtgattca ggcgcgcgaa tcgaaataca    9360
tcatgatgca cgcgccaagt gaacgcctgg aagaggttat cgccctgctg ccaggcgccg    9420
aaaggccgac aattctgccg ctggcaggcg agcaacagcg cgtggcgatg cacatggtca    9480
gcagcgaaac gttgttctgg gaaccatgg agaaactgaa agcgcttggc gccagctcga    9540
ttctggtact gccgatcgag aagatgatgg agtgatctga cgcctgatgg cgctgcgctt    9600
atcaggccta cgtaatgcgt tgaaaaactg tattataagt aaatgcatgt atactaaact    9660
cacaaattag agcttcaatt taattatatc agttattacc cgggaatctc ggtcgtaatg    9720
atttctataa tgacgaaaaa aaaaaaattg gaaagaaaaa gcttcatggc ctttataaaa    9780
aggaactatc caatacctcg ccagaaccaa gtaacagtat tttacggggc acaaatcaag    9840
aacaataaga caggactgta aagatggacg cattgaactc caaagaacaa caagagttcc    9900
aaaaagtagt ggaacaaaag caaatgaagg atttcatgcg tttgtactct aatctggtag    9960
aaagatgttt cacagactgt gtcaatgact tcacaacatc aaagctaacc aataaggaac   10020
```

```
aaacatgcat catgaagtgc tcagaaaagt tcttgaagca tagcgaacgt gtagggcagc    10080
gtttccaaga acaaaacgct gccttgggac aaggcttggg ccgataaggt gtactggcgt    10140
atatatatct aattatgtat ctctggtgta gcccattttt agcatgtaaa tataaagaga    10200
aaccatatct aatctaacca aatccaaaca aaattcaata gttactatcg cttttttctt    10260
tctgtatcgc aaataagtga aaattaaaaa agaaagatta aattggaagt tggatatggg    10320
ctggaacagc agcagtaatc ggtatcgggt tcgccactaa tgacgtccta cgattgcact    10380
caacagacct tgacgctcac gccgtagcgg gcgacaagtc aaacggaaca accgttgccg    10440
ttcccatcgg agtccgacct aggccgaact ccgtgaattt ctgataacaa cggtcggtaa    10500
agactggttc cccagtatat ttcttctctc aggagcaggg gccaatgcca aaagcgacat    10560
taacccggag gacaaggctc cactgtgttc caccgaattt cccacctgat aatatctgat    10620
aac                                                                  10623
```

<210> SEQ ID NO 97
<211> LENGTH: 8479
<212> TYPE: DNA
<213> ORGANISM: Artificial Sequence
<220> FEATURE:
<223> OTHER INFORMATION: Synthetic, Integration construct i467

<400> SEQUENCE: 97

```
gacggcacgg ccacgcgttt aaaccgccct ccaagctgac ataaatcgca ctttgtatct      60 acttttttt attcgaaaac aaggcacaac aatgaatcta tcgccctgtg agattttcaa     120
tctcaagttt gtgtaataga tagcgttata ttatagaact ataaaggtcc ttgaatatac    180
atagtgtttc attcctatta ctgtatatgt gactttacat tgttacttcc gcggctattt    240
gacgttttct gcttcaggtg cggcttggag ggcaaagtgt cagaaaatcg gccaggccgt    300
atgacacaaa agagtagaaa acgagatctc aaatatctcg aggcctgtcc tctatacaac    360
cgcccagctc tctgacaaag ctccagaacg gttgtctttt gtttcgaaaa gccaaggtcc    420
cttataattg ccctccattt tgtgtcacct atttaagcaa aaaattgaaa gtttactaac    480 cttttcattaa agagaaataa caatattata aaaagcgctt aaagctcaca cgcggccagg    540
gggagccgtt catcatctca tggatctgca catgaacaaa caccagagtc aaacgacgtt    600
gaaattgagg ctactgcgcc aattgatgac aatacagacg atgataacaa accgaagtta    660
tctgatgtag aaaaggatta aagatgctaa gagatagtga tgatatttca taaataatgt    720
aattctatat atgttaatta ccttttttgc gaggcatatt tatggtgaag ataagttttt    780
gaccatcaaa gaaggttaat gtggctgtgg tttcagggtc cataaagctt tcaattcat    840 ctttttttt tttgttcttt tttttgattc cggtttcttt gaaattttt tgattcggta    900 atctccgagc agaaggaaga acgaaggaag gagcacagac ttagattggt atatatacgc    960
atatgtggtt tgaagaaaac atgaaattgc ccagtattct taacccaact gcacagaaca   1020
aaaacctgca ggaaacgaag ataaatcatg tcgaaagcta catataagga acgtgctgct   1080
actcatccta gtcctgttgc tgccaagcta tttaatatca tgcacgaaaa gcaaacaaac   1140
ttgtgtgctt cattggatgt tcgtaccacc aaggaattac tggagttagt tgaagcatta   1200
ggtcccaaaa tttgttttact aaaaacacat gtggatatct tgactgattt ttccatggag   1260
ggcacagtta agccgctaaa ggcattatcc gccaagtaca atttttttact cttcgaagac   1320 agaaaatttg ctgacattgg taatacagtc aaattgcagt actctgcggg tgtatacaga   1380
atagcagaat gggcagacat tacgaatgca cacggtgtgg tgggcccagg tattgttagc   1440
```

```
ggtttgaagc aggcggcaga agaagtaaca aaggaaccta gaggccttt  gatgttagca    1500 gaattgtcat gcaagggctc cctatctact ggagaatata ctaagggtac tgttgacatt    1560
gcgaagagtg acaaagattt tgttatcggc tttattgctc aaagagacat gggtggaaga    1620
gatgaaggtt acgattggtt gattatgaca cccggtgtgg gtttagatga caagggagac    1680
gcattgggtc aacagtatag aaccgtggat gatgtggtct ctacaggatc tgacattatt    1740
attgttggaa gaggactatt tgcaaaggga agggatgcta aggtagaggg tgaacgttac    1800
agaaaagcag gctgggaagc atatttgaga agatgcggcc agcaaaacta aaaaactgta    1860
ttataagtaa atgcatgtat actaaactca caaattagag cttcaattta attatatcag    1920
ttattacccg ggaatctcgg tcgtaatgat ttctataatg acgaaaaaaa aaaaattgga    1980
aagaaaaagc ttcatggcct ttataaaaag gaactatcca atacctcgcc agaaccaagt    2040
aacagtattt tacggggcac aaatcaagaa caataagaca ggactgtaaa gatggacgca    2100
tcgctcgtcc aacgccggcg gacctgtttt caatagttcg gtaatattaa cggatacccta    2160 ctattatccc ctagtaggct cttttcacgg agaaattcgg gagtgttttt tttccgtgcg    2220
catttcttta gctatattct tccagcttcg cctgctgccc ggtcatcgtt cctgtcacgt    2280 agttttccg  gattcgtccg gctcatataa taccgcaata acacggaat  atctcgttcc    2340 gcggattcgg ttaaactctc ggtcgcggat tatcacagag aaagcttcgt ggagaatttt    2400
tccagatttt ccgctttccc cgatgttggt atttccggag gtcattatac tgaccgccat    2460
tataatgact gtacaacgac cttctggaga aagaaacaac tcaataacga tgtgggacat    2520
tgggggccca ctcaaaaaat ctggggacta tatccccaga gaatttctcc agaagagaag    2580
aaaagtcaaa gtttttttt  gcttgggggt tgcatataaa tacaggcgct gttttatctt    2640
cagcatgaat attccataat tttacttaat agcttttcat aaataataga atcacaaaca    2700
aaatttacat ctgagttaaa caatcatgac aatcaaggaa cataaagtag tttatgaagc    2760
tcacaacgta aaggctctta aggctcctca acatttttac aacagccaac ccggcaaggg    2820
ttacgttact gatatgcaac attatcaaga aatgtatcaa caatctatca atgagccaga    2880
aaaattcttt gataagatgg ctaaggaata cttgcattgg gatgctccat acaccaaagt    2940
tcaatctggt tcattgaaca atggtgatgt tgcatggttt ttgaacggta aattgaatgc    3000
atcatacaat tgtgttgaca gacatgcctt tgctaatccc gacaagccag cttttgatcta    3060 tgaagctgat gacgaatccg acaacaaaat catcacattt ggtgaattac tcagaaaagt    3120
ttcccaaatc gctggtgtct taaaaagctg gggcgttaag aaaggtgaca cagtggctat    3180
ctatttgcca atgattccag aagcggtcat tgctatgttg gctgtggctc gtattggtgc    3240
tattcactct gttgtctttg ctgggttctc cgctggttcg ttgaaagatc gtgtcgttga    3300
cgctaattct aaagtggtca tcacttgtga tgaaggtaaa agaggtggta agaccatcaa    3360
cactaaaaaa attgttgacg aaggtttgaa cggagtcgat ttggtttccc gtatcttggt    3420
tttccaaaga actggtactg aaggtattcc aatgaaggcc ggtagagatt actggtggca    3480
tgaggaggcc gctaagcaga gaacttacct acctcctgtt tcatgtgacg ctgaagatcc    3540
tctattttta ttatacactt ccggttccac tggttctcca aagggtgtcg ttcacactac    3600
aggtggttat ttattaggtg ccgctttaac aactagatac gttttgata  ttcacccaga    3660 agatgttctc ttcactgccg gtgacgtcgg ctggatcacg ggtcacacct atgctctata    3720
tggtccatta accttgggta ccgcctcaat aattttcgaa tccactcctg cctacccaga    3780
ttatggtaga tattggagaa ttatccaacg tcacaaggct acccatttct atgtggctcc    3840
```

```
aactgcttta agattaatca aacgtgtagg tgaagccgaa attgccaaat atgacacttc    3900
ctcattacgt gtcttgggtt ccgtcggtga accaatctct ccagacttat gggaatggta    3960
tcatgaaaaa gtgggtaaca aaaactgtgt catttgtgac actatgtggc aaacagagtc    4020
tggttctcat ttaattgctc ctttggcagg tgctgtccca acaaaacctg gttctgctac    4080
cgtgccattc tttggtatta acgcttgtat cattgaccct gttacaggtg tggaattaga    4140
aggtaatgat gtcgaaggtg tccttgccgt taaatcacca tggccatcaa tggctagatc    4200
tgtttggaac caccacgacc gttacatgga tacttacttg aaaccttatc ctggtcacta    4260
tttcacaggt gatggtgctg gtagagatca tgatggttac tactggatca ggggtagagt    4320
tgacgacgtt gtaaatgttt ccggtcatag attatccaca tcagaaattg aagcatctat    4380
ctcaaatcac gaaaacgtct cggaagctgc tgttgtcggt attccagatg aattgaccgg    4440
tcaaaccgtc gttgcatatg tttccctaaa agatggttat ctacaaaaca cgctactga    4500 aggtgatgca gaacacatca caccagataa tttacgtaga gaattgatct tacaagttag    4560
gggtgagatt ggtccttcg cctcaccaaa aaccattatt ctagttagag atctaccaag    4620
aacaaggtca ggaaagatta tgagaagagt tctaagaaag gttgcttcta acgaagccga    4680
acagctaggt gacctaacta ctttggccaa cccagaagtt gtacctgcca tcatttctgc    4740
tgtagagaac caattttct ctcaaaaaaa gaaataaatt gaattgaatt gaaatcgata    4800
gatcaatttt tttcttttct ctttccccat cctttacgct aaaataatag tttatttat    4860 tttttgaata ttttttattt atatacgtat atatagacta ttatttatct tttaatgatt    4920
attaagattt ttattaaaaa aaattcgct cctcttttaa tgcctttatg cagttttttt    4980
ttcccattcg atatttctat gttcgggttc agcgtatttt aagtttaata actcgaaaat    5040
tctgcgttcg ttaaagcttt cgagaaggat attatttcga aataaaccgt gttgtgtaag    5100
cttgaagcct ttttgcgctg ccaatattct tatccatcta ttgtactctt tagatccagt    5160
atagtgtatt cttcctgctc caagctcatc ccatccccgc gtgcttggcc ggccgttttg    5220
ccagcttact atccttcttg aaaatatgca ctctatatct tttagttctt aattgcaaca    5280
catagatttg ctgtataacg aatttatgc tattttttaa atttggagtt cagtgataaa    5340
agtgtcacag cgaattcct cacatgtagg gaccgaattg tttacaagtt ctctgtacca    5400
ccatggagac atcaaaaatt gaaaatctat ggaaagatat ggacggtagc aacaagaata    5460
tagcacgagc cgcggagttc atttcgttac ttttgatatc actcacaact attgcgaagc    5520
gcttcagtga aaaaatcata aggaaaagtt gtaaatatta ttggtagtat tcgtttggta    5580
aagtagaggg ggtaatttt ccccttatt ttgttcatac attcttaaat tgctttgcct    5640
ctccttttgg aaagctatac ttcggagcac tgttgagcga aggctcatta gatatatttt    5700
ctgtcatttt ccttaaccca aaaataaggg aaagggtcca aaaagcgctc ggacaactgt    5760
tgaccgtgat ccgaaggact ggctatacag tgttcacaaa atagccaagc tgaaaataat    5820
gtgtagctat gttcagttag tttggctagc aaagatataa aagcaggtcg aaatattta    5880 tgggcattat tatgcagagc atcaacatga taaaaaaaaa cagttgaata ttccctcaaa    5940
aatgtcttac accgtcggaa cctacttggc cgagaggttg gtccagatcg gattgaagca    6000
ccacttcgcc gtcgccggtg actacaactt ggtcttgttg gacaacttgt tgttgaacaa    6060
gaacatggag caggtctatt gctgcaacga gttgaactgc ggtttctcag cagaaggtta    6120
tgcaagagcc aagggagcag ccgctgccgt cgtcacctac tcagtcggtg cattatcagc    6180
attcgatgca attggaggtg cttacgctga gaacttgcca gtcatcttga tctctggagc    6240
```

```
acctaacaac aacgaccatg ctgctggtca cgtattgcac cacgccttgg gtaaaacaga    6300
ctaccactac cagttggaaa tggcaaaaaa tattaccgca gccgcagagg ccatctacac    6360
cccagaggaa gcacctgcca aaattgacca cgtcataaag accgctttga gagagaagaa    6420
gcctgtttac ttggagatcg cctgcaacat cgcttctatg ccatgcgccg cacctggtcc    6480
agcctctgct ttgttcaacg acgaggcctc tgacgaagct tcattgaacg ccgcagtcga    6540
agagacatta aagttcatcg ccaacaggga caaagttgcc gtcttagtcg gttcaaagtt    6600
gagggccgct ggtgccgaag aggcagctgt caagttcgct gacgccttgg gaggagccgt    6660
cgccaccatg gccgcagcaa aatctttctt tcctgaggag aacccacatt acatcggaac    6720
ctcatggggt gaagtatcat atcctggagt agaaaaaacc atgaaagagg ccgatgccgt    6780
aatagcattg gctcctgtct tcaacgacta ctcaaccaca ggatggactg atataccaga    6840
tccaaagaaa ttagtcttgg ctgagcctag gtctgtcgtc gtaaacggta tcaggttccc    6900
ttctgttcat ttgaaggact acttaacaag attgggccaa aaggtatcta aaaagactgg    6960
tgccttggac ttcttcaagt cattaaacgc aggagaattg aaaaaagcag caccagccga    7020
tccatcagcc ccattagtta acgctgaaat cgctagacaa gtagaggctt tgttgactcc    7080
aaacactacc gtcatagctg agacaggtga ctcttggttc aacgcacaga gaatgaaatt    7140
gccaaatggt gccagggtcg agtatgaaat gcagtgggga catataggtt ggtcagtccc    7200
agccgccttt ggatacgcag taggtgcccc tgagaggagg aacatattga tggttggtga    7260
tggttcattc caattaacag cccaggaggt agcccaaatg gtcaggttga agttgcctgt    7320
catcatcttc ttgatcaaca attacggata caccatcgag gtcatgatcc acgacggacc    7380
ttacaacaac atcaaaaact gggactacgc cggtttgatg gaggttttca acggtaacgg    7440
tggttatgac tcaggagccg gtaagggatt aaaggctaag accggtggtg aattggctga    7500
agcaattaag gtcgcattgg ccaacaccga tggacctaca ttgattgaat gcttcatcgg    7560
aagggaggac tgcaccgagg aattggttaa atggggtaaa agggtagccg ctgctaattc    7620
aagaaaacca gttaataaat tattataata agtgaattta ctttaaatct tgcatttaaa    7680
taaattttct ttttatagct ttatgactta gtttcaattt atatactatt ttaatgacat    7740
tttcgattca ttgattgaaa gctttgtgtt ttttcttgat gcgctattgc attgttcttg    7800
tcttttttcgc cacatgtaat atctgtagta gatacctgat acattgtgga tgctgagtga    7860
aattttagtt aataatggag gcgctcttaa taattttggg gatattggct taacctgcag    7920
gccgcgagcg ccgatataaa ctaatgattt taaatcgtta aaaaaatatg cgaattctgt    7980
ggatcgaaca caggacctcc agataacttg accgaagttt tttcttcagt ctggcgctct    8040
cccaactgag ctaaatccgc ttactatttg ttatcagttc ccttcatatc tacatagaat    8100
aggttaagta ttttattagt tgccagaaga actactgata gttgggaata tttggtgaat    8160
aatgaagatt gggtgaataa tttgataatt ttgagattca attgttaatc aatgttacaa    8220
tattatgtat acagagtata ctagaagttc tcttcggaga tcttgaagtt cacaaagggg    8280
aatcgatatt tctacataat attatcatta cttcttcccc atcttatatt tgtcattcat    8340
tattgattat gatcaatgca ataatgattg gtagttgcca aacatttaat acgatcctct    8400
gtaatatttc tatgaataat tatcacagca acgttcaatt atcttcaatt ccggtgttta    8460
aaccccagcg cctggcggg                                                 8479
```

<210> SEQ ID NO 98
<211> LENGTH: 10959
<212> TYPE: DNA

<213> ORGANISM: Artificial Sequence
<220> FEATURE:
<223> OTHER INFORMATION: Synthetic, Integration construct i601

<400> SEQUENCE: 98

| | | | | | |
|---|---|---|---|---|---|
| gacggcacgg | ccacgcgttt | aaaccgccct | ccaagctgac | ataaatcgca | ctttgtatct | 60 |
| acttttttt | attcgaaaac | aaggcacaac | aatgaatcta | tcgccctgtg | agattttcaa | 120 |
| tctcaagttt | gtgtaataga | tagcgttata | ttatagaact | ataaaggtcc | ttgaatatac | 180 |
| atagtgtttc | attcctatta | ctgtatatgt | gactttacat | tgttacttcc | gcggctattt | 240 |
| gacgttttct | gcttcaggtg | cggcttggag | ggcaaagtgt | cagaaaatcg | gccaggccgt | 300 |
| atgacacaaa | agagtagaaa | acgagatctc | aaatatctcg | aggcctgtcc | tctatacaac | 360 |
| cgcccagctc | tctgacaaag | ctccagaacg | gttgtctttt | gtttcgaaaa | gccaaggtcc | 420 |
| cttataattg | ccctccattt | tgtgtcacct | atttaagcaa | aaaattgaaa | gtttactaac | 480 |
| ctttcattaa | agagaaataa | caatattata | aaaagcgctt | aaagctcaca | cgcggccagg | 540 |
| gggagccgtt | catcatctca | tggatctgca | catgaacaaa | caccagagtc | aaacgacgtt | 600 |
| gaaattgagg | ctactgcgcc | aattgatgac | aatacagacg | atgataacaa | accgaagtta | 660 |
| tctgatgtag | aaaaggatta | aagatgctaa | gagatagtga | tgatatttca | taaataatgt | 720 |
| aattctatat | atgttaatta | cctttttgc | gaggcatatt | tatggtgaag | gataagtttt | 780 |
| gaccatcaaa | gaaggttaat | gtggctgtgg | tttcagggtc | cataaagctt | ttcaattcat | 840 |
| ctttttttt | tttgttcttt | ttttgattc | cggtttcttt | gaatttttt | tgattcggta | 900 |
| atctccgagc | agaaggaaga | acgaaggaag | gagcacagac | ttagattggt | atatatacgc | 960 |
| atatgtggtg | ttgaagaaac | atgaaattgc | ccagtattct | taacccaact | gcacagaaca | 1020 |
| aaaacctgca | ggaaacgaag | ataaatcatg | tcgaaagcta | catataagga | acgtgctgct | 1080 |
| actcatccta | gtcctgttgc | tgccaagcta | tttaatatca | tgcacgaaaa | gcaaacaaac | 1140 |
| ttgtgtgctt | cattggatgt | tcgtaccacc | aaggaattac | tggagttagt | tgaagcatta | 1200 |
| ggtcccaaaa | tttgtttact | aaaaacacat | gtggatatct | tgactgattt | ttccatggag | 1260 |
| ggcacagtta | agccgctaaa | ggcattatcc | gccaagtaca | attttttact | cttcgaagac | 1320 |
| agaaaatttg | ctgacattgg | taatacagtc | aaattgcagt | actctgcggg | tgtatacaga | 1380 |
| atagcagaat | gggcagacat | tacgaatgca | cacggtgtgg | tgggcccagg | tattgttagc | 1440 |
| ggtttgaagc | aggcggcaga | agaagtaaca | aaggaaccta | gaggcctttt | gatgttagca | 1500 |
| gaattgtcat | gcaagggctc | cctatctact | ggagaatata | ctaagggtac | tgttgacatt | 1560 |
| gcgaagagtg | acaaagattt | tgttatcggc | tttattgctc | aaagagacat | gggtggaaga | 1620 |
| gatgaaggtt | acgattggtt | gattatgaca | cccggtgtgg | gtttagatga | caagggagac | 1680 |
| gcattgggtc | aacagtatag | aaccgtggat | gatgtggtct | ctacaggatc | tgacattatt | 1740 |
| attgttggaa | gcgctcgtcc | aacgccggcg | gacctatggc | gcaagttttc | cgctttgtaa | 1800 |
| tatatattta | taccccttc | ttctctcccc | tgcaatataa | tagtttaatt | ctaatattaa | 1860 |
| taatatccta | tatttcttc | atttaccggc | gcactctcgc | ccgaacgacc | tcaaaatgtc | 1920 |
| tgctacattc | ataataacca | aaagctcata | acttttttt | ttgaacctga | atatatatac | 1980 |
| atcacatgtc | actgctggtc | cttgccgacc | agcgtataca | atctcgatag | ttggtttccc | 2040 |
| gttcttttcca | ctcccgtcat | ggactacaac | aagagatctt | cggtctcaac | cgtgcctaat | 2100 |
| gcagctccca | taagagtcgg | attcgtcggt | ctcaacgcag | ccaaaggatg | ggcaatcaag | 2160 |
| acacattacc | ccgccatact | gcaactatcg | tcacaatttc | aaatcactgc | cttatacagt | 2220 |

```
ccaaaaattg agacttctat tgccaccatc cagcgtctaa aattgagtaa tgccactgct   2280
tttcccactt tagagtcatt tgcatcatct tccactatag atatgatagt gatagctatc   2340
caagtggcca gtcattatga cgttgttatg cctctcttgg aattctccaa aaataatccg   2400
aacctcaagt atcttttcgt agaatgggcc cttgcatgtt cactagatca agccgaatcc   2460
atttataagg ctgctgctga acgtgggtt caaaccatca tctctttaca aggtcgtaaa    2520
tcaccatata ttttgagagc aaaagaatta atatctcaag ctatatcgg cgacattaat    2580 tctatcgaga ttgctggaaa tggcggttgg tacggctacg aaaggcctgt aaatcacca    2640 aaatacatct atgaaatcgg gaacggtgta gatctggtaa ccacaacatt tggtcacaca   2700
atcgatattt tacaatacat gacaagttcg tacttttcca ggataaatgc aatggttttc   2760
aataatattc cagagcaaga gctgatagat gagcgtggta accgattggg ccagcgagtc   2820
ccaaagacag taccggatca tcttttattc caaggcacat tgttaaatgg caatgttcca   2880
gtgtcatgca gtttcaaagg tggcaaacct accaaaaaat ttaccaaaaa tttggtcatt   2940
gatattcacg gtaccaaggg agatttgaaa cttgaaggcg atgccggatt cgcagaaatt   3000
tcaaatctgg tcctttacta cagtggaact agagcaaacg acttcccgct agctaatgga   3060
caacaagctc ctttagaccc ggggtatgat gcaggtaaag aaatcatgaa agtatatcat   3120
ttacgaaatt ataatgccat tgtcggtaat attcatcgac tgtatcaatc tatctctgac   3180
ttccacttca atacaaagaa aattcctgaa ttaccctcac aatttgtaat gcaaggtttc   3240
gatttcgaag ctttcccac cttgatggat gctctgatat tacacaggtt aatcgagagc    3300
gtttataaaa gtaacatgat gggctccaca ttaaacgtta gcaatatctc gcattatagt   3360
ttataaaagc atcttgccct gtgcttggcc cccagtgcag cgaacgttat aaaaacgaat   3420
actgagtata tatctatgta aacaaccat atcatttctt gttctgaact ttgtttacct    3480
aactagtttt aaatttccct ttttcgtgca tgcgggtgtt cttatttatt agcatactac   3540
atttgaaata tcaaatttcc ttagtagaaa agtgagagaa ggtgcactga cacaaaaaat   3600
aaaatccccg cgtgcttggc cggccgtctt cattggatgt tcgtaccacc aaggaattac   3660
tggagttagt tgaagcatta ggtcccaaaa tttgtttact aaaaacacat gtggatatct   3720
tgactgattt ttccatggag ggcacagtta agccgctaaa ggcattatcc gccaagtaca   3780 atttttact cttcgaagac agaaaatttg ctgacattgg taatacagtc aaattgcagt    3840
actctgcggg tgtatacaga atagcagaat gggcagacat tacgaatgca cacggtgtgg   3900
tgggcccagg tattgttagc ggtttgaagc aggcggcaga agaagtaaca aaggaaccta   3960
gaggcctttt gatgttagca gaattgtcat gcaagggctc cctatctact ggagaatata   4020
ctaagggtac tgttgacatt gcgaagagtg acaaagattt tgttatcggc tttattgctc   4080
aaagagacat gggtggaaga gatgaaggtt acgattggtt gattatgaca cccggtgtgg   4140
gtttagatga caaggagac gcattgggtc aacagtatag aaccgtggat gatgtggtct    4200
ctacaggatc tgacattatt attgttggaa gaggactatt tgcaagggca agggatgcta   4260
aggtagaggg tgaacgttac agaaaagcag gctgggaagc atatttgaga agatgcggcc   4320
agcaaaacta aaaaactgta ttataagtaa atgcatgtat actaaactca caaattagag   4380
cttcaattta attatatcag ttattacccg ggaatctcgg tcgtaatgat ttctataatg   4440
acgaaaaaaa aaaaattgga aagaaaaagc ttcatggcct ttataaaaag gaactatcca   4500
atacctcgcc agaaccaagt aacagtattt tacgggcac aaatcaagaa caataagaca    4560
ggactgtaaa gatggacgca tcgctcgtcc aacgccggcg gacctgtttt caatagttcg   4620
```

```
gtaatattaa cggataccta ctattatccc ctagtaggct cttttcacgg agaaattcgg   4680
gagtgttttt tttccgtgcg cattttctta gctatattct tccagcttcg cctgctgccc   4740
ggtcatcgtt cctgtcacgt agttttccg gattcgtccg gctcatataa taccgcaata    4800
aacacggaat atctcgttcc gcggattcgg ttaaactctc ggtcgcggat tatcacagag   4860
aaagcttcgt ggagaatttt tccagatttt ccgctttccc cgatgttggt atttccggag   4920
gtcattatac tgaccgccat tataatgact gtacaacgac cttctggaga agaaacaac    4980 tcaataacga tgtgggacat tgggggccca ctcaaaaaat ctggggacta tatccccaga   5040
gaatttctcc agaagagaag aaaagtcaaa gttttttttc gcttgggggt tgcatataaa   5100
tacaggcgct gttttatctt cagcatgaat attccataat tttacttaat agcttttcat   5160
aaataataga atcacaaaca aaatttacat ctgagttaaa caatcatgac aatcaaggaa   5220
cataaagtag tttatgaagc tcacaacgta aaggctctta aggctcctca acatttttac   5280
aacagccaac ccggcaaggg ttacgttact gatatgcaac attatcaaga aatgtatcaa   5340
caatctatca atgagccaga aaaattcttt gataagatgg ctaaggaata cttgcattgg   5400
gatgctccat acaccaaagt tcaatctggt tcattgaaca atggtgatgt tgcatggttt   5460
ttgaacggta aattgaatgc atcatacaat tgtgttgaca gacatgcctt tgctaatccc   5520
gacaagccag ctttgatcta tgaagctgat gacgaatccg acaacaaaat catcacattt   5580
ggtgaattac tcagaaaagt ttcccaaatc gctggtgtct taaaaagctg ggcgttaag    5640 aaaggtgaca cagtggctat ctatttgcca atgattccag aagcggtcat tgctatgttg   5700
gctgtggctc gtattggtgc tattcactct gttgtctttg ctgggttctc cgctggttcg   5760
ttgaaagatc gtgtcgttga cgctaattct aaagtggtca tcacttgtga tgaaggtaaa   5820
agaggtggta agaccatcaa cactaaaaaa attgttgacg aaggtttgaa cggagtcgat   5880
ttggtttccc gtatcttggt tttccaaaga actggtactg aaggtattcc aatgaaggcc   5940
ggtagagatt actggtggca tgaggaggcc gctaagcaga gaacttacct acctcctgtt   6000
tcatgtgacg ctgaagatcc tctatttta ttatacactt ccggttccac tggttctcca    6060
aagggtgtcg ttcacactac aggtggttat ttattaggtg ccgctttaac aactagatac   6120 gttttttgata ttcacccaga agatgttctc ttcactgccg gtgacgtcgg ctggatcacg   6180
ggtcacacct atgctctata tggtccatta accttgggta ccgcctcaat aattttcgaa   6240
tccactcctg cctacccaga ttatggtaga tattggagaa ttatccaacg tcacaaggct   6300
acccatttct atgtggctcc aactgcttta agattaatca acgtgtagg tgaagccgaa    6360 attgccaaat atgacacttc ctcattacgt gtcttgggtt ccgtcggtga accaatctct   6420
ccagacttat gggaatggta tcatgaaaaa gtgggtaaca aaaactgtgt catttgtgac   6480
actatgtggc aaacagagtc tggttctcat ttaattgctc ctttggcagg tgctgtccca   6540
acaaaacctg gttctgctac cgtgccattc ttggtatta acgcttgtat cattgaccct   6600
gttacaggtg tggaattaga aggtaatgat gtcgaaggtg tccttgccgt aaatcacca    6660 tggccatcaa tggctagatc tgtttggaac caccacgacc gttacatgga tacttacttg   6720
aaaccttatc ctggtcacta tttcacaggt gatggtgctg gtagagatca tgatggttac   6780
tactggatca ggggtagagt tgacgacgtt gtaaatgttt ccggtcatag attatccaca   6840
tcagaaattg aagcatctat ctcaaatcac gaaaacgtct cggaagctgc tgttgtcggt   6900
attccagatg aattgaccgg tcaaaccgtc gttgcatatg tttccctaaa agatggttat   6960
ctacaaaaca acgctactga aggtgatgca gaacacatca caccagataa tttacgtaga   7020
```

```
gaattgatct tacaagttag gggtgagatt ggtcctttcg cctcaccaaa aaccattatt    7080
ctagttagag atctaccaag aacaaggtca ggaaagatta tgagaagagt tctaagaaag    7140
gttgcttcta acgaagccga acagctaggt gacctaacta ctttggccaa cccagaagtt    7200
gtacctgcca tcattctgc tgtagagaac caatttttct ctcaaaaaaa gaataaatt     7260 gaattgaatt gaaatcgata gatcaatttt tttctttct cttcccat cctttacgct      7320 aaaataatag tttattttat tttttgaata ttttttattt atatacgtat atatagacta    7380
ttatttatct tttaatgatt attaagattt ttattaaaaa aaaattcgct cctcttttaa    7440
tgcctttatg cagtttttt ttcccattcg atatttctat gttcgggttc agcgtatttt     7500
aagtttaata actcgaaaat tctgcgttcg ttaaagcttt cgagaaggat attatttcga    7560
aataaaccgt gttgtgtaag cttgaagcct ttttgcgctg ccaatattct tatccatcta    7620
ttgtactctt tagatccagt atagtgtatt cttcctgctc caagctcatc ccatccccgc    7680
gtgcttggcc ggccgttttg ccagcttact atccttcttg aaaatatgca ctctatatct    7740
tttagttctt aattgcaaca catagatttg ctgtataacg aattttatgc tattttttaa    7800
atttggagtt cagtgataaa agtgtcacag cgaatttcct cacatgtagg gaccgaattg    7860
tttacaagtt ctctgtacca ccatggagac atcaaaaatt gaaaatctat ggaaagatat    7920
ggacggtagc aacaagaata tagcacgagc cgcggagttc atttcgttac ttttgatatc    7980
actcacaact attgcgaagc gcttcagtga aaaaatcata aggaaaagtt gtaaatatta    8040
ttggtagtat tcgtttggta aagtagaggg ggtaatttt ccccttatt ttgttcatac      8100 attcttaaat tgctttgcct ctccttttgg aaagctatac ttcggagcac tgttgagcga    8160
aggctcatta gatatatttt ctgtcatttt ccttaaccca aaaataaggg aaagggtcca    8220
aaaagcgctc ggacaactgt tgaccgtgat ccgaaggact ggctatacag tgttcacaaa    8280
atagccaagc tgaaaataat gtgtagctat gttcagttag tttggctagc aaagatataa    8340
aagcaggtcg gaaatattta tgggcattat tatgcagagc atcaacatga taaaaaaaa    8400 cagttgaata ttccctcaaa aatgtcttac accgtcggaa cctacttggc cgagaggttg    8460
gtccagatcg gattgaagca ccacttcgcc gtcgccggtg actacaactt ggtcttgttg    8520
gacaacttgt tgttgaacaa gaacatggag caggtctatt gctgcaacga gttgaactgc    8580
ggtttctcag cagaaggtta tgcaagagcc aagggagcag ccgctgccgt cgtcacctac    8640
tcagtcggtg cattatcagc attcgatgca attggaggtg cttacgctga gaacttgcca    8700
gtcatcttga tctctggagc acctaacaac aacgaccatg ctgctggtca cgtattgcac    8760
cacgccttgg gtaaaacaga ctaccactac cagttggaaa tggcaaaaaa tattaccgca    8820
gccgcagagg ccatctacac cccagaggaa gcacctgcca aaattgacca cgtcataaag    8880
accgctttga gagagaagaa gcctgtttac ttggagatcg cctgcaacat cgcttctatg    8940
ccatgcgccg cacctggtcc agcctctgct ttgttcaacg acgaggcctc tgacgaagct    9000
tcattgaacg ccgcagtcga agagacatta aagttcatcg ccaacaggga caaagttgcc    9060
gtcttagtcg gttcaaagtt gagggccgct ggtgccgaag aggcagctgt caagttcgct    9120
gacgccttgg gaggagccgt cgccaccatg gccgcagcaa atctttctt tcctgaggag    9180 aacccacatt acatcggaac ctcatggggt gaagtatcat atcctggagt agaaaaaacc    9240
atgaaagagg ccgatgccgt aatagcattg gctcctgtct tcaacgacta ctcaaccaca    9300
ggatggactg atataccaga tccaaagaaa ttagtcttgg ctgagcctag gtctgtcgtc    9360
gtaaacggta tcaggttccc ttctgttcat ttgaaggact acttaacaag attggcccaa    9420
```

```
aaggtatcta aaaagactgg tgccttggac ttcttcaagt cattaaacgc aggagaattg    9480
aaaaaagcag caccagccga tccatcagcc ccattagtta acgctgaaat cgctagacaa    9540
gtagaggctt tgttgactcc aaacactacc gtcatagctg agacaggtga ctcttggttc    9600
aacgcacaga gaatgaaatt gccaaatggt gccaggtcg agtatgaaat gcagtgggga     9660
catataggtt ggtcagtccc agccgccttt ggatacgcag taggtgcccc tgagaggagg    9720
aacatattga tggttggtga tggttcattc caattaacag cccaggaggt agcccaaatg    9780
gtcaggttga agttgcctgt catcatcttc ttgatcaaca attacggata caccatcgag    9840
gtcatgatcc acgacggacc ttacaacaac atcaaaaact gggactacgc cggtttgatg    9900
gaggttttca acgtaacgg tggttatgac tcaggagccg gtaagggatt aaaggctaag     9960
accggtggtg aattggctga agcaattaag gtcgcattgg ccaacaccga tggacctaca   10020
ttgattgaat gcttcatcgg aagggaggac tgcaccgagg aattggttaa atggggtaaa   10080
agggtagccg ctgctaattc aagaaaacca gttaataaat tattataata agtgaattta   10140
ctttaaatct tgcatttaaa taaattttct ttttatagct ttatgactta gtttcaattt   10200
atatactatt ttaatgacat tttcgattca ttgattgaaa gctttgtgtt ttttcttgat   10260
gcgctattgc attgttcttg tcttttttcgc cacatgtaat atctgtagta gatacctgat  10320
acattgtgga tgctgagtga aattttagtt aataatggag gcgctcttaa taattttggg   10380
gatattggct taacctgcag gccgcgagcg ccgatataaa ctaatgattt taaatcgtta   10440
aaaaaatatg cgaattctgt ggatcgaaca caggacctcc agataacttg accgaagttt   10500
tttcttcagt ctggcgctct cccaactgag ctaaatccgc ttactatttg ttatcagttc   10560
ccttcatatc tacatagaat aggttaagta ttttattagt tgccagaaga actactgata   10620
gttgggaata tttggtgaat aatgaagatt gggtgaataa tttgataatt ttgagattca   10680
attgttaatc aatgttacaa tattatgtat acagagtata ctagaagttc tcttcggaga   10740
tcttgaagtt cacaaaaggg aatcgatatt tctacataat attatcatta cttcttcccc   10800
atcttatatt tgtcattcat tattgattat gatcaatgca ataatgattg gtagttgcca   10860
aacatttaat acgatcctct gtaatatttc tatgaataat tatcacagca acgttcaatt   10920
atcttcaatt ccggtgttta aaccccagcg cctggcggg                          10959
```

<210> SEQ ID NO 99
<211> LENGTH: 7329
<212> TYPE: DNA
<213> ORGANISM: Artificial Sequence
<220> FEATURE:
<223> OTHER INFORMATION: Synthetic, Integration construct i2125

<400> SEQUENCE: 99

```
taattttaca agtagtgtct tcatgacgga ttcatagtct atccaagcgt ttgcccaaaa      60
ttttgcagta aatttaatgt tttctgtata ggataatggt gcgccattca agtcccgcga     120
aaaatgactg atgtctacag gacaggggcg caatatatgt tctctgacat tgcacctttt    180
gaatatatca tgtgtttgtt ctgctatctg cttgtagaag ggtacgctaa cagagccggc    240
ggcattgtaa aaagttctcc tttcgcggaa ggatgagtca aaaagcatgt gacaatgaaa    300
taatcaaatt gtgacatctg ctgacgcggg atcgttcctt cgtattgtct agattgtaat    360
ctatataaca tactacgaat ataaaagagg gactacaaga tatttctagc gcaaactact    420
gctttactgt ctcacaatgt ctctgattgg aagataccta agaaaattat ttaactacat    480
atctacaaaa tcaaagcatc taggataatt atactctatt tctcaacaag taattggttg    540
```

```
tttggccgag cggtctaagg cgcctgattc aagaaatatc ttgaccgcag ttaactgtgg    600
gaatactcag gtatcgtaag atgcaagagt tcgaatctct tagcaaccat tatttttttc    660
ctcaacataa cgagaacaca caggggcgct atcgcacaga atcaaattcg atgactggaa    720
atttttttgtt aatttcagag gtcgcctgac gcatatacct ttttcaactg aaaaattggg    780
agaaaaagga aaggtgagag cgccggaacc ggcttttcat atagaataga gaagcgttca    840
tgactaaatg cttgcatcac aatacttgaa gttgacaata ttatttaagg acctattgtt    900
ttttccaata ggtggttagc aatcgtctta ctttctaact tttcttacct tttacatttc    960
agcaatatat atatatatat ttcaaggata taccattcta atgtctgccc ctaagaagat   1020
cgtcgttttg ccaggtgacc acgttggtca agaaatcaca gccgaagcca ttaaggttct   1080
taaagctatt tctgatgttc gttccaatgt caagttcgat ttcgaaaatc atttaattgg   1140
tggtgctgct atcgatgcta caggtgttcc acttccagat gaggcgctgg aagcctccaa   1200
gaaggctgat gccgttttgt taggtgctgt gggtggtcct aaatggggta ccggtagtgt   1260
tagacctgaa caaggtttac taaaaatccg taaagaactt caattgtacg ccaacttaag   1320
accatgtaac tttgcatccg actctctttt agacttatct ccaatcaagc cacaatttgc   1380
taaaggtact gacttcgttg ttgtcagaga attagtggga ggtatttact ttggtaagag   1440
aaaggaagac gatggtgatg gtgtcgcttg ggatagtgaa caatacaccg ttccagaagt   1500
gcaaagaatc acaagaatgg ccgctttcat ggccctacaa catgagccac cattgcctat   1560
ttggtccttg gataaagcta atgttttggc ctcttcaaga ttatggagaa aaactgtgga   1620
ggaaaccatc aagaacgaat tccctacatt gaaggttcaa catcaattga ttgattctgc   1680
cgccatgatc ctagttaaga acccaaccca cctaaatggt attataatca ccagcaacat   1740
gtttggtgat atcatctccg atgaagcctc cgttatccca ggttccttgg gtttgttgcc   1800
atctgcgtcc ttggcctctt tgccagacaa gaacaccgca tttggtttgt acgaaccatg   1860
ccacggttct gctccagatt tgccaaagaa taaggtcaac cctatcgcca ctatcttgtc   1920
tgctgcaatg atgttgaaat tgtcattgaa cttgccgtaa gaaggtaagg ccattgaaga   1980
tgcagttaaa aaggttttgg atgcaggtat cagaactggt gatttaggtg gttccaacag   2040
taccaccgaa gtcggtgatg ctgtcgccga agaagttaag aaaatccttg cttaaaaaga   2100
ttctcttttt ttatgatatt tgtacataaa ctttataaat gaaattcata atagaaacga   2160
cacgaaatta caaaatggaa tatgttcata gggtagacga aactatatac gcaatctaca   2220
tacatttatc aagaaggaga aaaggagga tgtaaaggaa tacaggtaag caaattgata   2280
ctaatggctc aacgtgataa ggaaaagaa ttgcactta acattaatat tgacaaggag   2340
gagggcttcg agcgtcccaa aaccttctca agcaaggttt tcagtataat gttacatgcg   2400
tacacgcgtc tgtacagaaa aaaagaaaa atttgaaata taaataacgt tcttaatact   2460
aacataacta taaaaaaata aatagggacc tagacttcag gttgtctaac tccttccttt   2520
tcggttagag cggatcttag ctagctcaaa cgaccatcgg gtggacgaag aatgacttca   2580
tgtaagactt catatctcct tctgcatgtg taaatccgtc gtttacacta tagagaacct   2640
cacacattct agccaaattg atggcaggca taagcaaagg aaacggaacg gcagttggac   2700
gcaacgactc tcggttgata actttccatg catcctcaac cttacggcta atgtactcgc   2760
aggcctcttc ttcactggcc ccagattctt tcgaatagca ttcgatagaa cttgcaacat   2820
gccctcgttc ttgttcttct ttatgagaca cgatatcatc catcagacgg ataataacac   2880
acgacgcttt tacgataggc gggtacgaag acacccactt aaacgtatct tcattgacga   2940
```

```
tgtccccacg accaacgtaa ctccgagcgg tcataagccc gtaagtcccc gtaaccatgc   3000
taacgctcat gtactcctct aaagtaggca tgtagccttc ctttaaccat ctagcttcaa   3060
ctagataatt tcttaccagt tctttggcca tttccttaac gtagtggatt tgataagttt   3120
taccttcttt ctcaagactc tcctccattt caacgtgaag gttgacaagc tcttgataga   3180
tcaatttcat gtattctggt agcatgtcga gacatgatat tgaccacctc tcgacagctt   3240
gcgtgaaaat ctccaactcc tcgtatgttc cgtagttatc aaatgtatca tccaggacta   3300
ccagccacat acacgacttc ataagaaaca tacgagtacg tgcatgctga ggttcataat   3360
aaatactcaa aatccaaaaa tatccctcga cgactctgtc acgaacaaac ggtagtttgt   3420
tctgcaaatc gaggtccttc caccacttac aaatatgcga caattccttt ttgtgcatag   3480
attggagcac agaaaaatcc agcttcgcta gcttcaataa aacttcatca tgactagtct   3540
cctgttgata gattggcata tagtgaagag cttctattcg agccagtctg cgtctgagtg   3600
gctgctttaa tgcctgatga atctgtgtac gtagagatga atcacagctt ggatctttag   3660
caattatatc gagatgaacc ttactgaact ccaaggcgtt atctaagata gtttcatcct   3720
caaccctcat aaacgccgcc tcatagagag ctaaaatacc ttgagcatca ttacagaggc   3780 tttcttaaa ctttcccttt tcgtccataa aatctttaaa cactccactc gaaacgttga   3840
atccctgttg tctaagtaat cgaaaccata gcgagattga ctgaagattt tctttatcga   3900
cccactgctc tccgtaagta acgtgaatat gttgcaaagc ttcctcaatt tcctcctcaa   3960
aatggtaagc aattccaaga cgctgcacgg catcgatcag ctcgatgagt ttaacatgtt   4020
gcataggctc atttgatcct ttgattgtaa taagttcttt cttaacctct tccttcagtt   4080
cctctacgag ttgcttcttc ataaccaaat cctcgggttc atcgtatgtt aaaaactggt   4140 cacccccaaat agacgcgttg aaatttgtgg tatgtctgat tacgtccggt ttagtagaat   4200
ccttgtcatc gactaccaat ggggaggtac tagaagatga ggaaacagaa gaaataggta   4260
aagtagacat ttatattgaa ttttcaaaaa ttcttacttt tttttttggat ggacgcaaag   4320 aagtttaata atcatattac atggcaatac caccatatac atatccatat ctaatcttac   4380
ttatatgttg tggaaatgta aagagcccca ttatcttagc ctaaaaaaac cttctctttg   4440
gaactttcag taatacgctt aactgctcat tgctatattg aagtacggat tagaagccgc   4500
cgagcgggcg acagccctcc gacggaagac tctcctccgt gcgtcctggt cttcaccggt   4560
cgcgttcctg aaacgcagat gtgcctcgcg ccgcactgct ccgaacaata aagattctac   4620
aatactagct tttatggtta tgaagaggaa aaattggcag taacctggcc ccacaaacct   4680
tcaaatcaac gaatcaaatt aacaaccata ggataataat gcgattagtt ttttagcctt   4740
atttctgggg taattaatca gcgaagcgat gattttgat ctattaacag atatataaat   4800
gcaaaagctg cataaccact ttaactaata cttttcaacat tttcggtttg tattacttct   4860
tattcaaatg tcataaaagt atcaacaaaa aattgttaat atacctctat actttaacgt   4920
caaggagaaa aaactataat gtcaaccttg cctatttctt ctgtctcatc ttcttcatct   4980
acctctccat tggtcgtaga cgataaggac tctactaaac cagacgtcat caggcacacc   5040
acgaatttca acgcttctat atggggagac cagttttttaa cttacgacga acctgaggat   5100
ttggtcatga aaaacagtt ggtcgaagaa ttgaaggagg aggtcaagaa ggagttgatt   5160
acaatcaagg gatcaaacga acctatgcag cacgttaagt tgatcgaatt aatagatgct   5220
gtccaaagat tgggtatagc ctaccacttc gaggaggaaa tcgaggaggc tttacaacat   5280
atacacgtca catacggtga acagtgggtc gataaagaga atttgcagtc tatctcattg   5340
```

```
tggttcaggt tgttaaggca acaaggtttt aatgtttcat ctggagtttt caaggacttt      5400
atggacgaga aagtaaatt caaggagtct ttgtgcaacg atgctcaggg tattttagca       5460
ttgtatgagg ccgcatttat gagggttgaa gacgagacta tcttagataa cgcattggag      5520
ttctccaagg tccacttaga cattattgct aaagacccat catgtgactc ttctttgaga      5580
actcaaatac accaggcatt aaagcaacct tgaggagaa ggttggctag aatcgaagca       5640
ttacactata tgccaatata tcagcaggaa acctcacacg acgaagtttt gttaaagtta      5700
gcaaaattgg acttctctgt cttgcagtca atgcataaga aggagttgtc tcatatctgc      5760
aagtggtgga aggatttaga tttacaaaat aagttgccat cgtcagaga tagggttgta      5820 gagggatact tctggatctt gtctatatac tatgagcctc agcacgccag aaccagaatg      5880
ttcttaatga gtcctgcat gtggttagta gtattagacg acaccttcga caattatgga      5940
acatacgagg aattggagat ctttactcaa gccgttgaga gatggtctat ttcttgcttg      6000
gacatgttgc cagagtatat gaagttgatc taccaggagt tagttaactt gcacgtcgaa      6060
atggaggaat ctttggagaa agagggaaag acataccaga ttcactatgt caaggaaatg      6120
gccaaagagt tggtaaggaa ctatttggtt gaggccagat ggttgaaaga gggttatatg      6180
cctaccttgg aggagtacat gtcagtctca atggttactg gtacctatgg tttgatgact      6240
gccagatcat acgtcggaag aggtgatatc gtaaatgagg ataccttcaa gtgggtttct      6300
tcatacccct ctatcgttaa ggcctcttgc gtcataatta ggttgatgga tgacattgtt      6360
tctcataagg aggaacagga gagggtcac gtagcctcat caatagagtg ctattcaaaa      6420
gagtctggtg catcagagga agaggcatgt gaatacatct ctagaaaagt agaggatgcc      6480
tggaaggtca ttaacaggga gtcattgaga cctactgctg tacctttcc tttgttgatg       6540 cctgctatca acttggcaag gatgtgcgaa gttttgtatt cagtaaacga tggtttcact      6600
cacgccgaag gtgatatgaa atcatatatg aaatcttttt tcgtacatcc tatggtagta      6660
taagcgaatt tcttatgatt tatgattttt attattaaat aagttataaa aaaaataagt      6720
gtatacaaat tttaaagtga ctcttaggtt ttaaaacgaa aattcttatt cttgagtaac      6780
tctttcctgt aggtcaggtt gctttctcag gtatagcatg aggtcgctct cttttgtaac      6840
gaatttgatg aatatatttt actttttat ataagctatt ttgtagatat tgacttttta      6900
cgatttattt gtaacaatga gaattactcc atttctgaac ttcagtaaat agcgagtgat      6960
tctgtacttt gcgagaaccg gtggacattt ggtattttgc cttacaagaa caacctatac      7020
aaacgtttca atatctaatt cttcgtaatc cattgtttta cgagacatat aatgtgatat      7080
atagatgaac tttacgtata aaatgatata tttaaaacta gcaactgcgt gcgtaagaca      7140
aactgaaata ggccatttac ggaaaagaaa tttaataatg tcgactggaa actgaaacca      7200
ggaggagtag aaattggtta aattgattag ctaaaattta ctcgttgtgg acagagtttg      7260
agccaagcgg aatgttttca aggctttctt tgtttcgaag ggcagctctg gctcctgccc      7320
ctatgagaa                                                              7329

<210> SEQ ID NO 100
<211> LENGTH: 4016
<212> TYPE: DNA
<213> ORGANISM: Artificial Sequence
<220> FEATURE:
<223> OTHER INFORMATION: Synthetic, Integration construct i2608

<400> SEQUENCE: 100
tggaacacgg agtaaaatat tgtgtgtatg ggcacaaacc cttggaaata gcttagcatt        60
```

```
tgccgttggc ctgatgatct gaccattccc tttagtagag aaagaaagtc gcttcaagct    120
aacccagttt tctttttttt ttatcactta tcagtcctat tcggagatac aggcaacaag    180
tgatagaggg cccattatga atacgcacct ctatgtattt ccgagatacg attactccag    240
ttcctcttac aagaaatgca taaaaatagt tacaattaat tagaacaaga acttatttag    300
aacacgttca cactgagtaa gaactcttgt cccttattag ccttgatagt gctgaaaaaa    360
agaaaaaaaa caaaaaaaag aaataaaata acggcaaaca gcaaaggcca cagatctgta    420
ttcatgctac ttctgcaata tcaatcactt actggcaagt gcgtataaat taaacctatg    480
acggcacggc cacgcgttta aaccgccttc tttatcatca tatttactta tatctttaac    540
agattccaaa ccctaaagtg tccgaatttt caatagggcg aacttgaaga ataaccaagg    600
tcaataatat atcttttagt ataaccctga aatttgccct ataaaaatct agggtttctg    660
tgtggtttcc gggtgagtca tacggctttt ttgaatttct ttttttgcag ttgtctctat    720
caatgaaaat ttcgaggaag acgataaggt taagataagt agataagaga atgatacgag    780
ataaagcaca aattagcaga aagaagagtg gttgcgaaca gagtaaaccg aatcagggaa    840 tcccttttg caaaaacatc aattatcctt ttctttttt tacgtatata tctggaacag    900
aaatatataa gttactatta tacttatagt tggatccagt ttttaatctg tcgtcaatcg    960
aaagtttatt tcagagttct tcagacttct taactcctgt aaaaacaaaa aaaaaaaag   1020 gcatagcagc tcacacgcgg ccaggggag ccaccatata catatccata tctaatctta   1080
cttatatgtt gtggaaatgt aaagagcccc attatcttag cctaaaaaaa ccttctcttt   1140
ggaactttca gtaatacgct taactgctca ttgctatatt gaagtacgga ttagaagccg   1200
ccgagcgggc gacagccctc cgacggaaga ctctcctccg tgcgtcctgg tcttcaccgg   1260
tcgcgttcct gaaacgcaga tgtgcctcgc gccgcactgc tccgaacaat aaagattcta   1320
caatactagc ttttatggtt atgaagagga aaaattggca gtaacctggc cccacaaacc   1380
ttcaaatcaa cgaatcaaat taacaaccat aggataataa tgcgattagt ttttttagcct   1440 tatttctggg gtaattaatc agcgaagcga tgattttga tctattaaca gatatataaa   1500
tgcaaaagct gcataaccac tttaactaat actttcaaca ttttcggttt gtattacttc   1560
ttattcaaat gtcataaaag tatcaacaaa aaattgttaa tatacctcta tactttaacg   1620
tcaaggagaa aaaactataa tggaaaactt tccaaccgag tacttcttga acaccaccgt   1680
caggttgttg gagtacatta ggtacaggga ctcaaactat accagggagg agaggattga   1740
gaacttacac tacgcctaca acaaagccgc ccaccacttc gcccagccaa gacagcagca   1800
gttgttgaag gtcgacccta agagattgca agcttcattg cagaccattg tcggtatggt   1860
tgtatattca tgggccaagg tatctaaaga gtgtatggca gacttgtcaa tccactatac   1920
ctacaccttg gtattggacg attcaaaaga cgacccatac cctactatgg taaactactt   1980
cgatgactta caagcaggta gagaacaggc tcatccttgg tgggctttag taaacgagca   2040 cttttccaaac gtattgaggc attttggtcc ttttttgctca ttgaacttga tcaggtctac   2100
cttagacttc ttcgagggtt gctggataga acaatacaat tttggaggat tcccaggttc   2160
tcacgactac ccacagttct tgagaagaat gaacggttta ggacactgcg tcggtgcctc   2220
tttgtggcca aaggagcagt tcaatgaaag atcattgttt ttggagatca cttcagccat   2280
agctcaaatg gaaaattgga tggtctgggt taatgatttg atgtcatttt acaaggagtt   2340
cgacgacgag agggatcaga tctctttggt aaagaactac gttgtttctg acgagatatc   2400
attacacgag gccttagaaa aattgaccca ggataccttg cactcttcaa agcaaatggt   2460
```

```
tgcagttttc tcagacaagg accctcaagt aatggacacc atagagtgct tcatgcatgg   2520
ttatgtcaca tggcatttat gcgacaggag gtacaggttg tctgaaatct acgagaaagt   2580
caaggaggaa aagactgagg atgcccaaaa attttgcaag ttctacgagc aagctgccaa   2640
tgtaggagcc gtttcacctt ctgagtgggc ctatccacca gtcgcccagt tagctaacgt   2700
aagatcaaag gacgtcaaag aggtccagaa accatttta tcatctatag aattagttga   2760
ataagctagc taagatccgc tctaaccgaa aaggaaggag ttagacaacc tgaagtctag   2820
gtccctattt attttttat agttatgtta gtattaagaa cgttatttat atttcaaatt   2880 tttcttttt ttctgtacag acgcgtgtac gcatgtaaca ttatactgaa aaccttgctt   2940
gagaaggttt tgggacgctc gaagaacctg caggccgcga gcgccgatat atgacgtttt   3000
attacctttg atcacatttc cacgccattt cgcattctca ccctcataag tcatacaccg   3060
aaaagaaagt ttaagggatc aatgagctta ctataatctc agtatattta tttttatcga   3120
tgattcacca caacaatctt gctcccgaaa agaaagcaga cggagtagaa gcatttgaaa   3180
ctccttcaga ccttcaagta tatatatata tatatatata tgtatatgtg tacattttca   3240
cgctaatact aatgtataat tagaagataa ttttttactca tttttcgtta tcttcacgtc   3300
acccgaacct agaaccaaat gtcattttca cgatatgtaa atagtgaaat aggcaaaaac   3360
gccaaaaagt agtaagcgca acatacaccg gtgtttaaac cccagcgcct ggcgggtaaa   3420
ccattaaaga atatctcgac cagaatctaa cagatataca tgttccgata atgtctgagt   3480
taggtgagta ttctaaatta gaaaacaaag agcttagaac ggagtttgaa ttgacaaatt   3540 ttcctttcc aggcacaact gataacgact ccgatgacgg aagccaaggg cagaactctt   3600
tgaatatcat tactcctgac atggatgata ctctggttaa tgatgtactt cgagaaaacg   3660
ataaaaagtc tagtatgaga atggctttta tgaatctagc aaactctatt cttggtgccg   3720
gaataattac tcagccgttc gcgatcaaaa atgctggtat attaggcggg ctattatcat   3780
acgtagccct cggatttata gttgattgga cgttaagact tattgtcatt aacttgactc   3840
ttgctggcaa gagaacatac cagggtacgg tcgaacatgt aatgggtaaa aagggaaat   3900 tgctgattct atttacaaac gggttatttg catttggtgg atgtattggt tattgcataa   3960
ttattgggga tacgataccc cacgtactca gagctatatt cagccagaac gatggt        4016
```

<210> SEQ ID NO 101
<211> LENGTH: 11880
<212> TYPE: DNA
<213> ORGANISM: Artificial Sequence
<220> FEATURE:
<223> OTHER INFORMATION: Synthetic, Integration construct i2127

<400> SEQUENCE: 101

```
gacggcacgg ccacgcgttt aaaccgcctc atagtctatc caagcgtttg cccaaaattt    60
tgcagtaaat ttaatgtttt ctgtatagga taatggtgcg ccattcaagt cccgcgaaaa   120
atgactgatg tctacaggac aggggcgcaa tatatgttct ctgacattgc acctttgaa   180 tatatcatgt gtttgttctg ctatctgctt gtagaagggt acgctaacag agccggcggc   240
attgtaaaaa gttctccttt cgcggaagga tgagtcaaaa agcatgtgac aatgaaataa   300
tcaaattgtg acatctgctg acgcgggatc gttccttcgt attgtctaga ttgtaatcta   360
tataacatac tacgaatata aaagagggac tacaagatat ttctagcgca aactactgct   420
ttactgtctc acaatgtctc tgattggaag atacctaaga aaattattta actacatatc   480
tacaaaatca aagcatccgc tcgtccaacg ccggcggacc tgagcgacct catgctatac   540
```

```
ctgagaaagc aacctgacct acaggaaaga gttactcaag aataagaatt ttcgttttaa      600
aacctaagag tcactttaaa atttgtatac acttattttt tttataactt atttaataat      660
aaaaatcata aatcataaga aattcgctta gactaccata gggtgaacaa agaatgactt      720
catgtatgat ttcatgtcac cctcggcgtg ggtgaaaccg tcattaactg aatataagac      780
ttcgcacatt cttgctaagt ttatggcagg cattaataat gggaaaggga ctgcggttgg      840
cctcaatgac tctctgttga taactttcca tgcatcttcg acttttctag agatgtactc      900
acaggcttct tcttcagatg ctcctgattc ttttgaataa cactcgatag atgatgctac      960
atgtcccctc tcttgttcct ctttgtgaga tacaatatca tccatcaacc ttataataac     1020
gcatgaggcc tttacgatag gtggataaga tgatacccac ttgaatgtgt cttcgtttac     1080
aatgtctcct ctaccgacat aagatctagc agtcattaat ccgtaggttc cagtgaccat     1140
agaaacagac atatattcct ccaaggtagg catgtaaccc tccttcaacc atctagcttc     1200
taccaagtag tttcttacca actcttttgc catctccttg acatagtgga tctgataagt     1260
tttaccctct ttctccaaag attcttccat ctcgacgtgt aagttgacta actcctggta     1320
gatcaacttc atatactctg gtaacatgtc caagcatgaa attgaccatc tctctacagc     1380
ttgagtgaag atctctaatt cctcgtaggt accgtaattg tcaaaagtgt cgtctaaaac     1440
gaccaaccac atgcaagact tcattaagaa cattcttgtt ctagcgtgct gaggctcgta     1500
gtagatagac aatatccaga aatatccctc aacgactctg tctctaacaa aaggcaactt     1560
attctgcaaa tccaaatcct tccaccattt gcagatatga gacaattcct ttttatgcat     1620
tgactgcaat acagagaagt ccaatttggc caacttcaac aaaacttcat catgtgatgt     1680
ttcctgctga tagataggca tatagtgcaa ggcttctatc cttgctaacc ttctcctcaa     1740
aggttgcttc aatgcttgat gtatttgtgt tcttaaagaa gagtcgcatg aaggatcctt     1800
tgcgatgatg tctaagtgga ctttagagaa ttccaatgcg ttgtctaata tagtctcgtc     1860
ctctaccctc ataaaggcag cttcatataa tgccaaaatt ccttgagcat cgttgcataa     1920
tgactcctta aactttccct tttcgtccat gaaatctttta aagacacctg aagagacgtt     1980
gaatccctgt tgccttaaca acctaaacca taaagagatt gattgcaagt tctccttgtc     2040
aacccattgt tctccataag taacatgaat atgctgcaat gcctcttcaa tctcctcttc     2100
gaaatgatat gcaattccta accttttgaac agcgtcaatt aactctatca acttgacgtg     2160
ttgcataggc tcgtttgaac ctttatggt gatcaactcc ttcttaacct cctcctttaa      2220
ctcctcgacc aactgttttt tcatgactaa atccctctggt tcgtcatagg tcaagaactg     2280
gtctccccat atagaggcgt tgaagttcgt tgtatgcctt atgacgtctg gctttgtaga     2340
atctttgtcg tctacaacca atggtgaggt agaagatgag gatgagactg aagatatagg     2400
caatgttgac attgtaaagt tagttggttg cgcgacttcg ggtggggtaa gtatagaggt     2460
atattaacaa ttttttgttg atacttttat gacatttgaa taagaagtaa tacaaaccga     2520
aaatgttgaa agtattagtt aaagtggtta tgcagctttt gcatttatat atctgttaat     2580
agatcaaaaa tcatcgcttc gctgattaat taccccagaa ataaggctaa aaaactaatc     2640
gcattattat cctatggttg ttaatttgat tcgttgattt gaaggtttgt ggggccaggt     2700
tactgccaat ttttcctctt cataaccata aaagctagta ttgtagaatc tttattgttc     2760
ggagcagtgc ggcgcgaggc acatctgcgt ttcaggaacg cgaccggtga agaccaggac     2820
gcacggagga gagtcttccg tcggagggct gtcgcccgct cggcggcttc taatccgtac     2880
ttcaatatag caatgagcag ttaagcgtat tactgaaagt tccaaagaga aggttttttt     2940
```

```
aggctaagat aatggggctc tttacatttc cacaacatat aagtaagatt agatatggat    3000
atgtatatgg tggtattgcc atgtaatatg attattaaac ttctttgcgt ccatccaaaa    3060
aaaaagtaac gcacgcacac tcccgacaga caactagctt gataatgtca actttgccta    3120
tttcttctgt gtcatcttcc tcttctacat caccattagt cgtggacgac aaagattcaa    3180
ccaagcccga cgttatcaga catacaacga atttcaatgc ttctatttgg ggagatcaat    3240
tcttgaccta tgatgagcct gaagatttag ttatgaagaa acaattagtg gaggaattaa    3300
aagaggaagt taagaaggaa ttgataacta tcaaaggttc aaatgagccc atgcagcatg    3360
tgaaattgat tgaattaatt gatgctgttc aacgttaggg tatagcttac cattttgaag    3420
aagagatcga ggaagctttg caacatatgc atgttaccta tggtgaacag tgggtggata    3480
aggaaaattt acagagtatt tcattgtggt tcaggttgtt gcgtcaacag gctttaacg     3540 tctcctctgg cgttttcaaa gactttatgg acgaaaaagg taaattcaaa gagtctttat    3600
gcaatgatgc acaaggaata ttagccttat atgaagctgc atttatgagg gttgaagatg    3660
aaaccatctt agacaatgct ttggaattct caaaagttca tttagatatc atagcaaaag    3720
acccatcttg cgattcttca ttgcgtacac aaatccatca agccttaaaa caacctttaa    3780
gaaggagatt agcaaggatt gaagcattac attacatgcc aatctaccaa caggaaacat    3840
ctcatgatga agtattgttg aaattagcca agttggattt cagtgttttg cagtctatgc    3900
ataaaaagga attgtcacat atctgtaagt ggtggaaaga tttagattta caaaataagt    3960 tacctttgt acgtgatcgt gttgtcgaag gctacttctg gatattgtcc atatactatg     4020
agccacaaca cgctagaaca agaatgtttt tgatgaaatc atgcatgtgg ttagtagttt    4080
tggacgatac ttttgataat tatggaacat acgaagaatt ggagattttt actcaagccg    4140
tcgagagatg gtctatctca tgcttagata tgttgcccga atatatgaaa ttaatctacc    4200
aagaattagt caatttgcat gtggaaatgg aagaatcttt ggaaaaggag ggaaagacct    4260
atcagattca ttacgttaag gagatggcta agaattagt tcgtaattac ttagtagaag     4320
caagatggtt gaaggaaggt tatatgccta ctttagaaga atacatgtct gtttctatgg    4380
ttactggtac ttatggttg atgactgcaa ggtcctatgt tggcagagga gacattgtta     4440
atgaagacac attcaaatgg gtttctagtt acccacctat tgttaaagct tcctgtgtaa    4500
taattagatt aatggacgat attgtatctc acaaggaaga acaagaaaga ggacatgtgg    4560
cttcatctat agaatgttac tctaaagaat caggtgcttc tgaagaggaa gcatgtgaat    4620
atattagtag gaaagttgag gatgcctgga agtaatcaa tagagaatct ttgcgtccaa     4680
cagccgttcc cttcccttg ttaatgccag caataaactt agctagaatg tgtgaggtct     4740
tgtactctgt taatgatggt tttactcatg ctgagggtga catgaaatct tatatgaagt    4800
ccttcttcgt tcatcctatg gtcgtttgag ctagctaaga tccgctctaa ccgaaaagga    4860
aggagttaga caacctgaag tctaggtccc tatttatttt tttatagtta tgttagtatt    4920
aagaacgtta tttatatttc aaatttttct ttttttctg tacagacgcg tgtacgcatg     4980
taacattata ctgaaaacct tgcttgagaa ggttttggga cgctcgaaga acctgcaggc    5040
cgcgagcgcc gatggtctaa ggcgcctgat tcaagaaata tcttgaccgc agttaactgt    5100
gggaatactc aggtatcgta agatgcaaga gttcgaatct cttagcaacc attatttttt    5160
tcctcaacat aacgagaaca cacaggggcg ctatcgcaca gaatcaaatt cgatgactgg    5220 aaatttttg ttaatttcag aggtcgcctg acgcatatac cttttcaac tgaaaaattg      5280 ggagaaaaag gaaaggtgag agcgccggaa ccggcttttc atatagaata gagaagcgtt    5340
```

```
catgactaaa tgcttgcatc acaatacttg aagttgacaa tattatttaa ggacctattg   5400
ttttttccaa taggtggtta gcaatcgtct tactttctaa cttttcttac cttttacatt   5460
tcagcaatat atatatatat atttcaagga tataccattc taatgtctgc ccctaagaag   5520
atcgtcgttt tgccaggtga ccacgttggt caagaaatca cagccgaagc cattaaggtt   5580
cttaaagcta tttctgatgt tcgttccaat gtcaagttcg atttcgaaaa tcatttaatt   5640
ggtggtgctg ctatcgatgc tacaggtgtt ccacttccag atgaggcgct ggaagcctcc   5700
aagaaggctg atgccgtttt gttaggtgct gtgggtggtc ctaaatgggg tactggtagt   5760
gttagacctg aacaaggttt actaaaaatc cgtaaagaac ttcaattgta cgccaactta   5820
agaccatgta actttgcatc cgactctctt ttagacttat ctccaatcaa gccacaattt   5880
gctaaaggta ctgacttcgt tgttgtcaga gaattagtgg gaggtattta ctttggtaag   5940
agaaaggaag acgatggtga tggtgtcgct tgggatagtg aacaatacac cgttccagaa   6000
gtgcaaagaa tcacaagaat ggccgctttc atggccctac aacatgagcc accattgcct   6060
atttggtcct tggataaagc taatgttttg gcctcttcaa gattatggag aaaaactgtg   6120
gaggaaacca tcaagaacga attccctaca ttgaaggttc aacatcaatt gattgattct   6180
gccgccatga tcctagttaa gaacccaacc cacctaaatg gtattataat caccagcaac   6240
atgtttggtg atatcatctc cgatgaagcc tccgttatcc caggttcctt gggtttgttg   6300
ccatctgcgt ccttggcctc tttgccagac aagaacaccg catttggttt gtacgaacca   6360
tgccacggtt ctgctccaga tttgccaaag aataaggtca accctatcgc cactatcttg   6420
tctgctgcaa tgatgttgaa attgtcattg aacttgcctg aagaaggtaa ggccattgaa   6480
gatgcagtta aaaaggtttt ggatgcaggt atcagaactg gtgatttagg tggttccaac   6540
agtaccaccg aagtcggtga tgctgtcgcc gaagaagtta agaaaatcct tgcttaaaaa   6600
gattctcttt ttttatgata tttgtacata aactttataa atgaaattca taatagaaac   6660
gacacgaaat tacaaaatgg aatatgttca tagggtagac gaaactatat acgcaatcta   6720 catacatttta tcaagaagga gaaaaaggag gatgtaaagg aatacaggta agcaaattga   6780
tactaatggc tcaacgtgat cggcgctcgc ggcctgcagg ttcttcgagc gtcccaaaac   6840
cttctcaagc aaggttttca gtataatgtt acatgcgtac acgcgtctgt acagaaaaaa   6900
aagaaaaatt tgaaatataa ataacgttct taatactaac ataactataa aaaataaat   6960 agggacctag acttcaggtt gtctaactcc ttccttttcg gttagagcgg atcttagcta   7020
gctcaaacga ccatcgggtg gacgaagaat gacttcatgt aagacttcat atctccttct   7080
gcatgtgtaa atccgtcgtt tacactatag agaacctcac acattctagc caaattgatg   7140
gcaggcataa gcaaggaaa cggaacggca gttggacgca acgactctcg gttgataact   7200
ttccatgcat cctcaacctt acggctaatg tactcgcagg cctcttcttc actggcccca   7260 gattcttcg aatagcattc gatagaactt gcaacatgcc ctcgttcttg ttcttcttta   7320
tgagacacga tatcatccat cagacggata ataacacacg acgcttttac gataggcggg   7380
tacgaagaca cccacttaaa cgtatcttca ttgacgatgt ccccacgacc aacgtaactc   7440
cgagcggtca taagcccgta agtccccgta accatgctaa cgctcatgta ctcctctaaa   7500
gtaggcatgt agccttcctt taaccatcta gcttcaacta gataatttct taccagttct   7560
ttggccattt ccttaacgta gtggatttga taagttttac cttcttttctc aagactctcc   7620 tccatttcaa cgtgaaggtt gacaagctct tgatagatca atttcatgta ttctggtagc   7680
atgtcgagac atgatattga ccacctctcg acagcttgcg tgaaaatctc caactcctcg   7740
```

-continued

```
tatgttccgt agttatcaaa tgtatcatcc aggactacca gccacataca cgacttcata      7800
agaaacatac gagtacgtgc atgctgaggt tcataataaa tactcaaaat ccaaaaatat      7860
ccctcgacga ctctgtcacg aacaaacggt agtttgttct gcaaatcgag gtccttccac      7920
cacttacaaa tatgcgacaa ttcctttttg tgcatagatt ggagcacaga aaaatccagc      7980
ttcgctagct tcaataaaac ttcatcatga ctagtctcct gttgatagat tggcatatag      8040
tgaagagctt ctattcgagc cagtctgcgt ctgagtggct gctttaatgc ctgatgaatc      8100
tgtgtacgta gagatgaatc acagcttgga tctttagcaa ttatatcgag atgaacctta      8160
ctgaactcca aggcgttatc taagatagtt tcatcctcaa ccctcataaa cgccgcctca      8220
tagagagcta aaataccttg agcatcatta cagaggcttt cttttaaactt tcccttttcg      8280 tccataaaat ctttaaacac tccactcgaa acgttgaatc cctgttgtct aagtaatcga      8340
aaccatagcg agattgactg aagattttct ttatcgaccc actgctctcc gtaagtaacg      8400
tgaatatgtt gcaaagcttc ctcaatttcc tcctcaaaat ggtaagcaat tccaagacgc      8460
tgcacggcat cgatcagctc gatgagttta acatgttgca taggctcatt tgatcctttg      8520
attgtaataa gttctttctt aacctcttcc ttcagttcct ctacgagttg cttcttcata      8580
accaaatcct cgggttcatc gtatgttaaa aactggtcac cccaaataga cgcgttgaaa      8640
tttgtggtat gtctgattac gtccggttta gtagaatcct tgtcatcgac taccaatggg      8700
gaggtactag aagatgagga aacagaagaa ataggtaaag tagacattat caagctagtt      8760
gtctgtcggg agtgtgcgtg cgttactttt tttttggatg gacgcaaaga agtttaataa      8820
tcatattaca tggcaatacc accatataca tatccatatc taatcttact tatatgttgt      8880
ggaaatgtaa agagccccat tatcttagcc taaaaaaacc ttctctttgg aactttcagt      8940
aatacgctta actgctcatt gctatattga agtacggatt agaagccgcc gagcgggcga      9000
cagccctccg acggaagact ctcctccgtg cgtcctggtc ttcaccgtc gcgttcctga      9060 aacgcagatg tgcctcgcgc cgcactgctc cgaacaataa agattctaca atactagctt      9120
ttatggttat gaagaggaaa aattggcagt aacctggccc cacaaacctt caaatcaacg      9180
aatcaaatta acaaccatag gataataatg cgattagttt tttagcctta tttctggggt      9240
aattaatcag cgaagcgatg attttttgatc tattaacaga tatataaatg caaaagctgc      9300
ataaccactt taactaatac tttcaacatt ttcggtttgt attacttctt attcaaatgt      9360
cataaaagta tcaacaaaaa attgttaata tacctctata cttaccccac ccgaagtcgc      9420
gcaaccaact aactttacaa tgtcaacctt gcctatttct tctgtctcat cttcttcatc      9480
tacctctcca ttggtcgtag acgataagga ctctactaaa ccagacgtca tcaggcacac      9540
cacgaatttc aacgcttcta tatggggaga ccagttttta acttacgacg aacctgagga      9600
tttggtcatg aaaaaacagt tggtcgaaga attgaaggag gaggtcaaga aggagttgat      9660
tacaatcaag ggatcaaacg aacctatgca gcacgttaag ttgatcgaat taatagatgc      9720
tgtccaaaga ttgggtatag cctaccactt cgaggaggaa atcgaggagg ctttacaaca      9780
tatacacgtc acatacggtg aacagtgggt cgataaagag aatttgcagt ctatctcatt      9840
gtggttcagg ttgttaaggc aacaaggttt taatgtttca tctggagttt tcaaggactt      9900
tatggacgag aaaggtaaat tcaaggagtc tttgtgcaac gatgctcagg gtattttagc      9960
attgtatgag gccgcattta tgagggttga agacgagact atcttagata acgcattgga      10020
gttctccaag gtccacttag acattattgc taaagaccca tcatgtgact cttcttttgag      10080 aactcaaata caccaggcat taaagcaacc tttgaggaga aggttggcta gaatcgaagc      10140
```

```
attacactat atgccaatat atcagcagga aacctcacac gacgaagttt tgttaaagtt    10200
agcaaaattg gacttctctg tcttgcagtc aatgcataag aaggagttgt ctcatatctg    10260
caagtggtgg aaggatttag atttacaaaa taagttgcca ttcgtcagag atagggttgt    10320
agagggatac ttctggatct tgtctatata ctatgagcct cagcacgcca gaaccagaat    10380
gttcttaatg aagtcctgca tgtggttagt agtattagac gacaccttcg acaattatgg    10440
aacatacgag gaattggaga tctttactca agccgttgag agatggtcta tttcttgctt    10500
ggacatgttg ccagagtata tgaagttgat ctaccaggag ttagttaact tgcacgtcga    10560
aatggaggaa tctttggaga aagagggaaa gacataccag attcactatg tcaaggaaat    10620
ggccaaagag ttggtaagga actatttggt tgaggccaga tggttgaaag agggttatat    10680
gcctaccttg gaggagtaca tgtcagtctc aatggttact ggtacctatg gtttgatgac    10740
tgccagatca tacgtcggaa gaggtgatat cgtaaatgag gataccttca agtgggtttc    10800
ttcataccct cctatcgtta aggcctcttg cgtcataatt aggttgatgg atgacattgt    10860
ttctcataag gaggaacagg agaggggtca cgtagcctca tcaatagagt gctattcaaa    10920
agagtctggt gcatcagagg aagaggcatg tgaatacatc tctagaaaag tagaggatgc    10980
ctggaaggtc attaacaggg agtcattgag acctactgct gtaccttttc ctttgttgat    11040
gcctgctatc aacttggcaa ggatgtgcga agttttgtat tcagtaaacg atggtttcac    11100
tcacgccgaa ggtgatatga atcatatat gaaatctttt ttcgtacatc ctatggtagt    11160
ataagcgaat tcttatgat ttatgatttt tattattaaa taagttataa aaaaaataag    11220
tgtatacaaa ttttaaagtg actcttaggt tttaaaacga aaattcttat tcttgagtaa    11280
ctctttcctg taggtcaggt tgcttttctca ggtatagcat gaggtcgctc aggtccgccg    11340
gcgttggacg agcgtctttt gtaacgaatt tgatgaatat atttttactt tttatataag    11400
ctattttgta gatattgact ttttacgatt tatttgtaac aatgagaatt actccatttc    11460
tgaacttcag taaatagcga gtgattctgt actttgcgag aaccggtgga catttggtat    11520
tttgccttac aagaacaacc tatacaaacg tttcaatatc taattctttg taatccattg    11580
ttttacgaga catataatgt gatatataga tgaactttac gtataaaatg atatatttaa    11640
aactagcaac tgcgtgcgta agacaaactg aaataggcca tttacggaaa agaaatttaa    11700
taatgtcgac tggaaactga aaccaggagg agtagaaatt ggttaaattg attagctaaa    11760
atttactcgt tgtggacaga gtttgagcca agcggaatgt tttcaaggct ttctttgttt    11820
cgaagggcag ctctggctcc tgccctatg agggcggttt aaacgcgtgg ccgtgccgtc    11880
```

<210> SEQ ID NO 102
<211> LENGTH: 6896
<212> TYPE: DNA
<213> ORGANISM: Artificial Sequence
<220> FEATURE:
<223> OTHER INFORMATION: Synthetic, Integration construct i569

<400> SEQUENCE: 102

```
gacggcacgg ccacgcgttt aaaccgcccct ccaagctgac ataaatcgca ctttgtatct      60 acttttttttt attcgaaaac aaggcacaac aatgaatcta tcgccctgtg agattttcaa     120
tctcaagttt gtgtaataga tagcgttata ttatagaact ataaaggtcc ttgaatatac     180
atagtgtttc attcctatta ctgtatatgt gactttacat tgttacttcc gcggctattt     240
gacgttttct gcttcaggtg cggcttggag ggcaaagtgt cagaaaatcg gccaggccgt     300
atgacacaaa agagtagaaa acgagatctc aaatatctcg aggcctgtcc tctatacaac     360
```

-continued

```
cgcccagctc tctgacaaag ctccagaacg gttgtctttt gtttcgaaaa gccaaggtcc    420
cttataattg ccctccattt tgtgtcacct atttaagcaa aaaattgaaa gtttactaac    480
cttttcattaa agagaaataa caatattata aaaagcgccg ctcgtccaac gccggcggac   540
ctgttttcaa tagttcggta atattaacgg atacctacta ttatcccta gtaggctctt     600
ttcacggaga aattcgggag tgttttttttt ccgtgcgcat tttcttagct atattcttcc   660
agcttcgcct gctgcccggt catcgttcct gtcacgtagt ttttccggat tcgtccggct   720
catataatac cgcaataaac acggaatatc tcgttccgcg gattcggtta aactctcggt   780
cgcggattat cacagagaaa gcttcgtgga gaatttttcc agattttccg ctttccccga   840
tgttggtatt tccggaggtc attatactga ccgccattat aatgactgta caacgacctt   900
ctggagaaag aaacaactca ataacgatgt gggacattgg gggcccactc aaaaaatctg    960
gggactatat ccccagagaa tttctccaga agagaagaaa agtcaaagtt ttttttcgct   1020
tgggggttgc atataaatac aggcgctgtt ttatcttcag catgaatatt ccataatttt   1080
acttaatagc ttttcataaa taatagaatc acaaacaaaa tttacatctg agttaaacaa   1140
tcatgacaat caaggaacat aaagtagttt atgaagctca caacgtaaag gctcttaagg   1200
ctcctcaaca ttttttacaac agccaacccg gcaagggtta cgttactgat atgcaacatt  1260
atcaagaaat gtatcaacaa tctatcaatg agccagaaaa attctttgat aagatggcta   1320
aggaatactt gcattgggat gctccataca ccaaagttca atctggttca ttgaacaatg   1380
gtgatgttgc atggttttg aacggtaaat tgaatgcatc atacaattgt gttgacagac    1440
atgcctttgc taatcccgac aagccagctt tgatctatga agctgatgac gaatccgaca   1500
acaaaatcat cacatttggt gaattactca gaaaagtttc ccaaatcgct ggtgtcttaa   1560
aaagctgggg cgttaagaaa ggtgacacag tggctatcta tttgccaatg attccagaag   1620
cggtcattgc tatgttggct gtggctcgta ttggtgctat tcactctgtt gtctttgctg   1680
ggttctccgc tggttcgttg aaagatcgtg tcgttgacgc taattctaaa gtggtcatca   1740
cttgtgatga aggtaaaaga ggtggtaaga ccatcaacac taaaaaaatt gttgacgaag   1800
gtttgaacgg agtcgatttg gtttcccgta tcttggtttt ccaaagaact ggtactgaag   1860
gtattccaat gaaggccggt agagattact ggtggcatga ggaggccgct aagcagagaa   1920
cttacctacc tcctgtttca tgtgacgctg aagatcctct attttttatta tacacttccg   1980
gttccactgg ttctccaaag ggtgtcgttc acactacagg tggttattta ttaggtgccg   2040
ctttaacaac tagatacgtt tttgatattc acccagaaga tgttctcttc actgccggtg   2100
acgtcggctg gatcacgggt cacacctatg ctctatatgg tccattaacc ttgggtaccg   2160
cctcaataat tttcgaatcc actcctgcct acccagatta tggtagatat tggagaatta   2220
tccaacgtca caaggctacc catttctatg tggctccaac tgctttaaga ttaatcaaac   2280
gtgtaggtga agccgaaatt gccaaatatg acacttcctc attacgtgtc ttgggttccg   2340
tcggtgaacc aatctctcca gacttatggg aatggtatca tgaaaaagtg ggtaacaaaa   2400
actgtgtcat ttgtgacact atgtggcaaa cagagtctgg ttctcattta attgctcctt   2460
tggcaggtgc tgtcccaaca aaacctggtt ctgctaccgt gccattcttt ggtattaacg   2520
cttgtatcat tgaccctgtt acaggtgtgg aattagaagg taatgatgtc gaaggtgtcc   2580
ttgccgttaa atcaccatgg ccatcaatgg ctagatctgt ttggaaccac cacgaccgtt   2640
acatggatac ttacttgaaa cctttatcctg tcactatttt cacaggtgat ggtgctggta   2700
gagatcatga tggttactac tggatcaggg gtagagttga cgacgttgta aatgtttccg   2760
```

```
gtcatagatt atccacatca gaaattgaag catctatctc aaatcacgaa aacgtctcgg    2820
aagctgctgt tgtcggtatt ccagatgaat tgaccggtca aaccgtcgtt gcatatgttt    2880
ccctaaaaga tggttatcta caaaacaacg ctactgaagg tgatgcagaa cacatcacac    2940
cagataattt acgtagagaa ttgatcttac aagttagggg tgagattggt cctttcgcct    3000
caccaaaaac cattattcta gttagagatc taccaagaac aaggtcagga aagattatga    3060
gaagagttct aagaaaggtt gcttctaacg aagccgaaca gctaggtgac ctaactactt    3120
tggccaaccc agaagttgta cctgccatca tttctgctgt agagaaccaa ttttctctc    3180 aaaaaaagaa ataaattgaa ttgaattgaa atcgatagat caattttttt cttttctctt    3240
tccccatcct ttacgctaaa ataatagttt attttatttt ttgaatattt tttatttata    3300
tacgtatata tagactatta tttatctttt aatgattatt aagattttta ttaaaaaaaa    3360
attcgctcct cttttaatgc ctttatgcag ttttttttt ccattcgata tttctatgtt    3420
cgggttcagc gtattttaag tttaataact cgaaaattct gcgttcgtta aagcttttcga   3480 gaaggatatt atttcgaaat aaaccgtgtt gtgtaagctt gaagcctttt tgcgctgcca    3540
atattcttat ccatctattg tactctttag atccagtata gtgtattctt cctgctccaa    3600
gctcatccca tccccgcgtg cttggccggc cgttttgcca gcttactatc cttcttgaaa    3660
atatgcactc tatatctttt agttcttaat tgcaacacat agatttgctg tataacgaat    3720
tttatgctat ttttaaatt tggagttcag tgataaaagt gtcacagcga atttcctcac     3780
atgtagggac cgaattgttt acaagttctc tgtaccacca tggagacatc aaaaattgaa    3840
aatctatgga aagatatgga cggtagcaac aagaatatag cacgagccgc ggagttcatt    3900
tcgttacttt tgatatcact cacaactatt gcgaagcgct tcagtgaaaa aatcataagg    3960
aaaagttgta aatattattg gtagtattcg tttggtaaag tagagggggt aattttttccc    4020 cttatttttg ttcatacatt cttaaattgc tttgcctctc cttttggaaa gctatacttc     4080
ggagcactgt tgagcgaagg ctcattagat atatttttctg tcattttcct taacccaaaa    4140
ataagggaaa gggtccaaaa agcgctcgga caactgttga ccgtgatccg aaggactggc    4200
tatacagtgt tcacaaaata gccaagctga aaataatgtg tagctatgtt cagttagttt    4260
ggctagcaaa gatataaaag caggtcggaa atatttatgg gcattattat gcagagcatc    4320
aacatgataa aaaaaaacag ttgaatattc cctcaaaaat gtcttacacc gtcggaacct    4380
acttggccga gaggttggtc cagatcggat tgaagcacca cttcgccgtc gccggtgact    4440
acaacttggt cttgttggac aacttgttgt tgaacaagaa catggagcag gtctattgct    4500
gcaacgagtt gaactgcggt ttctcagcag aaggttatgc aagagccaag ggagcagccg    4560
ctgccgtcgt cacctactca gtcggtgcat tatcagcatt cgatgcaatt ggaggtgctt    4620
acgctgagaa cttgccagtc atcttgatct ctggagcacc taacaacaac gaccatgctg    4680
ctggtcacgt attgcaccac gccttgggta aaacagacta ccactaccag ttggaaatgg    4740
caaaaaatat taccgcagcc gcagaggcca tctacacccc agaggaagca cctgccaaaa    4800
ttgaccacgt cataaagacc gctttgagag agaagaagcc tgtttacttg gagatcgcct    4860
gcaacatcgc ttctatgcca tgcgccgcac ctggtccagc ctctgctttg ttcaacgacg    4920
aggcctctga cgaagcttca ttgaacgccg cagtcgaaga gacattaaag ttcatcgcca    4980
acagggacaa agttgccgtc ttagtcggtt caaagttgag ggccgctggt gccgaagagg    5040
cagctgtcaa gttcgctgac gccttgggag gagccgtcgc caccatggcc gcagcaaaat    5100
ctttctttcc tgaggagaac ccacattaca tcggaacctc atggggtgaa gtatcatatc    5160
```

```
ctggagtaga aaaaaccatg aaagaggccg atgccgtaat agcattggct cctgtcttca    5220
acgactactc aaccacagga tggactgata taccagatcc aaagaaatta gtcttggctg    5280
agcctaggtc tgtcgtcgta aacggtatca ggttcccttc tgttcatttg aaggactact    5340
taacaagatt ggcccaaaag gtatctaaaa agactggtgc cttggacttc ttcaagtcat    5400
taaacgcagg agaattgaaa aaagcagcac cagccgatcc atcagcccca ttagttaacg    5460
ctgaaatcgc tagacaagta gaggctttgt tgactccaaa cactaccgtc atagctgaga    5520
caggtgactc ttggttcaac gcacagagaa tgaaattgcc aaatggtgcc agggtcgagt    5580
atgaaatgca gtggggacat ataggttggt cagtcccagc cgcctttgga tacgcagtag    5640
gtgcccctga gaggaggaac atattgatgg ttggtgatgg ttcattccaa ttaacagccc    5700
aggaggtagc ccaaatggtc aggttgaagt tgcctgtcat catcttcttg atcaacaatt    5760
acggatacac catcgaggtc atgatccacg acggacctta caacaacatc aaaaactggg    5820
actacgccgg tttgatggag gttttcaacg gtaacggtgg ttatgactca ggagccggta    5880
agggattaaa ggctaagacc ggtggtgaat tggctgaagc aattaaggtc gcattggcca    5940
acaccgatgg acctcattg attgaatgct tcatcggaag ggaggactgc accgaggaat    6000
tggttaaatg gggtaaaagg gtagccgctg ctaattcaag aaaaccagtt aataaattat    6060
tataataagt gaattacctt taaatcttgc atttaaataa attttctttt tatagcttta    6120
tgacttagtt tcaatttata tactatttta atgacatttt cgattcattg attgaaagct    6180
ttgtgttttt tcttgatgcg ctattgcatt gttcttgtct ttttcgccac atgtaatatc    6240
tgtagtagat acctgataca ttgtggatgc tgagtgaaat tttagttaat aatggaggcg    6300
ctcttaataa ttttggggat attggcttaa cctgcaggcc gcgagcgccg atataaacta    6360
atgattttaa atcgttaaaa aaatatgcga attctgtgga tcgaacacag gacctccaga    6420
taacttgacc gaagtttttt cttcagtctg gcgctctccc aactgagcta aatccgctta    6480
ctatttgtta tcagttccct tcatatctac atagaatagg ttaagtattt tattagttgc    6540
cagaagaact actgatagtt gggaatattt ggtgaataat gaagattggg tgataatttt    6600
gataattttg agattcaatt gttaatcaat gttacaatat tatgtataca gagtatacta    6660
gaagttctct tcggagatct tgaagttcac aaaagggaat cgatatttct acataatatt    6720
atcattactt cttccccatc ttatatttgt cattcattat tgattatgat caatgcaata    6780
atgattggta gttgccaaac atttaatacg atcctctgta atatttctat gaataattat    6840
cacagcaacg ttcaattatc ttcaattccg gtgtttaaac cccagcgcct ggcggg       6896
```

<210> SEQ ID NO 103
<211> LENGTH: 7038
<212> TYPE: DNA
<213> ORGANISM: Artificial Sequence
<220> FEATURE:
<223> OTHER INFORMATION: Synthetic, Integration construct i2124

<400> SEQUENCE: 103

```
aagaaggacg tgagaaaact ttaacatctg cttggtaagg gcctcattta attctggatt      60
attgtacccg tgaataacac accaccacga cgacatggcg tcgatcacct cgacgtccac     120
tggtgagtcg gtatccaaca ccagcttgca tccgtgagca ctctttaccg gataaacgtt     180
caatggtgaa ctcaatgacg tataaggatg ccaaatatgt ttttatcaa  agtctagcag     240
ttccgcgaca tctggtgtat atgaaatttc ttgagacatt agttgttatc ctagcaatag     300
aaaacgaatt gcgctgttga catcctcccg accaaaagaa aatgaaatat acaaacaatg     360
```

```
gctatttata attcaaaatt attgggcaaa acaaaataaa atcccgctgg tagttcgttt    420
actgaagtat ataaagagat atacttttt  ccacaagtag gccagtgaaa agaactcaaa    480
aaatcactag cgcacaggtc gttcatcatc tcatggatct gcacatgaac aaacaccaga    540
gtcaaacgac gttgaaattg aggctactgc gccaattgat gacaatacag acgatgataa    600
caaaccgaag ttatctgatg tagaaaagga ttaaagatgc taagagatag tgatgatatt    660
tcataaataa tgtaattcta tatatgttaa ttaccttttt tgcgaggcat atttatggtg    720
aaggataagt tttgaccatc aaagaaggtt aatgtggctg tggtttcagg gtccataaag    780
cttttcaatt catcttttt  ttttttgttc tttttttga  ttccggtttc tttgaaattt    840
ttttgattcg gtaatctccg agcagaagga agaacgaagg aaggagcaca gacttagatt    900
ggtatatata cgcatatgtg gtgttgaaga aacatgaaat tgcccagtat tcttaaccca    960
actgcacaga acaaaaacct gcaggaaacg aagataaatc atgtcgaaag ctacatataa   1020
ggaacgtgct gctactcatc ctagtcctgt tgctgccaag ctatttaata tcatgcacga   1080
aaagcaaaca aacttgtgtg cttcattgga tgttcgtacc accaaggaat tactggagtt   1140
agttgaagca ttaggtccca aaatttgttt actaaaaaca catgtggata tcttgactga   1200 ttttccatg  gagggcacag ttaagccgct aaaggcatta tccgccaagt acaatttttt   1260
actcttcgaa gacagaaaat ttgctgacat tggtaataca gtcaaattgc agtactctgc   1320
gggtgtatac agaatagcag aatgggcaga cattacgaat gcacacggtg tggtgggccc   1380
aggtattgtt agcggtttga agcaggcggc agaagaagta acaaaggaac ctagaggcct   1440
tttgatgtta gcagaattgt catgcaaggg ctccctatct actggagaat atactaaggg   1500
tactgttgac attgcgaaga gcgacaaaga ttttgttatc ggcttttattg ctcaaagaga   1560 catgggtgga agagatgaag gttacgattg gttgattatg acacccggtg tgggtttaga   1620
tgacaaggga gacgcattgg gtcaacagta tagaaccgtg gatgatgtgg tctctacagg   1680
atctgacatt attattgttg gaagaggact atttgcaaag ggaagggatg ctaaggtaga   1740
gggtgaacgt tacagaaaag caggctggga agcatatttg agaagatgcg gccagcaaaa   1800
ctaaaaaact gtattataag taaatgcatg tatactaaac tcacaaatta gagcttcaat   1860
ttaattatat cagttattac ccgggaatct cggtcgtaat gatttctata atgacgaaaa   1920
aaaaaaaatt ggaaagaaaa agcttcatgg cctttataaa aaggaactat ccaatacctc   1980
gccagaacca agtaacagta ttttacgggg cacaaatcaa gaacaataag acaggactgt   2040
aaagatggac gcatgagcga cctcatgcta tacctgagaa agcaacctga cctacaggaa   2100
agagttactc aagaataaga atttcgttt  taaaacctaa gagtcacttt aaaatttgta   2160
tacacttatt tttttataa  cttatttaat aataaaaatc ataaatcata agaaattcgc   2220
ttagactacc atagggtgaa caaagaatga cttcatgtat gatttcatgt caccctcggc   2280
gtgggtgaaa ccgtcattaa ctgaatataa gacttcgcac attcttgcta agtttatggc   2340
aggcattaat aatgggaaag ggactgcggt tggcctcaat gactctctgt tgataacttt   2400
ccatgcatct tcgactttc  tagagatgta ctcacaggct tcttcttcag atgctcctga   2460
ttcttttgaa taacactcga tagatgatgc tacatgtccc ctctcttgtt cctctttgtg   2520
agatacaata tcatccatca accttataat aacgcatgag gcctttacga taggtggata   2580
agatgatacc cacttgaatg tgtcttcgtt tacaatgtct cctctaccga cataagatct   2640
agcagtcatt aatccgtagg ttccagtgac catagaaaca gacatatatt cctccaaggt   2700
aggcatgtaa ccctccttca accatctagc ttctaccaag tagtttctta ccaactcttt   2760
```

```
tgccatctcc ttgacatagt ggatctgata agttttaccc tctttctcca aagattcttc    2820
catctcgacg tgtaagttga ctaactcctg gtagatcaac ttcatatact ctggtaacat    2880
gtccaagcat gaaattgacc atctctctac agcttgagtg aagatctcta attcctcgta    2940
ggtaccgtaa ttgtcaaaag tgtcgtctaa acgaccaac cacatgcaag acttcattaa     3000
gaacattctt gttctagcgt gctgaggctc gtagtagata gacaatatcc agaaatatcc    3060
ctcaacgact ctgtctctaa caaaaggcaa cttattctgc aaatccaaat ccttccacca    3120
tttgcagata tgagacaatt ccttttatg cattgactgc aatacagaga agtccaattt     3180
ggccaacttc aacaaaactt catcatgtga tgtttcctgc tgatagatag gcatatagtg    3240
caaggcttct atccttgcta accttctcct caaaggttgc ttcaatgctt gatgtatttg    3300
tgttcttaaa gaagagtcgc atgaaggatc ctttgcgatg atgtctaagt ggactttaga    3360
gaattccaat gcgttgtcta atatagtctc gtcctctacc ctcataaagg cagcttcata    3420
taatgccaaa attccttgag catcgttgca taatgactcc ttaaactttc ccttttcgtc    3480
catgaaatct ttaaagacac ctgaagagac gttgaatccc tgttgcctta caacctaaa    3540
ccataaagag attgattgca agttctcctt gtcaacccat tgttctccat aagtaacatg    3600
aatatgctgc aatgcctctt caatctcctc ttcgaaatga tatgcaattc ctaacctttg    3660
aacagcgtca attaactcta tcaacttgac gtgttgcata ggctcgtttg aaccttttat    3720
ggtgatcaac tccttcttaa cctcctcctt taactcctcg accaactgtt ttttcatgac    3780
taaatcctct ggttcgtcat aggtcaagaa ctggtctccc catatagagg cgttgaagtt    3840
cgttgtatgc cttatgacgt ctggctttgt agaatctttg tcgtctacaa ccaatggtga    3900
ggtagaagat gaggatgaga ctgaagatat aggcaatgtt gacatttata ttgaattttc    3960
aaaaattctt actttttttt tggatggacg caaagaagtt taataatcat attacatggc    4020
aataccacca tatacatatc catatctaat cttacttata tgttgtggaa atgtaaagag    4080
ccccattatc ttagcctaaa aaaaccttct ctttggaact ttcagtaata cgcttaactg    4140
ctcattgcta tattgaagta cggattagaa gccgccgagc gggcgacagc cctccgacgg    4200
aagactctcc tccgtgcgtc ctggtcttca ccggtcgcgt tcctgaaacg cagatgtgcc    4260
tcgcgccgca ctgctccgaa caataaagat tctacaatac tagctttat ggttatgaag     4320
aggaaaaatt ggcagtaacc tggccccaca aaccttcaaa tcaacgaatc aaattaacaa    4380
ccataggata ataatgcgat tagttttta gccttatttc tggggtaatt aatcagcgaa     4440
gcgatgattt ttgatctatt aacagatata taaatgcaaa agctgcataa ccactttaac    4500
taatactttc aacattttcg gtttgtatta cttcttattc aaatgtcata aaagtatcaa    4560
caaaaaattg ttaatatacc tctatacttt aacgtcaagg agaaaaaact ataatgtcaa    4620
ctttgcctat ttcttctgtg tcatcttcct cttctacatc accattagtc gtggacgaca    4680
aagattcaac caagcccgac gttatcagac atacaacgaa tttcaatgct tctatttggg    4740
gagatcaatt cttgacctat gatgagcctg aagatttagt tatgaagaaa caattagtgg    4800
aggaattaaa agaggaagtt aagaaggaat tgataactat caaaggttca aatgagccca    4860
tgcagcatgt gaaattgatt gaattaattg atgctgttca acgtttaggt atagcttacc    4920
attttgaaga agagatcgag gaagcttgc aacatatgca tgttacctat ggtgaacagt     4980
gggtggataa ggaaaattta cagagtattt cattgtggtt caggttgttg cgtcaacagg    5040
gctttaacgt ctcctctggc gttttcaaag actttatgga cgaaaaaggt aaattcaaag    5100
agtctttatg caatgatgca caaggaatat tagccttata tgaagctgca tttatgaggg    5160
```

```
ttgaagatga aaccatctta gacaatgctt tggaattctc aaaagttcat ttagatatca    5220
tagcaaaaga cccatcttgc gattcttcat tgcgtacaca aatccatcaa gccttaaaac    5280
aacctttaag aaggagatta gcaaggattg aagcattaca ttacatgcca atctaccaac    5340
aggaaacatc tcatgatgaa gtattgttga aattagccaa gttggatttc agtgttttgc    5400
agtctatgca taaaaaggaa ttgtcacata tctgtaagtg gtggaaagat ttagatttac    5460
aaaataagtt acctttttgta cgtgatcgtg ttgtcgaagg ctacttctgg atattgtcca    5520
tatactatga gccacaacac gctagaacaa gaatgttttt gatgaaatca tgcatgtggt    5580
tagtagtttt ggacgatact tttgataatt atggaacata cgaagaattg gagatttta    5640 ctcaagccgt cgagagatgg tctatctcat gcttagatat gttgcccgaa tatatgaaat    5700
taatctacca agaattagtc aatttgcatg tggaaatgga agaatctttg gaaaaggagg    5760
gaaagaccta tcagattcat tacgttaagg agatggctaa agaattagtt cgtaattact    5820
tagtagaagc aagatggttg aaggaaggtt atatgcctac tttagaagaa tacatgtctg    5880
tttctatggt tactggtact tatggtttga tgactgcaag gtcctatgtt ggcagaggag    5940
acattgttaa tgaagacaca ttcaaatggg tttctagtta cccacctatt gttaaagctt    6000
cctgtgtaat aattagatta atggacgata ttgtatctca caaggaagaa caagaaagag    6060
gacatgtggc ttcatctata gaatgttact ctaaagaatc aggtgcttct gaagaggaag    6120
catgtgaata tattagtagg aaagttgagg atgcctggaa agtaatcaat agagaatctt    6180
tgcgtccaac agccgttccc ttccctttgt taatgccagc aataaactta gctagaatgt    6240
gtgaggtctt gtactctgtt aatgatggtt ttactcatgc tgagggtgac atgaaatctt    6300
atatgaagtc cttcttcgtt catcctatgg tcgtttgagc tagctaagat ccgctctaac    6360
cgaaaaggaa ggagttagac aacctgaagt ctaggtccct atttattttt ttatagttat    6420
gttagtatta agaacgttat ttatatttca aatttttctt ttttttctgt acagacgcgt    6480
gtacgcatgt aacattatac tgaaaacctt gcttgagaag gttttgggac gctcgaagtt    6540
taaataaaaa agttgcaagg ctttcatcag ctatatataa gtagcatggt atgaacagag    6600
taggggcagt gttcctattt gtatatgaaa gaaatttttt tttgtctatt gttccagatc    6660
gtcacaggac ggaaataaga atgtctagtt cagaaaggtc agaagtcaag tttgacaagc    6720
actttaattg gtggtcccta ttaggtatcg cgttctcatt aagttgctca tgggtcggta    6780
tctcagcgtc gatggccgtt ggtattgcca gtggagggcc actgcttatc atctatgggt    6840
tgataattgc tgcttttttc agtctcatgt gtggtatatc tctgggagat tttgctgcta    6900
tcctgccaaa cagcagcggt ggttcatttt gggttcttaa aatgttggaa caagaatcag    6960
tcactttgaa aaccoctgag tacgaggacc cttctgacga tgatgaagaa gtgttcctcg    7020
agaattattg tcaaactt                                                  7038
```

<210> SEQ ID NO 104
<211> LENGTH: 4376
<212> TYPE: DNA
<213> ORGANISM: Artificial Sequence
<220> FEATURE:
<223> OTHER INFORMATION: Synthetic, Integration construct i65

<400> SEQUENCE: 104

```
gtttaaaccc tggaaattcg gtgtccttct cattatctat cagcatgtac tcggcggtaa      60
aaacatcctt tgaaggattt tgaatgatgg gtcccaaaaa tcttttttctg tggaaagaac     120 cgatactact atgattcgca ttaacgccgt tattaacggt taactgatag tctttgttgc     180
```

```
ataaactaaa cttacccttc gaaatacgat tagcatacct gccgatcgtg gcgcctatat    240
aagcactatc aggattcaaa tacccttcct cattttcata gccaagaaca actgattgtc    300
cgttcacttt caggtcaaca atgctggcgc ccaaattggc aaacgtggct tgaaatctgg    360
tgccggcacc aatagtcaca aatcttgcgt cataacgcat atcttcagcg gaaaatctgg    420
cctcgacacc ccttaactgg taaccaaaag gattctcagt agtccatttc cataaatcct    480
tgcaggagtc ttcaacctgc aactcggtct gccatttcag ttcgcgtttg ccctatctg     540 gtttagccgt caagttcaaa acatcacctg ctcttctgcc cgtaactttg tatggaagat    600
caataccaga agctttgcag aatgcatgat aaacttcaaa aactgtagaa cctttaccgg    660
aacccaagtt ccactcacga cacaaacctt cattttcatt gtaggcctct aggtattgca    720
gggctgcaat atgaccttt gctagatcaa ctacgtggat ataatccctg atcggggtac     780
catctctgga atcataatcg tctccgaaga tgtaaagctt ctcgcgccta ccaacagcta    840
cttgagccat atatggcaac aaattgtttg gtatacctag cggatcttct ccgattaatc    900
cagagggatg tgcgccaatt gggttaaaat aacgcaagat agcaaacttc caacttttt     960 tgtcgctatt gtaaagatca ttcaagatat tctcaatggc gtatttcgta tgaccatacg   1020
gattagtagg ccctaaggga cattcttctg ggataggaat catatttggg aatctcgtag   1080
catcaccata gacagtagca gaagatgaaa aaacaaattt ggaaacgttg tattgttgca   1140
ttaactctaa taaaacgaca gttcccaaaa tgttattgtg atagtatctc agcgggattt   1200
gtgtagattc acctacagcc tttaaaccag caaagtgaat taccgaatca attttatatt   1260
ctttgaaaac cttttccaga ccttttcggt cacacaaatc aacctcatag aagggaatgt   1320
gatgcttggt caagacctct aacctggcta cagaatcata agttgaattc gacaggttat   1380
cagcaacaac acagtcatat ccattctcaa ttagctctac cacagtgtgt gaaccaatgt   1440
atccagcacc acctgtaacc aaaacaattt tagaagtact ttcactttgt aactgagctg   1500
tgtcgacact agtaatacac atcatcgtcc tacaagttca tcaaagtgtt ggacagacaa   1560
ctataccagc atggatctct tgtatcggtt cttttctccc gctctctcgc aataacaatg   1620
aacactgggt caatcatagc ctacacaggt gaacagagta gcgtttatac agggtttata   1680
cggtgattcc tacggcaaaa attttcatt tctaaaaaaa aaagaaaaa ttttctttc     1740 caacgctaga aggaaaagaa aaatctaatt aaattgattt ggtgattttc tgagagttcc   1800 cttttttcata tatcgaattt tgaatataaa aggagatcga aaaattttt ctattcaatc    1860 tgttttctgg ttttatttga tagtttttt gtgtattatt attatggatt agtactggtt    1920 tatatggggtt tttctgtata acttcttttt attttagttt gtttaatctt attttgagtt   1980
acattatagt tccctaactg caagagaagt aacattaaaa atgaaaaagc ctgaactcac   2040
cgcgacgtct gtcgagaagt ttctgatcga aaagttcgac agcgtctccg acctgatgca   2100
gctctcggag ggcgaagaat ctcgtgcttt cagcttcgat gtaggagggc gtggatatgt   2160
cctgcgggta aatagctgcg ccgatggttt ctacaaagat cgttatgttt atcggcactt   2220
tgcatcggcc gcgctcccga ttccggaagt gcttgacatt ggggaattca gcgagagcct   2280
gacctattgc atctcccgcc gtgcacaggg tgtcacgttg caagacctgc ctgaaaccga   2340
actgcccgct gttctgcagc cggtcgcgga ggccatggat gcgatcgctg cggccgatct   2400
tagccagacg agcgggttcg gcccattcgg accgcaagga atcggtcaat acactacatg   2460
gcgtgatttc atatgcgcga ttgctgatcc ccatgtgtat cactggcaaa ctgtgatgga   2520
cgacaccgtc agtgcgtccg tcgcgcaggc tctcgatgag ctgatgcttt gggccgagga   2580
```

```
ctgccccgaa gtccggcacc tcgtgcacgc ggatttcggc tccaacaatg tcctgacgga    2640
caatggccgc ataacagcgg tcattgactg gagcgaggcg atgttcgggg attcccaata    2700
cgaggtcgcc aacatcttct tctggaggcc gtggttggct tgtatggagc agcagacgcg    2760
ctacttcgag cggaggcatc cggagcttgc aggatcgccg cggctccggg cgtatatgct    2820
ccgcattggt cttgaccaac tctatcagag cttggttgac ggcaatttcg atgatgcagc    2880
ttgggcgcag ggtcgatgcg acgcaatcgt ccgatccgga gccgggactg tcgggcgtac    2940
acaaatcgcc cgcagaagcg cggccgtctg gaccgatggc tgtgtagaag tactcgccga    3000
tagtggaaac cgacgcccca gcactcgtcc gagggcaaag gaataggttt aacttgatac    3060
tactagattt tttctcttca tttataaaat ttttggttat aattgaagct ttagaagtat    3120
gaaaaaatcc tttttttttca ttctttgcaa ccaaaataag aagcttcttt tattcattga    3180
aatgatgaat ataaacctaa caaagaaaa agactcgaat atcaaacatt aaaaaaaaat    3240
aaaagaggtt atctgttttc ccatttagtt ggagtttgca ttttctaata gatagaactc    3300
tcaattaatg tggatttagt ttctctgttc gtttttttttt gttttgttct cactgtattt    3360
acatttctat ttagtattta gttattcata taatcttaac ttctcgagac tcataacttt    3420
agcatcacaa aatacgcaat aataacgagt agtaacactt ttatagttca tacatgcttc    3480
aactacttaa taaatgattg tatgataatg ttttcaatgt aagagatttc gattatccac    3540
aaactttaaa acacagggac aaaattcttg atatgctttc aaccgctgcg ttttggatac    3600
ctattcttga catgatatga ctaccatttt gttattgtac gtggggcagt tgacgtctta    3660
tcatatgtca aagtcatttg cgaagttctt ggcaagttgc caactgacga gatgcagtaa    3720
aaagagattg ccgtcttgaa acttttttgtc cttttttttt tccggggact ctacgagaac    3780
cctttgtcct actgattaat tttgtactga atttggacaa ttcagatttt agtagacaag    3840
cgcgaggagg aaaagaaatg acagaaaaat tccgatggac aagaagatag gaaaaaaaaa    3900
aagctttcac cgatttccta gaccggaaaa aagtcgtatg acatcagaat gaaaaatttt    3960
caagttagac aaggacaaaa tcaggacaaa ttgtaaagat ataataaact atttgattca    4020
gcgccaattt gcccttttcc attttccatt aaatctctgt tctctcttac ttatatgatg    4080
attaggtatc atctgtataa aactcctttc ttaatttcac tctaaagcat accccataga    4140
gaagatcttt cggttcgaag acattcctac gcataataag aataggaggg aataatgcca    4200
gacaatctat cattacattt aagcggctct tcaaaaagat tgaactctcg ccaacttatg    4260
gaatcttcca atgagacctt tgcgccaaat aatgtggatt tggaaaaaga gtataagtca    4320
tctcagagta atataactac cgaagtttat gaggcatcga gctttgaagt ttaaac        4376
```

<210> SEQ ID NO 105
<211> LENGTH: 7686
<212> TYPE: DNA
<213> ORGANISM: Artificial Sequence
<220> FEATURE:
<223> OTHER INFORMATION: Synthetic, Integration construct i10

<400> SEQUENCE: 105

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagcttg     240
gtaccgagct cggatccact agtaacggcc gccagtgtgc tggaattcgc ccttctcgag     300
```

```
aagttaagat tatatgaata actaaatact aaatagaaat gtaaatacag tgagaacaaa      360
acaaaaaaaa acgaacagag aaactaaatc cacattaatt gagagttcta tctattagaa      420
aatgcaaact ccaactaaat gggaaaacag ataacctctt ttatttttt ttaatgtttg       480 atattcgagt ctttttcttt tgttaggttt atattcatca tttcaatgaa taaaagaagc      540
ttcttatttt ggttgcaaag aatgaaaaaa aaggatttt tcatacttct aaagcttcaa       600
ttataaccaa aaattttata aatgaagaga aaaaatctag tagtatcaag ttaaacttaa      660
cggccttttg ccagatattg attcatctct tcttccggca ccattccacc tcccgtcgcc      720
cacaccagat gagtggtatt acgcagttgt tctgcgctga aaccgtgcat ctgttggtaa      780
cttactgatg cacacacgcg ctgaggtccg gccatacccg ccagtgccga aggttcaaga      840
cgaataccct tcctgcgc cagccagcca agcatgtcat acatggttg atcgctaagg         900 gtatagaagc catccagcag acgctccatt gcccgcccga caaagcctga tgcgcgacca      960
actgcaaggc catccgctgc ggtaaggttg tcgataccaa tatcctgaac agaaatctga     1020
tcgtgtaatc ctgtatggac gcctaacaac atacaagggg agtgcgttgg ttcggcaaaa     1080
aagcagtgaa catgatcgcc aaacgccagt ttaagcccga atgcgacgcc accaggacca     1140
ccgccaacac cacacggcag atagacaaac agagggttat cagcatcgac gatacggcct     1200
tgctgggcaa attgcgcttt aagacgctgg ccagcgacgg aatacccaag gaacaacgtg     1260
cgggaatttt cgtcatcaat aaagaaacag ttcgggtcag actgcgctgc tttacgtcct     1320
tcctcgacgg caacaccata atcttgctca tattccacga ccgtaacgcc atgcgtgcgc     1380
agtttcgctt ttttccatgc ccgggcatca gcagacatat gaactgtcac cttaaagcca     1440
atgcgggcgc tcataatgcc gattgataac cccagatttc cggttgagcc cacagcaatg     1500
ctgtattggc taaagaactg tttaaactcc ggagaaagca gtttgctgta gtcatcatca     1560
agcgtcagca accccgcttc cagagccagt ttttctgcgt gtgccaggac ttcataaatc     1620
ccgccgcgtg cttttatgga gccggaaatg ggcaaatggc tatcttttt cagtaacagt      1680 tgcccgctga tcggttgctg atattctttt tccagccgtt tttgcatagc tcgaatggca     1740
accagttctg attcaataat cccccccagtg gcagcagttt caggaaatgc ttttgccaga    1800
tagggtgcaa aacgggataa gcgcgcatgg gcgtcctgaa catcctgttc ggtcaggcca     1860
acataaggta aaccttcagc caatgaggtc gtgccaggat taaaccaggt ggtttcttta     1920
agagcaacca gatcctttac caacggatac tgggcgatga gcgagttcat tttagcgttt     1980 tccatttta atgttacttc tcttgcagtt agggaactat aatgtaactc aaaataagat      2040
taaacaaact aaaataaaaa gaagttatac agaaaaaccc atataaacca gtactaatcc     2100
ataataataa tacacaaaaa aactatcaaa taaaaccaga aaacagattg aatagaaaaa     2160
ttttttcgat ctccttttat attcaaaatt cgatatatga aaaagggaac tctcagaaaa     2220
tcaccaaatc aatttaatta gatttttctt ttccttctag cgttggaaag aaaaatttt     2280 cttttttttt ttagaaatga aaaattttg ccgtaggaat caccgtataa accctgtata      2340
aacgctactc tgttcacctg tgtaggctat gattgaccca gtgttcattg ttattgcgag     2400
agagcgggag aaaagaaccg atacaagaga tccatgctgg tatagttgtc tgtccaacac     2460
tttgatgaac ttgtaggacg atgatgtgta ttactagtgt cgacgtattc caatgagaat     2520
cgctagaaat gctttaccag aactagacta cttgtcgcag atcacttttg aactgtatga     2580
gagtacggat gcttctggtc aaaaatcgca ttccattaga ctgaaaatgt ctcctgggtg     2640
tcatactcaa gatccgttag atgttcaatt agatgacagg cattatatta gttgtattcc     2700
```

```
aaagatttcc ctgacgaagc atttggatat ggactacgtt caacagaaat tgagaaacaa    2760
atttaccagg gtcattatgc ctccgaaatt tacaccagta acattacga gccccaactt    2820 gagtttccag aaacgcaaaa ccagaagaaa gtcggtatct gttgagaagt tgaagcttcc    2880
tgcctcgtcc ggatcttcat catctacctc cgttaacaag acattagatt agtgatcaca    2940
cccaattttt aatttagcaa cccaaaataa ataagtattt actcaacttt ttttaataa    3000 aaaaaaactt aattgaattt tgctcgcgat ctttaggtcc ggggttttcg ttgaacccttt    3060 agacgagcaa attagcgcca taaggatata cgtcagagca cattaattag tgacatatac    3120
ctatataaag agcaaccttc tccgatagac ttgtaattta tcttatttca tttcctaaca    3180
ctttggtcga agaagaggga taaaaacaga cgaaaacaca tttaagggct atacaaagat    3240
gggaaagcta ttacaattgg cattgcatcc ggtcgagatg aaggcagctt tgaagctgaa    3300
gttttgcaga acaccgctat tctccatcta tgatcagtcc acgtctccat atctcttgca    3360
ctgtttcgaa ctgttgaact tgacctccag atcgtttgct gctgtgatca gagagctgca    3420
tccagaattg agaaactgtg ttactctctt ttatttgatt ttaagggctt tggataccat    3480
cgaagacgat atgtccatcg aacacgattt gaaaattgac ttgttgcgtc acttccacga    3540
gaaattgttg ttaactaaat ggagtttcga cggaaatgcc cccgatgtga aggacagagc    3600
cgttttgaca gatttcgaat cgattcttat tgaattccac aaattgaaac cagaatatca    3660
agaagtcatc aaggagatca ccgagaaaat gggtaatggt atggccgact acatcttaga    3720
tgaaaattac aacttgaatg ggttgcaaac cgtccacgac tacgacgtgt actgtcacta    3780
cgtagctggt ttggtcggtg atggtttgac ccgtttgatt gtcattgcca agtttgccaa    3840
cgaatctttg tattctaatg agcaattgta tgaaagcatg ggtcttttcc tacaaaaaac    3900
caacatcatc agagattaca atgaagattt ggtcgatggt agatccttct ggcccaagga    3960
aatctggtca caatacgctc ctcagttgaa ggacttcatg aaacctgaaa acgaacaact    4020
ggggttggac tgtataaacc acctcgtcta agggcgaatt ctgcagatat ccatcacact    4080
ggcggccgct cgagcatgca tctagagggc ccaattcgcc ctatagtgag tcgtattaca    4140
attcactggc cgtcgtttta caacgtcgtg actgggaaaa ccctggcgtt acccaactta    4200
atcgccttgc agcacatccc cctttcgcca gctggcgtaa tagcgaagag gcccgcaccg    4260 atcgccttc ccaacagttg cgcagcctga atggcgaatg gacgcgccct gtagcggcgc    4320
attaagcgcg gcgggtgtgg tggttacgcg cagcgtgacc gctacacttg ccagcgccct    4380
agcgcccgct cctttcgctt tcttcccttc ctttctcgcc acgttcgccg gctttccccg    4440
tcaagctcta aatcgggggc tccctttagg gttccgattt agtgctttac ggcacctcga    4500
ccccaaaaaa cttgattagg gtgatggttc acgtagtggg ccatcgccct gatagacggt    4560
ttttcgccct ttgacgttgg agtccacgtt ctttaatagt ggactcttgt tccaaactgg    4620
aacaacactc aaccctatct cggtctattc ttttgattta agggatttt gccgatttc    4680 ggcctattgg ttaaaaaatg agctgattta acaaaatttt aacgcgaatt ttaacaaaat    4740
tcagggcgca agggctgcta aggaagcgg aacacgtaga aagccagtcc gcagaaacgg    4800
tgctgacccc ggatgaatgt cagctactgg gctatctgga caagggaaaa cgcaagcgca    4860
aagagaaagc aggtagcttg cagtgggctt acatggcgat agctagactg gcggttttta    4920
tggacagcaa gcgaaccgga attgccagct ggggcgccct ctggtaaggt tgggaagccc    4980
tgcaaagtaa actggatggc tttcttgccg ccaaggatct gatggcgcag gggatcaaga    5040
tctgatcaag agacaggatg aggatcgttt cgcatgattg aacaagatgg attgcacgca    5100
```

```
ggttctccgg ccgcttgggt ggagaggcta ttcggctatg actgggcaca acagacaatc    5160
ggctgctctg atgccgccgt gttccggctg tcagcgcagg ggcgcccggt tcttttttgtc   5220 aagaccgacc tgtccggtgc cctgaatgaa ctgcaggacg aggcagcgcg gctatcgtgg    5280
ctggccacga cgggcgttcc ttgcgcagct gtgctcgacg ttgtcactga agcgggaagg    5340
gactggctgc tattgggcga agtgccgggg caggatctcc tgtcatccca ccttgctcct    5400
gccgagaaag tatccatcat ggctgatgca atgcggcggc tgcatacgct tgatccggct    5460
acctgcccat tcgaccacca agcgaaacat cgcatcgagc gagcacgtac tcggatggaa    5520
gccggtcttg tcgatcagga tgatctggac gaagagcatc aggggctcgc gccagccgaa    5580
ctgttcgcca ggctcaaggc gcgcatgccc gacggcgagg atctcgtcgt gacccatggc    5640
gatgcctgct tgccgaatat catggtggaa aatggccgct ttctggatt catcgactgt     5700 ggccggctgg gtgtggcgga ccgctatcag gacatagcgt tggctacccg tgatattgct    5760
gaagagcttg gcggcgaatg ggctgaccgc ttcctcgtgc tttacggtat cgccgctccc    5820
gattcgcagc gcatcgcctt ctatcgcctt cttgacgagt tcttctgaat tgaaaagga    5880 agagtatgag tattcaacat ttccgtgtcg cccttattcc cttttttgcg gcattttgcc    5940
ttcctgtttt tgctcaccca gaaacgctgg tgaaagtaaa agatgctgaa gatcagttgg    6000
gtgcacgagt gggttacatc gaactggatc tcaacagcgg taagatcctt gagagttttc    6060
gccccgaaga acgttttcca atgatgagca cttttaaagt tctgctatgt ggcgcggtat    6120
tatcccgtat tgacgccggg caagagcaac tcggtcgccg catacactat tctcagaatg    6180
acttggttga gtactcacca gtcacagaaa agcatcttac ggatggcatg acagtaagag    6240
aattatgcag tgctgccata accatgagtg ataacactgc ggccaactta cttctgacaa    6300
cgatcggagg accgaaggag ctaaccgctt ttttgcacaa catgggggat catgtaactc    6360
gccttgatcg ttgggaaccg gagctgaatg aagccatacc aaacgacgag cgtgacacca    6420
cgatgcctgt agcaatggca acaacgttgc gcaaactatt aactggcgaa ctacttactc    6480
tagcttcccg gcaacaatta atagactgga tggaggcgga taaagttgca ggaccacttc    6540
tgcgctcggc ccttccggct ggctggttta ttgctgataa atctggagcc ggtgagcgtg    6600
ggtctcgcgg tatcattgca gcactggggc cagatggtaa gccctcccgt atcgtagtta    6660
tctacacgac ggggagtcag gcaactatgg atgaacgaaa tagacagatc gctgagatag    6720
gtgcctcact gattaagcat tggtaactgt cagaccaagt ttactcatat atactttaga    6780
ttgatttaaa acttcatttt taatttaaaa ggatctaggt gaagatcctt tttgataatc    6840
tcatgaccaa aatcccttaa cgtgagtttt cgttccactg agcgtcagac cccgtagaaa    6900
agatcaaagg atcttcttga gatcctttt ttctgcgcgt aatctgctgc ttgcaaacaa    6960
aaaaaccacc gctaccagcg gtggtttgtt tgccggatca agagctacca actctttttc    7020
cgaaggtaac tggcttcagc agagcgcaga taccaaatac tgttcttcta gtgtagccgt    7080
agttaggcca ccacttcaag aactctgtag caccgcctac atacctcgct ctgctaatcc    7140
tgttaccagt ggctgctgcc agtggcgata agtcgtgtct taccgggttg gactcaagac    7200
gatagttacc ggataaggcg cagcggtcgg gctgaacggg gggttcgtgc acacagccca    7260
gcttggagcg aacgacctac accgaactga gatacctaca gcgtgagcta tgagaaagcg    7320
ccacgcttcc cgaagggaga aaggcggaca ggtatccggt aagcggcagg gtcggaacag    7380
gagagcgcac gagggagctt ccagggggaa acgcctggta tctttatagt cctgtcgggt    7440
ttcgccacct ctgacttgag cgtcgatttt tgtgatgctc gtcaggggg cggagcctat    7500
```

```
ggaaaaacgc cagcaacgcg gccttttac ggttcctggc cttttgctgg ccttttgctc      7560
acatgttctt tcctgcgtta tccctgatt ctgtggataa ccgtattacc gcctttgagt      7620
gagctgatac cgctcgccgc agccgaacga ccgagcgcag cgagtcagtg agcgaggaag     7680
cggaag                                                                7686

<210> SEQ ID NO 106
<211> LENGTH: 33
<212> TYPE: DNA
<213> ORGANISM: Artificial Sequence
<220> FEATURE:
<223> OTHER INFORMATION: Synthetic, Primer LX-268-139-S2D-F

<400> SEQUENCE: 106
ggtcaccata tggacactct gccgatctct tcc                                    33

<210> SEQ ID NO 107
<211> LENGTH: 34
<212> TYPE: DNA
<213> ORGANISM: Artificial Sequence
<220> FEATURE:
<223> OTHER INFORMATION: Synthetic, Primer LX-268-139-S2D-R

<400> SEQUENCE: 107
gtataaggat cctcatacga ccatagggtg tacg                                   34

<210> SEQ ID NO 108
<211> LENGTH: 1725
<212> TYPE: DNA
<213> ORGANISM: Artificial Sequence
<220> FEATURE:
<223> OTHER INFORMATION: Synthetic, FS_D_3.5 coding sequence

<400> SEQUENCE: 108
atgtctactt tacctatttc ttctgtttcc tcatcttcta gtacctcccc attggtagtc        60
gatgacaagg attctactaa accggacgta atcagacata ccacaaattt caacgcgtct       120
atttggggtg accagttttt aacatacgat gaacccgagg atttggttat gaagaagcaa       180
ctcgtagagg aactgaagga agaggttaag aaagaactta ttacaatcaa aggatcaaat       240
gagcctatgc aacatgttaa actcatcgag ctgatcgatg ccgtgcagcg tcttggaatt       300
gcttaccatt tgaggagga aattgaggaa gctttgcaac atattcacgt tacttacgga       360
gagcagtggg tcgataaaga aaatcttcag tcaatctcgc tatggtttcg attacttaga      420
caacagggat tcaacgtttc gagtggagtg tttaaagatt ttatgacga aaagggaaag       480 tttaaagaaa gcctctgtaa tgatgctcaa ggtattttag ctctctatga ggcggcgttt      540
atgagggttg aggatgaaac tatcttagat aacgccttgg agttcagtaa ggttcatctc     600
gatataattg ctaaagatcc aagctgtgat tcatctctac gtacacagat tcatcaggca     660
ttaaagcagc cactcagacg cagactggct cgaatagaag ctcttcacta tgccaatc        720 tatcaacagg agactagtca tgatgaagtt ttattgaagc tagcgaagct ggattttcct     780
gtgctccaat ctatgcacaa aaaggaattg tcgcatattt gtaagtggtg gaaggacctc     840
gatttgcaga acaaactacc gtttgttcgt gacagagtcg tcgagggata tttttggatt     900
ttgagtattt attatgaacc tcagcatgca cgtactcgta tgtttcttat gaagtcgtgt     960
atgtggctgg tagtcctgga tgatacattt gataactacg gaacatacga ggagttggag    1020
attttcacgc aagctgtcga gaggtggtca atatcatgtc tcgacatgct accagaatac    1080
atgaaattga tctatcaaga gcttgtcaac cttcacgttg aaatggagga gagtcttgag    1140
```

-continued

```
aaagaaggta aaacttatca aatccactac gttaaggaaa tggccaaaga actggtaaga      1200
aattatctag ttgaagctag atggttaaag gaaggctaca tgcctacttt agaggagtac      1260
atgagcgtta gcatggttac ggggacttac gggcttatga ccgctcggag ttacgttggt      1320
cgtggggaca tcgtcaatga agatacgttt aagtgggtgt cttcgtaccc gcctatcgta      1380
aaagcgtcgt gtgttattat ccgtctgatg gatgatatcg tgtctcataa agaagaacaa      1440
gaacgagggc atgttgcaag ttctatcgaa tgctattcga agaatctggg ggccagtgaa      1500
gaagaggcct gcgagtacat tagccgtaag gttgaggatg catggaaagt tatcaaccga      1560
gagtcgttgc gtccaactgc cgttccgttt cctttgctta tgcctgccat caatttggct      1620
agaatgtgtg aggttctcta tagtgtaaac gacggattta cacatgcaga aggagatatg      1680
aagtcttaca tgaagtcatt cttcgtccac ccgatggtcg tttga                     1725
```

<210> SEQ ID NO 109
<211> LENGTH: 56
<212> TYPE: DNA
<213> ORGANISM: Artificial Sequence
<220> FEATURE:
<223> OTHER INFORMATION: Synthetic, Primer LX-268-130-4-S2D-R

<400> SEQUENCE: 109

```
ctttaacgtc aaggagaaaa aaccccggat ccatggacac tctgccgatc tcttcc          56
```

<210> SEQ ID NO 110
<211> LENGTH: 59
<212> TYPE: DNA
<213> ORGANISM: Artificial Sequence
<220> FEATURE:
<223> OTHER INFORMATION: Synthetic, Primer LX-268-130-3-S2D-F

<400> SEQUENCE: 110

```
ccttcctttt cggttagagc ggatcttagc tagctcatac gaccataggg tgtacgaag       59
```

<210> SEQ ID NO 111
<211> LENGTH: 574
<212> TYPE: PRT
<213> ORGANISM: Artificial Sequence
<220> FEATURE:
<223> OTHER INFORMATION: Synthetic, A. annua b-farnesene synthase amino
      acid sequence

<400> SEQUENCE: 111

```
Met Ser Thr Leu Pro Ile Ser Ser Val Ser Phe Ser Ser Ser Thr Ser
1               5                  10                  15

Pro Leu Val Val Asp Asp Lys Val Ser Thr Lys Pro Asp Val Ile Arg
            20                  25                  30

His Thr Met Asn Phe Asn Ala Ser Ile Trp Gly Asp Gln Phe Leu Thr
        35                  40                  45

Tyr Asp Glu Pro Glu Asp Leu Val Met Lys Lys Gln Leu Val Glu Glu
    50                  55                  60

Leu Lys Glu Glu Val Lys Lys Glu Leu Ile Thr Ile Lys Gly Ser Asn
65                  70                  75                  80

Glu Pro Met Gln His Val Lys Leu Ile Glu Leu Ile Asp Ala Val Gln
                85                  90                  95

Arg Leu Gly Ile Ala Tyr His Phe Glu Glu Glu Ile Glu Glu Ala Leu
            100                 105                 110

Gln His Ile His Val Thr Tyr Gly Glu Gln Trp Val Asp Lys Glu Asn
        115                 120                 125

Leu Gln Ser Ile Ser Leu Trp Phe Arg Leu Leu Arg Gln Gln Gly Phe
```

-continued

```
              130                 135                 140
Asn Val Ser Ser Gly Val Phe Lys Asp Phe Met Asp Glu Lys Gly Lys
145                 150                 155                 160

Phe Lys Glu Ser Leu Cys Asn Asp Ala Gln Gly Ile Leu Ala Leu Tyr
                165                 170                 175

Glu Ala Ala Phe Met Arg Val Glu Asp Glu Thr Ile Leu Asp Asn Ala
                180                 185                 190

Leu Glu Phe Thr Lys Val His Leu Asp Ile Ile Ala Lys Asp Pro Ser
                195                 200                 205

Cys Asp Ser Ser Leu Arg Thr Gln Ile His Gln Ala Leu Lys Gln Pro
210                 215                 220

Leu Arg Arg Arg Leu Ala Arg Ile Glu Ala Leu His Tyr Met Pro Ile
225                 230                 235                 240

Tyr Gln Gln Glu Thr Ser His Asp Glu Val Leu Leu Lys Leu Ala Lys
                245                 250                 255

Leu Asp Phe Ser Val Leu Gln Ser Met His Lys Lys Glu Leu Ser His
                260                 265                 270

Ile Cys Lys Trp Trp Lys Asp Leu Asp Leu Gln Asn Lys Leu Pro Tyr
                275                 280                 285

Val Arg Asp Arg Val Val Glu Gly Tyr Phe Trp Ile Leu Ser Ile Tyr
                290                 295                 300

Tyr Glu Pro Gln His Ala Arg Thr Arg Met Phe Leu Met Lys Thr Cys
305                 310                 315                 320

Met Trp Leu Val Val Leu Asp Asp Thr Phe Asp Asn Tyr Gly Thr Tyr
                325                 330                 335

Glu Glu Leu Glu Ile Phe Thr Gln Ala Val Glu Arg Trp Ser Ile Ser
                340                 345                 350

Cys Leu Asp Met Leu Pro Glu Tyr Met Lys Leu Ile Tyr Gln Glu Leu
                355                 360                 365

Val Asn Leu His Val Glu Met Glu Glu Ser Leu Glu Lys Glu Gly Lys
                370                 375                 380

Thr Tyr Gln Ile His Tyr Val Lys Glu Met Ala Lys Glu Leu Val Arg
385                 390                 395                 400

Asn Tyr Leu Val Glu Ala Arg Trp Leu Lys Glu Gly Tyr Met Pro Thr
                405                 410                 415

Leu Glu Glu Tyr Met Ser Val Ser Met Val Thr Gly Thr Tyr Gly Leu
                420                 425                 430

Met Ile Ala Arg Ser Tyr Val Gly Arg Gly Asp Ile Val Thr Glu Asp
                435                 440                 445

Thr Phe Lys Trp Val Ser Ser Tyr Pro Pro Ile Ile Lys Ala Ser Cys
                450                 455                 460

Val Ile Val Arg Leu Met Asp Asp Ile Val Ser His Lys Glu Glu Gln
465                 470                 475                 480

Glu Arg Gly His Val Ala Ser Ser Ile Glu Cys Tyr Ser Lys Glu Ser
                485                 490                 495

Gly Ala Ser Glu Glu Glu Ala Cys Glu Tyr Ile Ser Arg Lys Val Glu
                500                 505                 510

Asp Ala Trp Lys Val Ile Asn Arg Glu Ser Leu Arg Pro Thr Ala Val
                515                 520                 525

Pro Phe Pro Leu Leu Met Pro Ala Ile Asn Leu Ala Arg Met Cys Glu
                530                 535                 540

Val Leu Tyr Ser Val Asn Asp Gly Phe Thr His Ala Glu Gly Asp Met
545                 550                 555                 560
```

```
Lys Ser Tyr Met Lys Ser Phe Phe Val His Pro Met Val Val
            565                 570
```

<210> SEQ ID NO 112
<211> LENGTH: 1725
<212> TYPE: DNA
<213> ORGANISM: Artificial Sequence
<220> FEATURE:
<223> OTHER INFORMATION: Synthetic, A. annua b-farnesene synthase
      nucleotide sequence

<400> SEQUENCE: 112

```
atgtcgactc ttcctatttc tagtgtttca ttctcttcat ctacgtcacc tttggttgtt      60
gacgataaag ttagcacgaa accagatgtt atccgccata ccatgaattt caatgctagc     120
atatggggag atcaatttct tacatatgat gagccagaag atttggttat gaagaaacaa     180
cttgttgaag agctcaaaga ggaagtcaag aaagagctaa taacgatcaa aggttcaaat     240
gaaccgatgc agcatgtcaa gttgatagaa cttattgatg cagtccaacg gcttggcata     300
gcctatcatt ttgaagagga gattgaagaa gccttgcaac atatccatgt tacatatggc     360
gagcagtggg tcgataaaga aaacctacaa agcatttctc tttggttccg actcctacga     420
caacaaggct tcaacgtctc atcaggagta ttcaaggact ttatggacga agggaaaa       480
tttaaggaat ccttatgtaa tgatgctcag ggaattcttg ctctgtatga agcggcattt     540
atgagggtgg aagatgaaac aatactagat aatgcgctcg agttcactaa agttcacctt     600
gacatcatag ccaaggatcc ttcttgtgac tcttccctaa gaacccaaat acaccaagcg     660
ttaaagcagc cacttaggag aaggctggca aggattgagg cgttgcatta catgcctatc     720
taccaacaag aaacatccca cgatgaggtc ttactgaagc ttgcaaaatt agattttagc     780
gtgcttcagt cgatgcacaa aaaggaactt agccacattt gcaaatggtg aaggatttg      840
gacctccaaa ataagcttcc ttatgttcga gacagggtgg tggaaggcta tttttggata     900
ctatccatct attacgagcc tcaacatgct cgaacaagaa tgttcctaat gaaaacatgc     960
atgtggttag tcgttttaga tgatacattt gataattatg gtacttatga agaactcgaa    1020
atctttacac aagctgttga agatggtca ataagctgcc tggatatgct tccagaatac    1080
atgaaactaa tatatcaaga gcttgtgaat cttcacgtgg aaatggagga atcacttgaa    1140
aaggagggaa aaacatatca aattcactat gtcaaggaga tggcaaaaga gttggttcgc    1200
aattacttgg tagaagccag atggctaaaa gaggggtaca tgccaactct tgaggagtac    1260
atgtctgtgt caatggtgac tggtacctat ggcttgatga tagcgagatc ttatgtcggc    1320
aggggtgata tcgtcaccga ggatacccttt aaatgggtgt cctcgtatcc tcctattata    1380
aaagcttcat gtgtgattgt aagacttatg gatgatattt tcagccacaa ggaggaacaa    1440
gagagaggcc atgttgcttc aagcatcgaa tgctattcta aggaaagtgg tgcatcagag    1500
gaggaagcgt gtgaatatat ctcaagaaaa gttgaagatg catggaaagt tataaaccga    1560
gagtcgctca ggcctacagc tgtcccattt cctctactta tgcctgcaat caaccttgca    1620
cgtatgtgtg aagtcctata tagcgtcaac gatggcttca ctcatgctga gggagacatg    1680
aaaagttaca tgaaatcgtt cttcgttcac cctatggttg tctaa                    1725
```

<210> SEQ ID NO 113
<211> LENGTH: 47
<212> TYPE: DNA
<213> ORGANISM: Artificial Sequence
<220> FEATURE:
<223> OTHER INFORMATION: Synthetic, Primer AM-288-160-CPK2090

```
<400> SEQUENCE: 113
cacgttcgcc ggccaaatta aagcagatct agatcggtga aaacatc            47

<210> SEQ ID NO 114
<211> LENGTH: 50
<212> TYPE: DNA
<213> ORGANISM: Artificial Sequence
<220> FEATURE:
<223> OTHER INFORMATION: Synthetic, Primer AM-288-160-CPK2091

<400> SEQUENCE: 114
gaagaaatag gcaaagttga catggatccg tttagtccgt attgctattg            50

<210> SEQ ID NO 115
<211> LENGTH: 50
<212> TYPE: DNA
<213> ORGANISM: Artificial Sequence
<220> FEATURE:
<223> OTHER INFORMATION: Synthetic, Primer AM-288-160-CPK2092

<400> SEQUENCE: 115
cacgttcgcc ggccaaatta aagcagatct ctctacaacc gcagggaaat            50

<210> SEQ ID NO 116
<211> LENGTH: 4309
<212> TYPE: DNA
<213> ORGANISM: Artificial Sequence
<220> FEATURE:
<223> OTHER INFORMATION: Synthetic, Construct D

<400> SEQUENCE: 116
gaagatccga ggcctagctt taacgaacgc agaattttcg agttattaaa cttaaaatac    60
gctgaacccg aacatagaaa tatcgaatgg gaaaaaaaaa ctgcataaag cattaaaag   120
aggagcgaat tttttttaa taaaaatctt aataatcatt aaaagataaa taatagtcta   180
tatatacgta tataataaa aaatattcaa aaaataaaat aaactattat tttagcgtaa   240
aggatgggga agagaaaag aaaaaaattg atctatcgat ttcaattcaa ttcaatttat   300
ttcttttcgg ataagaaagc aacacctggc aattccttac cttccaataa ttccaaagaa   360
gcaccaccac cagtagagac atgggagagt caaacgacca taggatgaac gaagaaggac   420
ttcatataag atttcatgtc accctcagca tgagtaaaac catcattaac agagtacaag   480
acctcacaca ttctagctaa gtttattgct ggcattaaca aagggaaggg aacggctgtt   540
ggacgcaaag attctctatt gattactttc caggcatcct caactttcct actaatatat   600
tcacatgctt cctcttcaga agcacctgat tctttagagt aacattctat agatgaagcc   660
acatgtcctc tttcttgttc ttccttgtga gatacaatat cgtccattaa tcttactatt   720
acacaggaag ctttaataat aggtgggtaa ctagaaaccc atttgaatgt gtcttcagta   780
acaatgtctc ctctgccaac ataggacctt gcaatcatca aaccataagt accagtaacc   840
atagaaacag acatgtattc ttctaaagta ggcatataac cttccttcaa ccatcttgct   900
tctactaagt aattacgaac taattcttta gccatctcct taacgtaatg aatctgatag   960
gtctttccct cctttttccaa agattcttcc atttccacat gcaaattgac taattcttgg  1020
tagattaatt tcatatattc gggcaacata tctaagcatg agatagacca tctctcgacg  1080
gcttgagtaa aaatctccaa ttcttcgtat gttccataat tatcaaaagt atcgtccaaa  1140
actactaacc acatgcatgt tttcatcaaa acattcttg ttctagcgtg ttgtggctca  1200
tagtatatgg acaatatcca gaagtagcct tcgacaacac gatcacgtac ataaggtaac  1260
```

```
ttatttttgta aatctaaatc tttccaccac ttacagatat gtgacaattc cttttatgc    1320 atagactgca aaacactgaa atccaacttg gctaatttca acaatacttc atcatgagat    1380
gtttcctgtt ggtagattgg catgtaatgt aatgcttcaa tccttgctaa tctccttctt    1440
aaaggttgtt ttaaggcttg atggatttgt gtacgcaatg aagaatcgca agatgggtct    1500
tttgctatga tatctaaatg aacttttgtg aattccaaag cattgtctaa gatggtttca    1560
tcttcaaccc tcataaatgc agcttcatat aaggctaata ttccttgtgc atcattgcat    1620
aaagactctt tgaatttacc ttttttcgtcc ataaagtctt tgaaaacgcc agaggagacg    1680
ttaaagccct gttgacgcaa caacctgaac cacaatgaaa tactctgtaa attttccta    1740 tccacccact gttcaccata ggtaacatgt atatgttgca aagcttcctc gatctcttct    1800
tcaaaatggt aagctatacc taaacgttga acagcatcaa ttaattcaat caatttcaca    1860
tgctgcatgg gctcatttga acctttgata gttatcaatt ccttcttaac ttcctctttt    1920
aattcctcca ctaattgttt cttcataact aaatcttcag gctcatcata ggtcaagaat    1980
tgatctcccc aaatagaagc attgaaattc attgtatgtc tgataacgtc gggcttggtt    2040
gagactttgt cgtccacgac taatggtgat gtagaagagg aaaatgacac agaagaaata    2100
ggcaaagttg acatggatcc ggggtttttt ctccttgacg ttaaagtata gaggtatatt    2160
aacaattttt tgttgatact tttattacat ttgaataaga agtaatacaa accgaaaatg    2220
ttgaaagtat tagttaaagt ggttatgcag ttttttgcatt tatatatctg ttaatagatc    2280
aaaaatcatc gcttcgctga ttaattaccc cagaaataag gctaaaaaac taatcgcatt    2340
atcatcctat ggttgttaat ttgattcgtt catttgaagg tttgtgggggc caggttactg    2400 ccaattttttc ctcttcataa ccataaaagc tagtattgta gaatctttat tgttcggagc    2460
agtgcggcgc gaggcacatc tgcgtttcag gaacgcgacc ggtgaagacg aggacgcacg    2520
gaggagagtc ttccttcgga gggctgtcac ccgctcggcg gcttctaatc cgtactagat    2580
ctgctttaat ttggccggcg aacgtggcga gaaaggaagg gaagaaagcg aaaggagcgg    2640
gcgctagggc gctggcaagt gtagcggtca cgctgcgcgt aaccaccaca cccgccgcgc    2700
ttaatgcgcc gctacagggc gcgtcgcgcc attcgccatt caggctgcgc aactgttggg    2760
aagggcgatc ggtgcgggcc tcttcgctat tacgccagct gaattggagc gacctcatgc    2820
tatacctgag aaagcaacct gacctacagg aaagagttac tcaagaataa gaattttcgt    2880
tttaaaacct aagagtcact ttaaaatttg tatacactta ttttttttat aacttattta    2940
ataataaaaa tcataaatca taagaaattc gcttattcaa ctaattctat agatgataaa    3000
aatggtttct ggacctcttt gacgtccttt gatcttacgt tagctaactg ggcgactggt    3060
ggataggccc actcagaagg tgaaacggct cctacattgg cagcttgctc gtagaacttg    3120
caaaattttt gggcatcctc agtcttttcc tccttgactt tctcgtagat ttcagacaac    3180
ctgtacctcc tgtcgcataa atgccatgtg acataaccat gcatgaagca ctctatggtg    3240
tccattactt gagggtcctt gtctgagaaa actgcaacca tttgctttga agagtgcaag    3300
gtatcctggg tcaattttttc taaggcctcg tgtaatgata tctcgtcaga aacaacgtag    3360
ttctttacca aagagatctg atccctctcg tcgtcgaact ccttgtaaaa tgacatcaaa    3420
tcattaaccc agaccatcca atttccatt tgagctatgg ctgaagtgat ctccaaaaac    3480
aatgatcttt cattgaactg ctcctttggc cacaaagagg caccgacgca gtgtcctaaa    3540
ccgttcattc ttctcaagaa ctgtgggtag tcgtgagaac ctgggaatcc tccaaaattg    3600
tattgttcta tccagcaacc ctcgaagaag tctaaggtag acctgatcaa gttcaatgag    3660
```

```
caaaaaggac caaaatgcct caatacgttt ggaaagtgct cgtttactaa agcccaccaa    3720
ggatgagcct gttctctacc tgcttgtaag tcatcgaagt agtttaccat agtagggtat    3780
gggtcgtctt ttgaatcgtc caataccaag gtgtaggtat agtggattga caagtctgcc    3840
atacactctt tagatacctt ggcccatgaa tatacaacca taccgacaat ggtctgcaat    3900
gaagcttgca atctcttagg gtcgaccttc aacaactgct gctgtcttgg ctgggcgaag    3960
tggtgggcgg ctttgttgta ggcgtagtgt aagttctcaa tcctctcctc cctggtatag    4020
tttgagtccc tgtacctaat gtactccaac aacctgacgg tggtgttcaa gaagtactcg    4080
gttggaaagt tttccatgaa ttcgaatttt caaaaattct tacttttttt ttggatggac    4140
gcaaagaagt ttaataatca tattacatgg cattaccacc atatacatat ccatatacat    4200
atccatatct aatcttactt atatgttgtg gaaatgtaaa gagccccatt atcttagcct    4260
aaaaaaacct tctctttgga actttcagta atacgcttaa ctgctcatt              4309
```

<210> SEQ ID NO 117
<211> LENGTH: 5714
<212> TYPE: DNA
<213> ORGANISM: Artificial Sequence
<220> FEATURE:
<223> OTHER INFORMATION: Synthetic, Expression plasmid pAM1490

<400> SEQUENCE: 117

```
ttcttgaaga cgaaagggcc tcgtgatacg cctatttta taggttaatg tcatgataat      60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttgata atctcatgac caaaatccct taacgtgagt ttcgttcca    1200 ctgagcgtca gaccccgtag aaaagatcaa aggatcttct tgagatcctt ttttctgcg    1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
```

```
tacatacctc gctctgctaa tcctgttacc agtggctgct gccagtggcg ataagtcgtg    1500
tcttaccggg ttggactcaa gacgatagtt accggataag gcgcagcggt cgggctgaac    1560
ggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggccttt tacggttcct    1860
ggccttttgc tggccttttg ctcacatgtt ctttcctgcg ttatccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
tgtctgcctg ttcatccgcg tccagctcgt tgagtttctc cagaagcgtt aatgtctggc    2400
ttctgataaa gcgggccatg ttaagggcgg ttttttcctg tttggtcact gatgcctccg    2460
tgtaaggggg atttctgttc atggggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag gcggcgccct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga aagaatcat    3360
aatgggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag gcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
```

```
gcgtattggg cgccagggtg gttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt gcgacggcg    4620 cgtgcagggc cagactggag gtggcaacgc caatcagcaa cgactgtttg cccgccagtt    4680
gttgtgccac gcggttggga atgtaattca gctccgccat cgccgcttcc acttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg    5100 aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actataggg aattgtgagc ggataacaat tcccctctag    5280
aaataatttt gtttaacttt aagaaggaga tataccatgg gcagcagcca tcatcatcat    5340
catcacagca gcggcctgga agttctgttc caggggcccc atatgctcga ggatccggct    5400
gctaacaaag cccgaaagga agctgagttg gctgctgcca ccgctgagca ataactagca    5460
taaccccttg gggcctctaa acgggtcttg aggggttttt tgctgaaagg aggaactata    5520
tccggatatc ccgcaagagg cccggcagta ccggcataac caagcctatg cctacagcat    5580
ccagggtgac ggtgccgagg atgacgatga gcgcattgtt agatttcata cacggtgcct    5640
gactgcgtta gcaatttaac tgtgataaac taccgcatta agcttatcg atgataagct    5700 gtcaaacatg agaa                                                    5714
```

<210> SEQ ID NO 118
<211> LENGTH: 1725
<212> TYPE: DNA
<213> ORGANISM: Artificial Sequence
<220> FEATURE:
<223> OTHER INFORMATION: Synthetic, FS_A coding sequence

<400> SEQUENCE: 118

```
atgtcaactt tgcctatttc ttctgtgtca tttcctctt ctacatcacc attagtcgtg      60
gacgacaaag tctcaaccaa gcccgacgtt atcagacata caatgaattt caatgcttct     120
atttggggag atcaattctt gacctatgat gagcctgaag atttagttat gaagaaacaa     180
```

```
ttagtggagg aattaaaaga ggaagttaag aaggaattga taactatcaa aggttcaaat      240
gagcccatgc agcatgtgaa attgattgaa ttaattgatg ctgttcaacg tttaggtata      300
gcttaccatt ttgaagaaga gatcgaggaa gctttgcaac atatacatgt tacctatggt      360
gaacagtggg tggataagga aaatttacag agtatttcat tgtggttcag gttgttgcgt      420
caacagggct ttaacgtctc ctctggcgtt ttcaaagact ttatggacga aaaaggtaaa      480
ttcaaagagt ctttatgcaa tgatgcacaa ggaatattag ccttatatga agctgcattt      540
atgagggttg aagatgaaac catcttagac aatgctttgg aattcacaaa agttcattta      600
gatatcatag caaaagaccc atcttgcgat tcttcattgc gtacacaaat ccatcaagcc      660
ttaaaacaac ctttaagaag gagattagca aggattgaag cattacatta catgccaatc      720
taccaacagg aaacatctca tgatgaagta ttgttgaaat tagccaagtt ggatttcagt      780
gttttgcagt ctatgcataa aaaggaattg tcacatatct gtaagtggtg aaagattta       840 gatttacaaa ataagttacc ttatgtacgt gatcgtgttg tcgaaggcta cttctggata      900
ttgtccatat actatgagcc acaacacgct agaacaagaa tgttttttgat gaaaacatgc      960 atgtggttag tagttttgga cgatactttt gataattatg gaacatacga agaattggag     1020 attttttactc aagccgtcga gagatggtct atctcatgct agatatgtt gcccgaatat      1080 atgaaattaa tctaccaaga attagtcaat ttgcatgtgg aaatggaaga atctttggaa     1140
aaggagggaa agacctatca gattcattac gttaaggaga tggctaaaga attagttcgt     1200
aattacttag tagaagcaag atggttgaag gaaggttata tgcctacttt agaagaatac     1260
atgtctgttt ctatggttac tggtacttat ggtttgatga ttgcaaggtc ctatgttggc     1320
agaggagaca ttgttactga agacacattc aaatggggtt ctagttaccc acctattatt     1380
aaagcttcct gtgtaatagt aagattaatg gacgatattg tatctcacaa ggaagaacaa     1440
gaaagaggac atgtggcttc atctatagaa tgttactcta aagaatcagg tgcttctgaa     1500
gaggaagcat gtgaatatat tagtaggaaa gttgaggatg cctggaaagt aatcaataga     1560
gaatctttgc gtccaacagc cgttcccttc ccttttgttaa tgccagcaat aaacttagct     1620
agaatgtgtg aggtcttgta ctctgttaat gatggtttta ctcatgctga gggtgacatg     1680
aaatcttata tgaagtcctt cttcgttcat cctatggtcg tttga                     1725
```

<210> SEQ ID NO 119  
<211> LENGTH: 1725  
<212> TYPE: DNA  
<213> ORGANISM: Artificial Sequence  
<220> FEATURE:  
<223> OTHER INFORMATION: Synthetic, FS_B coding sequence

<400> SEQUENCE: 119

```
atgtcaacat tgcctatatc ttcagtctca ttctcatctt ctacctcacc attggttgta       60
gacgacaaag tttctacaaa gccagacgtc ataaggcata caatgaactt caacgcctct      120
atatggggag accagttctt gacctatgac gaaccagagg atttagtcat gaaaaaacag      180
ttggtcgagt agtaaagga ggaggttaag aaggagttga tcaccataaa aggttcaaac      240
gagcctatgc aacacgtcaa gttgatagag ttaattgacg ctgttcaaag gttaggaatt      300
gcatatcatt tcgaagagga gattgaagag gcattcagc atattcatgt tacttatgga      360
gaacaatggg ttgacaagga gaacttgcaa tcaatctctt tatggtttag gttgttaagg     420
caacagggat tcaacgtctc ttcaggtgtc tttaaagatt tcatggacga aagggaaag      480 tttaaggagt cattatgcaa cgatgctcaa ggaatttggg cattatatga agctgccttt      540
```

```
atgagggtag aggacgagac tatattagac aacgcattgg aattcactaa agtccactta    600
gacatcatcg caaaggatcc ttcatgcgac tcttctttaa gaacacaaat acatcaagca    660
ttgaagcaac ctttgaggag aaggttagca aggatagaag ccttgcacta tatgcctatc    720
tatcagcagg aaacatcaca tgatgaagtt ttgttgaagt tggccaaatt ggacttctct    780
gtattgcagt caatgcataa aaaggaattg tctcatatct gcaaatggtg aaggatttg     840
gatttgcaga taagttgcc ttatgttaga gacagagtcg ttgagggata tttctggata    900
ttgtctatct actacgagcc tcagcacgct agaacaagaa tgttcttaat gaagacttgc    960
atgtggttgg tcgttttaga cgacactttt gacaattacg gtacctacga ggaattagag   1020
atcttcactc aagctgtaga gagatggtca atttcatgct tggacatgtt accagagtat   1080
atgaagttga tctaccagga gttagtcaac ttacacgtcg atgtgaaga atctttggag    1140
aaagagggta aaacttatca gatccactat gtcaaggaga tggcaaaaga gttggtaaga   1200
aactacttgg tagaagctag atggttgaag gagggttaca tgcctacctt ggaggaatat   1260
atgtctgttt ctatggtcac tggaacctac ggattaatga ttgctagatc ttatgtcggt   1320
agaggagaca ttgtaaccga agacacattc aagtgggtat catcttatcc acctatcata   1380
aaggcctcat gcgttattgt aaggttgatg gatgatattg tatctcacaa agaggaacaa   1440
gagaggggac atgtagcatc atctatcgag tgttattcaa aagaatcagg agcatctgaa   1500
gaagaagcct gtgagtacat ctctagaaaa gtcgaagatg catggaaagt tatcaacaga   1560
gagtcattga ggccaaccgc agtcccttc ccattattaa tgcctgccat aaacttagca    1620
agaatgtgcg aagtcttata ttcagttaat gacggtttca cccacgccga gggtgacatg   1680
aaatcataca tgaagtcatt ctttgttcac cctatggtag tctaa                   1725
```

<210> SEQ ID NO 120  
<211> LENGTH: 1725  
<212> TYPE: DNA  
<213> ORGANISM: Artificial Sequence  
<220> FEATURE:  
<223> OTHER INFORMATION: Synthetic, FS_C coding sequence

<400> SEQUENCE: 120

```
atgtcaacct tgcctatttc ttctgtctca ttctcttcat ctacctctcc attggtcgta     60
gacgataagg tctctactaa accagacgtc atcaggcaca ccatgaattt caacgcttct    120
atatggggag accagttttt aacttacgac gaacctgagg atttggtcat gaaaaaacag    180
ttggtcgaag aattgaagga ggaggtcaag aaggagttga ttacaatcaa gggatcaaac    240
gaacctatgc agcacgttaa gttgatcgaa ttaatagatg ctgtccaaag attgggtata    300
gcctaccact tcgaggagga aatcgaggag gctttacaac atatacacgt cacatacggt    360
gaacagtggg tcgataaaga gaatttgcag tctatctcat tgtggttcag gttgttaagg    420
caacaaggtt ttaatgtttc atctggagtt ttcaaggact ttatgacga  aaaggtaaa    480
ttcaaggagt ctttgtgcaa cgatgctcag ggtattttag cattgtatga ggccgcattt    540
atgagggttg aagacgagac tatcttagat aacgcattgg agttcaccaa ggtccactta    600
gacattattg ctaaagaccc atcatgtgac tcttctttga aactcaaat acaccaggca    660
ttaaagcaac ctttgaggag aaggttggct agaatcgaag cattacacta tatgccaata    720
tatcagcagg aaacctcaca cgacgaagtt ttgttaaagt tagcaaaatt ggacttctct    780
gtcttgcagt caatgcataa gaaggagttg tctcatatct gcaagtggtg gaaggattta    840
gatttacaaa ataagttgcc atacgtcaga gataggggttg tagagggata cttctggatc   900
```

-continued

```
ttgtctatat actatgagcc tcagcacgcc agaaccagaa tgttcttaat gaagacctgc       960
atgtggttag tagtattaga cgacaccttc gacaattatg aacatacga ggaattggag      1020 atctttactc aagccgttga gagatggtct atttcttgct tggacatgtt gccagagtat      1080
atgaagttga tctaccagga gttagttaac ttgcacgtcg aaatggagga atctttggag      1140
aaagagggaa agacatacca gattcactat gtcaaggaaa tggccaaaga gttggtaagg      1200
aactatttgg ttgaggccag atggttgaaa gagggttata tgcctacctt ggaggagtac      1260
atgtcagtct caatggttac tggtacctat ggtttgatga ttgccagatc atacgtcgga      1320
agaggtgata tcgtaacaga ggataccttc aagtgggttt cttcataccc tcctatcatt      1380
aaggcctctt gcgtcatagt caggttgatg gatgacattg tttctcataa ggaggaacag      1440
gagaggggtc acgtagcctc atcaatagag tgctattcaa aagagtctgg tgcatcagag      1500
gaagaggcat gtgaatacat ctctagaaaa gtagaggatg cctggaaggt cattaacagg      1560
gagtcattga gacctactgc tgtaccttt cctttgttga tgcctgctat caacttggca      1620
aggatgtgcg aagttttgta ttcagtaaac gatggtttca ctcacgccga aggtgatatg      1680
aaatcatata tgaaatcttt tttcgtacat cctatggtag tataa                    1725
```

```
<210> SEQ ID NO 121
<211> LENGTH: 29
<212> TYPE: DNA
<213> ORGANISM: Artificial Sequence
<220> FEATURE:
<223> OTHER INFORMATION: Synthetic, Primer AM-288-110-CPK1849

<400> SEQUENCE: 121
gacacagaag aaataggcaa agttgacat                                          29

<210> SEQ ID NO 122
<211> LENGTH: 29
<212> TYPE: DNA
<213> ORGANISM: Artificial Sequence
<220> FEATURE:
<223> OTHER INFORMATION: Synthetic, Primer AM-288-110-CPK1903

<400> SEQUENCE: 122
cggatccatg tcaactttgc ctatttctt                                          29

<210> SEQ ID NO 123
<211> LENGTH: 20
<212> TYPE: DNA
<213> ORGANISM: Artificial Sequence
<220> FEATURE:
<223> OTHER INFORMATION: Synthetic, Primer AM-288-160-CPK2039

<400> SEQUENCE: 123
gaagatccga ggcctagctt                                                    20

<210> SEQ ID NO 124
<211> LENGTH: 44
<212> TYPE: DNA
<213> ORGANISM: Artificial Sequence
<220> FEATURE:
<223> OTHER INFORMATION: Synthetic, Primer AM-288-160-CPK2040

<400> SEQUENCE: 124
ccaccagtag agacatggga gagtcaaacg accataggat gaac                         44

<210> SEQ ID NO 125
<211> LENGTH: 44
<212> TYPE: DNA
```

<210> SEQ ID NO 125
<211> LENGTH: 44
<212> TYPE: DNA
<213> ORGANISM: Artificial Sequence
<220> FEATURE:
<223> OTHER INFORMATION: Synthetic, Primer AM-288-160-CPK2041

<400> SEQUENCE: 125
gttcatccta tggtcgtttg actctcccat gtctctactg gtgg        44

<210> SEQ ID NO 126
<211> LENGTH: 39
<212> TYPE: DNA
<213> ORGANISM: Artificial Sequence
<220> FEATURE:
<223> OTHER INFORMATION: Synthetic, Primer AM-288-160-CPK2042

<400> SEQUENCE: 126
ggcttctaat ccgtactaga tctgctttaa tttggccgg        39

<210> SEQ ID NO 127
<211> LENGTH: 39
<212> TYPE: DNA
<213> ORGANISM: Artificial Sequence
<220> FEATURE:
<223> OTHER INFORMATION: Synthetic, Primer AM-288-160-CPK2043

<400> SEQUENCE: 127
ccggccaaat taaagcagat ctagtacgga ttagaagcc        39

<210> SEQ ID NO 128
<211> LENGTH: 33
<212> TYPE: DNA
<213> ORGANISM: Artificial Sequence
<220> FEATURE:
<223> OTHER INFORMATION: Synthetic, Primer AM-288-160-CPK2044

<400> SEQUENCE: 128
caggtatagc atgaggtcgc tccaattcag ctg        33

<210> SEQ ID NO 129
<211> LENGTH: 33
<212> TYPE: DNA
<213> ORGANISM: Artificial Sequence
<220> FEATURE:
<223> OTHER INFORMATION: Synthetic, Primer AM-288-160-CPK2045

<400> SEQUENCE: 129
cagctgaatt ggagcgacct catgctatac ctg        33

<210> SEQ ID NO 130
<211> LENGTH: 20
<212> TYPE: DNA
<213> ORGANISM: Artificial Sequence
<220> FEATURE:
<223> OTHER INFORMATION: Synthetic, Primer AM-288-160-CPK2046

<400> SEQUENCE: 130
aatgagcagt taagcgtatt        20

<210> SEQ ID NO 131
<211> LENGTH: 45
<212> TYPE: DNA
<213> ORGANISM: Artificial Sequence
<220> FEATURE:
<223> OTHER INFORMATION: Synthetic, Primer AM-288-160-CPK2051

<400> SEQUENCE: 131
gaagaaatag gcaaagttga catggatccg ttctcgaggc agccg        45

```
<210> SEQ ID NO 132
<211> LENGTH: 50
<212> TYPE: DNA
<213> ORGANISM: Artificial Sequence
<220> FEATURE:
<223> OTHER INFORMATION: Synthetic, Primer AM-288-160-CPK2052

<400> SEQUENCE: 132
cacgttcgcc ggccaaatta aagcagatct ccacgatgtt gataatgagc          50

<210> SEQ ID NO 133
<211> LENGTH: 50
<212> TYPE: DNA
<213> ORGANISM: Artificial Sequence
<220> FEATURE:
<223> OTHER INFORMATION: Synthetic, Primer AM-288-160-CPK2053

<400> SEQUENCE: 133
gaagaaatag gcaaagttga catggatccg ttcttaattg ttattcgtac          50

<210> SEQ ID NO 134
<211> LENGTH: 50
<212> TYPE: DNA
<213> ORGANISM: Artificial Sequence
<220> FEATURE:
<223> OTHER INFORMATION: Synthetic, Primer AM-288-160-CPK2054

<400> SEQUENCE: 134
cacgttcgcc ggccaaatta aagcagatct tccaggtatg ggtttgagga          50

<210> SEQ ID NO 135
<211> LENGTH: 50
<212> TYPE: DNA
<213> ORGANISM: Artificial Sequence
<220> FEATURE:
<223> OTHER INFORMATION: Synthetic, Primer AM-288-160-CPK2055

<400> SEQUENCE: 135
gaagaaatag gcaaagttga catggatccg tgtgatgatg ttttatttgt          50

<210> SEQ ID NO 136
<211> LENGTH: 42
<212> TYPE: DNA
<213> ORGANISM: Artificial Sequence
<220> FEATURE:
<223> OTHER INFORMATION: Synthetic, Primer AM-288-160-CPK2056

<400> SEQUENCE: 136
ccggccaaat taaagcagat ctaacggcgg gattcctcta tg          42

<210> SEQ ID NO 137
<211> LENGTH: 50
<212> TYPE: DNA
<213> ORGANISM: Artificial Sequence
<220> FEATURE:
<223> OTHER INFORMATION: Synthetic, Primer AM-288-160-CPK2059

<400> SEQUENCE: 137
gaagaaatag gcaaagttga catggatccg tttgattgat ttgactgtgt          50

<210> SEQ ID NO 138
<211> LENGTH: 50
<212> TYPE: DNA
<213> ORGANISM: Artificial Sequence
<220> FEATURE:
<223> OTHER INFORMATION: Synthetic, Primer AM-288-160-CPK2060
```

<400> SEQUENCE: 138
cacgttcgcc ggccaaatta aagcagatct gtaataaaca caccccgcgt    50

<210> SEQ ID NO 139
<211> LENGTH: 50
<212> TYPE: DNA
<213> ORGANISM: Artificial Sequence
<220> FEATURE:
<223> OTHER INFORMATION: Synthetic, Primer AM-288-160-CPK2061

<400> SEQUENCE: 139
gaagaaatag gcaaagttga catggatccg ttttagttta tgtatgtgtt    50

<210> SEQ ID NO 140
<211> LENGTH: 46
<212> TYPE: DNA
<213> ORGANISM: Artificial Sequence
<220> FEATURE:
<223> OTHER INFORMATION: Synthetic, Primer AM-288-160-CPK2062

<400> SEQUENCE: 140
cacgttcgcc ggccaaatta aagcagatct acgaagagtt tgaatc    46

<210> SEQ ID NO 141
<211> LENGTH: 50
<212> TYPE: DNA
<213> ORGANISM: Artificial Sequence
<220> FEATURE:
<223> OTHER INFORMATION: Synthetic, Primer AM-288-160-CPK2063

<400> SEQUENCE: 141
gaagaaatag gcaaagttga catggatccg tttgaatatg tattacttgg    50

<210> SEQ ID NO 142
<211> LENGTH: 50
<212> TYPE: DNA
<213> ORGANISM: Artificial Sequence
<220> FEATURE:
<223> OTHER INFORMATION: Synthetic, Primer AM-288-160-CPK2064

<400> SEQUENCE: 142
cacgttcgcc ggccaaatta aagcagatct cctcctttcc ccatgtttcc    50

<210> SEQ ID NO 143
<211> LENGTH: 50
<212> TYPE: DNA
<213> ORGANISM: Artificial Sequence
<220> FEATURE:
<223> OTHER INFORMATION: Synthetic, Primer AM-288-160-CPK2065

<400> SEQUENCE: 143
gaagaaatag gcaaagttga catggatccg tgttgtattt agtttttttt    50

<210> SEQ ID NO 144
<211> LENGTH: 50
<212> TYPE: DNA
<213> ORGANISM: Artificial Sequence
<220> FEATURE:
<223> OTHER INFORMATION: Synthetic, Primer AM-288-160-CPK2066

<400> SEQUENCE: 144
cacgttcgcc ggccaaatta aagcagatct tccttctttt cctcttgata    50

<210> SEQ ID NO 145
<211> LENGTH: 50
<212> TYPE: DNA

```
<213> ORGANISM: Artificial Sequence
<220> FEATURE:
<223> OTHER INFORMATION: Synthetic, Primer AM-288-160-CPK2067

<400> SEQUENCE: 145
gaagaaatag gcaaagttga catggatccg cttgactata cttttttata          50

<210> SEQ ID NO 146
<211> LENGTH: 44
<212> TYPE: DNA
<213> ORGANISM: Artificial Sequence
<220> FEATURE:
<223> OTHER INFORMATION: Synthetic, Primer AM-288-160-CPK2068

<400> SEQUENCE: 146
cacgttcgcc ggccaaatta aagcagatct ttgcatcgcc ctgc                44

<210> SEQ ID NO 147
<211> LENGTH: 50
<212> TYPE: DNA
<213> ORGANISM: Artificial Sequence
<220> FEATURE:
<223> OTHER INFORMATION: Synthetic, Primer AM-288-160-CPK2073

<400> SEQUENCE: 147
gaagaaatag gcaaagttga catggatccg gtttagttaa ttatagttcg          50

<210> SEQ ID NO 148
<211> LENGTH: 50
<212> TYPE: DNA
<213> ORGANISM: Artificial Sequence
<220> FEATURE:
<223> OTHER INFORMATION: Synthetic, Primer AM-288-160-CPK2074

<400> SEQUENCE: 148
cacgttcgcc ggccaaatta aagcagatct acccaaaatg tgaaagaaat          50

<210> SEQ ID NO 149
<211> LENGTH: 49
<212> TYPE: DNA
<213> ORGANISM: Artificial Sequence
<220> FEATURE:
<223> OTHER INFORMATION: Synthetic, Primer AM-288-160-CPK2079

<400> SEQUENCE: 149
gaagaaatag gcaaagttga catggatccg tgttttatat ttgttgtaa           49

<210> SEQ ID NO 150
<211> LENGTH: 38
<212> TYPE: DNA
<213> ORGANISM: Artificial Sequence
<220> FEATURE:
<223> OTHER INFORMATION: Synthetic, Primer AM-288-160-CPK2080

<400> SEQUENCE: 150
ccaaattaaa gcagatctgg catttgcaag aattactc                       38

<210> SEQ ID NO 151
<211> LENGTH: 50
<212> TYPE: DNA
<213> ORGANISM: Artificial Sequence
<220> FEATURE:
<223> OTHER INFORMATION: Synthetic, Primer AM-288-160-CPK2085

<400> SEQUENCE: 151
gaagaaatag gcaaagttga catggatccg ggctatttgc ttatatgtat          50
```

<210> SEQ ID NO 152
<211> LENGTH: 50
<212> TYPE: DNA
<213> ORGANISM: Artificial Sequence
<220> FEATURE:
<223> OTHER INFORMATION: Synthetic, Primer AM-288-160-CPK2086

<400> SEQUENCE: 152
cacgttcgcc ggccaaatta aagcagatct atttcctttt cttcctctta    50

<210> SEQ ID NO 153
<211> LENGTH: 46
<212> TYPE: DNA
<213> ORGANISM: Artificial Sequence
<220> FEATURE:
<223> OTHER INFORMATION: Synthetic, Primer AM-288-160-CPK2087

<400> SEQUENCE: 153
gaagaaatag gcaaagttga catggatccg tttgttcttt ctggaa    46

<210> SEQ ID NO 154
<211> LENGTH: 50
<212> TYPE: DNA
<213> ORGANISM: Artificial Sequence
<220> FEATURE:
<223> OTHER INFORMATION: Synthetic, Primer AM-288-160-CPK2088

<400> SEQUENCE: 154
cacgttcgcc ggccaaatta aagcagatct tgtgttacgt atctttgatg    50

<210> SEQ ID NO 155
<211> LENGTH: 49
<212> TYPE: DNA
<213> ORGANISM: Artificial Sequence
<220> FEATURE:
<223> OTHER INFORMATION: Synthetic, Primer AM-288-160-CPK2089

<400> SEQUENCE: 155
gaagaaatag gcaaagttga catggatccg gttttagtgt gtgaatgaa    49

<210> SEQ ID NO 156
<211> LENGTH: 11151
<212> TYPE: DNA
<213> ORGANISM: Artificial Sequence
<220> FEATURE:
<223> OTHER INFORMATION: Synthetic, Expression plasmid pAM552

<400> SEQUENCE: 156
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatcga ctacgtcgta aggccgtttc tgacagagta aaattcttga ggaactttc    240 accattatgg gaaatgcttc aagaaggtat tgacttaaac tccatcaaat ggtcaggtca    300
ttgagtgttt tttatttgtt gtattttttt tttttagag aaaatcctcc aatatcaaat    360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctaccctat gaacatattc catttgtaa tttcgtgtcg    600 tttctattat gaatttcatt tataaagttt atgtacaaat atcataaaaa aagagaatct    660

```
tttttaagcaa ggattttctt aacttcttcg gcgacagcat caccgacttc ggtggtactg    720
ttggaaccac ctaaatcacc agttctgata cctgcatcca aaacctttt aactgcatct      780 tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct aactaggat  catggcggca   1080 gaatcaatca attgatgttg aaccttcaat gtagggaatt cgttcttgat ggtttcctcc   1140 acagttttc  tccataatct tgaagaggcc aaaagattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaatacctcc cactaattct ctgacaacaa cgaagtcagt acctttagca   1380
aattgtggct tgattggaga taagtctaaa agagagtcgg atgcaaagtt acatggtctt   1440
aagttggcgt acaattgaag ttcttttacg attttagta  aaccttgttc aggtctaaca   1500
ctaccggtac cccatttagg accagccaca gcacctaaca aaacggcatc aaccttcttg   1560
gaggcttcca gcgcctcatc tggaagtggg acacctgtag catcgatagc agcaccacca   1620
attaaatgat tttcgaaatc gaacttgaca ttggaacgaa catcagaaat agctttaaga   1680
accttaatgg cttcggctgt gatttcttga ccaacgtggt cacctggcaa aacgacgatc   1740
ttcttagggg cagacattac aatggtatat ccttgaaata tatataaaaa aaggcgcctt   1800
agaccgctcg gccaaacaac caattacttg ttgagaaata gagtataatt atcctataaa   1860
tataacgttt ttgaacacac atgaacaagg aagtacagga caattgattt tgaagagaat   1920
gtggattttg atgtaattgt tgggattcca ttttttaataa ggcaataata ttaggtatgt   1980
ggatatacta gaagttctcc tcgaccgtcg atatgcggtg tgaaataccg cacagatgcg   2040
taaggagaaa ataccgcatc aggaaattgt aaacgttaat attttgttaa aattcgcgtt   2100
aaatttttgt taaatcagct cattttttaa ccaataggcc gaaatcggca aaatccctta   2160
taaatcaaaa gaatagaccg agatagggtt gagtgttgtt ccagtttgga caagagtcc    2220 actattaaag aacgtggact ccaacgtcaa agggcgaaaa accgtctatc agggcgatgg   2280
cccactacgt ggaagatccg aggcctagct ttaacgaacg cagaattttc gagttattaa   2340
acttaaaata cgctgaaccc gaacatgaaa atatcgaatg gaaaaaaaa  actgcataaa   2400 ggcattaaaa gaggagcgaa tttttttta  ataaaaatct taataatcat taaaagataa   2460
ataatagtct atatatacgt atataaataa aaaatattca aaaaataaaa taaactatta   2520
ttttagcgta aaggatgggg aaagagaaaa gaaaaaaatt gatctatcga tttcaattca   2580
attcaattta tttcttttcg gataagaaag caacacctgg caattcctta ccttccaata   2640
attccaaaga agcaccacca ccagtagaga catgggagac ccgggccatg gttagataga   2700 cataggtaa  actagcaatg atttgatcaa atgcttgtat tcatctccca ttctcgtaaa   2760
attgtcttta cctgcatatt ggacctctaa aaattggcaa agatatataa cagccataag   2820
taaaggtctt gggatattct tgttgttaa  atactctctg tttatgtctt tccaaacgtc   2880
ctccacttcc ttataaatca gtgtctgagc atattcttcg ttgacattgt attccttcat   2940
gtaagattct aaagagcttg aactatgttt tctctcctgt tccgctttat gagtcatcag   3000
gtcatttaat ctcctaccca gaataccact gtaacggaat aaaggcggag cagatacagc   3060
```

```
ccactcaact gattccttag tgaaaatatc gctcattcct agataacagg tagttgttag    3120
caagtttgca ccaccagtga taataactac gggatcgtgc tcttcagttg tcggtatgtg    3180
tccttcatta gcccatttcg cttctaccat tagattcctt acgaattctt taacgaactc    3240
cttcccacag ttgaataaat cagttctacc ttctttggcc agaaactcct ccatttctgt    3300
gtaggtatcc atgaataatt tgtaaatagg cttcatgtat tccggcaacg tgtctaagca    3360
ggtgatcgac catcttttcca cggcttcagt gaaaatcttt aactcctcgt aagttccata    3420
tgcgtcatac gtgtcatcaa taagtgttat cacagcaact gccttagtga aaaaaactct    3480
agctcttgaa tactggggtt cgtaaccaga acctaaaccc caaaaatagc attcaacgat    3540
acgatctctc agacatgggg cattttttctt aatatcaaat gccttccacc acttgcatac    3600
gtgactcaac tcttccttat gtaggctctg caatagattg aactccagtt tagctaactt    3660
tagcagagtt ttattatggg agtcttgttg ctgatagaag ggtatgtact gggcggcctc    3720
gatccttggc aatctcttcc acaatggttg ctttaaagct ctctggattt cagtgaataa    3780
agcggggttt gtactaaacg cgtcctttgt cataatcgat agccttgatc ttgtgaatcc    3840
cagggcatct tcaagaatta tttcgcccgg aactctcatg gacgtagcct catataattc    3900
caacaatcct tcaacatcat tcgctaacga ttgtttaaaa gcaccattct tgtctttata    3960
gttattaaac acatcacacg tgacatagta tccttgttta cgcatcagcc taaaccataa    4020
gctagacctg tcgccattcc aattatcacc ataggtctcg taaatacatt gcaatgcatg    4080
atcaatttca cgttcaaaat gatacggaat acctaaacgt tgaatctcgt caatcagctt    4140
caacaaattt gcatgtttca taggaatatc caatgcttcc tttaacaact gtcttacttc    4200
cttctttaga tcgtttacta tttgctccac accctgttca acttgtttct cataaatcaa    4260
aaattgatcg ccccaaatag aaggtgggaa atttgcaatt ggccttatag gtttctcttc    4320
agtcaaggcc attgttttct gcagatccgg ggttttttct ccttgacgtt aaagtataga    4380
ggtatattaa caatttttttg ttgatacttt tattacattt gaataagaag taatacaaac    4440
cgaaaatgtt gaaagtatta gttaaagtgg ttatgcagtt tttgcattta tatatctgtt    4500
aatagatcaa aaatcatcgc ttcgctgatt aattacccca gaaataaggc taaaaaacta    4560
atcgcattat catcctatgg ttgttaattt gattcgttca tttgaaggtt tgtggggcca    4620
ggttactgcc aattttttcct cttcataacc ataaaagcta gtattgtaga atctttattg    4680
ttcggagcag tgcggcgcga ggcacatctg cgtttcagga acgcgaccgg tgaagacgag    4740
gacgcacgga ggagagtctt ccttcggagg gctgtcaccc gctcggcggc ttctaatccg    4800
tactaagatc tgctttaatt tggccggcga acgtggcgag aaaggaaggg aagaaagcga    4860
aaggagcggg cgctagggcg ctggcaagtg tagcggtcac gctgcgcgta accaccacac    4920
ccgccgcgct taatgcgccg ctacagggcg cgtcgcgcca ttcgccattc aggctgcgca    4980
actgttggga agggcgatcg gtgcgggcct cttcgctatt acgccagctg aattggagcg    5040
acctcatgct atacctgaga aagcaacctg acctacagga aagagttact caagaataag    5100
aattttcgtt ttaaaaccta agagtcactt taaaatttgt atacacttat ttttttttata    5160 acttatttaa taataaaaat cataaatcat aagaaattcg cttatttaga agtgtcaaca    5220
acgtatctac caacgatttg acccttttcc atcttttcgt aaatttctgg caaggtagac    5280
aagccgacaa ccttgattgg agacttgacc aaacctctgg cgaagaattg ttaattaaga    5340
gtcagtcgac ttaaaaacta gggaccaata gcaattctgt tttacgttgc attgttgcac    5400
ctgaactttc cgtcatgtca atttgatcat atgaaactcc attgggcaac ttccagttga    5460
```

```
aatgataaag aatgttggct agtggcagtt gaacattggc caaacctaac gcagcgccag   5520
gacacatacg acgtccagcc ccaaatggta aatattcata ttcggcgccc atcactgttg   5580
ccgaagagtt ttcaaatctt tcaggtataa acgcttctgc atccttccag tattcaggat   5640
ctctattgat cgcaaacaca ttaacgatta atttcgtttt gttagggata ttataaccag   5700
ccaagtttac tggctgacga cattctctag gtagcactaa cggcaagggt gggtgtagtc   5760
taagagtctc tttgatgacc atattcaagt aggacaattc ttgtatatct tcttcatgta   5820
ttttttcttt cccattcaag gccttacgta attcagcctg aaccttttcc attgctttcg   5880 gacatttat  tagctcgctt atagcccatt ctatggtaga acttgaagtg tcggtccctg   5940
caccgaacat gtccaaaatt attgctttga tattatccga agtcagagga aactcagcag   6000
aatcctttaa tctaagtaat acatctaata gggtttcgtt ggttttggat gacgtattta   6060
cggtatgttc agctaccaaa ttgtcaatta agttatcaat cttttt acgt aggctagtta   6120 atcttgctct cttaccgctc aagtgatgca agaactttt agatgggaaa atatcggcaa   6180
catcgaaacc gcctgtttgt ctcagtattt ctttaacaat ttcagtaagt tccttttgat   6240
ctttaattcc cttaccaaac gcagcacggg atagtatagt ggcaattagt ttaaaaacgt   6300
tttcacttaa atttactggt ctaccactac ctgaagcctt tatttcctgg actaaattcc   6360
aacattcttc ttccctcaac gattgaaatg acttaacctt ttttacagac aacaattcaa   6420
gagtacaaat cttccttaat tgtctccagt attccccata tggagcaagg acaacatcag   6480
tgttatgata taaaactatt tccccagtta agtttcgggg tctattagcg aaagtaatat   6540
cgtaggttgt aagaatttcc ttagcccact taggactcga cacgactatt gtgggtacct   6600
ctcccaattg aaggtgcatt agcgaaccat attttctcgc taaatccctt acacccctgt   6660
gtggtgtggt tccgatcaaa tggtgcatgt gaccaatgat gggtagcctc caaggttccg   6720
gcaaggactt tttagttgac ttacttctag tggcaaattt gtacgaac aacaaaatag    6780 ttgctaaagc aattgatgta gttaaagata gtgccatagc ctttaaaatt gacttcattg   6840
ttttcctagg cctttagtga gggttgaatt cgaattttca aaaattctta ctttttttt    6900 ggatggacgc aaagaagttt aataatcata ttacatggca ttaccaccat atacatatcc   6960
atatacatat ccatatctaa tcttacttat atgttgtgga aatgtaaaga gccccattat   7020
cttagcctaa aaaaaccttc tctttggaac tttcagtaat acgcttaact gctcattgct   7080
atattgaagt acggattaga agccgccgag cgggtgacag ccctccgaag gaagactctc   7140
ctccgtgcgt cctcgtcttc accggtcgcg ttcctgaaac gcagatgtgc ctcgcgccgc   7200
actgctccga acaataaaga ttctacaata ctagctttta tggttatgaa gaggaaaaat   7260
tggcagtaac ctggccccac aaaccttcaa atgaacgaat caaattaaca accataggat   7320
gataatgcga ttagttttt agccttattt ctggggtaat taatcagcga agcgatgatt    7380
tttgatctat taacagatat ataaatgcaa aaactgcata accactttaa ctaatacttt   7440
caacattttc ggtttgtatt acttcttatt caaatgtaat aaaagtatca acaaaaaatt   7500
gttaatatac ctctatactt taacgtcaag gagaaaaaac cccaagctct agctaagatc   7560
cgctctaacc gaaaggaag  gagttagaca acctgaagtc taggtcccta tttattttt    7620 tatagttatg ttagtattaa gaacgttatt tatatttcaa attttttcttt tttttctgta   7680 cagacgcgtg tacgcatgta acattatact gaaaaccttg cttgagaagg ttttgggacg   7740
ctcgaagatc cagctgcatt aatgaatcgg ccaacgcgcg gggagaggcg gtttgcgtat   7800
tgggcgctct tccgcttcct cgctcactga ctcgctgcgc tcggtcgttc ggctgcggcg   7860
```

```
agcggtatca gctcactcaa aggcggtaat acggttatcc acagaatcag gggataacgc    7920
aggaaagaac atgtgagcaa aaggccagca aaaggccagg aaccgtaaaa aggccgcgtt    7980
gctggcgttt ttccataggc tccgcccccc tgacgagcat cacaaaaatc gacgctcaag    8040
tcagaggtgg cgaaacccga caggactata aagataccag gcgtttcccc ctggaagctc    8100
cctcgtgcgc tctcctgttc cgaccctgcc gcttaccgga tacctgtccg cctttctccc    8160
ttcgggaagc gtggcgcttt ctcatagctc acgctgtagg tatctcagtt cggtgtaggt    8220
cgttcgctcc aagctgggct gtgtgcacga accccccgtt cagcccgacc gctgcgcctt    8280
atccggtaac tatcgtcttg agtccaaccc ggtaagacac gacttatcgc cactggcagc    8340
agccactggt aacaggatta gcagagcgag gtatgtaggc ggtgctacag agttcttgaa    8400
gtggtggcct aactacggct acactagaag gacagtattt ggtatctgcg ctctgctgaa    8460
gccagttacc ttcggaaaaa gagttggtag ctcttgatcc ggcaaacaaa ccaccgctgg    8520
tagcggtggt ttttttgttt gcaagcagca gattacgcgc agaaaaaaag gatctcaaga    8580
agatcctttg atcttttcta cggggtctga cgctcagtgg aacgaaaact cacgttaagg    8640
gattttggtc atgagattat caaaaaggat cttcacctag atccttttaa attaaaaatg    8700
aagttttaaa tcaatctaaa gtatatatga gtaaacttgg tctgacagtt accaatgctt    8760
aatcagtgag gcacctatct cagcgatctg tctatttcgt tcatccatag ttgcctgact    8820
ccccgtcgtg tagataacta cgatacggga gggcttacca tctggcccca gtgctgcaat    8880
gataccgcga gacccacgct caccggctcc agatttatca gcaataaacc agccagccgg    8940
aagggccgag cgcagaagtg gtcctgcaac tttatccgcc tccatccagt ctattaattg    9000
ttgccgggaa gctagagtaa gtagttcgcc agttaatagt ttgcgcaacg ttgttgccat    9060
tgctacaggc atcgtggtgt cacgctcgtc gtttggtatg gcttcattca gctccggttc    9120
ccaacgatca aggcgagtta catgatcccc catgttgtgc aaaaaagcgg ttagctcctt    9180
cggtcctccg atcgttgtca gaagtaagtt ggccgcagtg ttatcactca tggttatggc    9240
agcactgcat aattctctta ctgtcatgcc atccgtaaga tgcttttctg tgactggtga    9300
gtactcaacc aagtcattct gagaatagtg tatgcggcga ccgagttgct cttgcccggc    9360
gtcaatacgg gataataccg cgccacatag cagaacttta aaagtgctca tcattggaaa    9420
acgttcttcg gggcgaaaac tctcaaggat cttaccgctg ttgagatcca gttcgatgta    9480
acccactcgt gcacccaact gatcttcagc atcttttact ttcaccagcg tttctgggtg    9540
agcaaaaaca ggaaggcaaa atgccgcaaa aaagggaata agggcgacac ggaaatgttg    9600
aatactcata ctcttccttt ttcaatatta ttgaagcatt tatcagggtt attgtctcat    9660
gagcggatac atatttgaat gtatttagaa aaataaacaa ataggggttc cgcgcacatt    9720
tccccgaaaa gtgccacctg aacgaagcat ctgtgcttca ttttgtagaa caaaaatgca    9780
acgcgagagc gctaattttt caaacaaaga atctgagctg catttttaca gaacagaaat    9840
gcaacgcgaa agcgctattt taccaacgaa gaatctgtgc ttcatttttg taaacaaaa    9900
atgcaacgcg agagcgctaa ttttcaaac aaagaatctg agctgcattt ttacagaaca    9960
gaaatgcaac gcgagagcgc tattttacca acaaagaatc tatacttctt ttttgttcta    10020
caaaaatgca tcccgagagc gctatttttc taacaaagca tcttagatta cttttttttct    10080
cctttgtgcg ctctataatg cagtctcttg ataactttt gcactgtagg tccgttaagg    10140
ttagaagaag gctactttgg tgtctatttt ctcttccata aaaaaagcct gactccactt    10200
cccgcgttta ctgattacta gcgaagctgc gggtgcattt tttcaagata aaggcatccc    10260
```

-continued

```
cgattatatt ctataccgat gtggattgcg catactttgt gaacagaaag tgatagcgtt    10320
gatgattctt cattggtcag aaaattatga acgtttctt ctattttgtc tctatatact    10380
acgtatagga aatgtttaca ttttcgtatt gttttcgatt cactctatga atagttctta    10440
ctacaatttt tttgtctaaa gagtaatact agagataaac ataaaaaatg tagaggtcga    10500
gtttagatgc aagttcaagg agcgaaaggt ggatgggtag gttatatagg gatatagcac    10560
agagatatat agcaaagaga tacttttgag caatgtttgt ggaagcggta ttcgcaatat    10620
tttagtagct cgttacagtc cggtgcgttt ttggtttttt gaaagtgcgt cttcagagcg    10680
cttttggttt tcaaaagcgc tctgaagttc ctatactttc tagagaatag gaacttcgga    10740
ataggaactt caaagcgttt ccgaaaacga gcgcttccga aaatgcaacg cgagctgcgc    10800
acatacagct cactgttcac gtcgcaccta tatctgcgtg ttgcctgtat atatatatac    10860
atgagaagaa cggcatagtg cgtgtttatg cttaaatgcg tacttatatg cgtctattta    10920
tgtaggatga aaggtagtct agtacctcct gtgatattat cccattccat gcggggtatc    10980
gtatgcttcc ttcagcacta ccctttagct gttctatatg ctgccactcc tcaattggat    11040
tagtctcatc cttcaatgct atcatttcct ttgatattgg atcatactaa gaaaccatta    11100
ttatcatgac attaacctat aaaaataggc gtatcacgag gccctttcgt c              11151
```

<210> SEQ ID NO 157
<211> LENGTH: 79
<212> TYPE: DNA
<213> ORGANISM: Artificial Sequence
<220> FEATURE:
<223> OTHER INFORMATION: Synthetic, Primer ADS-A13-F
<220> FEATURE:
<221> NAME/KEY: misc_feature
<222> LOCATION: (57)..(58)
<223> OTHER INFORMATION: n is a, c, g, or t

<400> SEQUENCE: 157

```
ggagaaaaaa ccccggatcc atggccttga ctgaagagaa acctataagg ccaattnnka    60
atttcccacc ttctatttg                                                  79
```

<210> SEQ ID NO 158
<211> LENGTH: 53
<212> TYPE: DNA
<213> ORGANISM: Artificial Sequence
<220> FEATURE:
<223> OTHER INFORMATION: Synthetic, Primer ADS-C260-F
<220> FEATURE:
<221> NAME/KEY: misc_feature
<222> LOCATION: (27)..(28)
<223> OTHER INFORMATION: n is a, c, g, or t

<400> SEQUENCE: 158

```
catttgatat taagaaaaat gccccannkc tgagagatcg tatcgttgaa tgc             53
```

<210> SEQ ID NO 159
<211> LENGTH: 30
<212> TYPE: DNA
<213> ORGANISM: Artificial Sequence
<220> FEATURE:
<223> OTHER INFORMATION: Synthetic, Primer ADS-C260-R

<400> SEQUENCE: 159

```
cattttctt aatatcaaat gccttccacc                                       30
```

<210> SEQ ID NO 160
<211> LENGTH: 51
<212> TYPE: DNA

```
<213> ORGANISM: Artificial Sequence
<220> FEATURE:
<223> OTHER INFORMATION: Synthetic, Primer ADS-A291-F
<220> FEATURE:
<221> NAME/KEY: misc_feature
<222> LOCATION: (27)..(28)
<223> OTHER INFORMATION: n is a, c, g, or t

<400> SEQUENCE: 160
caagagctag agttttttc actaagnnkg ttgctgtgat aacacttatt g         51

<210> SEQ ID NO 161
<211> LENGTH: 25
<212> TYPE: DNA
<213> ORGANISM: Artificial Sequence
<220> FEATURE:
<223> OTHER INFORMATION: Synthetic, Primer ADS-A291-R

<400> SEQUENCE: 161
gaaaaaaact ctagctcttg aatac                                     25

<210> SEQ ID NO 162
<211> LENGTH: 46
<212> TYPE: DNA
<213> ORGANISM: Artificial Sequence
<220> FEATURE:
<223> OTHER INFORMATION: Synthetic, Primer ADS-M341-F
<220> FEATURE:
<221> NAME/KEY: misc_feature
<222> LOCATION: (26)..(27)
<223> OTHER INFORMATION: n is a, c, g, or t

<400> SEQUENCE: 162
catgaagcct atttacaaat tattcnnkga tacctacaca gaaatg              46

<210> SEQ ID NO 163
<211> LENGTH: 26
<212> TYPE: DNA
<213> ORGANISM: Artificial Sequence
<220> FEATURE:
<223> OTHER INFORMATION: Synthetic, Primer ADS-M341-R

<400> SEQUENCE: 163
aatttgtaaa taggcttcat gtattc                                    26

<210> SEQ ID NO 164
<211> LENGTH: 49
<212> TYPE: DNA
<213> ORGANISM: Artificial Sequence
<220> FEATURE:
<223> OTHER INFORMATION: Synthetic, Primer ADS-M406-F
<220> FEATURE:
<221> NAME/KEY: misc_feature
<222> LOCATION: (31)..(32)
<223> OTHER INFORMATION: n is a, c, g, or t

<400> SEQUENCE: 164
gttattatca ctggtggtgc aaacttgcta nnkactacct gttatctag           49

<210> SEQ ID NO 165
<211> LENGTH: 30
<212> TYPE: DNA
<213> ORGANISM: Artificial Sequence
<220> FEATURE:
<223> OTHER INFORMATION: Synthetic, Primer ADS-M406-R

<400> SEQUENCE: 165
gtttgcacca ccagtgataa taactacggg                                30
```

```
<210> SEQ ID NO 166
<211> LENGTH: 49
<212> TYPE: DNA
<213> ORGANISM: Artificial Sequence
<220> FEATURE:
<223> OTHER INFORMATION: Synthetic, Primer ADS-M418-F
<220> FEATURE:
<221> NAME/KEY: misc_feature
<222> LOCATION: (27)..(28)
<223> OTHER INFORMATION: n is a, c, g, or t

<400> SEQUENCE: 166
gttatctagg aatgagcgat attttcnnka aggaatcagt tgagtgggc                49

<210> SEQ ID NO 167
<211> LENGTH: 24
<212> TYPE: DNA
<213> ORGANISM: Artificial Sequence
<220> FEATURE:
<223> OTHER INFORMATION: Synthetic, Primer ADS-M418-R

<400> SEQUENCE: 167
cgctcattcc tagataacag gtag                                          24

<210> SEQ ID NO 168
<211> LENGTH: 44
<212> TYPE: DNA
<213> ORGANISM: Artificial Sequence
<220> FEATURE:
<223> OTHER INFORMATION: Synthetic, Primer ADS-F432-F
<220> FEATURE:
<221> NAME/KEY: misc_feature
<222> LOCATION: (24)..(25)
<223> OTHER INFORMATION: n is a, c, g, or t

<400> SEQUENCE: 168
gggctgtatc tgctccgcct ttannkcgtt acagtggtat tctg                    44

<210> SEQ ID NO 169
<211> LENGTH: 26
<212> TYPE: DNA
<213> ORGANISM: Artificial Sequence
<220> FEATURE:
<223> OTHER INFORMATION: Synthetic, Primer ADS-F432-R

<400> SEQUENCE: 169
ggcggagcag atacagccca ctcaac                                        26

<210> SEQ ID NO 170
<211> LENGTH: 50
<212> TYPE: DNA
<213> ORGANISM: Artificial Sequence
<220> FEATURE:
<223> OTHER INFORMATION: Synthetic, Primer ADS-G439-F
<220> FEATURE:
<221> NAME/KEY: misc_feature
<222> LOCATION: (27)..(28)
<223> OTHER INFORMATION: n is a, c, g, or t

<400> SEQUENCE: 170
ctttattccg ttacagtggt attctgnnka ggagattaaa tgacctgatg              50

<210> SEQ ID NO 171
<211> LENGTH: 24
<212> TYPE: DNA
<213> ORGANISM: Artificial Sequence
<220> FEATURE:
<223> OTHER INFORMATION: Synthetic, Primer ADS-G439-R
```

```
<400> SEQUENCE: 171
gaataccact gtaacggaat aaag                                              24

<210> SEQ ID NO 172
<211> LENGTH: 39
<212> TYPE: DNA
<213> ORGANISM: Artificial Sequence
<220> FEATURE:
<223> OTHER INFORMATION: Synthetic, Primer ADS-SM-5'

<400> SEQUENCE: 172 gaaaaaccc cggatccatg gccttgactg aagagaaac                               39

<210> SEQ ID NO 173
<211> LENGTH: 44
<212> TYPE: DNA
<213> ORGANISM: Artificial Sequence
<220> FEATURE:
<223> OTHER INFORMATION: Synthetic, Primer ADS-SM-3'

<400> SEQUENCE: 173
ggttagagcg gatcttagct agcttagata gacatagggt aaac                        44

<210> SEQ ID NO 174
<211> LENGTH: 546
<212> TYPE: PRT
<213> ORGANISM: Artificial Sequence
<220> FEATURE:
<223> OTHER INFORMATION: Synthetic, Artemisia annua Amorpha-4,11-diene
      Synthase A291V mutant

<400> SEQUENCE: 174
```

Met Ala Leu Thr Glu Glu Lys Pro Ile Arg Pro Ile Ala Asn Phe Pro
1               5                   10                  15

Pro Ser Ile Trp Gly Asp Gln Phe Leu Ile Tyr Glu Lys Gln Val Glu
                20                  25                  30

Gln Gly Val Glu Gln Ile Val Asn Asp Leu Lys Lys Glu Val Arg Gln
            35                  40                  45

Leu Leu Lys Glu Ala Leu Asp Ile Pro Met Lys His Ala Asn Leu Leu
    50                  55                  60

Lys Leu Ile Asp Glu Ile Gln Arg Leu Gly Ile Pro Tyr His Phe Glu
65                  70                  75                  80

Arg Glu Ile Asp His Ala Leu Gln Cys Ile Tyr Glu Thr Tyr Gly Asp
                85                  90                  95

Asn Trp Asn Gly Asp Arg Ser Ser Leu Trp Phe Arg Leu Met Arg Lys
            100                 105                 110

Gln Gly Tyr Tyr Val Thr Cys Asp Val Phe Asn Asn Tyr Lys Asp Lys
        115                 120                 125

Asn Gly Ala Phe Lys Gln Ser Leu Ala Asn Asp Val Glu Gly Leu Leu
    130                 135                 140

Glu Leu Tyr Glu Ala Thr Ser Met Arg Val Pro Gly Glu Ile Ile Leu
145                 150                 155                 160

Glu Asp Ala Leu Gly Phe Thr Arg Ser Arg Leu Ser Ile Met Thr Lys
                165                 170                 175

Asp Ala Phe Ser Thr Asn Pro Ala Leu Phe Thr Glu Ile Gln Arg Ala
            180                 185                 190

Leu Lys Gln Pro Leu Trp Lys Arg Leu Pro Arg Ile Glu Ala Ala Gln
        195                 200                 205

Tyr Ile Pro Phe Tyr Gln Gln Gln Asp Ser His Asn Lys Thr Leu Leu
    210                 215                 220

Lys Leu Ala Lys Leu Glu Phe Asn Leu Leu Gln Ser Leu His Lys Glu
225                 230                 235                 240

Glu Leu Ser His Val Cys Lys Trp Trp Lys Ala Phe Asp Ile Lys Lys
            245                 250                 255

Asn Ala Pro Cys Leu Arg Asp Arg Ile Val Glu Cys Tyr Phe Trp Gly
        260                 265                 270

Leu Gly Ser Gly Tyr Glu Pro Gln Tyr Ser Arg Ala Arg Val Phe Phe
    275                 280                 285

Thr Lys Val Val Ala Val Ile Thr Leu Ile Asp Asp Thr Tyr Asp Ala
290                 295                 300

Tyr Gly Thr Tyr Glu Glu Leu Lys Ile Phe Thr Glu Ala Val Glu Arg
305                 310                 315                 320

Trp Ser Ile Thr Cys Leu Asp Thr Leu Pro Glu Tyr Met Lys Pro Ile
            325                 330                 335

Tyr Lys Leu Phe Met Asp Thr Tyr Thr Glu Met Glu Glu Phe Leu Ala
        340                 345                 350

Lys Glu Gly Arg Thr Asp Leu Phe Asn Cys Gly Lys Glu Phe Val Lys
    355                 360                 365

Glu Phe Val Arg Asn Leu Met Val Glu Ala Lys Trp Ala Asn Glu Gly
370                 375                 380

His Ile Pro Thr Thr Glu Glu His Asp Pro Val Val Ile Ile Thr Gly
385                 390                 395                 400

Gly Ala Asn Leu Leu Thr Thr Thr Cys Tyr Leu Gly Met Ser Asp Ile
            405                 410                 415

Phe Thr Lys Glu Ser Val Glu Trp Ala Val Ser Ala Pro Leu Phe
        420                 425                 430

Arg Tyr Ser Gly Ile Leu Gly Arg Arg Leu Asn Asp Leu Met Thr His
    435                 440                 445

Lys Ala Glu Gln Glu Arg Lys His Ser Ser Ser Leu Glu Ser Tyr
450                 455                 460

Met Lys Glu Tyr Asn Val Asn Glu Glu Tyr Ala Gln Thr Leu Ile Tyr
465                 470                 475                 480

Lys Glu Val Glu Asp Val Trp Lys Asp Ile Asn Arg Glu Tyr Leu Thr
            485                 490                 495

Thr Lys Asn Ile Pro Arg Pro Leu Leu Met Ala Val Ile Tyr Leu Cys
        500                 505                 510

Gln Phe Leu Glu Val Gln Tyr Ala Gly Lys Asp Asn Phe Thr Arg Met
    515                 520                 525

Gly Asp Glu Tyr Lys His Leu Ile Lys Ser Leu Leu Val Tyr Pro Met
530                 535                 540

Ser Ile
545

<210> SEQ ID NO 175
<211> LENGTH: 585
<212> TYPE: PRT
<213> ORGANISM: Artificial Sequence
<220> FEATURE:
<223> OTHER INFORMATION: Synthetic, Artemisia annua Amorpha-4,11-diene
      Synthase A291C mutant

<400> SEQUENCE: 175

Ala Arg Thr Glu Met Ile Ser Ile Ala Ala Asn Asn Ala Ala Met Arg
1               5                   10                  15

Pro His Ala Asp Ile Glu Asn Glu Ser Tyr Asn Thr His Ala Ser Glu
            20                  25                  30

```
Ala Cys Met Thr Ala Asn Thr Met Ala Leu Thr Glu Glu Lys Pro Ile
         35                  40                  45

Arg Pro Ile Ala Asn Phe Pro Pro Ser Ile Trp Gly Asp Gln Phe Leu
 50                  55                  60

Ile Tyr Glu Lys Gln Val Glu Gln Gly Val Glu Gln Ile Val Asn Asp
 65                  70                  75                  80

Leu Lys Lys Glu Val Arg Gln Leu Leu Lys Glu Ala Leu Asp Ile Pro
                 85                  90                  95

Met Lys His Ala Asn Leu Leu Lys Leu Ile Asp Glu Ile Gln Arg Leu
            100                 105                 110

Gly Ile Pro Tyr His Phe Glu Arg Glu Ile Asp His Ala Leu Gln Cys
            115                 120                 125

Ile Tyr Glu Thr Tyr Gly Asp Asn Trp Asn Gly Asp Arg Ser Ser Leu
            130                 135                 140

Trp Phe Arg Leu Met Arg Lys Gln Gly Tyr Tyr Val Thr Cys Asp Val
145                 150                 155                 160

Phe Asn Asn Tyr Lys Asp Lys Asn Gly Ala Phe Lys Gln Ser Leu Ala
                165                 170                 175

Asn Asp Val Glu Gly Leu Leu Glu Leu Tyr Glu Ala Thr Ser Met Arg
            180                 185                 190

Val Pro Gly Glu Ile Ile Leu Glu Asp Ala Leu Gly Phe Thr Arg Ser
            195                 200                 205

Arg Leu Ser Ile Met Thr Lys Asp Ala Phe Ser Thr Asn Pro Ala Leu
            210                 215                 220

Phe Thr Glu Ile Gln Arg Ala Leu Lys Gln Pro Leu Trp Lys Arg Leu
225                 230                 235                 240

Pro Arg Ile Glu Ala Ala Gln Tyr Ile Pro Phe Tyr Gln Gln Gln Asp
            245                 250                 255

Ser His Asn Lys Thr Leu Leu Lys Leu Ala Lys Leu Glu Phe Asn Leu
            260                 265                 270

Leu Gln Ser Leu His Lys Glu Glu Leu Ser His Val Cys Lys Trp Trp
            275                 280                 285

Lys Ala Phe Asp Ile Lys Lys Asn Ala Pro Cys Leu Arg Asp Arg Ile
            290                 295                 300

Val Glu Cys Tyr Phe Trp Gly Leu Gly Ser Gly Tyr Glu Pro Gln Tyr
305                 310                 315                 320

Ser Arg Ala Arg Val Phe Phe Thr Lys Cys Val Ala Val Ile Thr Leu
                325                 330                 335

Ile Asp Asp Thr Tyr Asp Ala Tyr Gly Thr Tyr Glu Glu Leu Lys Ile
            340                 345                 350

Phe Thr Glu Ala Val Glu Arg Trp Ser Ile Thr Cys Leu Asp Thr Leu
            355                 360                 365

Pro Glu Tyr Met Lys Pro Ile Tyr Lys Leu Phe Met Asp Thr Tyr Thr
            370                 375                 380

Glu Met Glu Glu Phe Leu Ala Lys Gly Arg Thr Asp Leu Phe Asn
385                 390                 395                 400

Cys Gly Lys Glu Phe Val Lys Glu Phe Val Arg Asn Leu Met Val Glu
                405                 410                 415

Ala Lys Trp Ala Asn Glu Gly His Ile Pro Thr Thr Glu Glu His Asp
            420                 425                 430

Pro Val Val Ile Ile Thr Gly Gly Ala Asn Leu Leu Thr Thr Thr Cys
            435                 440                 445

Tyr Leu Gly Met Ser Asp Ile Phe Thr Lys Glu Ser Val Glu Trp Ala
```

```
            450                 455                 460
Val Ser Ala Pro Pro Leu Phe Arg Tyr Ser Gly Ile Leu Gly Arg Arg
465                 470                 475                 480

Leu Asn Asp Leu Met Thr His Lys Ala Glu Gln Glu Arg Lys His Ser
                485                 490                 495

Ser Ser Ser Leu Glu Ser Tyr Met Lys Glu Tyr Asn Val Asn Glu Glu
                500                 505                 510

Tyr Ala Gln Thr Leu Ile Tyr Lys Glu Val Glu Asp Val Trp Lys Asp
                515                 520                 525

Ile Asn Arg Glu Tyr Leu Thr Thr Lys Asn Ile Pro Arg Pro Leu Leu
530                 535                 540

Met Ala Val Ile Tyr Leu Cys Gln Phe Leu Glu Val Gln Tyr Ala Gly
545                 550                 555                 560

Lys Asp Asn Phe Thr Arg Met Gly Asp Glu Tyr Lys His Leu Ile Lys
                565                 570                 575

Ser Leu Leu Val Tyr Pro Met Ser Ile
                580                 585

<210> SEQ ID NO 176
<211> LENGTH: 585
<212> TYPE: PRT
<213> ORGANISM: Artificial Sequence
<220> FEATURE:
<223> OTHER INFORMATION: Synthetic, Artemisia annua Amorpha-4,11-diene
      Synthase A291I mutant

<400> SEQUENCE: 176

Ala Arg Thr Glu Met Ile Ser Ile Ala Ala Asn Asn Ala Ala Met Arg
1               5                   10                  15

Pro His Ala Asp Ile Glu Asn Glu Ser Tyr Asn Thr His Ala Ser Glu
                20                  25                  30

Ala Ile Met Thr Ala Asn Thr Met Ala Leu Thr Glu Glu Lys Pro Ile
                35                  40                  45

Arg Pro Ile Ala Asn Phe Pro Pro Ser Ile Trp Gly Asp Gln Phe Leu
50                  55                  60

Ile Tyr Glu Lys Gln Val Glu Gln Gly Val Glu Gln Ile Val Asn Asp
65                  70                  75                  80

Leu Lys Lys Glu Val Arg Gln Leu Leu Lys Glu Ala Leu Asp Ile Pro
                85                  90                  95

Met Lys His Ala Asn Leu Leu Lys Leu Ile Asp Glu Ile Gln Arg Leu
                100                 105                 110

Gly Ile Pro Tyr His Phe Glu Arg Glu Ile Asp His Ala Leu Gln Cys
                115                 120                 125

Ile Tyr Glu Thr Tyr Gly Asp Asn Trp Asn Gly Asp Arg Ser Ser Leu
                130                 135                 140

Trp Phe Arg Leu Met Arg Lys Gln Gly Tyr Tyr Val Thr Cys Asp Val
145                 150                 155                 160

Phe Asn Asn Tyr Lys Asp Lys Asn Gly Ala Phe Lys Gln Ser Leu Ala
                165                 170                 175

Asn Asp Val Glu Gly Leu Leu Glu Leu Tyr Glu Ala Thr Ser Met Arg
                180                 185                 190

Val Pro Gly Glu Ile Ile Leu Glu Asp Ala Leu Gly Phe Thr Arg Ser
                195                 200                 205

Arg Leu Ser Ile Met Thr Lys Asp Ala Phe Ser Thr Asn Pro Ala Leu
                210                 215                 220

Phe Thr Glu Ile Gln Arg Ala Leu Lys Gln Pro Leu Trp Lys Arg Leu
```

-continued

```
            225                 230                 235                 240
Pro Arg Ile Glu Ala Ala Gln Tyr Ile Pro Phe Tyr Gln Gln Gln Asp
                    245                 250                 255

Ser His Asn Lys Thr Leu Leu Lys Leu Ala Lys Leu Glu Phe Asn Leu
                260                 265                 270

Leu Gln Ser Leu His Lys Glu Glu Leu Ser His Val Cys Lys Trp Trp
            275                 280                 285

Lys Ala Phe Asp Ile Lys Lys Asn Ala Pro Cys Leu Arg Asp Arg Ile
        290                 295                 300

Val Glu Cys Tyr Phe Trp Gly Leu Gly Ser Gly Tyr Glu Pro Gln Tyr
305                 310                 315                 320

Ser Arg Ala Arg Val Phe Phe Thr Lys Ile Val Ala Val Ile Thr Leu
                    325                 330                 335

Ile Asp Asp Thr Tyr Asp Ala Tyr Gly Thr Tyr Glu Glu Leu Lys Ile
                340                 345                 350

Phe Thr Glu Ala Val Glu Arg Trp Ser Ile Thr Cys Leu Asp Thr Leu
            355                 360                 365

Pro Glu Tyr Met Lys Pro Ile Tyr Lys Leu Phe Met Asp Thr Tyr Thr
        370                 375                 380

Glu Met Glu Glu Phe Leu Ala Lys Glu Gly Arg Thr Asp Leu Phe Asn
385                 390                 395                 400

Cys Gly Lys Glu Phe Val Lys Glu Phe Val Arg Asn Leu Met Val Glu
                    405                 410                 415

Ala Lys Trp Ala Asn Glu Gly His Ile Pro Thr Thr Glu Glu His Asp
                420                 425                 430

Pro Val Val Ile Ile Thr Gly Gly Ala Asn Leu Leu Thr Thr Thr Cys
            435                 440                 445

Tyr Leu Gly Met Ser Asp Ile Phe Thr Lys Glu Ser Val Glu Trp Ala
        450                 455                 460

Val Ser Ala Pro Pro Leu Phe Arg Tyr Ser Gly Ile Leu Gly Arg Arg
465                 470                 475                 480

Leu Asn Asp Leu Met Thr His Lys Ala Glu Gln Glu Arg Lys His Ser
                    485                 490                 495

Ser Ser Ser Leu Glu Ser Tyr Met Lys Glu Tyr Asn Val Asn Glu Glu
                500                 505                 510

Tyr Ala Gln Thr Leu Ile Tyr Lys Glu Val Glu Asp Val Trp Lys Asp
            515                 520                 525

Ile Asn Arg Glu Tyr Leu Thr Thr Lys Asn Ile Pro Arg Pro Leu Leu
        530                 535                 540

Met Ala Val Ile Tyr Leu Cys Gln Phe Leu Glu Val Gln Tyr Ala Gly
545                 550                 555                 560

Lys Asp Asn Phe Thr Arg Met Gly Asp Glu Tyr Lys His Leu Ile Lys
                    565                 570                 575

Ser Leu Leu Val Tyr Pro Met Ser Ile
                580                 585
```